(12) United States Patent
Keler et al.

(10) Patent No.: US 11,332,537 B2
(45) Date of Patent: May 17, 2022

(54) ANTI-CD27 AND ANTI-PD-L1 ANTIBODIES AND BISPECIFIC CONSTRUCTS

(71) Applicant: Celldex Therapeutics, Inc., Hampton, NJ (US)

(72) Inventors: Tibor Keler, Pipersville, PA (US); Joel Goldstein, Hopewell, NJ (US); Laura A. Vitale, Doylestown, PA (US); Lizhen He, Fujian (CN)

(73) Assignee: Celldex Therapeutics, Inc., Hampton, NJ (US)

( * ) Notice: Subject to any disclaimer, the term of this patent is extended or adjusted under 35 U.S.C. 154(b) by 0 days.

(21) Appl. No.: 17/405,861

(22) Filed: Aug. 18, 2021

(65) Prior Publication Data

US 2022/0025063 A1  Jan. 27, 2022

Related U.S. Application Data

(62) Division of application No. 16/387,228, filed on Apr. 17, 2019.

(60) Provisional application No. 62/826,091, filed on Mar. 29, 2019, provisional application No. 62/658,899, filed on Apr. 17, 2018.

(51) Int. Cl.
| | | |
|---|---|---|
| C07K 16/28 | (2006.01) | |
| A61P 35/00 | (2006.01) | |
| A61K 39/00 | (2006.01) | |

(52) U.S. Cl.
CPC .......... *C07K 16/2878* (2013.01); *A61P 35/00* (2018.01); *C07K 16/2827* (2013.01); *A61K 2039/505* (2013.01); *A61K 2039/507* (2013.01); *A61K 2039/545* (2013.01); *C07K 2317/21* (2013.01); *C07K 2317/31* (2013.01); *C07K 2317/33* (2013.01); *C07K 2317/34* (2013.01); *C07K 2317/35* (2013.01); *C07K 2317/565* (2013.01); *C07K 2317/622* (2013.01); *C07K 2317/732* (2013.01); *C07K 2317/734* (2013.01); *C07K 2317/74* (2013.01); *C07K 2317/76* (2013.01); *C07K 2317/90* (2013.01); *C07K 2317/92* (2013.01)

(58) Field of Classification Search
CPC .......... C07K 16/2878; C07K 2317/565; C07K 2317/622
USPC ............................. 424/133.1, 135.1
See application file for complete search history.

(56) References Cited

U.S. PATENT DOCUMENTS

| | | | |
|---|---|---|---|
| 5,182,368 A | 1/1993 | Ledbetter et al. | |
| 5,506,126 A | 4/1996 | Seed et al. | |
| 5,830,731 A | 11/1998 | Seed et al. | |
| 5,849,898 A | 12/1998 | Seed et al. | |
| 6,010,853 A | 1/2000 | Kanteti et al. | |
| 6,111,093 A | 8/2000 | Seed et al. | |
| 6,218,525 B1 | 4/2001 | Seed et al. | |
| 6,787,688 B2 | 9/2004 | Watkins et al. | |
| 6,808,192 B1 | 10/2004 | Chen | |
| 6,936,704 B1 | 8/2005 | Freeman et al. | |
| 7,038,013 B2 | 5/2006 | Freeman et al. | |
| 7,041,474 B2 | 5/2006 | Kingsbury | |
| 7,101,550 B2 | 9/2006 | Wood et al. | |
| 7,105,328 B2 | 9/2006 | Wood et al. | |
| 7,119,183 B2 | 10/2006 | Seed et al. | |
| 7,385,036 B2 | 6/2008 | Kingsbury | |
| 7,432,351 B1 | 10/2008 | Chen | |
| 7,635,757 B2 | 12/2009 | Freeman et al. | |
| 7,638,492 B2 | 12/2009 | Wood et al. | |
| 7,700,301 B2 | 4/2010 | Wood et al. | |
| 7,709,214 B2 | 5/2010 | Freeman et al. | |
| 7,767,206 B2 | 8/2010 | Tocker et al. | |
| 7,786,284 B2 | 8/2010 | Tocker et al. | |
| 7,794,710 B2 | 9/2010 | Chen et al. | |
| 7,892,540 B2 | 2/2011 | Chen et al. | |
| 7,943,743 B2 | 5/2011 | Korman et al. | |
| 8,163,503 B2 | 4/2012 | Kingsbury | |
| 8,168,179 B2 | 5/2012 | Honjo et al. | |
| 8,287,870 B2 | 10/2012 | Lanzavecchia et al. | |
| 8,481,029 B2 | 7/2013 | Glennie et al. | |
| 8,664,360 B2 | 3/2014 | Mikesell et al. | |
| 8,779,108 B2 | 7/2014 | Queva et al. | |
| 8,993,727 B2 | 3/2015 | Walker et al. | |
| 9,102,737 B2 | 8/2015 | Chen et al. | |

(Continued)

FOREIGN PATENT DOCUMENTS

| | | |
|---|---|---|
| EP | 0330191 A2 | 8/1989 |
| EP | 0739980 A2 | 10/1996 |

(Continued)

OTHER PUBLICATIONS

Chen et al. (Adv Drug Deliv Rev. 65(10):1357-1369 (Oct. 15, 2013)).*

(Continued)

*Primary Examiner* — Lynn A Bristol

(74) *Attorney, Agent, or Firm* — Nelson Mullins Riley & Scarborough LLP; Jane E. Remillard, Esq.; Jeanne M. DiGiorgio, Esq.

(57) ABSTRACT

Provided herein are anti-CD27 and anti-PD-L1 antibodies, and binding domains thereof, as well as bispecific constructs and anti-CD27 binding domain linked to an anti-PD-L1 binding domain. Also provided herein are methods of stimulating T cell activity, methods of inducing or enhancing an immune response, and methods of treating a disease or condition by administering the bispecific constructs, antibodies, or antigen binding fragments thereof, or compositions described herein to a patient in need thereof.

26 Claims, 40 Drawing Sheets

Specification includes a Sequence Listing.

(56) References Cited

U.S. PATENT DOCUMENTS

| | | |
|---|---|---|
| 9,169,325 B2 | 10/2015 | Keler et al. |
| 9,493,561 B2 | 11/2016 | Mak et al. |
| 9,493,565 B2 | 11/2016 | Queva et al. |
| 9,527,916 B2 | 12/2016 | Van Eenennaam et al. |
| 9,683,046 B2 | 6/2017 | Chen et al. |
| 9,938,342 B2 | 4/2018 | Di Padova et al. |
| 10,556,957 B2 | 2/2020 | Beebe et al. |
| 10,633,444 B2 | 4/2020 | Keler et al. |
| 11,180,566 B2 | 11/2021 | Keler et al. |
| 2003/0035790 A1 | 2/2003 | Chen et al. |
| 2004/0072283 A1 | 4/2004 | Seed et al. |
| 2004/0110226 A1 | 6/2004 | Lazar et al. |
| 2004/0170982 A1 | 9/2004 | Morris et al. |
| 2005/0003469 A1 | 1/2005 | Watkins et al. |
| 2006/0228366 A1 | 10/2006 | Watkins |
| 2006/0228710 A1 | 10/2006 | Morris et al. |
| 2007/0149449 A1 | 6/2007 | Morris et al. |
| 2007/0212351 A1 | 9/2007 | Morris et al. |
| 2008/0213267 A1 | 9/2008 | Young et al. |
| 2009/0176317 A1 | 7/2009 | Kwon et al. |
| 2009/0274666 A1 | 11/2009 | Chen |
| 2009/0317368 A1 | 12/2009 | Chen |
| 2010/0151492 A1 | 6/2010 | Ahmed et al. |
| 2010/0173324 A1 | 7/2010 | Mori et al. |
| 2011/0033449 A1 | 2/2011 | Glennie et al. |
| 2011/0052579 A1 | 3/2011 | Weiss et al. |
| 2011/0064743 A1 | 3/2011 | Hammond et al. |
| 2011/0159023 A1 | 6/2011 | Langermann |
| 2011/0195068 A1 | 8/2011 | Langermann et al. |
| 2011/0200620 A1 | 8/2011 | Chen et al. |
| 2011/0223188 A1 | 9/2011 | Langermann |
| 2011/0271358 A1 | 11/2011 | Freeman et al. |
| 2011/0274685 A1 | 11/2011 | Keler et al. |
| 2012/0021377 A1 | 1/2012 | Chen |
| 2012/0027759 A1 | 2/2012 | Chen et al. |
| 2012/0064626 A1 | 3/2012 | Chen |
| 2012/0100139 A1 | 4/2012 | Thompson et al. |
| 2012/0114648 A1 | 5/2012 | Langermann et al. |
| 2012/0195900 A1 | 8/2012 | Ghayur et al. |
| 2012/0201746 A1 | 8/2012 | Liu et al. |
| 2012/0213771 A1 | 8/2012 | Keler et al. |
| 2012/0251514 A1 | 10/2012 | Fowler et al. |
| 2012/0251537 A1 | 10/2012 | Ahmed et al. |
| 2012/0269859 A1 | 10/2012 | Minato et al. |
| 2013/0017199 A1 | 1/2013 | Langermann |
| 2013/0039911 A1 | 2/2013 | Bedi et al. |
| 2013/0183316 A1 | 7/2013 | Van Eenennaam et al. |
| 2013/0266514 A1 | 10/2013 | Nitsch et al. |
| 2013/0266585 A1 | 10/2013 | Nitsch et al. |
| 2013/0336976 A1 | 12/2013 | Glennie et al. |
| 2014/0079691 A1 | 3/2014 | McConnell et al. |
| 2014/0112942 A1 | 4/2014 | Van Eenennaam et al. |
| 2014/0220040 A1 | 8/2014 | Abo et al. |
| 2014/0341917 A1 | 11/2014 | Nastri et al. |
| 2015/0299330 A1 | 10/2015 | Chen et al. |
| 2015/0337047 A1 | 11/2015 | Keler et al. |
| 2016/0185870 A1 | 6/2016 | Van Eenennaam et al. |
| 2016/0194402 A1 | 7/2016 | Van Eenennaam et al. |
| 2016/0208018 A1 | 7/2016 | Chen et al. |
| 2016/0376373 A1 | 12/2016 | Ahmadi et al. |
| 2017/0044265 A1 | 2/2017 | Ahmadi et al. |
| 2017/0267771 A1 | 9/2017 | Van Eenennaam et al. |
| 2017/0032095 A1 | 11/2017 | Chen et al. |
| 2017/0319690 A1 | 11/2017 | Wang et al. |
| 2018/0044429 A1 | 2/2018 | Keler et al. |
| 2018/0066053 A1 | 3/2018 | Keler et al. |
| 2018/0127502 A1 | 5/2018 | Brentjens et al. |
| 2018/0147279 A1 | 5/2018 | Dar et al. |
| 2018/0148496 A1 | 5/2018 | Sui et al. |
| 2018/0161464 A1 | 6/2018 | Kelly et al. |
| 2018/0186883 A1 | 7/2018 | Papadopoulos et al. |
| 2018/0186890 A1 | 7/2018 | Dimitrov et al. |
| 2018/0214548 A1 | 8/2018 | Liu et al. |
| 2019/0010233 A1 | 1/2019 | Liu et al. |
| 2019/0322743 A1 | 10/2019 | Keler et al. |
| 2020/0109207 A1* | 4/2020 | Keler ............... C07K 16/2827 |
| 2021/0198374 A1* | 7/2021 | Keler ............... C07K 16/2827 |
| 2022/0016168 A1 | 1/2022 | He et al. |

FOREIGN PATENT DOCUMENTS

| | | |
|---|---|---|
| EP | 2090320 A1 | 8/2009 |
| EP | 2591001 | 5/2013 |
| EP | 2619226 A2 | 7/2013 |
| EP | 2088858 B1 | 12/2013 |
| EP | 2698382 A1 | 2/2014 |
| EP | 2825200 | 1/2015 |
| JP | 2005-507635 A | 3/2005 |
| WO | 89/08114 A1 | 9/1989 |
| WO | 92/01049 A2 | 1/1992 |
| WO | 96/34096 A1 | 10/1996 |
| WO | 98/54323 A1 | 12/1998 |
| WO | 00/41508 A2 | 7/2000 |
| WO | 02064634 A2 | 8/2002 |
| WO | 2003044036 A1 | 5/2003 |
| WO | 03/068268 A2 | 8/2003 |
| WO | 04023973 A2 | 3/2004 |
| WO | 04/074320 A2 | 9/2004 |
| WO | 04/074321 A2 | 9/2004 |
| WO | 2007102230 A1 | 9/2007 |
| WO | 08/051424 A2 | 5/2008 |
| WO | 2009058564 A2 | 5/2009 |
| WO | 09/100942 A1 | 8/2009 |
| WO | 10/001908 A1 | 1/2010 |
| WO | 2010080463 A1 | 7/2010 |
| WO | 2011/130434 A2 | 10/2011 |
| WO | 2012/004367 A1 | 1/2012 |
| WO | 2012/058460 A2 | 5/2012 |
| WO | 2012/177624 A2 | 12/2012 |
| WO | 2013/138586 A1 | 9/2013 |
| WO | 2015/016718 A1 | 2/2015 |
| WO | 2016/145085 A2 | 9/2016 |
| WO | 2017/079112 A1 | 5/2017 |
| WO | 2017186928 A1 | 11/2017 |
| WO | 2018020273 A1 | 2/2018 |
| WO | 2018129332 A1 | 7/2018 |
| WO | 2018162749 A1 | 9/2018 |
| WO | 2018/183927 A1 | 10/2018 |
| WO | 2018195283 A1 | 10/2018 |
| WO | 2018/223101 A1 | 12/2018 |
| WO | 2019/204462 A2 | 10/2019 |

OTHER PUBLICATIONS

Buchan et al. (J Immunol 194 (1):125-133 (Jan. 1, 2015)).*
Vitale et al. (Cancer Immunol Immunother 69(10):2125-2137 (Oct. 2020)).*
Vitale et al. (Cancer Research, (Jul. 2018) vol. 78, No. 13, Supp. Supplement 1. Abstract No. 5624; Meeting Info: 2018 Annual Meeting of the American Association for Cancer Research, AACR 2018. Chicago, IL, United States. Apr. 14, 2018-Apr. 18, 2018).*
Sanborn et al. (Journal of Clinical Oncology, (2021) vol. 39, No. 15 SUPPL. Abstract No. 2585; Meeting Info: Annual Meeting of the American Society of Clinical Oncology, ASCO 2021. Online. Jun. 4, 2021-Jun. 8, 2021).*
U.S. Appl. No. 17/047,656, filed Oct. 14, 2020, Tibor Keler.
U.S. Appl. No. 16/387,228, filed Apr. 17, 2019, Tibor Keler.
U.S. Appl. No. 17/507,895, filed Oct. 22, 2021, Tibor Keler.
U.S. Appl. No. 14/790,247, filed Jul. 2, 2015, Tibor Keler.
U.S. Appl. No. 13/086,286, filed Apr. 13, 2011, Tibor Keler.
U.S. Appl. No. 13/276,735, filed Oct. 19, 2011, Tibor Keler.
U.S. Appl. No. 15/557,035, filed Sep. 8, 2017, Tibor Keler.
Anonymous:, "Abstract 1246: Development of an agonistic antibody against the human T-cell costimulatory receptor CD27 as a potential immunotherapeutic tool," Cancer Research, XP055283844, 3 pages (2013).
Bigler, Robert D. et all., "A Novel Disulfide-Linked Cell Surface Molecule Present on Resting and Activated Human T Lymphocytes," Leukocyte Typing II, vol. 1, Human T Lymphocytes, Ellis L. Reinherz (Ed.), Springer-Verlag, New York, Chpt. 41, pp. 503-512 (1986).

(56) References Cited

OTHER PUBLICATIONS

Buchan, S. et al., "OX40- and CD27-Mediated Costimulation Synergizes with Anti-PD-L1 Blockade by Forcing Exhausted CD8 + T Cells To Exit Quiescence," The Journal of Immunology, vol. 194(1):125-133 (2015).

Buchan, S. et al., "PD-1 Blockade and CD27 Stimulation Activate Distinct Transcriptional Programs That Synergize or CD8 + T-Cell-Driven Antitumor Immunity," Clinical Cancer Research, vol. 24 (10):2383-2394 (2018).

ClinicalTrials.gov (Identifier: NCT04440943; pp. 1-9; Jun. 22, 2020).

Daniel, et al., "Mapping of Linear Antigenic Sites on the S Glycoprotein of a Neurotropic Murine Coronavirus with Synthetic Peptides: A Combination of Nine Prediction Algorithms Fails To Identify Relevant Epitopes and Peptide Immunogenicity Is Drastically Influenced by the Nature of the Protein Carrier," (Virology, 202:540-549, 1994).

Florido, Manuela et al., "Contribution of CD30/CD153 but not of CD27/CD70, Cd134/OX40L, or CD137/4-1BBL to the optimal induction of protective immunity to *Mycobacterium avium*," Journal of Leukocyte Biology, vol. 76:1039-1046 (2004).

French, Ruth R. et al., "Eradication of lymphomoa by CD8 T cells following anti-CD40 monoclonal antibody therapy is critically dependent on CD27 costimulation," Blood, vol. 109(11):4810-4815 (2007).

Fujiwara, S. et al., "Clinical features of de novo CD25-positive follicular lymphoma," (Leukemia & Lymphoma vol. 55 (2): 307-313): (2014).

George, J., et al., "Differential Effects of Anti-B2-Glycoprotein I Antibodies on Endothelial Cells and on the Manifestations of Experimental Antiphospholipid Syndrome," Circulation, vol. 97: 900-906 (1998).

Gravestein, Loes A. et al., "Novel mAbs reveal potent co-stimulatory activity of murine CD27," International Immunology. vol. 7(4):551-557 (1995).

Greenspan, N. et al., "Defining Epitopes: It's not as Easy as It Seems," Nature Biotechnology, vol. 7: 936-937 (1999).

Gussow, et al., "Humanization of monoclonal antibodies," Methods in Enzymology, vol. 203: 99-121 (1991).

He, LiZhen et al., "Development of Novel Anti-CD27 Human Antibodies with Therapeutic Potential," 101st Annual Meeting of the American-Association-for-Cancer-Research, Abstract No. 5343 (2010).

He, LiZhen et al., "Development of Novel Anti-CD27 Human Antibodies with Therapeutic Potential," Proceedings of the American Association for Cancer Research Annual Meeting, vol. 51:1295 (2010).

Hirano, Testuo et al., "CD27 synergizes with CD40 to induce IgM, IgG, and IgA antibody responses of peripheral blood B cells in the presence of IL-2 and IL-10," Immunology Letters, vol. 89:251-257 (2003).

Hudson, P.J. et al., "High avidity scFv multimers; diabodies and triabodies," J. Immunological Methods, vol. 231: 177-189) (1999).

International Preliminary Report on Patentability, PCT/US2016/21569, dated Sep. 12, 2017, 8 pages.

International Preliminary Report on Patentability, PCT/US2019/027897, dated Oct. 20, 2020, 13 pages.

International Search Report and Written Opinion for Application No. PCT/US2011/032355, dated Jan. 17, 2012, 9 pages.

International Search Report and Written Opinion, PCT/US2016/21569, dated Sep. 15, 2016, 14 pages.

International Search Report and Written Opinion, PCT/US2019/027897, dated Nov. 26, 2019, 23 pages.

Invitation to Pay Additional Fees and, Where Applicable, Protest Fee, PCT/US2019/027897, dated Aug. 27, 2019, 18 pages.

Invitation to Pay Additional Fees for Application No. PCT/US2011/032355, dated Oct. 5, 2011, 4 pages.

Kobata, Tetsuji et al., "CD27 is a Signal-Transducing Molecule Involved in CD45RA+ Naive T Cell Costimulation," The Journal of Immunology, vol. 153:5422-5432 (1994).

Kobata, Tetsuji et al., "CD27-CD70 interactions regulate B-cell activation by T cells," Proc. Natl. Acad. Sci. USA, vol. 92:11249-11253 (1995).

Kolker "Antibodies and the written description requirement of 35 U.S.C.112(a)" pp. 1-36 (Sep. 17, 2020).

Kontemnann RE, "Dual targeting strategies with bispecific antibodies," mAbs, vol. 4:(2):182-197 (2012).

Lee, C. et al., "Novel antibodies targeting immune regulatory checkpoints for cancer therapy," British Journal of Clinical Pharmacology, vol. 76(2):233-247, XP055151740,(2013).

Lippincott-Schwartz, "Antibodies as Cell Biological Tools," (Current Protocols in Cell Biology, 16.0.1-16.0.2, 2002).

Mariuzza et al., "The structural basis of antigen-antibody recognition," Annu. Rev. Biophys. Biophys. Chem., vol. 16: 139-159 (1987).

Vatter, Matthias et al., "Elimination of chronic viral infection by blocking CD27 signaling," The Journal of Experimental Medicine, vol. 203(9):2145-2155 (2006).

McMichael, Andrew J. et al., "T-cell antigens: new and previously defined clusters," Leucocyte Typing III, White Cell Differentiation Antigens, A.J. McMichael (Ed.), Oxford University Press, Oxford, Chpt. 5.1, pp. 31-62 (1987).

Morrissey, KM et al., "Immunotherapy and Novel Combinations in Oncology: Current Landscape, Challenges, and Opportunities:Immunotherapy and Novel Combinations in Oncology," Clinical and Translational Science—CTS, vol. 9 (2);89-104 (2016).

Ramakrishna, Venky et al., "In vitro characterization of novel anti-human CD27 mAbs," The Journal of Immunology, vol. 184, Abstract No. 87.23 (2010).

Rudikoff, Stuart et al., "Single amino acid substitution altering antigen-binding specificity," Proc. Natl. Acad. Sci. USA, vol. 79:1979-1983 (1982).

Sakanishi, Tamami et al., "Anti-tumor effects of depleting and non-depleting anti-CD27 monoclonal antibodies in immune-competent mice," Biochemical and Biophysical Research Communication, vol. 393:829-835 (2010).

Sanborn, R. et al., "Clinical results with combination of anti-CD27 agonist antibody, varlilumab, with anti-PD1 antibody nivolumab in advanced cancer patients," Journal of Clinical Oncology, vol. 35(15-supp):3007-3007 (2017) Abstract Only).

Stewart, R. et al., "The role of Fc gamma receptors in the activity of immunomodulatory antibodies for cancer," Journal for Immunotherapy of Cancer, vol. 2(1): 10 pages (29), XP02119393 (2014).

Stockinger, Hannes et al., "T14, A Non-modulating 150-Kd T Cell Surface Antigen," Leukocyte Typing II, vol. 1, Human T Lymphocytes, Ellis L. Reinherz (Ed.), Springer-Verlag, New York, Chpt. 42, pp. 513-529 (1986).

Sugita, Kanji et al., "The 1A4 Molecule (CD27) is Involved in T Cell Activation," The Journal of Immunology, vol. 147 (5):1477-1483 (1991).

Takeda, Kazuyoshi et al., "CD27-Mediated Activation of Murine NK Cells," The Journal of Immunology, vol. 164:1741-1745 (2000).

Van Lier, Rene A.W. et al., "Tissue Distribution and Biochemical and Functional Properties of Tp55 (CD27), a Novel T Cell Differentiation Antigen," The Journal of Immunology, vol. 139:1589-1596 (1987).

Vitale, L et al., Abstract 2392: CDX-527: A novel bispecific immune-modulating antibody targeting CD27 and PD-L1, Jul. 2019, 1 page (Abstract Only) XP055612392, Retrieved from the Internet:URL:https://cancerres.aacijournals.org/content/79/13_Supplement/2392 [retrieved on Aug. 12, 2019].

Vitale, L. et al., Development of CDX-527: a bispecific antibody combining PD-1 blockade and CD27 costimulation for cancer immunotherapy: Cancer Immunol Immunother, vol. 69(10):2125-2137 (2020).

Winkler et al., "Changing the antigen binding specificity by single point mutations of an anti-p24 (HIV-1) antibody," J. Imm., vol. 265:4505-4514 (2000).

Yang, F.C. et al., "CD27/CD70 interaction directly induces natural killer cell killing activity," Immunology, vol. 88:289-293 (1996).

(56) References Cited

OTHER PUBLICATIONS

Yun, L.W.P., et al., "Blockade of protease-activated receptors on T cells correlates with altered proteolysis of CD27 by gingipains of Porphyromonas gingivalis," Clin Exp Immunol., vol. 150(2): 217-229 (2007).

Dronca, R. et al., "Immunomodulatory Antibody Therapy of Cancer: The Closer, the Better," Clin Cancer Res; vol. 21(5): 944-946 (2015).

International Preliminary Report on Patentability, PCT/US2019/065375, dated Jun. 8, 2021, 8 pages.

International Search Report and Written Opinion, PCT/US2019/065375, dated Jun. 5, 2020, 12 pages.

Mangsbo, S. et al., "ADC-1013, an agonistic CD40 antibody optimized for local immunotherapy of cancer," Journal for ImmunoTherapy of Cancer, 1(Suppl 1):P42 (2013).

Sandin, L. et al., "Locally Delivered CD40 Agonist Antibody Accumulates in Secondary Lymphoid Organs and Eradicates Experimental Disseminated Bladder Cancer," Cancer Immunol. Res., vol. 2(1):80-90 (2014).

Van De Ven, K. et al. "Targeting the T-cell co-stimulatory CD27/CD70 pathway in cancer immunotherapy: rationale and potential," Immunotherapy, vol. 7(6):655-667 (2015).

Vitale, L. et al. (Cancer Research, (Jul. 2018) vol. 78, No. 13, Supp. Supplement 1. Abstract No. 5624; Meeting Info: 2018 Annual Meeting of the American Association for Cancer Research, AACR 2018. Chicago, IL, United States. Apr. 14, 2018-Apr. 18, 2018), 2 pages.

Vonderheide, R. et al., "Agonistic CD40 Antibodies and Cancer Therapy," Clin Cancer Res; vol. 19(5): 1035-43 (2013).

Wasiuk, A. et al., "Conditioning Treatment with A CD27 Antibody Enhances in vivo Expansion and Antitumor Activity of Adoptively Transferred T Cells," Celldex Therapeutics, AACR Meeting Nov. 17-20, 2019 (Boston), Nov. 20, 2019 (Nov. 20, 2019), Retrieved from the Internet: URL:https://www.celldex.com/docs/AACR 2019poster CDX1127.pdf, retrieved on May 8, 2020.

* cited by examiner

| BsAb | Anti-CD27 mAb | Anti-PD-L1 mAb | Reactivity with mouse PD-L1 |
|---|---|---|---|
| CD27xAbX | 1F5 | AbX | Yes |
| CD27x8B1 | 2B3 | 8B1 | No |
| CD27x9H9 | 2B3 | 9H9 | No |

FIG. 15D

ANTI-CD27 AND ANTI-PD-L1 ANTIBODIES AND BISPECIFIC CONSTRUCTS

RELATED APPLICATIONS

This application is a divisional application of U.S. application Ser. No. 16/387,228, filed Apr. 17, 2019, which claims the benefit of priority of U.S. Provisional Application No. 62/658,899 (filed on Apr. 17, 2018) and U.S. Provisional Application No. 62/826,091 (filed on Mar. 29, 2019). The contents of the aforementioned applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on Feb. 13, 2022, is named CDJ_400ADV_ST25.txt and is 119,560 bytes in size.

I. BACKGROUND OF THE INVENTION

Interactions between T cells and antigen-presenting cells involve a variety of accessory molecules that facilitate in the generation of an immune response. One such molecule is CD27, which binds CD70 and belongs to the tumor necrosis factor receptor (TNF-R) superfamily (Ranheim, E. A. et al. (1995) *Blood*, 85(12):3556-65). CD27 typically exists as a glycosylated, type I transmembrane protein, frequently in the form of homodimers with a disulfide bridge linking the two monomers. The disulfide bridge is in the extracellular domain close to the membrane (Camerini et al. (1991) *J. Immunol.*, 147:3165-69). CD27 may also be expressed in a soluble form (see, e.g., van Oers, M. H. et al. (1993) *Blood* 82(11):3430-6 and Loenen, W. A. et al. (1992) *Eur. J. Immunol.*, 22:447). Cross-linking the CD27 antigen on T cells provides a costimulatory signal that, in concert with T-cell receptor crosslinking, can induce T-cell proliferation and cellular immune activation.

CD27 is expressed on mature thymocytes, on most CD4+ and CD8+ peripheral blood T cells, natural killer cells and B cells (Kobata, T. et al. (1995) *Proc. Natl. Acad. Sci. USA*, 92(24):11249-53). CD27 is also highly expressed on B cell non-Hodgkin's lymphomas and B cell chronic lymphocytic leukemias (Ranheim, E. A. et al. (1995) *Blood*, 85(12):3556-65). Additionally, increased levels of soluble CD27 protein have been identified in sera or sites of disease activity in parasitic infection, cytomegalovirus (CMV) infection, sarcoidosis, multiple sclerosis, and B-cell chronic lymphocytic leukemia (Loenen, W. A. et al. (1992) *Eur. J. Immunol*, 22:447).

Programmed death-ligand 1 (PD-L1) is a 40 kDa type 1 transmembrane protein that has been speculated to play a major role in suppressing the immune system during particular events such as pregnancy, tissue allografts, autoimmune disease, and other disease states such as hepatitis. Normally the immune system reacts to foreign antigens that are associated with exogenous or endogenous danger signals, which triggers a proliferation of antigen-specific CD8+ T cells and/or CD4+ helper cells. The binding of PD-L1 to PD-1 transmits an inhibitory signal that reduces the proliferation of these T cells and can also induce apoptosis, which is further mediated by a lower regulation of the gene Bcl-2. PD-L1 is abundant in a variety of human cancers (Dong et al. (2002) *Nat. Med.* 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) *J. Mol. Med.* 81:281-7; Blank et al. (2005) *Cancer Immunol. Immunother.* 54:307-314; Konishi et al. (2004) *Clin. Cancer Res.* 10:5094-100). Immune suppression can be reversed by inhibiting the local interaction of PD-1 with PD-L1, and the effect is additive when the interaction of PD-1 with PD-L2 is blocked as well (Iwai et al. (2002) *Proc. Nat'l. Acad. Sci. USA* 99:12293-7; Brown et al. (2003) *J. Immunol.* 170:1257-66).

Despite advances in multimodal therapy, there is a need in the art for new and improved therapeutic agents to treat conditions or diseases (e.g., in which stimulation of an immune response is desired). Accordingly, it is an object of the present invention to provide improved methods for treating subjects with such conditions or diseases (e.g., cancer).

II. SUMMARY OF THE INVENTION

Provided herein are novel anti-CD27 and anti-PD-L1 antibodies, and binding domains thereof, as well as bispecific constructs and multipsecific constructs comprising an anti-CD27 binding domain linked to an anti-PD-L1 binding domain. Also provided herein are methods of stimulating T cell activity, methods of inducing or enhancing an immune response, and methods of treating a disease or condition (e.g., cancer) by administering the bispecific or multispecific constructs, antibodies, or antigen binding fragments thereof, or compositions described herein to a patient in need thereof.

An exemplary anti-CD27 antibody is antibody 3C2 as described herein. In one embodiment, the anti-CD27 antibody or binding domain thereof comprises the heavy and light chain CDRs or variable regions of antibody 3C2. In another embodiment, the antibody or binding domain thereof comprises the CDR1, CDR2, and CDR3 domains of the heavy chain variable region of antibody 3C2 having the sequence set forth in SEQ ID NO:17, and the CDR1, CDR2 and CDR3 domains of the light chain variable region of antibody 3C2 having the sequence set forth in SEQ ID NO:18. In another embodiment, the antibody or binding domain thereof comprises heavy chain CDR1, CDR2 and CDR3 domains having the sequences set forth in SEQ ID NOs:1, 2, and 3, respectively, or conservative sequence modifications thereof, and light chain CDR1, CDR2 and CDR3 domains having the sequences set forth in SEQ ID NOs:4, 5, and 6, respectively, or conservative sequence modifications thereof. In another embodiment, the antibody or binding domain thereof comprises a heavy chain variable region having the amino acid sequence set forth in SEQ ID NO:17. In another embodiment, the antibody or binding domain thereof comprises a light chain variable region having the amino acid sequence set forth in SEQ ID NO:18. In another embodiment, the antibody or binding domain thereof comprises heavy and light chain variable regions having the amino acid sequences set forth in SEQ ID NO:17 and SEQ ID NO:18, respectively.

Another exemplary anti-CD27 antibody is antibody 2B3 as described herein. In one embodiment, the anti-CD27 antibody or binding domain thereof comprises the heavy and light chain CDRs or variable regions of antibody 2B3. In another embodiment, the antibody or binding domain thereof comprises the CDR1, CDR2, and CDR3 domains of the heavy chain variable region of antibody 2B3 having the sequence set forth in SEQ ID NO:19, and the CDR1, CDR2 and CDR3 domains of the light chain variable region of antibody 3C2 having the sequence set forth in SEQ ID NO:20. In another embodiment, the antibody or binding domain thereof comprises heavy chain CDR1, CDR2 and CDR3 domains having the sequences set forth in SEQ ID NOs:7, 8, and 9, respectively, or conservative sequence modifications thereof, and light chain CDR1, CDR2 and CDR3 domains having the sequences set forth in SEQ ID NOs: 10, 11, and 12, respectively, or conservative sequence modifications thereof. In another embodiment, the antibody or binding domain thereof comprises a heavy chain variable region having the amino acid sequences set forth in SEQ ID NO:19. In another embodiment, the antibody or binding domain thereof comprises a light chain variable region having the amino acid sequences set forth in SEQ ID NO:20. In another embodiment, the antibody or binding domain thereof comprises heavy and light chain variable regions having the amino acid sequences set forth in SEQ ID NO:19 and SEQ ID NO:20, respectively.

An exemplary anti-PD-L1 antibody is antibody 7H7 as described herein. In one embodiment, the anti-PD-L1 antibody or binding domain thereof comprises the heavy and light chain CDRs or variable regions of antibody 7H7. In another embodiment, the antibody or binding domain thereof comprises the CDR1, CDR2, and CDR3 domains of the heavy chain variable region of antibody 7H7 having the sequence set forth in SEQ ID NO:77, and the CDR1, CDR2 and CDR3 domains of the light chain variable region of antibody 7H7 having the sequence set forth in SEQ ID NO:78. In another embodiment, the antibody or binding domain thereof comprises heavy chain CDR1, CDR2 and CDR3 domains having the sequences set forth in SEQ ID NOs:29, 30, and 31, respectively, or conservative sequence modifications thereof, and light chain CDR1, CDR2 and CDR3 domains having the sequences set forth in SEQ ID NOs:32, 33, and 34, respectively, or conservative sequence modifications thereof. In another embodiment, the antibody or binding domain thereof comprises a heavy chain variable region having the amino acid sequence set forth in SEQ ID NO:77. In another embodiment, the antibody or binding domain thereof comprises a heavy chain variable region having the amino acid sequence set forth in SEQ ID NO:77. In another embodiment, the antibody or binding domain thereof comprises heavy and light chain variable regions having the amino acid sequences set forth in SEQ ID NO:77 and SEQ ID NO:78, respectively.

Another exemplary anti-PD-L1 antibody is antibody 1B3 as described herein. In one embodiment, the anti-PD-L1 antibody or binding domain thereof comprises the heavy and light chain CDRs or variable regions of antibody 1B3. In another embodiment, the antibody or binding domain thereof comprises the CDR1, CDR2, and CDR3 domains of the heavy chain variable region of antibody 1B3 having the sequence set forth in SEQ ID NO:79, and the CDR1, CDR2 and CDR3 domains of the light chain variable region of antibody 1B3 having the sequence set forth in SEQ ID NO:80. In another embodiment, the antibody or binding domain thereof comprises heavy chain CDR1, CDR2 and CDR3 domains having the sequences set forth in SEQ ID NOs:35, 36, and 37, respectively, or conservative sequence modifications thereof, and light chain CDR1, CDR2 and CDR3 domains having the sequences set forth in SEQ ID NOs:38, 39, and 40, respectively, or conservative sequence modifications thereof. In another embodiment, the antibody or binding domain thereof comprises a heavy chain variable region having the amino acid sequences set forth in SEQ ID NO:79. In another embodiment, the antibody or binding domain thereof comprises a light chain variable region having the amino acid sequences set forth in SEQ ID NO:80.

In another embodiment, the antibody or binding domain thereof comprises heavy and light chain variable regions having the amino acid sequences set forth in SEQ ID NO:79 and SEQ ID NO:80, respectively.

Another exemplary anti-PD-L1 antibody is antibody 3B6 as described herein. In one embodiment, the anti-PD-L1 antibody or binding domain thereof comprises the heavy and light chain CDRs or variable regions of antibody 3B6. In another embodiment, the antibody or binding domain thereof comprises the CDR1, CDR2, and CDR3 domains of the heavy chain variable region of antibody 3B6 having the sequence set forth in SEQ ID NO:81, and the CDR1, CDR2 and CDR3 domains of the light chain variable region of antibody 3B6 having the sequence set forth in SEQ ID NO:82. In another embodiment, the antibody or binding domain thereof comprises heavy chain CDR1, CDR2 and CDR3 domains having the sequences set forth in SEQ ID NOs:41, 42, and 43, respectively, or conservative sequence modifications thereof, and light chain CDR1, CDR2 and CDR3 domains having the sequences set forth in SEQ ID NOs:44, 45, and 46, respectively, or conservative sequence modifications thereof. In another embodiment, the antibody or binding domain thereof comprises a heavy chain variable region having the amino acid sequence set forth in SEQ ID NO:81. In another embodiment, the antibody or binding domain thereof comprises a light chain variable region having the amino acid sequence set forth in SEQ ID NO:82. In another embodiment, the antibody or binding domain thereof comprises heavy and light chain variable regions having the amino acid sequences set forth in SEQ ID NO:81 and SEQ ID NO:82, respectively.

Another exemplary anti-PD-L1 antibody is antibody 8B1 as described herein. In one embodiment, the anti-PD-L1 antibody or binding domain thereof comprises the heavy and light chain CDRs or variable regions of antibody 8B1. In another embodiment, the antibody or binding domain thereof comprises the CDR1, CDR2, and CDR3 domains of the heavy chain variable region of antibody 8B1 having the sequence set forth in SEQ ID NO:83, and the CDR1, CDR2 and CDR3 domains of the light chain variable region of antibody 8B1 having the sequence set forth in SEQ ID NO:84. In another embodiment, the antibody or binding domain thereof comprises heavy chain CDR1, CDR2 and CDR3 domains having the sequences set forth in SEQ ID NOs:47, 48, and 49, respectively, or conservative sequence modifications thereof, and light chain CDR1, CDR2 and CDR3 domains having the sequences set forth in SEQ ID NOs:50, 51, and 52, respectively, or conservative sequence modifications thereof. In another embodiment, the antibody or binding domain thereof comprises a heavy chain variable region having the amino acid sequences set forth in SEQ ID NO:83. In another embodiment, the antibody or binding domain thereof comprises a light chain variable region having the amino acid sequences set forth in SEQ ID NO:84. In another embodiment, the antibody or binding domain thereof comprises heavy and light chain variable regions having the amino acid sequences set forth in SEQ ID NO:83 and SEQ ID NO:84, respectively.

Another exemplary anti-PD-L1 antibody is antibody 4A3 as described herein. In one embodiment, the anti-PD-L1 antibody or binding domain thereof comprises the heavy and light chain CDRs or variable regions of antibody 4A3. In another embodiment, the antibody or binding domain thereof comprises the CDR1, CDR2, and CDR3 domains of the heavy chain variable region of antibody 4A3 having the sequence set forth in SEQ ID NO:85, and the CDR1, CDR2 and CDR3 domains of the light chain variable region of antibody 4A3 having the sequence set forth in SEQ ID NO:86. In another embodiment, the antibody or binding domain thereof comprises heavy chain CDR1, CDR2 and CDR3 domains having the sequences set forth in SEQ ID NOs:53, 54, and 55, respectively, or conservative sequence modifications thereof, and light chain CDR1, CDR2 and CDR3 domains having the sequences set forth in SEQ ID NOs:56, 57, and 58, respectively, or conservative sequence modifications thereof. In another embodiment, the antibody or binding domain thereof comprises a heavy chain variable region having the amino acid sequence set forth in SEQ ID NO:85. In another embodiment, the antibody or binding domain thereof comprises a light chain variable region having the amino acid sequence set forth in SEQ ID NO:86. In another embodiment, the antibody or binding domain thereof comprises heavy and light chain variable regions having the amino acid sequences set forth in SEQ ID NO:85 and SEQ ID NO:86, respectively.

Another exemplary anti-PD-L1 antibody is antibody 9H9 as described herein. In one embodiment, the anti-PD-L1 antibody or binding domain thereof comprises the heavy and light chain CDRs or variable regions of antibody 9H9. In another embodiment, the antibody or binding domain thereof comprises the CDR1, CDR2, and CDR3 domains of the heavy chain variable region of antibody 9H9 having the sequence set forth in SEQ ID NO:87, and the CDR1, CDR2 and CDR3 domains of the light chain variable region of antibody 9H9 having the sequence set forth in SEQ ID NO:88. In another embodiment, the antibody or binding domain thereof comprises heavy chain CDR1, CDR2 and CDR3 domains having the sequences set forth in SEQ ID NOs:59, 60, and 61, respectively, or conservative sequence modifications thereof, and light chain CDR1, CDR2 and CDR3 domains having the sequences set forth in SEQ ID NOs:62, 63, and 64, respectively, or conservative sequence modifications thereof. In another embodiment, the antibody or binding domain thereof comprises a heavy chain variable region having the amino acid sequence set forth in SEQ ID NO:87. In another embodiment, the antibody or binding domain thereof comprises a light chain variable region having the amino acid sequence set forth in SEQ ID NO:88. In another embodiment, the antibody or binding domain thereof comprises heavy and light chain variable regions having the amino acid sequences set forth in SEQ ID NO:87 and SEQ ID NO:88, respectively.

In one embodiment, the CDR1, 2, and/or 3 regions of the anti-C27 or anti-PD-L1 binding domains described herein can comprise the exact amino acid sequences as those of antibodies 3C2, 2B3, 7H7, 1B3, 3B6, 8B1, 4A3 and 9H9 disclosed herein. In another embodiment, the antibodies comprise derivatives from the exact CDR sequences of 3C2, 2B3, 7H7, 1B3, 3B6, 8B1, 4A3 and 9H9, yet still retain the ability of to bind either CD27 or PD-L1 effectively. Such sequence modifications may include one or more (e.g., 1, 2, 3, 4, 5, or 6) amino acid additions, deletions, or substitutions, e.g., conservative sequence modifications.

In another embodiment, the anti-C27 or anti-PD-L1 binding domains described herein can be composed of one or more CDRs that are, for example, 90%, 95%, 98% or 99.5% identical to one or more CDRs of antibodies 3C2, 2B3, 7H7, 1B3, 3B6, 8B1, 4A3 and 9H9. Ranges intermediate to the above-recited values, e.g., CDRs that are 90-95%, 95-98%, or 98-100% identical identity to one or more of the above sequences are also intended to be encompassed by the present invention.

The antibody sequences can also be consensus sequences of several antibodies. For example, in one embodiment, the anti-PD-L1 binding domain comprises a heavy chain variable region CDR1 comprising an amino acid sequence selected from the consensus sequence: (T,S)(S,Y,H)WMS (SEQ ID NO:167). In another embodiment, the anti-PD-L1 binding domain comprises a heavy chain variable region CDR2 comprising SEQ ID NO:168. In another embodiment, the anti-PD-L1 binding domain comprises a heavy chain variable region CDR3 comprising SEQ ID NO:169. In another embodiment, the anti-PD-L1 binding domain comprises a light chain variable region CDR1 comprising SEQ ID NO:170. In another embodiment, the anti-PD-L1 binding domain comprises a light chain variable region CDR2 comprising SEQ ID NO:171. In another embodiment, the anti-PD-L1 binding domain comprises a light chain variable region CDR3 comprising SEQ ID NO:172.

Sequences substantially identical to the anti-C27 and/or anti-PD-L1 binding domains described herein (e.g., at least 80%, 85%, 90%, 91%, 92%, 93%, 94%, 95%, 96%, 97%, 98% or 99% identical to the aforementioned sequences), are also encompassed by the invention. In one embodiment, the anti-CD27 binding domain comprises a heavy chain variable region comprising SEQ ID NO:17, SEQ ID NO: 19 or a sequence at least 90% identical thereto (e.g., at least 90%, 91%, 92%, 93%, 94%, 95%, 96%, 97%, 98% or 99% identical to the aforementioned sequences). In another embodiment, the anti-CD27 binding domain comprises a light chain variable region comprising SEQ ID NO:18, SEQ ID NO:20, or a sequence at least 90% identical thereto (e.g., at least 90%, 91%, 92%, 93%, 94%, 95%, 96%, 97%, 98% or 99% identical to the aforementioned sequences). In another embodiment, the anti-CD27 binding domain comprises a heavy chain variable region comprising SEQ ID NO:17 and a light chain variable region comprising SEQ ID NO:18 or sequences at least 90% identical thereto (e.g., at least 90%, 91%, 92%, 93%, 94%, 95%, 96%, 97%, 98% or 99% identical to the aforementioned sequences). In another embodiment, the anti-CD27 binding domain comprises a heavy chain variable region comprising SEQ ID NO:19 and a light chain variable region comprising SEQ ID NO:20 or sequences at least 90% identical thereto (e.g., at least 90%, 91%, 92%, 93%, 94%, 95%, 96%, 97%, 98% or 99% identical to the aforementioned sequences).

In another embodiment, the anti-PD-L1 binding domain comprises a heavy chain variable region comprising SEQ ID NO:77, SEQ ID NO:79, SEQ ID NO:81, SEQ ID NO:83, SEQ ID NO:85, SEQ ID NO:87, or a sequence at least 90% identical thereto (e.g., at least 90%, 91%, 92%, 93%, 94%, 95%, 96%, 97%, 98% or 99% identical to the aforementioned sequences). In another embodiment, the anti-PD-L1 binding domain comprises a light chain variable region comprising SEQ ID NO:78, SEQ ID NO:80, SEQ ID NO:82, SEQ ID NO:84, SEQ ID NO:86, SEQ ID NO:88 or a sequence at least 90% identical thereto (e.g., at least 90%, 91%, 92%, 93%, 94%, 95%, 96%, 97%, 98% or 99% identical to the aforementioned sequences). In another embodiment, the anti-PD-L1 binding domain comprises a heavy chain variable region comprising SEQ ID NO:77 and a light chain variable region comprising SEQ ID NO:78 or sequences at least 90% identical thereto (e.g., at least 90%, 91%, 92%, 93%, 94%, 95%, 96%, 97%, 98% or 99% identical to the aforementioned sequences). In another embodiment, the anti-PD-L1 binding domain comprises a heavy chain variable region comprising SEQ ID NO:79 and a light chain variable region comprising SEQ ID NO:80 or sequences at least 90% identical thereto (e.g., at least 90%, 91%, 92%, 93%, 94%, 95%, 96%, 97%, 98% or 99% identical to the aforementioned sequences). In another embodiment, the anti-PD-L1 binding domain comprises a heavy chain variable region comprising SEQ ID NO:81 and a light chain variable region comprising SEQ ID NO:82 or sequences at least 90% identical thereto (e.g., at least 90%, 91%, 92%, 93%, 94%, 95%, 96%, 97%, 98% or 99% identical to the aforementioned sequences). In another embodiment, the anti-PD-L1 binding domain comprises a heavy chain variable region comprising SEQ ID NO:83 and a light chain variable region comprising SEQ ID NO:84 or sequences at least 90% identical thereto (e.g., at least 90%, 91%, 92%, 93%, 94%, 95%, 96%, 97%, 98% or 99% identical to the aforementioned sequences). In another embodiment, the anti-PD-L1 binding domain comprises a heavy chain variable region comprising SEQ ID NO:85 and a light chain variable region comprising SEQ ID NO:86 or sequences at least 90% identical thereto (e.g., at least 90%, 91%, 92%, 93%, 94%, 95%, 96%, 97%, 98% or 99% identical to the aforementioned sequences). In another embodiment, the anti-PD-L1 binding domain comprises a heavy chain variable region comprising SEQ ID NO:87 and a light chain variable region comprising SEQ ID NO:88 or sequences at least 90% identical thereto (e.g., at least 90%, 91%, 92%, 93%, 94%, 95%, 96%, 97%, 98% or 99% identical to the aforementioned sequences).

Anti-CD27 and/or anti-PD-L1 antibodies or binding domains thereof that compete for binding with any of the antibodies or binding domains thereof described herein or that bind the same epitope as any of the antibodies or binding domains thereof described herein are also suitable for use and are encompassed by the invention. For example, in one embodiment, the anti-CD27 antibody or binding domain thereof competes for binding to CD27 with antibody 3C2 and/or antibody 2B3, as described herein. For example, as described in Example 28, antibodies of the invention (e.g., antibody 2B3) bind to one or more residues within amino acids 80-95 of the ECD of human CD27 (SEQ ID NO: 183), e.g., one or more residues within amino acids 85-89, e.g., amino acids 85, 87, 88, and/or 89 of the ECD of human CD27 (SEQ ID NO: 183).

In another embodiment, the antibodies bind to the wild-type ECD of human CD27, but not to a mutated version of the ECD having amino acid substitutions at one or more positions within amino acid residues 85-89 (e.g., A85S, R87A, N88A, and/or G89A) of the ECD of human CD27 (SEQ ID NO: 183). For example, the anti-CD27 antibody or antigen-binding fragment thereof, binds to the wildtype ECD of human CD27 (SEQ ID NO: 183), but does not bind to a mutated version of the wildtype ECD of human CD27 having the following amino acid substitutions: A85S, R87A, N88A, and G89A.

In another embodiment, the anti-CD27 antibody or binding domain binds to the same epitope on CD27 as antibody 3C2 and/or antibody 2B3, as described herein. In another embodiment, the antibody or anti-PD-L1 binding domain competes for binding to PD-L1 with antibody 7H7, 1B3, 3B6, 8B1, 4A3 and/or 9H9, as described herein. In another embodiment, the anti-PD-L1 antibody or binding domain binds to the same epitope on PD-L1 as antibody 7H7, 1B3, 3B6, 8B1, 4A3 and/or 9H9, as described herein.

In one aspect, a bispecific construct (or multispecific construct) comprising an anti-CD27 binding domain linked to an anti-PD-L1 binding domain is provided, wherein:
 (i) the anti-CD27 binding domain comprises:
  a. heavy chain variable region CDR1, CDR2 and CDR3 as set forth in SEQ ID NOs:1, 2, and 3, respectively, or conservative sequence modifications thereof, and light chain variable region CDR1, CDR2 and CDR3 as set forth in SEQ ID NOs:4, 5, and 6, respectively, or conservative sequence modifications thereof, or
  b. heavy chain variable region CDR1, CDR2 and CDR3 as set forth in SEQ ID NOs:7, 8, and 9, respectively, or conservative sequence modifications thereof, and light chain variable region CDR1, CDR2 and CDR3 as set forth in SEQ ID NOs:10, 11, and 12, respectively, or conservative sequence modifications thereof; and
 (ii) the anti-PD-L1 binding domain comprises:
  a. a heavy chain variable region CDR1 comprising an amino acid sequence selected from the consensus sequence: (T,S)(S,Y,H)WMS (SEQ ID NO:167);
  b. a heavy chain variable region CDR2 comprising SEQ ID NO:168;
  c. a heavy chain variable region CDR3 comprising SEQ ID NO:169;
  d. a light chain variable region CDR1 comprising SEQ ID NO:170;
  e. a light chain variable region CDR2 comprising SEQ ID NO:171; and
  f. a light chain variable region CDR3 comprising SEQ ID NO:172.

In another embodiment, a bispecific construct comprising an anti-CD27 binding domain linked to an anti-PD-L1 binding domain, wherein:
 (i) the anti-CD27 binding domain comprises:
  a. heavy chain variable region CDR1, CDR2 and CDR3 as set forth in SEQ ID NOs:1, 2, and 3, respectively, or conservative sequence modifications thereof, and light chain variable region CDR1, CDR2 and CDR3 as set forth in SEQ ID NOs:4, 5, and 6, respectively, or conservative sequence modifications thereof, or
  b. heavy chain variable region CDR1, CDR2 and CDR3 as set forth in SEQ ID NOs:7, 8, and 9, respectively, or conservative sequence modifications thereof, and light chain variable region CDR1, CDR2 and CDR3 as set forth in SEQ ID NOs:10, 11, and 12, respectively, or conservative sequence modifications thereof; and
 (ii) the anti-PD-L1 binding domain comprises:
  a. a heavy chain variable region comprising SEQ ID NO:77 and a light chain variable region comprising SEQ ID NO:78 or sequences at least 95% identical thereto;
  b. a heavy chain variable region comprising SEQ ID NO:79 and a light chain variable region comprising SEQ ID NO:80 or sequences at least 95% identical thereto;
  c. a heavy chain variable region comprising SEQ ID NO:81 and a light chain variable region comprising SEQ ID NO:82 or sequences at least 95% identical thereto;
  d. a heavy chain variable region comprising SEQ ID NO:83 and a light chain variable region comprising SEQ ID NO:84 or sequences at least 95% identical thereto;
  e. a heavy chain variable region comprising SEQ ID NO:85 and a light chain variable region comprising SEQ ID NO:86 or sequences at least 95% identical thereto; or
  f. a heavy chain variable region comprising SEQ ID NO:87 and a light chain variable region comprising SEQ ID NO:88 or sequences at least 95% identical thereto.

In another embodiment, the bispecific construct comprises (a) an anti-CD27 binding domain comprising heavy chain variable region CDR1, CDR2 and CDR3 as set forth in SEQ ID NOs:1, 2, and 3, respectively, or conservative sequence modifications thereof, and light chain variable region CDR1, CDR2 and CDR3 as set forth in SEQ ID NOs:4, 5, and 6, respectively, or conservative sequence modifications thereof, and (b) an anti-PD-L1 binding domain comprising heavy chain variable region CDR1, CDR2 and CDR3 as set forth in SEQ ID NOs:29, 30, and 31, respectively, and light chain variable region CDR1, CDR2 and CDR3 as set forth in SEQ ID NOs: 32, 33, and 34, respectively.

In another embodiment, the bispecific construct comprises (a) an anti-CD27 binding domain comprising a heavy chain variable region comprising SEQ ID NO:17 and a light chain variable region comprising SEQ ID NO:18 and (b) an anti-PD-L1 binding domain comprising a heavy chain variable region comprising SEQ ID NO:77 and a light chain variable region comprising SEQ ID NO:78.

In another embodiment, the bispecific construct comprises (a) an anti-CD27 binding domain comprising heavy chain variable region CDR1, CDR2 and CDR3 as set forth in SEQ ID NOs:1, 2, and 3, respectively, or conservative sequence modifications thereof, and light chain variable region CDR1, CDR2 and CDR3 as set forth in SEQ ID NOs:4, 5, and 6, respectively, or conservative sequence modifications thereof and (b) an anti-PD-L1 binding domain comprising heavy chain variable region CDR1, CDR2 and CDR3 as set forth in SEQ ID NOs:35, 36, and 37, respectively, and light chain variable region CDR1, CDR2 and CDR3 as set forth in SEQ ID NOs: 38, 39, and 40, respectively.

In another embodiment, the bispecific construct comprises (a) an anti-CD27 binding domain comprising a heavy chain variable region comprising SEQ ID NO:17 and a light chain variable region comprising SEQ ID NO:18 and (b) an anti-PD-L1 binding domain comprising a heavy chain variable region comprising SEQ ID NO:79 and a light chain variable region comprising SEQ ID NO:80.

In another embodiment, the bispecific construct comprises (a) an anti-CD27 binding domain comprising heavy chain variable region CDR1, CDR2 and CDR3 as set forth in SEQ ID NOs:1, 2, and 3, respectively, or conservative sequence modifications thereof, and light chain variable region CDR1, CDR2 and CDR3 as set forth in SEQ ID NOs:4, 5, and 6, respectively, or conservative sequence modifications thereof and (b) an anti-PD-L1 binding domain comprising heavy chain variable region CDR1, CDR2 and CDR3 as set forth in SEQ ID NOs:41, 42, and 43, respectively, and light chain variable region CDR1, CDR2 and CDR3 as set forth in SEQ ID NOs:44, 45, and 46, respectively.

In another embodiment, the bispecific construct comprises (a) an anti-CD27 binding domain comprising a heavy chain variable region comprising SEQ ID NO:17 and a light chain variable region comprising SEQ ID NO:18 and (b) an anti-PD-L1 binding domain comprising a heavy chain variable region comprising SEQ ID NO:81 and a light chain variable region comprising SEQ ID NO:82.

In another embodiment, the bispecific construct comprises (a) an the anti-CD27 binding domain comprising heavy chain variable region CDR1, CDR2 and CDR3 as set forth in SEQ ID NOs:1, 2, and 3, respectively, or conservative sequence modifications thereof, and light chain variable region CDR1, CDR2 and CDR3 as set forth in SEQ ID NOs:4, 5, and 6, respectively, or conservative sequence modifications thereof and (b) an anti-PD-L1 binding domain comprising heavy chain variable region CDR1, CDR2 and CDR3 as set forth in SEQ ID NOs:47, 48, and 49, respectively, or conservative sequence modifications thereof, and light chain variable region CDR1, CDR2 and CDR3 as set forth in SEQ ID NOs:50, 51, and 52, respectively, or conservative sequence modifications thereof.

In another embodiment, the bispecific construct comprises (a) an anti-CD27 binding domain comprising a heavy chain variable region comprising SEQ ID NO:17 and a light chain variable region comprising SEQ ID NO:18 and (b) an anti-PD-L1 binding domain comprising a heavy chain variable region comprising SEQ ID NO:83 and a light chain variable region comprising SEQ ID NO:84.

In another embodiment, the bispecific construct comprises (a) an anti-CD27 binding domain comprising heavy chain variable region CDR1, CDR2 and CDR3 as set forth in SEQ ID NOs:1, 2, and 3, respectively, or conservative sequence modifications thereof, and light chain variable region CDR1, CDR2 and CDR3 as set forth in SEQ ID NOs:4, 5, and 6, respectively, or conservative sequence modifications thereof, and (b) an anti-PD-L1 binding domain comprising heavy chain variable region CDR1, CDR2 and CDR3 as set forth in SEQ ID NOs:53, 54, and 55, respectively, or conservative sequence modifications thereof, and light chain variable region CDR1, CDR2 and CDR3 as set forth in SEQ ID NOs:56, 57, and 58, respectively, or conservative sequence modifications thereof.

In another embodiment, the bispecific construct comprises (a) an anti-CD27 binding domain comprising a heavy chain variable region comprising SEQ ID NO:17 and a light chain variable region comprising SEQ ID NO:18 and (b) an anti-PD-L1 binding domain comprising a heavy chain variable region comprising SEQ ID NO:85 and a light chain variable region comprising SEQ ID NO:86.

In another embodiment, the bispecific construct comprises (a) an anti-CD27 binding domain comprising heavy chain variable region CDR1, CDR2 and CDR3 as set forth in SEQ ID NOs:1, 2, and 3, respectively, or conservative sequence modifications thereof, and light chain variable region CDR1, CDR2 and CDR3 as set forth in SEQ ID NOs:4, 5, and 6, respectively, or conservative sequence modifications thereof, and an anti-PD-L1 binding domain comprising heavy chain variable region CDR1, CDR2 and CDR3 as set forth in SEQ ID NOs:59, 60, and 61, respectively, or conservative sequence modifications thereof, and light chain variable region CDR1, CDR2 and CDR3 as set forth in SEQ ID NOs: 62, 63, and 64, respectively, or conservative sequence modifications thereof.

In another embodiment, the bispecific construct comprises (a) an anti-CD27 binding domain comprising a heavy chain variable region comprising SEQ ID NO:17 and a light chain variable region comprising SEQ ID NO:18 and (b) an anti-PD-L1 binding domain comprising a heavy chain variable region comprising SEQ ID NO:87 and a light chain variable region comprising SEQ ID NO:88.

In another embodiment, the bispecific construct comprises (a) an anti-CD27 binding domain comprising heavy chain variable region CDR1, CDR2 and CDR3 as set forth in SEQ ID NOs:7, 8, and 9, respectively, or conservative sequence modifications thereof, and light chain variable region CDR1, CDR2 and CDR3 as set forth in SEQ ID NOs:10, 11, and 12, respectively, or conservative sequence modifications thereof, and (b) an anti-PD-L1 binding domain comprising heavy chain variable region CDR1, CDR2 and CDR3 as set forth in SEQ ID NOs:29, 30, and 31, respectively, or conservative sequence modifications thereof, and light chain variable region CDR1, CDR2

CDR3 as set forth in SEQ ID NOs:32, 33, and 34, respectively, or conservative sequence modifications thereof.

In another embodiment, the bispecific construct comprises (a) an anti-CD27 binding domain comprising a heavy chain variable region comprising SEQ ID NO:19 and a light chain variable region comprising SEQ ID NO:20 and (b) an anti-PD-L1 binding domain comprising a heavy chain variable region comprising SEQ ID NO:77 and a light chain variable region comprising SEQ ID NO:78.

In another embodiment, the bispecific construct comprises (a) an anti-CD27 binding domain comprising heavy chain variable region CDR1, CDR2 and CDR3 as set forth in SEQ ID NOs:7, 8, and 9, respectively, or conservative sequence modifications thereof, and light chain variable region CDR1, CDR2 and CDR3 as set forth in SEQ ID NOs:10, 11, and 12, respectively, or conservative sequence modifications thereof, and (b) an anti-PD-L1 binding domain comprising heavy chain variable region CDR1, CDR2 and CDR3 as set forth in SEQ ID NOs:35, 36, and 37, respectively, or conservative sequence modifications thereof, and light chain variable region CDR1, CDR2 and CDR3 as set forth in SEQ ID NOs:38, 39, and 40, respectively, or conservative sequence modifications thereof.

In another embodiment, the bispecific construct comprises (a) an anti-CD27 binding domain comprising a heavy chain variable region comprising SEQ ID NO:19 and a light chain variable region comprising SEQ ID NO:20 and (b) and anti-PD-L1 binding domain comprising a heavy chain variable region comprising SEQ ID NO:79 and a light chain variable region comprising SEQ ID NO:80.

In another embodiment, the bispecific construct comprises (a) an anti-CD27 binding domain comprising heavy chain variable region CDR1, CDR2 and CDR3 as set forth in SEQ ID NOs:7, 8, and 9, respectively, or conservative sequence modifications thereof, and light chain variable region CDR1, CDR2 and CDR3 as set forth in SEQ ID NOs:10, 11, and 12, respectively, or conservative sequence modifications thereof, and (b) an anti-PD-L1 binding domain comprising heavy chain variable region CDR1, CDR2 and CDR3 as set forth in SEQ ID NOs:41, 42, and 43, respectively, or conservative sequence modifications thereof, and light chain variable region CDR1, CDR2 and CDR3 as set forth in SEQ ID NOs:44, 45, and 46, respectively, or conservative sequence modifications thereof.

In another embodiment, the bispecific construct comprises (a) an anti-CD27 binding domain comprises a heavy chain variable region comprising SEQ ID NO:19 and a light chain variable region comprising SEQ ID NO:20 and an anti-PD-L1 binding domain comprising a heavy chain variable region comprising SEQ ID NO:81 and a light chain variable region comprising SEQ ID NO:82.

In another embodiment, the bispecific construct comprises (a) an anti-CD27 binding domain comprising heavy chain variable region CDR1, CDR2 and CDR3 as set forth in SEQ ID NOs:7, 8, and 9, respectively, or conservative sequence modifications thereof, and light chain variable region CDR1, CDR2 and CDR3 as set forth in SEQ ID NOs:10, 11, and 12, respectively, or conservative sequence modifications thereof and (b) an anti-PD-L1 binding domain comprising heavy chain variable region CDR1, CDR2 and CDR3 as set forth in SEQ ID NOs:47, 48, and 49, respectively, or conservative sequence modifications thereof, and light chain variable region CDR1, CDR2 and CDR3 as set forth in SEQ ID NOs:50, 51, and 52, respectively, or conservative sequence modifications thereof.

In another embodiment, the bispecific construct comprises (a) an anti-CD27 binding domain comprising a heavy chain variable region comprising SEQ ID NO:19 and a light chain variable region comprising SEQ ID NO:20 and (b) an anti-PD-L1 binding domain comprises a heavy chain variable region comprising SEQ ID NO:83 and a light chain variable region comprising SEQ ID NO:84.

In another embodiment, the bispecific construct comprises (a) an anti-CD27 binding domain comprising a heavy chain variable region CDR1, CDR2 and CDR3 as set forth in SEQ ID NOs:7, 8, and 9, respectively, or conservative sequence modifications thereof, and light chain variable region CDR1, CDR2 and CDR3 as set forth in SEQ ID NOs:10, 11, and 12, respectively, or conservative sequence modifications thereof and (b) an anti-PD-L1 binding domain comprising a heavy chain variable region CDR1, CDR2 and CDR3 as set forth in SEQ ID NOs:53, 54, and 55, respectively, or conservative sequence modifications thereof, and light chain variable region CDR1, CDR2 and CDR3 as set forth in SEQ ID NOs:56, 57, and 58, respectively, or conservative sequence modifications thereof.

In another embodiment, the bispecific construct comprises (a) an anti-CD27 binding domain comprising a heavy chain variable region comprising SEQ ID NO:19 and a light chain variable region comprising SEQ ID NO:20 and (b) an anti-PD-L1 binding domain comprising a heavy chain variable region comprising SEQ ID NO:85 and a light chain variable region comprising SEQ ID NO:86.

In another embodiment, the bispecific construct comprises (a) an anti-CD27 binding domain comprising a heavy chain variable region CDR1, CDR2 and CDR3 as set forth in SEQ ID NOs:7, 8, and 9, respectively, or conservative sequence modifications thereof, and light chain variable region CDR1, CDR2 and CDR3 as set forth in SEQ ID NOs:10, 11, and 12, respectively, or conservative sequence modifications thereof, and (b) an anti-PD-L1 binding domain comprising a heavy chain variable region CDR1, CDR2 and CDR3 as set forth in SEQ ID NOs:59, 60, and 61, respectively, or conservative sequence modifications thereof, and light chain variable region CDR1, CDR2 and CDR3 as set forth in SEQ ID NOs:62, 63, and 64, respectively, or conservative sequence modifications thereof.

In another embodiment, the bispecific construct comprises (a) an anti-CD27 binding domain comprising a heavy chain variable region comprising SEQ ID NO:19 and a light chain variable region comprising SEQ ID NO:20 and (b) an anti-PD-L1 binding domain comprises a heavy chain variable region comprising SEQ ID NO:87 and a light chain variable region comprising SEQ ID NO:88.

In one embodiment, the anti-PD-L1 binding domain and the anti-CD27 binding domain are genetically fused. The bispecific construct can be, for example, a fusion protein, which can be made by genetic engineering using standard recombinant DNA techniques to operatively link nucleic acid encoding the anti-CD27 and anti-PD-L1 binding domains. In another embodiment, the anti-PD-L1 binding domain and the anti-CD27 binding domain are chemically conjugated.

For example, the bispecific construct can be a chemical conjugate, which can be made by chemical conjugation of the anti-CD27 and anti-PD-L1 binding domains. In one embodiment, the anti-PD-L1 binding domain further comprises a human IgG1 constant domain. In another embodiment, the anti-CD27 binding domain is linked to the C-terminus of the heavy chain of the anti-PD-L1 binding domain. In another embodiment, the anti-CD27 binding domain is a scFv.

In another embodiment, the anti-CD27 binding domain further comprises a human IgG1 constant domain. In another embodiment, the anti-PD-L1 binding domain is linked to the C-terminus of the heavy chain of the anti-CD27 binding domain. In another embodiment, the anti-PD-L1 binding domain is a scFv.

In a particular embodiment, the bispecific construct comprises an anti-PD-L1 antibody linked to an anti-CD27 scFv, wherein:
(i) the anti-CD27 scFv comprises:
  a. heavy chain variable region CDR1, CDR2 and CDR3 as set forth in SEQ ID NOs:1, 2, and 3, respectively, and light chain variable region CDR1, CDR2 and CDR3 as set forth in SEQ ID NOs:4, 5, and 6, respectively, or
  b. heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively; and
(ii) the anti-PD-L1 antibody comprises:
  a. heavy chain variable region CDR1, CDR2 and CDR3 as set forth in SEQ ID NOs: 29, 30, and 31, respectively, and light chain variable region CDR1, CDR2 and CDR3 as set forth in SEQ ID NOs:32, 33, and 34, respectively;
  b. heavy chain variable region CDR1, CDR2 and CDR3 as set forth in SEQ ID NOs: 35, 36, and 37, respectively, and light chain variable region CDR1, CDR2 and CDR3 as set forth in SEQ ID NOs:38, 39, and 40, respectively;
  c. heavy chain variable region CDR1, CDR2 and CDR3 as set forth in SEQ ID NOs: 41, 42, and 43, respectively, and light chain variable region CDR1, CDR2 and CDR3 as set forth in SEQ ID NOs:44, 45, and 46, respectively;
  d. heavy chain variable region CDR1, CDR2 and CDR3 as set forth in SEQ ID NOs: 47, 48, and 49, respectively, and light chain variable region CDR1, CDR2 and CDR3 as set forth in SEQ ID NOs:50, 51, and 52, respectively;
  e. heavy chain variable region CDR1, CDR2 and CDR3 as set forth in SEQ ID NOs: 53, 54, and 55, respectively, and light chain variable region CDR1, CDR2 and CDR3 as set forth in SEQ ID NOs:56, 57, and 58, respectively; or
  f. heavy chain variable region CDR1, CDR2 and CDR3 as set forth in SEQ ID NOs: 59, 60, and 61, respectively, and light chain variable region CDR1, CDR2 and CDR3 as set forth in SEQ ID NOs:62, 63, and 64, respectively; and
  g. a human IgG1 constant domain.

In another particular embodiment, the bispecific construct comprises an anti-CD27 antibody linked to an anti-PD-L1 scFv, wherein:
(i) the anti-CD27 antibody comprises:
  a. heavy chain variable region CDR1, CDR2 and CDR3 as set forth in SEQ ID NOs:1, 2, and 3, respectively, and light chain variable region CDR1, CDR2 and CDR3 as set forth in SEQ ID NOs:4, 5, and 6, respectively, or
  b. heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively; and
  c. a human IgG1 constant domain; and
(ii) the anti-PD-L1 scFv comprises:
  a. heavy chain variable region CDR1, CDR2 and CDR3 as set forth in SEQ ID NOs: 29, 30, and 31, respectively, and light chain variable region CDR1, CDR2 and CDR3 as set forth in SEQ ID NOs:32, 33, and 34, respectively;
  b. heavy chain variable region CDR1, CDR2 and CDR3 as set forth in SEQ ID NOs: 35, 36, and 37, respectively, and light chain variable region CDR1, CDR2 and CDR3 as set forth in SEQ ID NOs:38, 39, and 40, respectively;
  c. heavy chain variable region CDR1, CDR2 and CDR3 as set forth in SEQ ID NOs: 41, 42, and 43, respectively, and light chain variable region CDR1, CDR2 and CDR3 as set forth in SEQ ID NOs:44, 45, and 46, respectively;
  d. heavy chain variable region CDR1, CDR2 and CDR3 as set forth in SEQ ID NOs: 47, 48, and 49, respectively, and light chain variable region CDR1, CDR2 and CDR3 as set forth in SEQ ID NOs:50, 51, and 52, respectively;
  e. heavy chain variable region CDR1, CDR2 and CDR3 as set forth in SEQ ID NOs: 53, 54, and 55, respectively, and light chain variable region CDR1, CDR2 and CDR3 as set forth in SEQ ID NOs:56, 57, and 58, respectively; or
  f. heavy chain variable region CDR1, CDR2 and CDR3 as set forth in SEQ ID NOs: 59, 60, and 61, respectively, and light chain variable region CDR1, CDR2 and CDR3 as set forth in SEQ ID NOs:62, 63, and 64, respectively.

In another embodiment, the bispecific construct comprises an anti-PD-L1 antibody linked to an anti-CD27 scFv, wherein:
(i) the anti-CD27 scFv comprises:
  a. a heavy chain variable region comprising SEQ ID NO:17 and a light chain variable region comprising SEQ ID NO:18; or
  b. a heavy chain variable region comprising SEQ ID NO:19 and a light chain variable region comprising SEQ ID NO:20; and
(ii) the anti-PD-L1 antibody comprises:
  a. a heavy chain variable region comprising SEQ ID NO:77 and a light chain variable region comprising SEQ ID NO:78;
  b. a heavy chain variable region comprising SEQ ID NO:79 and a light chain variable region comprising SEQ ID NO:80;
  c. a heavy chain variable region comprising SEQ ID NO:81 and a light chain variable region comprising SEQ ID NO:82;
  d. a heavy chain variable region comprising SEQ ID NO:83 and a light chain variable region comprising SEQ ID NO:84;
  e. a heavy chain variable region comprising SEQ ID NO:85 and a light chain variable region comprising SEQ ID NO:86; or
  f. a heavy chain variable region comprising SEQ ID NO:87 and a light chain variable region comprising SEQ ID NO:88; and g. a human IgG1 constant domain.

In another embodiment, the bispecific construct comprises an anti-CD27 antibody linked to an anti-PD-L1 scFv, wherein:
(i) the anti-CD27 antibody comprises:
  a. a heavy chain variable region comprising SEQ ID NO:17 and a light chain variable region comprising SEQ ID NO:18; or
  b. a heavy chain variable region comprising SEQ ID NO:19 and a light chain variable region comprising SEQ ID NO:20; and
  c. a human IgG1 constant domain; and
(ii) the anti-PD-L1 scFv comprises:
  a. a heavy chain variable region comprising SEQ ID NO:77 and a light chain variable region comprising SEQ ID NO:78;
  b. a heavy chain variable region comprising SEQ ID NO:79 and a light chain variable region comprising SEQ ID NO:80;
  c. a heavy chain variable region comprising SEQ ID NO:81 and a light chain variable region comprising SEQ ID NO:82;
  d. a heavy chain variable region comprising SEQ ID NO:83 and a light chain variable region comprising SEQ ID NO:84;
  e. a heavy chain variable region comprising SEQ ID NO:85 and a light chain variable region comprising SEQ ID NO:86; or
  f. a heavy chain variable region comprising SEQ ID NO:87 and a light chain variable region comprising SEQ ID NO:88.

In another embodiment, the bispecific construct comprises an anti-PD-L1 antibody linked to an anti-CD27 scFv, wherein:
(i) the anti-CD27 scFv comprises heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively; and
(ii) the anti-PD-L1 antibody comprises a heavy chain variable region CDR1, CDR2 and CDR3 as set forth in SEQ ID NOs: 47, 48, and 49, respectively, and light chain variable region CDR1, CDR2 and CDR3 as set forth in SEQ ID NOs:50, 51, and 52, respectively, and a human IgG1 constant domain.

In another embodiment, the bispecific construct comprises an anti-CD27 antibody linked to an anti-PD-L1 scFv, wherein:
(i) the anti-CD27 antibody comprises heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively, and a human IgG1 constant domain; and
(ii) the anti-PD-L1 scFv comprises a heavy chain variable region CDR1, CDR2 and CDR3 as set forth in SEQ ID NOs: 47, 48, and 49, respectively, and light chain variable region CDR1, CDR2 and CDR3 as set forth in SEQ ID NOs:50, 51, and 52, respectively.

In another embodiment, the bispecific construct comprises an anti-PD-L1 antibody linked to an anti-CD27 scFv, wherein:
(i) the anti-CD27 scFv comprises a heavy chain variable region comprising SEQ ID NO:19, a light chain variable region comprising SEQ ID NO:20; and
(ii) the anti-PD-L1 antibody comprises a heavy chain variable region comprising SEQ ID NO:83 and a light chain variable region comprising SEQ ID NO:84, and a human IgG1 constant domain.

In another embodiment, the bispecific construct comprises an anti-CD27 antibody linked to an anti-PD-L1 scFv, wherein:
(i) the anti-CD27 antibody comprises a heavy chain variable region comprising SEQ
ID NO:19, a light chain variable region comprising SEQ ID NO:20, and a human
IgG1 constant domain; and
(ii) the anti-PD-L1 scFv comprises a heavy chain variable region comprising SEQ ID
NO:83 and a light chain variable region comprising SEQ ID NO:84.

In another embodiment, the bispecific construct comprises an anti-PD-L1 antibody linked to an anti-CD27 scFv, wherein:
(i) the anti-CD27 scFv comprises heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively; and
(ii) the anti-PD-L1 antibody comprises heavy chain variable region CDR1, CDR2 and
CDR3 as set forth in SEQ ID NOs:59, 60, and 61, respectively, and light chain variable region CDR1, CDR2 and CDR3 as set forth in SEQ ID NOs:62, 63, and 64, respectively, and a human IgG1 constant domain.

In another embodiment, the bispecific construct comprises an anti-CD27 antibody linked to an anti-PD-L1 scFv, wherein:
(i) the anti-CD27 antibody comprises heavy chain variable region CDR1, CDR2 and
CDR3 as set forth in SEQ ID NOs:7, 8, and 9, respectively, and light chain variable region CDR1, CDR2 and CDR3 as set forth in SEQ ID NOs:10, 11, and 12, respectively, and a human IgG1 constant domain; and
(ii) the anti-PD-L1 scFv comprises heavy chain variable region CDR1, CDR2 and CDR3 as set forth in SEQ ID NOs:59, 60, and 61, respectively, and light chain variable region CDR1, CDR2 and CDR3 as set forth in SEQ ID NOs:62, 63, and 64, respectively.

In another embodiment, the bispecific construct comprises an anti-PD-L1 antibody linked to an anti-CD27 scFv, wherein:
(i) the anti-CD27 scFv comprises a heavy chain variable region comprising SEQ ID NO:19, a light chain variable region comprising SEQ ID NO:20; and
(ii) the anti-PD-L1 antibody comprises a heavy chain variable region comprising SEQ ID NO:87 and a light chain variable region comprising SEQ ID NO:88, and a human IgG1 constant domain.

In another embodiment, the bispecific construct comprises an anti-CD27 antibody linked to an anti-PD-L1 scFv, wherein:
(i) the anti-CD27 antibody comprises a heavy chain variable region comprising SEQ ID NO:19, a light chain variable region comprising SEQ ID NO:20, and a human IgG1 constant domain; and (ii) the anti-PD-L1 scFv comprises a heavy chain variable region comprising SEQ ID NO:87 and a light chain variable region comprising SEQ ID NO:88.

In another embodiment, the bispecific construct has one or more of the following functional features: induces NFκB activation, increases T cell proliferation, induces a CD8 T cell response, and/or increases IL-2 production. In another embodiment, the bispecific construct increases IL-2 production by at least about 1.5-fold (e.g., at least 2-fold, 2.5 fold, 3-fold, 3.5 fold, or 4-fold) compared to an anti-CD27 monoclonal antibody or anti-PD-L1 monoclonal antibody alone. In another embodiment, the bispecific construct induces a CD8 T cell response by at least about 2-fold greater (e.g., at least 2-fold, 2.5 fold, 3-fold, 3.5 fold, 4-fold, 4.5-fold, 5-fold, 5.5-fold, 6-fold, 6.5-fold, 7-fold, 7.5-fold, 8.0-fold, 8.5-fold, or 9-fold) than an anti-CD27 monoclonal antibody alone. In another embodiment, the bispecific construct increases survival by at least about 1.5-fold longer (e.g., at least 1.5-fold, 2.0-fold, 2.5 fold, 3-fold, 3.5 fold, 4-fold, 4.5-fold, or 5-fold) compared to an anti-CD27 monoclonal antibody or anti-PD-L1 monoclonal antibody alone. In another embodiment, the bispecific construct decreases tumor weight by at least about 1.5-fold (e.g., at least 1.5-fold, 2.0-fold, 2.5 fold, 3-fold, 3.5 fold, 4-fold, 4.5-fold, or 5-fold) compared to anti-CD27 monoclonal antibodies or anti-PD-L1 monoclonal antibodies alone or in combination. In another embodiment, the bispecific construct increases T cell production by at least about 1.5-fold (e.g., at least 1.5-fold, 2.0-fold, 2.5 fold, 3-fold, 3.5 fold, 4-fold, 4.5-fold, 5-fold, 5.5-fold, 6-fold, 6.5-fold, 7-fold, 7.5-fold, 8.0-fold, 8.5-fold, or 9-fold) compared to anti-CD27 monoclonal antibodies or anti-PD-L1 monoclonal antibodies alone or in combination.

In certain embodiments, the bispecific constructs described herein exhibit synergistic effects (e.g., in enhancing immune responses in vivo) as compared to use of anti-CD27 binding domains and anti-PD-L1 binding domains in combination (i.e., co-administration of unlinked antibodies).

In another aspect, novel anti-CD27 antibodies, or antigen-binding portions thereof, are provided which comprise any of the anti-CD27 binding domains described herein. In one embodiment, the anti-CD27 antibody, or antigen-binding fragment thereof, comprises heavy chain variable region CDR1, CDR2 and CDR3 as set forth in SEQ ID NOs:1, 2, and 3, respectively, and light chain variable region CDR1, CDR2 and CDR3 as set forth in SEQ ID NOs:4, 5, and 6, respectively. In another embodiment, the anti-CD27 antibody, or antigen-binding fragment thereof, comprises a heavy chain variable region comprising SEQ ID NO:17 and a light chain variable region comprising SEQ ID NO:18 or sequences at least 90% identical thereto (e.g., at least 90%, 91%, 92%, 93%, 94%, 95%, 96%, 97%, 98% or 99% identical to the aforementioned sequences).

In another embodiment, the anti-CD27 antibody, or antigen-binding fragment thereof, comprises heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively. In another embodiment, the anti-CD27 antibody, or antigen-binding fragment thereof, comprises a heavy chain variable region comprising SEQ ID NO:19 and a light chain variable region comprising SEQ ID NO:20 or sequences at least 95% identical thereto.

In another embodiment, the anti-CD27 antibody, or antigen-binding fragment thereof, has one or more of the following functional features: induces or enhances a T cell-mediated immune response, blocks binding of sCD70 to CD27 (e.g., partially or completely), induces NFκB activation, increases T cell proliferation, binds to human CD27 with an equilibrium dissociation constant Kd of $10^{-9}$ M or less, or alternatively, an equilibrium association constant Ka of $10^{+9}$ M$^{-1}$ or greater, induces specific complement mediated cytotoxicity (CDC) of CD27 expressing cells, induces antibody dependent cell-mediated cytotoxicity (ADCC) specific lysis of CD27 expressing cells, induces or enhances antigen-specific immune responses in vivo in combination with a vaccine or endogenous antigen, induces or enhances antigen-specific TH1 immune responses in vivo in combination with a vaccine or endogenous antigen, induces or enhances antigen-specific T-cell proliferation or activation in vivo in combination with a vaccine or endogenous antigen; and/or induces or enhances T-cell activity when combined with simultaneous, separate or sequential TCR activation.

In another aspect, a bispecific construct is provided, wherein the bispecific construct comprises any one of the anti-CD27 antibodies described herein linked to an anti-PD-L1 binding domain. In one embodiment, the anti-PD-L1 binding domain is selected from the group consisting of:

a. an anti-PD-L1 antibody, or antigen binding fragment thereof, comprising heavy chain variable region CDR1, CDR2 and CDR3 as set forth in SEQ ID NOs: 29, 30, and 31, respectively, and light chain variable region CDR1, CDR2 and CDR3 as set forth in SEQ ID NOs:32, 33, and 34, respectively;

b. an anti-PD-L1 antibody, or antigen binding fragment thereof, comprising heavy chain variable region CDR1, CDR2 and CDR3 as set forth in SEQ ID NOs: 35, 36, and 37, respectively, and light chain variable region CDR1, CDR2 and CDR3 as set forth in SEQ ID NOs:38, 39, and 40, respectively;

c. an anti-PD-L1 antibody, or antigen binding fragment thereof, comprising heavy chain variable region CDR1, CDR2 and CDR3 as set forth in SEQ ID NOs: 41, 42, and 43, respectively, and light chain variable region CDR1, CDR2 and CDR3 as set forth in SEQ ID NOs:44, 45, and 46, respectively;

d. an anti-PD-L1 antibody, or antigen binding fragment thereof, comprising heavy chain variable region CDR1, CDR2 and CDR3 as set forth in SEQ ID NOs: 47, 48, and 49, respectively, and light chain variable region CDR1, CDR2 and CDR3 as set forth in SEQ ID NOs:50, 51, and 52, respectively;

e. anti-PD-L1 antibody, or antigen binding fragment thereof, comprising heavy chain variable region CDR1, CDR2 and CDR3 as set forth in SEQ ID NOs: 53, 54, and 55, respectively, and light chain variable region CDR1, CDR2 and CDR3 as set forth in SEQ ID NOs:56, 57, and 58, respectively; and f. anti-PD-L1 antibody, or antigen binding fragment thereof, comprising heavy chain variable region CDR1, CDR2 and CDR3 as set forth in SEQ ID NOs: 59, 60, and 61, respectively, and light chain variable region CDR1, CDR2 and CDR3 as set forth in SEQ ID NOs:62, 63, and 64, respectively.

In another embodiment, the anti-PD-L1 binding domain is selected from the group consisting of: (a) a heavy chain variable region comprising SEQ ID NO:77 and a light chain variable region comprising SEQ ID NO:78; (b) a heavy chain variable region comprising SEQ ID NO:79 and a light chain variable region comprising SEQ ID NO:80; (c) a heavy chain variable region comprising SEQ ID NO:81 and a light chain variable region comprising SEQ ID NO:82; (d) a heavy chain variable region comprising SEQ ID NO:83 and a light chain variable region comprising SEQ ID NO:84; (e) a heavy chain variable region comprising SEQ ID NO:85 and a light chain variable region comprising SEQ ID NO:86; and (f) a heavy chain variable region comprising SEQ ID NO:87 and a light chain variable region comprising SEQ ID NO:88. In a particular embodiment, the anti-PD-L1 binding domain is an scFv.

In certain embodiments, the bispecific constructs described herein exhibit synergistic effects (e.g., in enhancing immune responses in vivo) as compared to use of anti-CD27 binding domains and anti-PD-L1 binding domains in combination (i.e., co-administration of unlinked antibodies).

In another aspect, novel anti-PD-L1 antibodies, or antigen-binding portions thereof, are provided, which comprise any of the anti-PD-L1 binding domains described herein. In one embodiment, the anti-PD-L1 antibody, or antigen-binding fragment thereof, comprises heavy chain variable region CDR1, CDR2 and CDR3 as set forth in SEQ ID NOs:29, 30, and 31, respectively, and light chain variable region CDR1, CDR2 and CDR3 as set forth in SEQ ID NOs:32, 33, and 34, respectively. In another embodiment, the anti-PD-L1 antibody, or antigen-binding fragment thereof, comprises a heavy chain variable region comprising SEQ ID NO:77 and a light chain variable region comprising SEQ ID NO:78 or sequences at least 90% identical thereto (e.g., at least 90%, 91%, 92%, 93%, 94%, 95%, 96%, 97%, 98% or 99% identical to the aforementioned sequences). In another embodiment, the anti-PD-L1 antibody, or antigen-binding fragment thereof, comprises heavy chain variable region CDR1, CDR2 and CDR3 as set forth in SEQ ID NOs:35, 36, and 37, respectively, and light chain variable region CDR1, CDR2 and CDR3 as set forth in SEQ ID NOs:38, 39, and 40, respectively. In another embodiment, the anti-PD-L1 antibody, or antigen-binding fragment thereof, comprises a heavy chain variable region comprising SEQ ID NO:79 and a light chain variable region comprising SEQ ID NO:80 or sequences at least 90% identical thereto (e.g., at least 90%, 91%, 92%, 93%, 94%, 95%, 96%, 97%, 98% or 99% identical to the aforementioned sequences). In another embodiment, the anti-PD-L1 antibody, or antigen-binding fragment thereof, comprises heavy chain variable region CDR1, CDR2 and CDR3 as set forth in SEQ ID NOs:41, 42, and 43, respectively, and light chain variable region CDR1, CDR2 and CDR3 as set forth in SEQ ID NOs:44, 45, and 46, respectively. In another embodiment, the anti-PD-L1 antibody, or antigen-binding fragment thereof, comprises a heavy chain variable region comprising SEQ ID NO:81 and a light chain variable region comprising SEQ ID NO:82 or sequences at least 90% identical thereto (e.g., at least 90%, 91%, 92%, 93%, 94%, 95%, 96%, 97%, 98% or 99% identical to the aforementioned sequences). In another embodiment, the anti-PD-L1 antibody, or antigen-binding fragment thereof, comprises heavy chain variable region CDR1, CDR2 and CDR3 as set forth in SEQ ID NOs:47, 48, and 49, respectively, and light chain variable region CDR1, CDR2 and CDR3 as set forth in SEQ ID NOs:50, 51, and 52, respectively. In another embodiment, the anti-PD-L1 antibody, or antigen-binding fragment thereof, comprises a heavy chain variable region comprising SEQ ID NO:83 and a light chain variable region comprising SEQ ID NO:84 or sequences at least 90% identical thereto (e.g., at least 90%, 91%, 92%, 93%, 94%, 95%, 96%, 97%, 98% or 99% identical to the aforementioned sequences). In another embodiment, the anti-PD-L1 antibody, or antigen-binding fragment thereof, comprises heavy chain variable region CDR1, CDR2 and CDR3 as set forth in SEQ ID NOs:53, 54, and 55, respectively, and light chain variable region CDR1, CDR2 and CDR3 as set forth in SEQ ID NOs:56, 57, and 58, respectively. In another embodiment, the anti-PD-L1 antibody, or antigen-binding fragment thereof, comprises a heavy chain variable region comprising SEQ ID NO:85 and a light chain variable region comprising SEQ ID NO:86 or sequences at least 90% identical thereto (e.g., at least 90%, 91%, 92%, 93%, 94%, 95%, 96%, 97%, 98% or 99% identical to the aforementioned sequences). In another embodiment, the anti-PD-L1 antibody, or antigen-binding fragment thereof, comprises heavy chain variable region CDR1, CDR2 and CDR3 as set forth in SEQ ID NOs:59, 60, and 61, respectively, and light chain variable region CDR1, CDR2 and CDR3 as set forth in SEQ ID NOs:62, 63, and 64, respectively. In another embodiment, the anti-PD-L1 antibody, or antigen-binding fragment thereof, comprises a heavy chain variable region comprising SEQ ID NO:87 and a light chain variable region comprising SEQ ID NO:88 or sequences at least 90% identical thereto (e.g., at least 90%, 91%, 92%, 93%, 94%, 95%, 96%, 97%, 98% or 99% identical to the aforementioned sequences).

In another embodiment, the anti-PD-L1 antibody, or antigen-binding fragment thereof, has one or more of the following functional features: (a) blocks binding of PD1 to PD-L1 (e.g., partially or completely), (b) induces NFAT pathway activation, and/or (c) induces a mixed lymphocyte response.

In another aspect, a bispecific construct is provided, wherein the bispecific construct comprises any one of the anti-PD-L1 antibodies, or antigen binding fragments thereof, described herein, linked to an anti-CD27 binding domain. In one embodiment, the anti-C27 binding domain comprises an anti-CD27 antibody comprising heavy chain variable region CDR1, CDR2 and CDR3 as set forth in SEQ ID NOs:1, 2, and 3, respectively, and light chain variable region CDR1, CDR2 and CDR3 as set forth in SEQ ID NOs:4, 5, and 6, respectively. In another embodiment, the anti-CD27 binding domain comprises an antibody comprising a heavy chain variable region comprising SEQ ID NO:17 and a light chain variable region comprising SEQ ID NO:18, or sequences at least 90% identical thereto (e.g., at least 90%, 91%, 92%, 93%, 94%, 95%, 96%, 97%, 98% or 99% identical to the aforementioned sequences). In another embodiment, the anti-C27 binding domain comprises an anti-CD27 antibody comprising heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively. In another embodiment, the anti-C27 binding domain comprises an anti-CD27 antibody comprising a heavy chain variable region comprising SEQ ID NO:19 and a light chain variable region comprising SEQ ID NO:20, or sequences at least 90% identical thereto (e.g., at least 90%, 91%, 92%, 93%, 94%, 95%, 96%, 97%, 98% or 99% identical to the aforementioned sequences). In one embodiment, the anti-CD27 binding domain further comprises a human IgG1 constant domain.

In certain embodiments, the bispecific constructs described herein exhibit synergistic effects (e.g., in enhancing immune responses in vivo) as compared to use of anti-CD27 binding domains and anti-PD-L1 binding domains in combination (i.e., co-administration of unlinked antibodies).

In another aspect, provided herein are compositions including any of the bispecific constructs (multispecific constructs), antibodies, or antigen binding fragments thereof, described herein and a pharmaceutically acceptable carrier. Also provided are kits comprising any of the bispecific constructs (multispecific constructs), antibodies, or antigen binding fragments thereof, described herein and instructions for use.

In a further aspect, isolated nucleic acid molecules encoding the binding domains, antibodies, or antigen-binding portions thereof, and bispecific or multispecific constructs described herein are also provided, as well as expression vectors comprising such nucleic acids and host cells comprising such expression vectors. In another embodiment, a nucleic acid molecule coding for any of the binding domains, antibodies, or antigen-binding portions thereof, or bispecific constructs described herein is provided. In another embodiment, the nucleic acid molecule is in the form of an expression vector. In another embodiment, the nucleic acid molecule is in the form of an expression vector which expresses the binding domain, antibody, or antigen-binding portion thereof, or bispecific construct when administered to a subject in vivo.

In one embodiment, the nucleic acid molecule comprises a nucleotide sequence encoding an antibody variable region, wherein the antibody variable region comprises the amino acid sequence depicted in SEQ ID NO:17, 18, 19, 20, 77, 78, 79, 80, 81, 82, 83, 84, 85, 86, 87, 88, or an amino acid sequence at least 90% identical thereto (e.g., at least 90%, 91%, 92%, 93%, 94%, 95%, 96%, 97%, 98% or 99% identical to one or more of the aforementioned sequences). In another embodiment, the nucleic acid molecule comprises a nucleotide sequence as set forth in SEQ ID NO:25, 26, 27, 28, 101, 102, 103, 104, 105, 106, 107, 108, 109, 110, 111, 112, or a nucleotide sequence at least 90% identical thereto (e.g., at least 90%, 91%, 92%, 93%, 94%, 95%, 96%, 97%, 98% or 99% identical to one or more of the aforementioned sequences).

In another embodiment, the nucleic acid molecule comprises a nucleotide sequence encoding heavy and light chain variable regions of an antibody, wherein the heavy and light chain variable regions comprise the amino acid sequences depicted in SEQ ID NOs:17 and 18, SEQ ID NOs:19 and 20, SEQ ID NOs:77 and 78, SEQ ID NOs:79 and 80, SEQ ID NOs:81 and 82, SEQ ID NOs: 83 and 84, SEQ ID NOs:85 and 86, or SEQ ID NOs:87 and 88, respectively, or amino acids sequences at least 90% identical thereto (e.g., at least 90%, 91%, 92%, 93%, 94%, 95%, 96%, 97%, 98% or 99% identical the aforementioned sequences).

In another aspect, methods of stimulating T cell activity are provided, which comprise contacting T cells with any one of the antibodies, or antigen binding fragments thereof, bispecific constructs, multispecific constructs, or the compositions of described herein. Stimulating T cell activity can comprise, for example, stimulating IFN-gamma production.

In yet another aspect, methods for inducing or enhancing an immune response (e.g., against an antigen) in a subject comprising administering to the subject any one of the antibodies, or antigen binding fragments thereof, bispecific constructs, multispecific constructs, or the compositions described herein, in an amount effective to induce or enhance an immune response in the subject (e.g., against an antigen).

In a further aspect, methods of for treating a condition or disease in a subject are provided, the method comprising administering to the subject any one of the antibodies, or antigen binding fragments thereof, bispecific constructs, multispecific constructs, or the compositions described herein, in an amount effective to treat the condition or disease.

In another aspect, methods for treating a condition or disease in a subject are provided, wherein the method comprises administering to the subject any one of the anti-CD27 antibodies, or antigen binding fragments thereof, described herein in combination with any one of the anti-PD-L1 antibodies, or antigen binding fragments thereof, described herein. For example, in one embodiment:
(i) the anti-CD27 antibody, or antigen binding fragment thereof, is selected from the group consisting of: (a) an anti-CD27 antibody, or antigen binding fragment thereof, comprising heavy chain variable region CDR1, CDR2 and CDR3 as set forth in SEQ ID NOs:1, 2, and 3, respectively, and light chain variable region CDR1, CDR2 and CDR3 as set forth in SEQ ID NOs:4, 5, and 6, respectively, and (b) an anti-CD27 antibody, or antigen binding fragment thereof, comprising heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively; and
(ii) the anti-PD-L1 antibody, or antigen binding fragment thereof, is selected from the group consisting of: (a) an anti-PD-L1 antibody, or antigen binding fragment thereof, comprising heavy chain variable region CDR1, CDR2 and CDR3 as set forth in SEQ ID NOs: 29, 30, and 31, respectively, and light chain variable region CDR1, CDR2 and CDR3 as set forth in SEQ ID NOs:32, 33, and 34, respectively; (b) an anti-PD-L1 antibody, or antigen binding fragment thereof, comprising heavy chain variable region CDR1, CDR2 and CDR3 as set forth in SEQ ID NOs: 35, 36, and 37, respectively, and light chain variable region CDR1, CDR2 and CDR3 as set forth in SEQ ID NOs:38, 39, and 40, respectively; (c) an anti-PD-L1 antibody, or antigen binding fragment thereof, comprising heavy chain variable region CDR1, CDR2 and CDR3 as set forth in SEQ ID NOs: 41, 42, and 43, respectively, and light chain variable region CDR1, CDR2 and CDR3 as set forth in SEQ ID NOs:44, 45, and 46, respectively; (d) an anti-PD-L1 antibody, or antigen binding fragment thereof, comprising heavy chain variable region CDR1, CDR2 and CDR3 as set forth in SEQ ID NOs: 47, 48, and 49, respectively, and light chain variable region CDR1, CDR2 and CDR3 as set forth in SEQ ID NOs:50, 51, and 52, respectively; (e) anti-PD-L1 antibody, or antigen binding fragment thereof, comprising heavy chain variable region CDR1, CDR2 and CDR3 as set forth in SEQ ID NOs: 53, 54, and 55, respectively, and light chain variable region CDR1, CDR2 and CDR3 as set forth in SEQ ID NOs:56, 57, and 58, respectively; and (f) anti-PD-L1 antibody, or antigen binding fragment thereof, comprising heavy chain variable region CDR1, CDR2 and CDR3 as set forth in SEQ ID NOs: 59, 60, and 61, respectively, and light chain variable region CDR1, CDR2 and CDR3 as set forth in SEQ ID NOs:62, 63, and 64, respectively.

In another embodiment,
(i) the anti-CD27 antibody, or antigen binding fragment thereof, is selected from the group consisting of: (a) an anti-CD27 antibody, or antigen-binding fragment thereof, comprising a heavy chain variable region comprising SEQ ID NO:17 and a light chain variable region comprising SEQ ID NO:18 and (b) an anti-CD27 antibody, or antigen-binding fragment thereof, comprising SEQ ID NO:19 and a light chain variable region comprising SEQ ID NO:20 or sequences; and (ii) the anti-PD-L1 antibody, or antigen binding fragment thereof, is selected from the group consisting of: (a) an anti-PD-L1 antibody, or antigen binding fragment thereof, comprising a heavy chain variable region comprising SEQ ID NO:77 and a light chain variable region comprising SEQ ID NO:78; (b) an anti-PD-L1 antibody, or antigen binding fragment thereof, comprising a heavy chain variable region comprising SEQ ID NO:79 and a light chain variable region comprising SEQ ID NO:80; (c) an anti-PD-L1 antibody, or antigen binding fragment thereof, comprising a heavy chain variable region comprising SEQ ID NO:81 and a light chain variable region comprising SEQ ID NO:82; (d) an anti-PD-L1 antibody, or antigen binding fragment thereof, comprising a heavy chain variable region comprising SEQ ID NO:83 and a light chain variable region comprising SEQ ID NO:84; (e) an anti-PD-L1 antibody, or antigen binding fragment thereof, comprising a heavy chain variable region comprising SEQ ID NO:85 and a light chain variable region comprising SEQ ID NO:86; and (f) an anti-PD-L1 antibody, or antigen binding fragment thereof, comprising a heavy chain variable region comprising SEQ ID NO:87 and a light chain variable region comprising SEQ ID NO:88.

In one embodiment, the anti-CD27 antibody, or antigen binding fragment thereof, and the anti-PD-L1 antibody, or antigen binding fragment thereof, are administered separately. In one embodiment, the anti-CD27 antibody, or antigen binding fragment thereof, and the anti-PD-L1 antibody, or antigen binding fragment thereof, are administered sequentially. For example, the anti-CD27 antibody, or antigen binding fragment thereof, can be administered first followed by (e.g., immediately followed by) administration of the anti-PD-L1 antibody, or antigen binding fragment thereof, or vice versa. In another embodiment, the anti-CD27 antibody, or antigen binding fragment thereof, and the anti-PD-L1 antibody, or antigen binding fragment thereof, are administered together. In another embodiment, the anti-CD27 antibody, or antigen binding fragment thereof, and the anti-PD-L1 antibody, or antigen binding fragment thereof, are administered simultaneously. In another embodiment, the anti-CD27 antibody, or antigen binding fragment thereof, and the anti-PD-L1 antibody, or antigen binding fragment thereof, are simultaneously administered in a single formulation. Alternatively, the anti-CD27 antibody, or antigen binding fragment thereof, and the anti-PD-L1 antibody, or antigen binding fragment thereof, are formulated for separate administration and are administered concurrently or sequentially. Such concurrent or sequential administration preferably results in both antibodies being simultaneously present in treated patients.

In certain embodiments, administration of any of the anti-CD27 antibodies, or antigen binding fragment thereof, described herein in combination with any of the anti-PD-L1 antibodies, or antigen binding fragments thereof, described herein results in synergistic effects (e.g., in enhancing immune responses in vivo) as compared to use of either antibody alone.

The subject can be, for example, one who suffers from a condition or disease in which stimulation of an immune response is desired. In one embodiment, the condition or disease in which stimulation of an immune response is desired is cancer. The method of inducing or enhancing an immune response (e.g., against an antigen) in a subject can further comprise administering the antigen to the subject. Preferred antigens to be co-administered with the antibodies, or antigen binding fragments thereof, bispecific constructs, multispecific constructs, or the compositions of described herein are tumor antigens.

III. BRIEF DESCRIPTION OF THE DRAWINGS

FIG. 15D is a table of representative anti-CD27/anti-PD-L1 bispecific constructs.

Figures 22A, 22B, 22C:
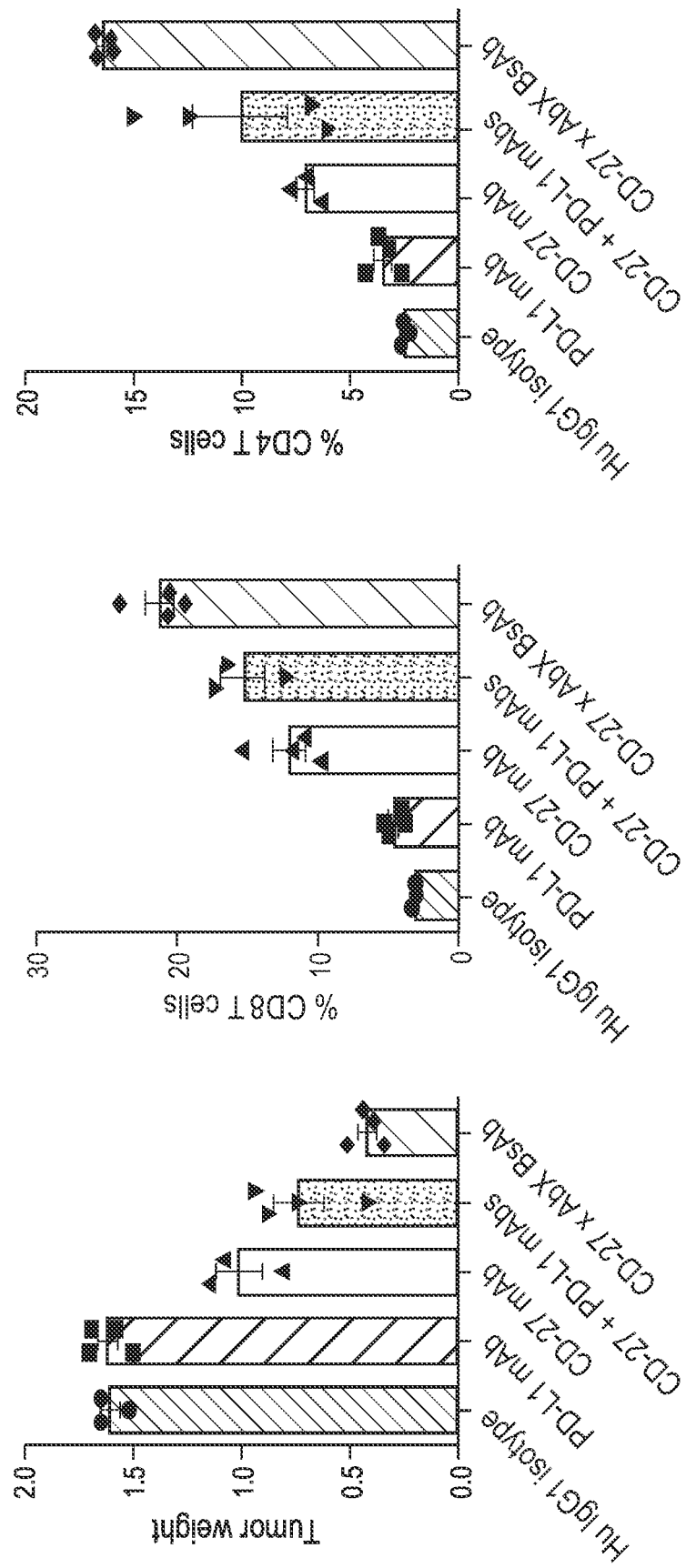
Figure 22D:
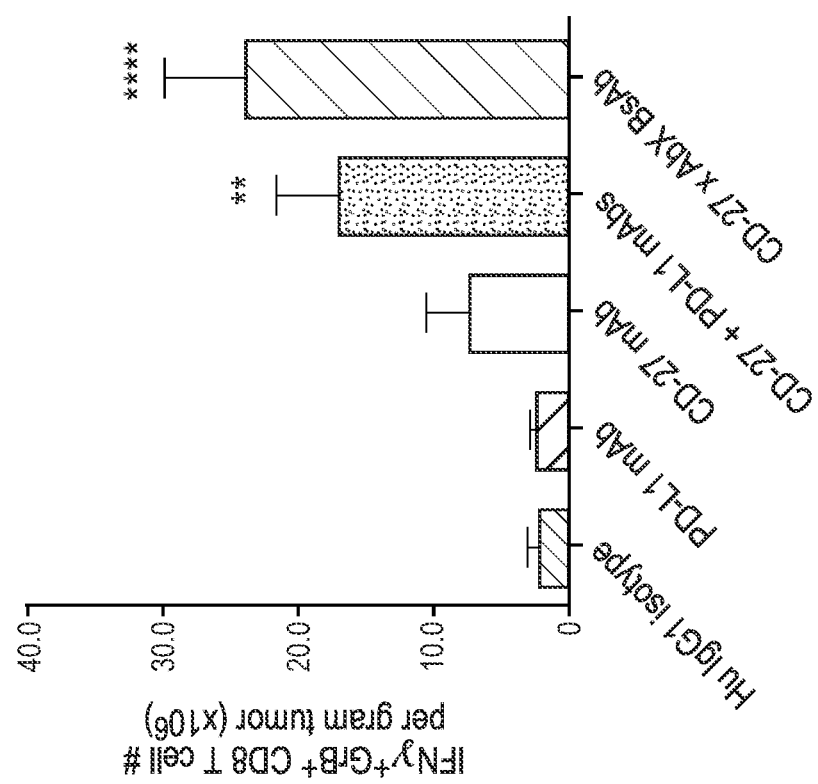

FIG. 22A is a graph showing decreased tumor weight in mice treated with a bispecific construct (e.g., CD27xAbX) compared to CD27 and PD-L1 antibodies administered alone or in combination. FIG. 22B is a graph showing increased percent CD8 T cells in mice treated with a bispecific construct (e.g., CD27xAbX) compared to CD27 and PD-L1 antibodies administered alone or in combination. FIG. 22C is a graph showing increased percent CD4 T cells in mice treated with a bispecific construct (e.g., CD27xAbX) compared to CD27 and PD-L1 antibodies administered alone or in combination. FIG. 22D is a graph showing increased activated CD8 T cells in mice treated with a bispecific construct (e.g., CD27xAbX) compared to CD27 and PD-L1 antibodies administered alone or in combination.

Figures 23A, 23B:
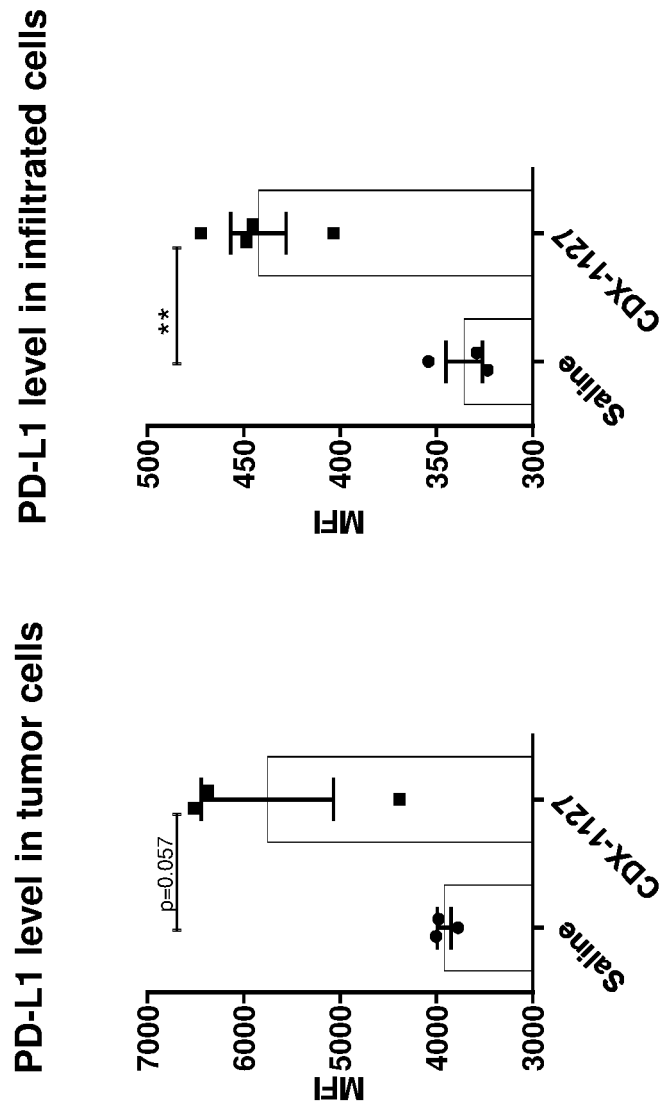

FIGS. 23A and 23B are graphs showing anti-CD27 Ab (e.g., CDX-1127) upregulates PD-L1 expression in tumor cells and tumor infiltrated cells.

Figure 24:
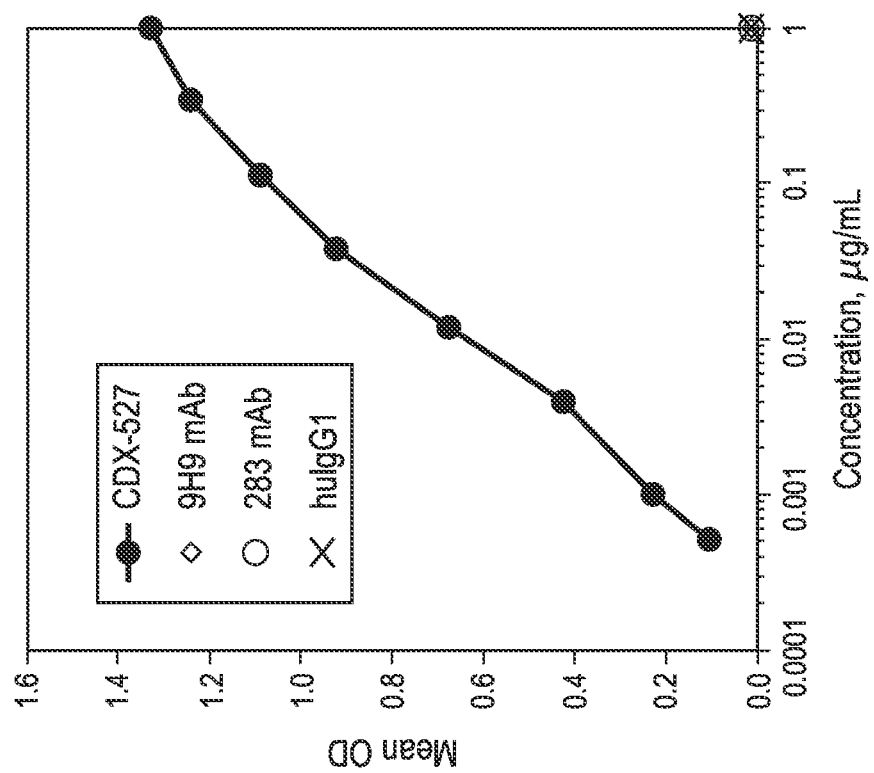

FIG. 24 is a graph showing binding of the anti-CD27/antiPD-L1 bispecific construct CDX-527 to CD27 and PD-L1 using a bifunctional ELISA.

Figure 25:
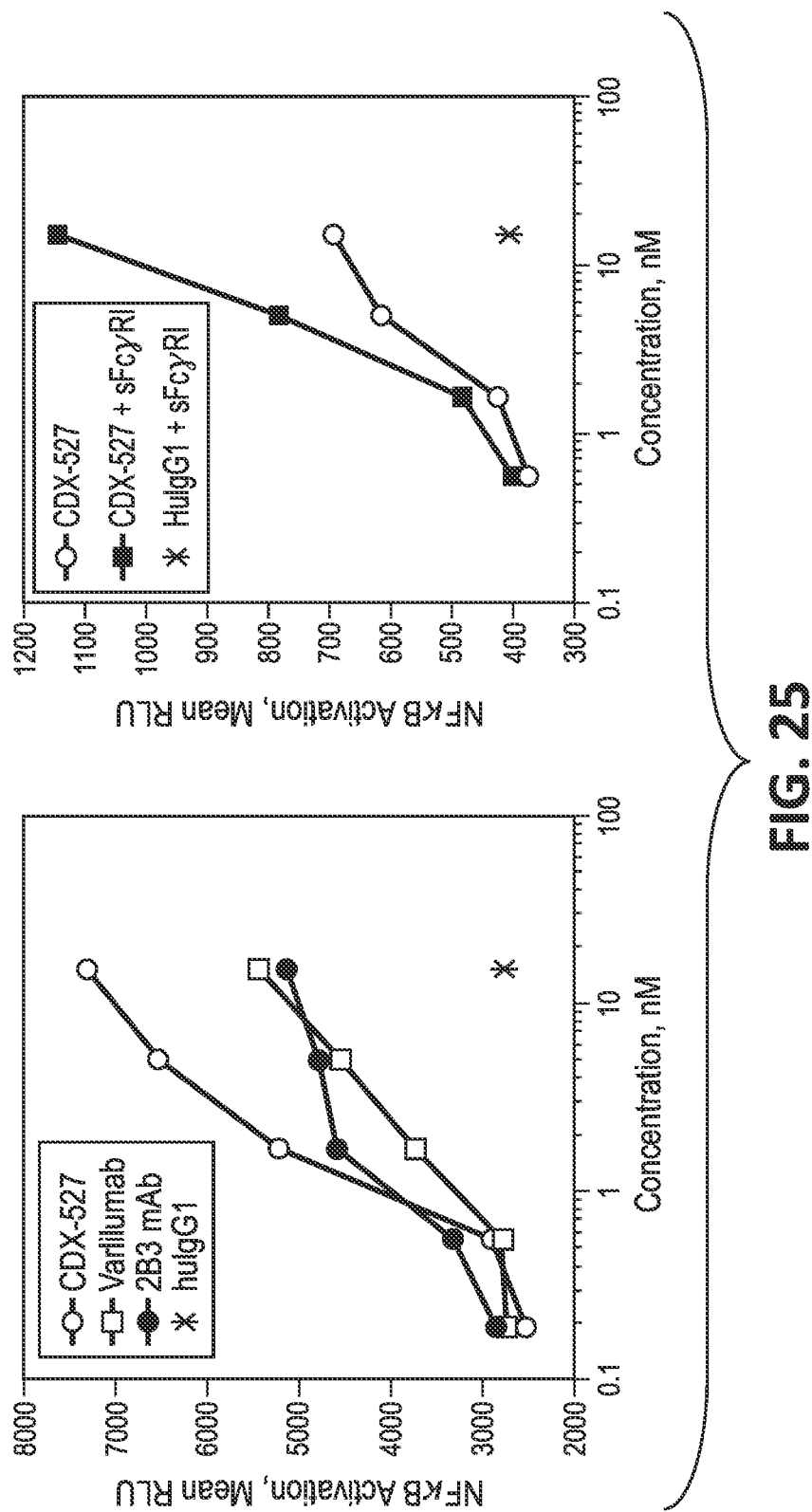

FIG. 25 are graphs showing increased NFκB activation induced by anti-CD27/anti-PD-L1 bispecific construct CDX-527 as compared to antibodies 1F5 or 2B3 alone (left graph) and also in presence of soluble Fcγ121 (right graph).

Figure 26:
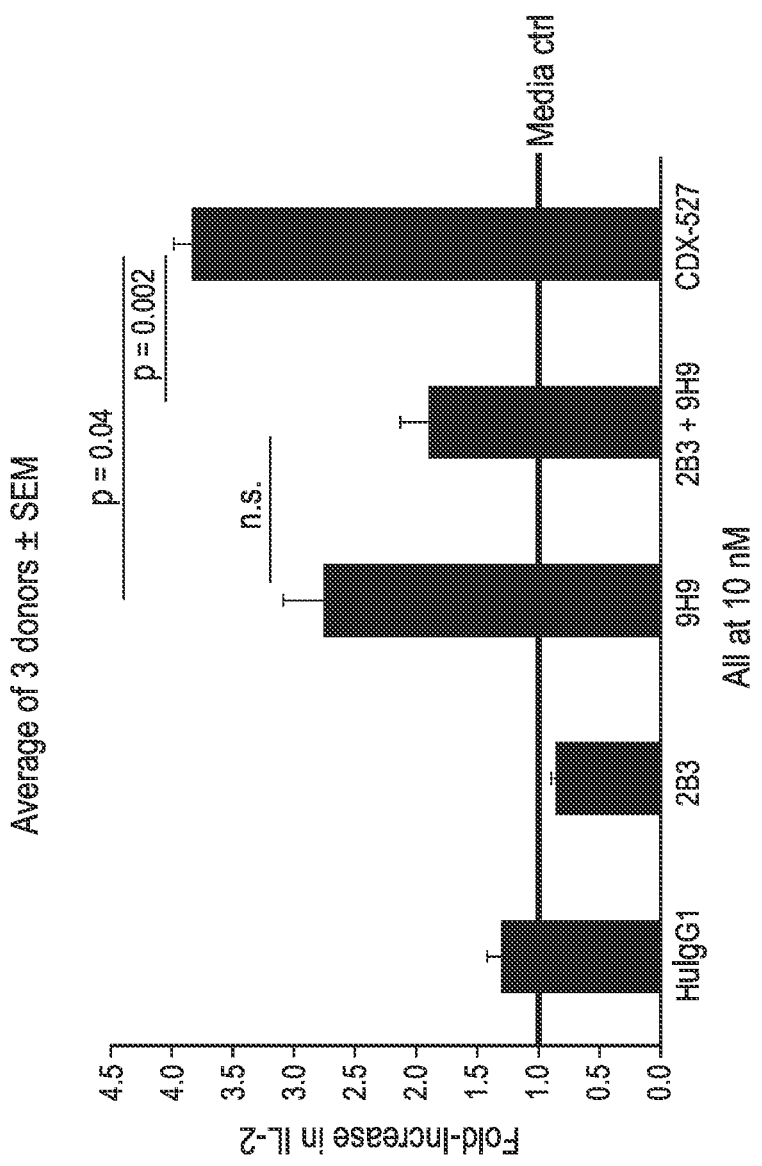

FIG. 26 is a graph showing increased IL-2 production/secretion in a mixed lymphocyte reaction by anti-CD27/anti-PD-L1 bispecific construct CDX-527 as compared to antibodies 2B3 or 9H9 alone or in combination.

Figure 27:
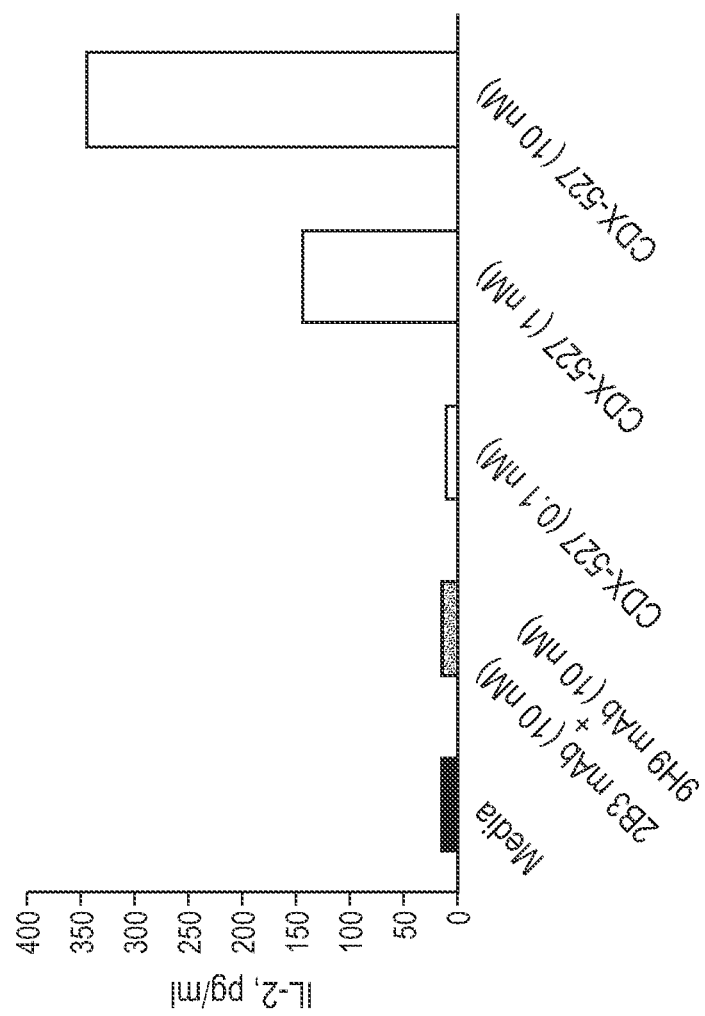

FIG. 27 is a graph showing increased IL-2 production/secretion in T-cells by anti-CD27/anti-PD-L1 bispecific construct CDX-527 as compared to antibodies 2B3 and 9H9 in combination.

Figure 28:
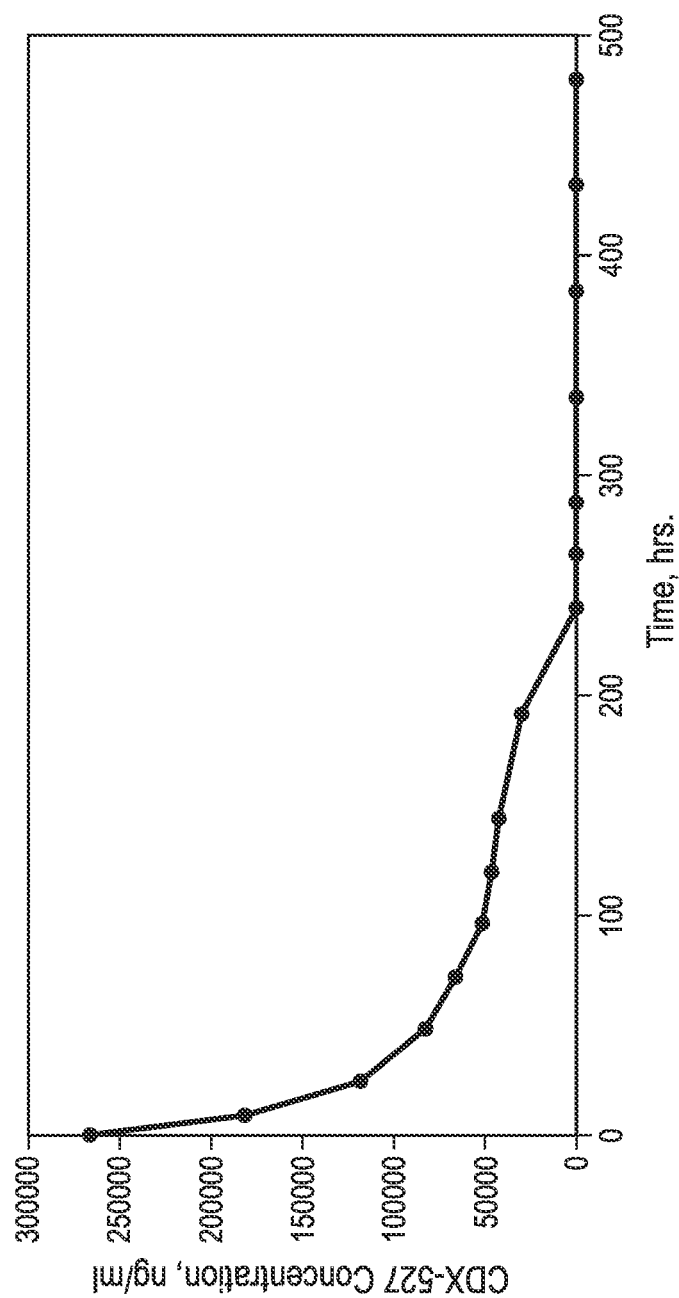

FIG. 28 is a graph showing serum levels of CDX-527 in a NHP pharmacokinetic study.

Figure 29:
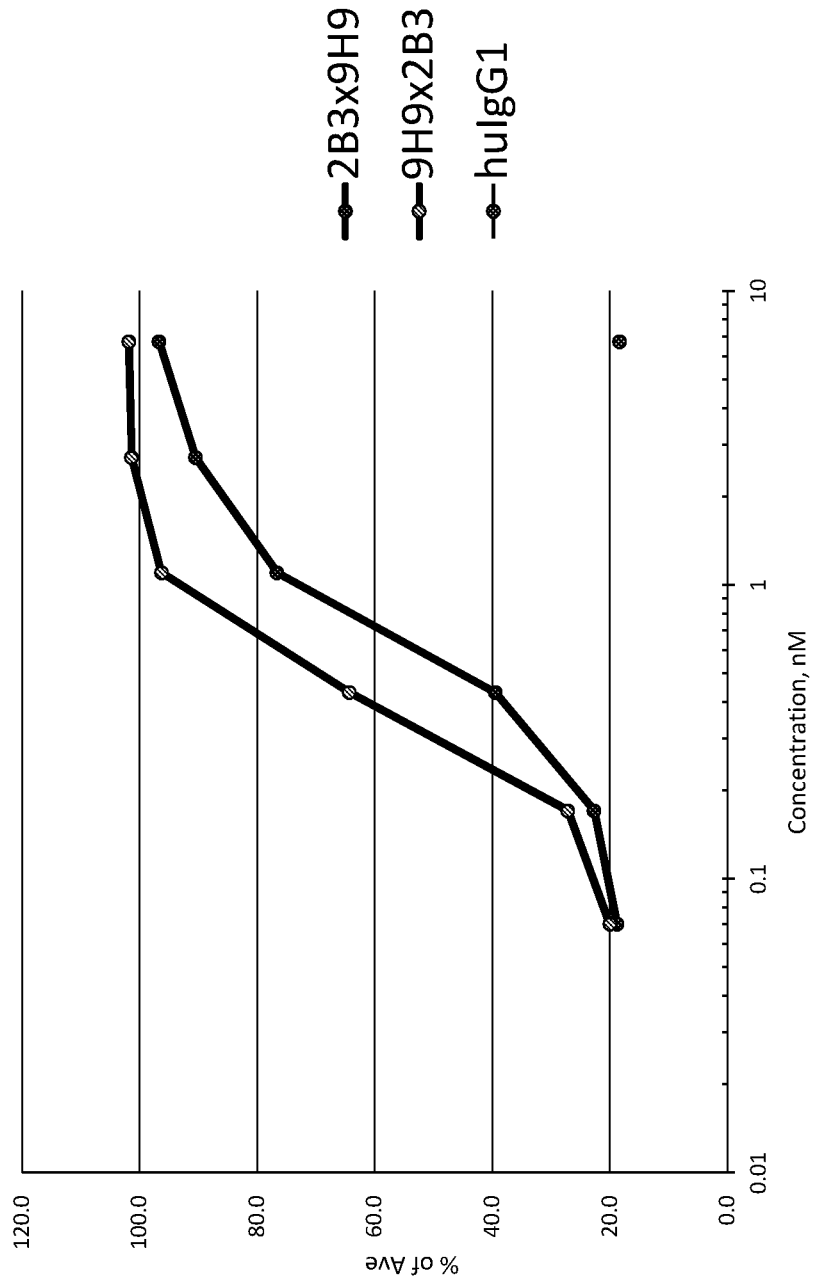

FIG. 29 is a graph showing increased blockade of PD-1 signaling by the 9H9x2B3 configuration as compared to the 2B3x9H9 configuration.

Figure 30:
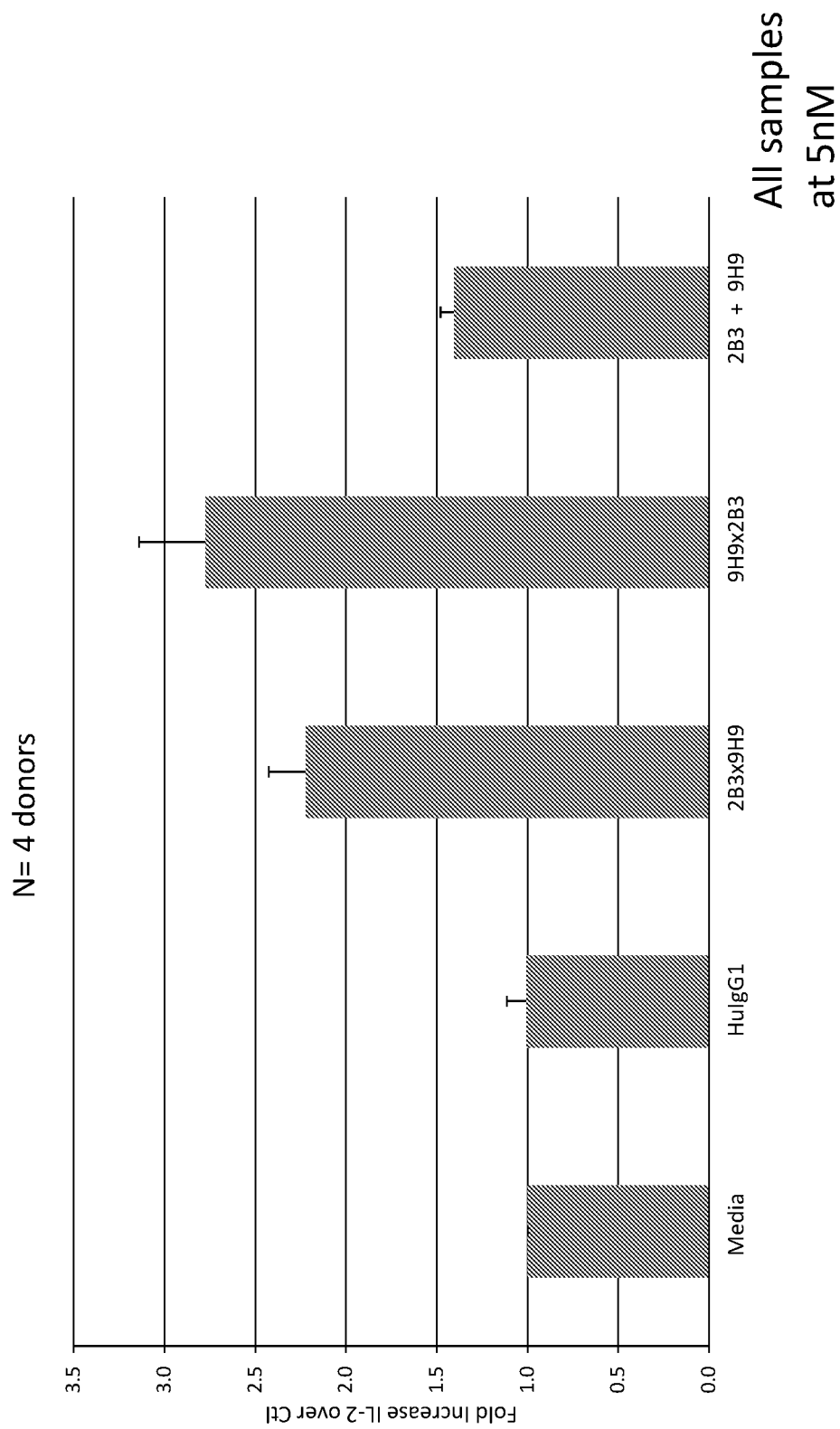

FIG. 30 is a graph showing increased T-cell activation by the 9H9x2B3 configuration as compared to the 2B3x9H9 configuration.

Figure 31:
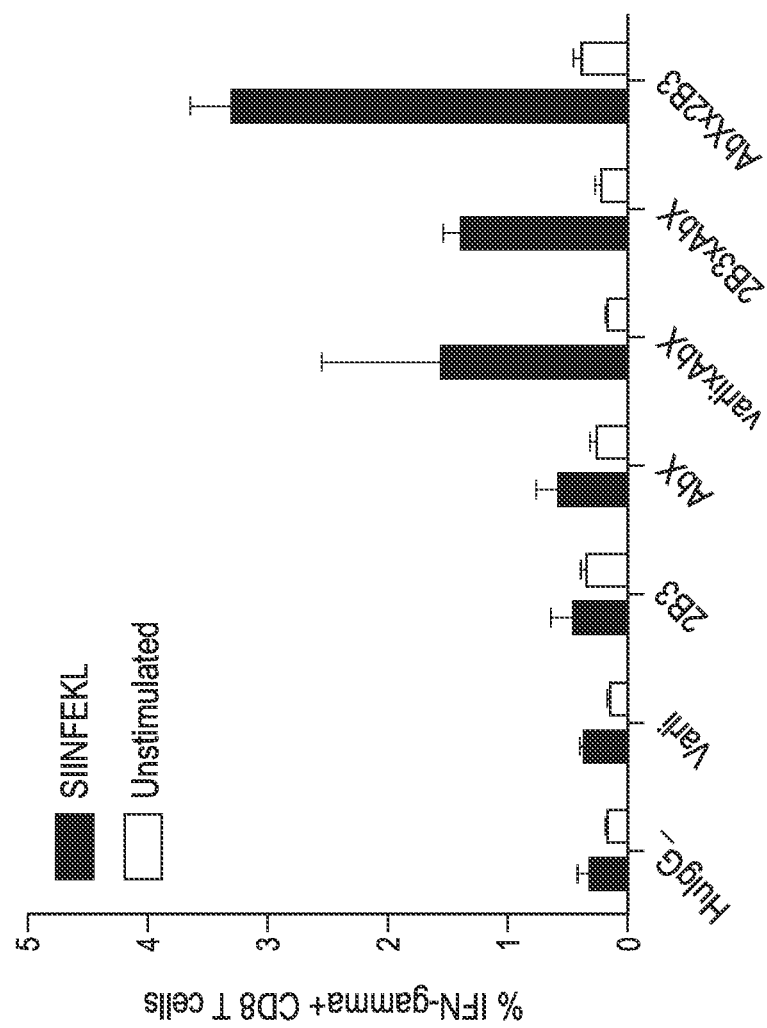

FIG. 31 is a graph showing increased stimulation (with and without ex-vivo stimulation of SIINFEKL peptide SEQ ID NO: SEQ ID NO: 188) of a vaccine induced CD8+ T-cell response by AbXx2B3 as compared to 2B3xAbX.

Figure 32:
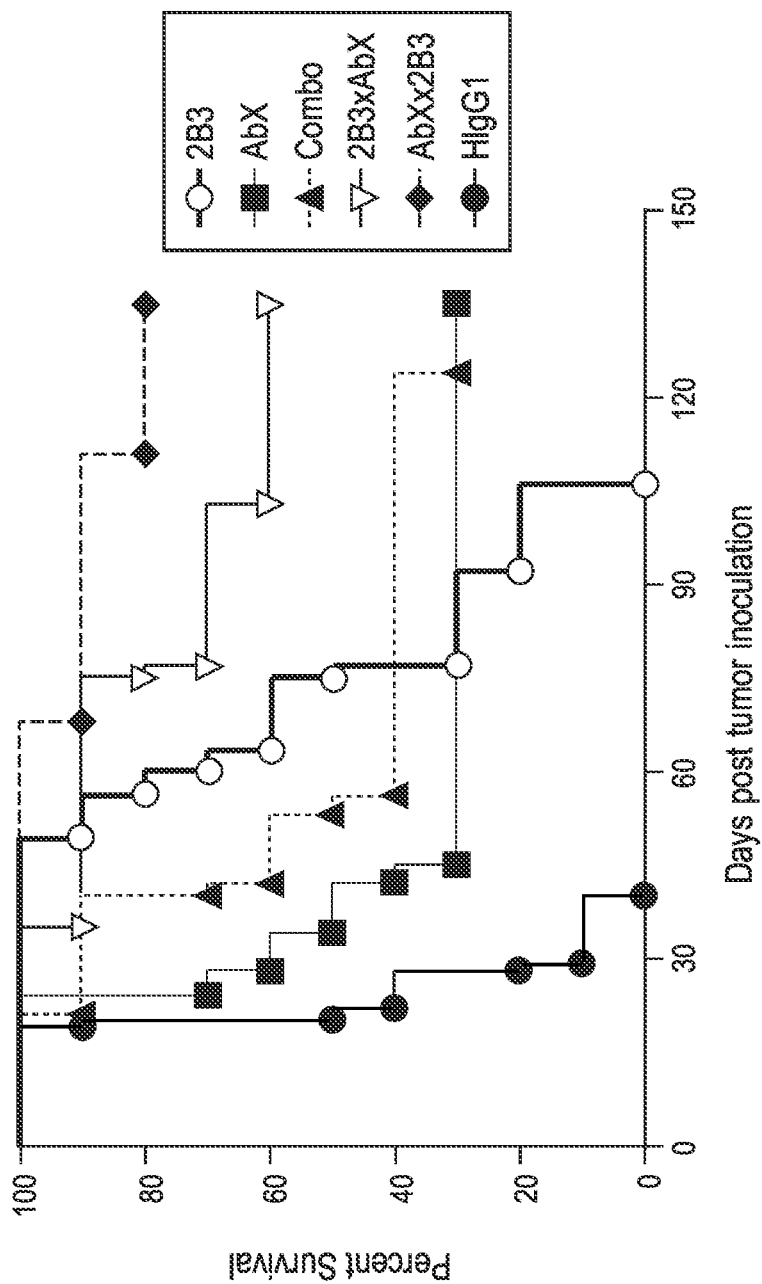

FIG. 32 is a graph showing increased anti-tumor activity by AbXx2B3 as compared to 2B3xAbX.

Figure 33:
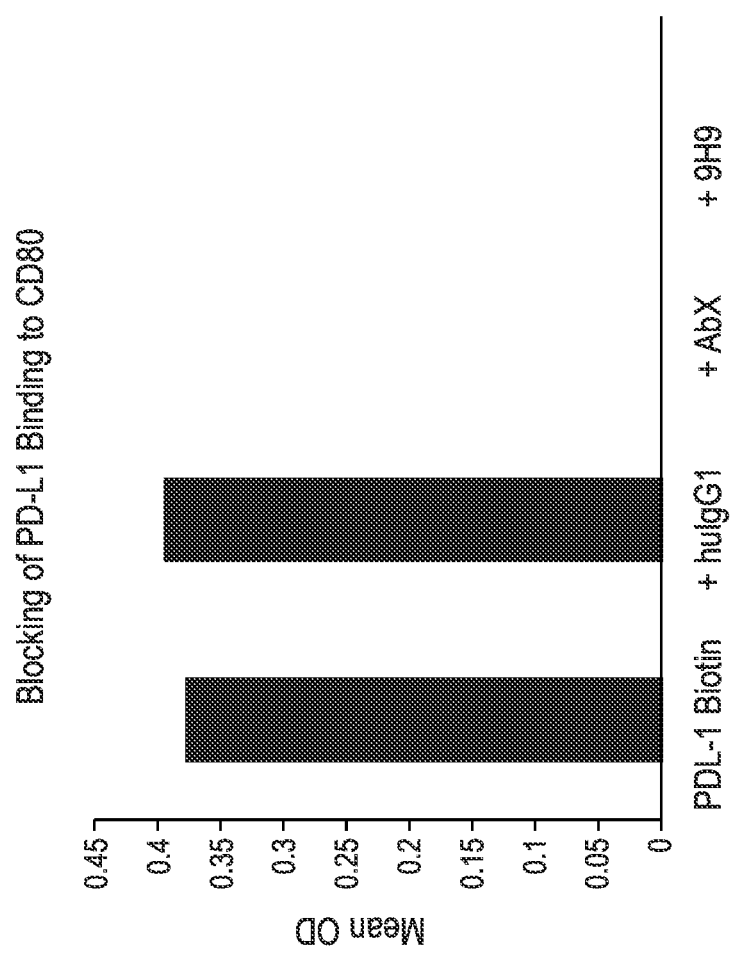

FIG. 33 is a graph showing blocking of PD-L1 Binding to CD80 by anti-PD-L1 antibodies AbX and 9H9.

Figure 34:
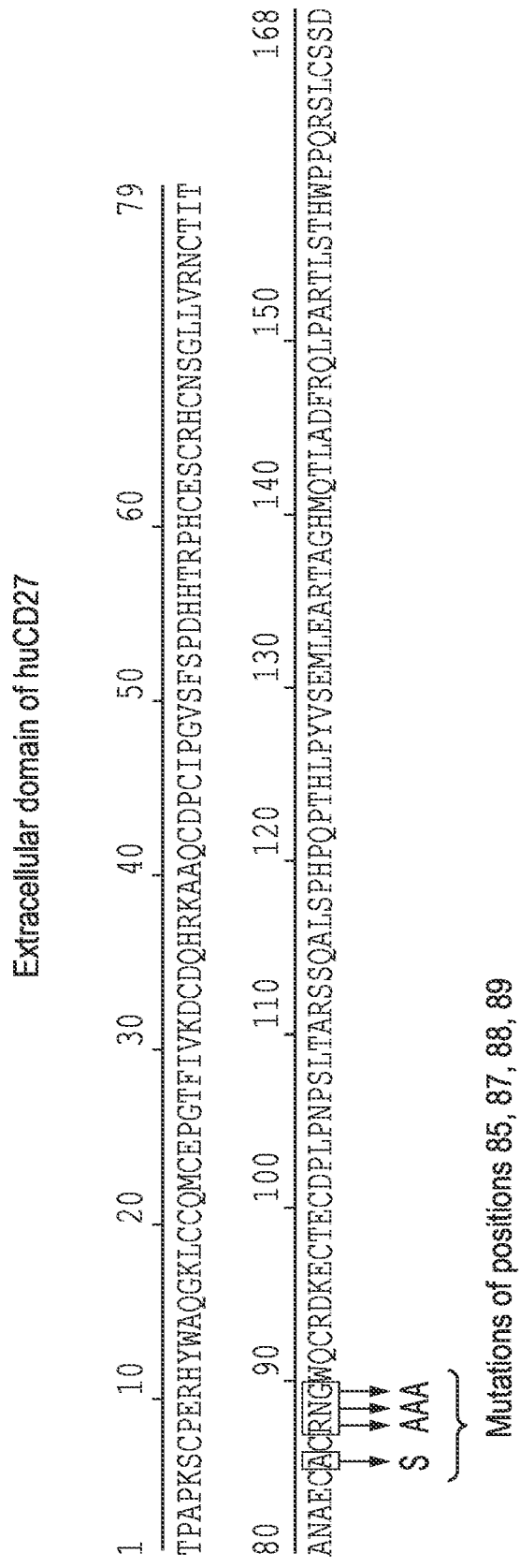

FIG. 34 (SEQ ID NO: 183) shows the sequence of the extracellular domain (ECD) of wild type huCD27 and a mutated version with substitutions at positions 85, 87, 88 and 89.

Figure 35:
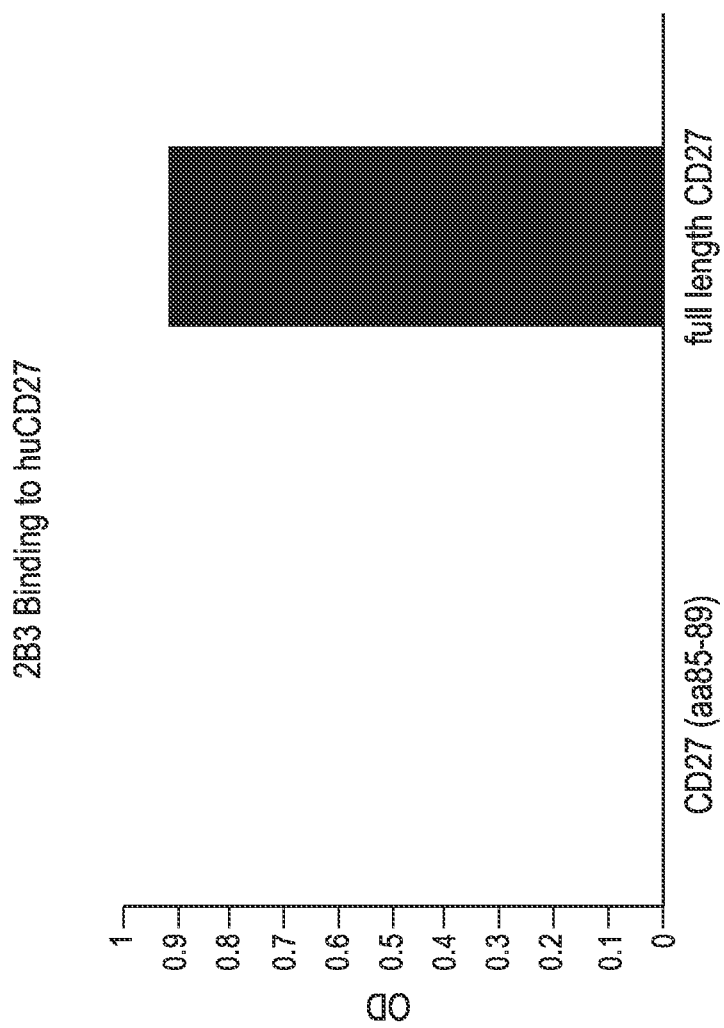

FIG. 35 is a graph showing binding of anti-CD27 antibody 2B3 to both wild type huCD27 and mutated huCD27 with sequences as shown in FIG. 34.

Figure 36:
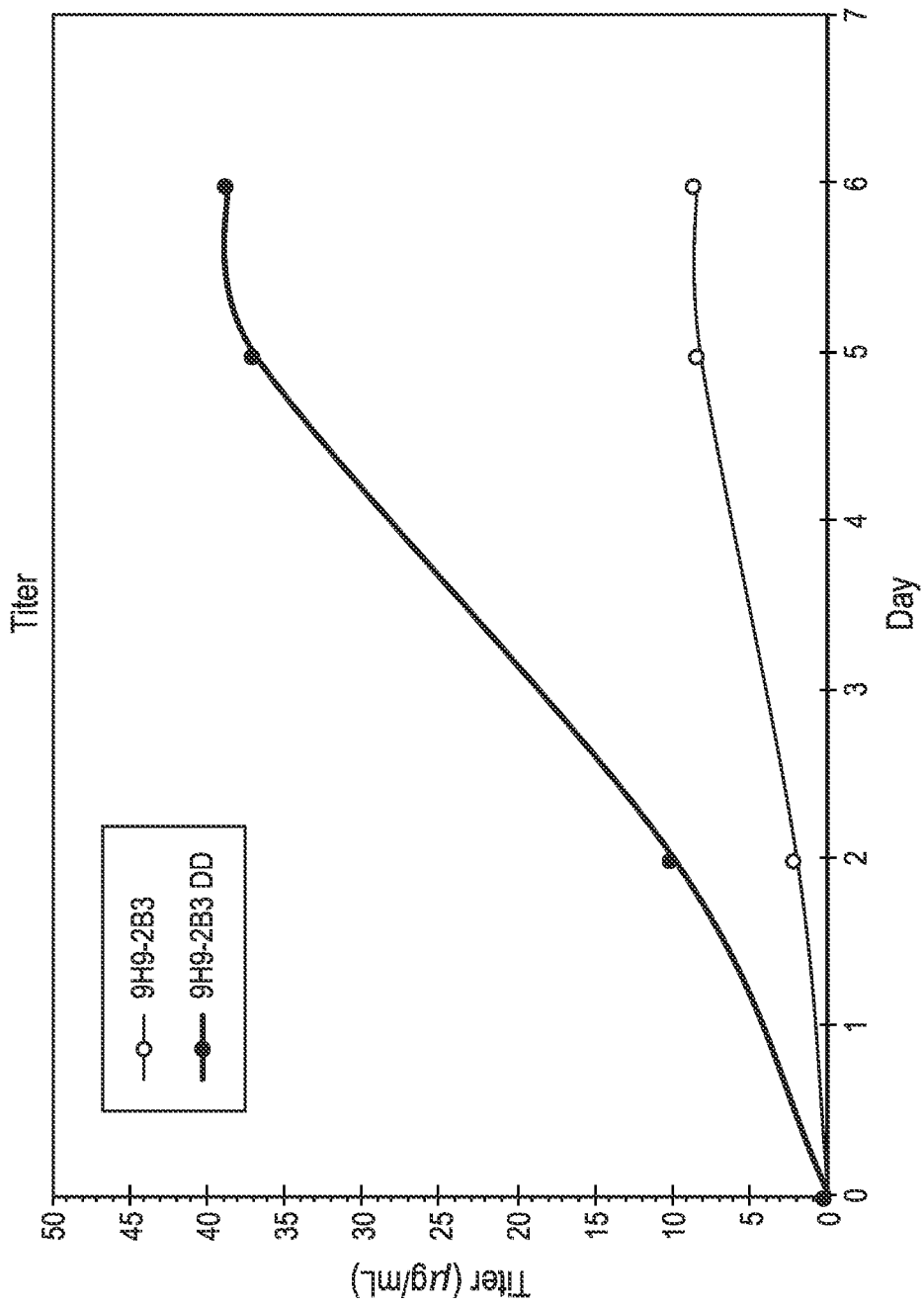

FIG. 36 is a graph showing improved production (expression) of a modified 9H9x2B3 (DD) construct compared to the original (unmodified) 9H9x2B3 construct.

IV. DETAILED DESCRIPTION OF THE INVENTION

CD27 is an important co-stimulatory receptor that can be exploited for immunotherapy using agonist molecules. CD27 plays a key role in diverse immunological processes, including the survival, activation and effector functions of T cells, as well as the proliferation and cytotoxic activity of natural killer (NK) cells. These events occur in response to appropriate interaction of the ligand (CD70) with CD27 resulting in intracellular signaling events that lead to an activation of NF-kB and expression of relevant genes. As with most co-stimulatory molecules, effective stimulation of T cells with either the ligand or agonist antibodies also requires simultaneous stimulation through the T cell receptor (TCR).

Most CD27 agonists molecules require multimerization or crosslinking for their activity. For example, anti-CD27 antibodies that are agonists are cross-linked through interaction of their Fc domains with Fc receptors through cis or trans interactions. In vitro this can also be performed artificially using a secondary anti-Ig antibody or by adsorbing the antibody to a solid phase matrix. The requirement for FcR interaction of anti-CD27 agonist antibodies implies that the T cell stimulating activity is at least partially dependent on the number FcR expressing cells.

To eliminate the requirement for FcR interactions, CD27 agonists have been invented that 1) eliminate the need for interaction with receptors other than CD27 (herein termed CD27 hyper-crosslinking agents), or 2) can provide the crosslinking through interaction of alternate receptors that may be on different specific cell types not expressing FcR, and which alternate receptors may also provide additional function (herein termed CD27 multi-specific agents).

In one aspect, the invention provides bispecific constructs (or multispecific constructs) that comprise an anti-CD27 antibody, or antigen-binding fragment thereof, linked to an anti-PD-L1 antibody, or antigen-binding fragment thereof. Such anti-CD27×anti-PD-L1 bispecific agents of the invention have now been shown to exhibit synergistic effects in vivo, such as in enhancing immune parameters and inhibiting tumor growth, as compared to co-administration of an anti-CD27 antibody with an anti-PD-L1 antibody (see Examples 9 and 10).

In order that the present invention may be more readily understood, certain terms are first defined. Additional definitions are set forth throughout the detailed description.

A. Definitions

As used herein, the term "subject" includes any human or non-human animal. For example, the methods and compositions of the present invention can be used to treat a subject with an immune disorder. The term "non-human animal" includes all vertebrates, e.g., mammals and non-mammals, such as non-human primates, sheep, dog, cow, chickens, amphibians, reptiles, etc.

As used herein, the term "binding domain" refers to the portion of a protein or antibody which comprises the amino acid residues that interact with an antigen. Binding domains include, but are not limited to, antibodies (e.g., full length antibodies), as well as antigen-binding portions thereof. The binding domain confers on the binding agent its specificity and affinity for the antigen. The term also covers any protein having a binding domain which is homologous or largely homologous to an immunoglobulin-binding domain. Such proteins may be derived from natural sources, or partly or wholly synthetically produced.

The term "antibody" as referred to herein includes whole antibodies and any antigen binding fragment (i.e., "antigen-binding portion") or single chain version thereof. An "antibody" refers, in one preferred embodiment, to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding fragment" of an antibody (or simply "antibody fragment"), as used herein, refers to one or more fragments or portions of an antibody that retain the ability to specifically bind to an antigen (e.g., human CD27). Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (sFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "monoclonal antibody," as used herein, refers to an antibody that displays a single binding specificity and affinity for a particular epitope. Accordingly, the term "human monoclonal antibody" refers to an antibody which displays a single binding specificity and which has variable and optional constant regions derived from human germline immunoglobulin sequences. In one embodiment, human monoclonal antibodies are produced by a hybridoma that includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) *Nature Biotech.* 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

The term "human antibody" includes antibodies having variable and constant regions (if present) of human germline immunoglobulin sequences. Human antibodies of the invention can include amino acid residues not encoded by human germline immunoglobulin sequences (e.g., mutations introduced by random or site-specific mutagenesis in vitro or by somatic mutation in vivo) (see, Lonberg, N. et al. (1994) *Nature* 368(6474): 856-859); Lonberg, N. (1994) *Handbook of Experimental Pharmacology* 113:49-101; Lonberg, N.

and Huszar, D. (1995) *Intern. Rev. Immunol.* Vol. 13: 65-93, and Harding, F. and Lonberg, N. (1995) *Ann. N.Y. Acad. Sci* 764:536-546). However, the term "human antibody" does not include antibodies in which CDR sequences derived from the germline of another mammalian species, such as a mouse, have been grafted onto human framework sequences (i.e., chimeric and humanized antibodies).

An "isolated antibody," as used herein, is intended to refer to an antibody which is substantially free of other antibodies having different antigenic specificities (e.g., an isolated antibody that specifically binds to human CD27 is substantially free of antibodies that specifically bind antigens other than human CD27; an isolated antibody that specifically binds to human PD-L1 is substantially free of antibodies that specifically bind antigens other than human PD-L1). An isolated antibody that specifically binds to an epitope may, however, have cross-reactivity to the same antigen from different species. In addition, an isolated antibody is typically substantially free of other cellular material and/or chemicals.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from the antigen (e.g., CD27 or PD-L1) are tested for reactivity with the given antibody (e.g., an anti-CD27 or anti-PD-L1 antibody. Methods of determining spatial conformation of epitopes include techniques in the art and those described herein, for example, x-ray crystallography and 2-dimensional nuclear magnetic resonance (see, e.g., *Epitope Mapping Protocols in Methods in Molecular Biology,* Vol. 66, G. E. Morris, Ed. (1996)).

The term "antibody that binds the same epitope" as another antibody is intended to encompass antibodies that interact with, i.e., bind to, the same structural region on human CD27 as a reference anti-CD27 antibody. The "same epitope" to which the antibodies bind may be a linear epitope or a conformational epitope formed by tertiary folding of the antigen.

The term "competing antibody" refers to an antibody that competes for binding to human CD27 with a reference anti-CD27 antibody, i.e., competitively inhibits binding of the reference anti-CD27 antibody to CD27. A "competing antibody" may bind the same epitope on CD27 as the reference anti-CD27 antibody, may bind to an overlapping epitope or may sterically hinder the binding of the reference anti-CD27 antibody to CD27.

Antibodies that recognize the same epitope or compete for binding can be identified using routine techniques. Such techniques include, for example, an immunoassay, which shows the ability of one antibody to block the binding of another antibody to a target antigen, i.e., a competitive binding assay. Competitive binding is determined in an assay in which the immunoglobulin under test inhibits specific binding of a reference antibody to a common antigen, such as CD27. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual,* Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

Other techniques include, for example, epitope mapping methods, such as, x-ray analyses of crystals of antigen: antibody complexes which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

As used herein, the terms "specific binding," "selective binding," "selectively binds," and "specifically binds," refer to antibody binding to an epitope on a predetermined antigen. Typically, the antibody binds with an equilibrium dissociation constant ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE™ 2000 instrument (e.g., using recombinant human CD27 as the analyte and the antibody as the ligand) and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

The term "$K_D$," as used herein, is intended to refer to the dissociation equilibrium constant of a particular antibody-antigen interaction. Typically, the human antibodies of the invention bind to CD27 with a dissociation equilibrium constant ($K_D$) of approximately $10^{-8}$ M or less, such as less than $10^{-9}$ M or $10^{-10}$ M or even lower when determined by surface plasmon resonance (SPR) technology in a BIACORE 2000 instrument (e.g., using recombinant human CD27 as the analyte and the antibody as the ligand).

The term "kd" as used herein, is intended to refer to the off rate constant for the dissociation of an antibody from the antibody/antigen complex.

The term "ka" as used herein, is intended to refer to the on rate constant for the association of an antibody with the antigen.

The term "EC50," as used herein, refers to the concentration of an antibody or an antigen-binding portion thereof, which induces a response, either in an in vitro or an in vivo assay, which is 50% of the maximal response, i.e., halfway between the maximal response and the baseline.

As used herein, "isotype" refers to the antibody class (e.g., IgM or IgG1) that is encoded by heavy chain constant region genes. In one embodiment, a human monoclonal antibody of the invention is of the IgG1 isotype. In another embodiment, a human monoclonal antibody of the invention is of the IgG2 isotype.

As used herein, the terms "inhibits" or "blocks" (e.g., referring to inhibition/blocking of binding of CD70 to CD27 and/or PD1 to PD-L1) are used interchangeably and encompass both partial and complete inhibition/blocking. The inhibition/blocking preferably reduces or alters the normal level or type of activity that occurs when binding occurs without inhibition or blocking. Inhibition and blocking are also intended to include any measurable decrease in the binding affinity of CD70 when in contact with an anti-CD27 antibody as compared to CD70 not in contact with an anti-CD27 antibody, e.g., inhibits binding of CD70 by at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%. In one embodiment, the anti-CD27 antibody inhibits binding of CD70 by at least about 70%. In another embodiment, the anti-CD27 antibody inhibits binding of CD70 by at least 80%. Inhibition and blocking are also intended to include any measurable decrease in the binding affinity of PD1 when in contact with an anti-PD-L1 antibody as compared to PD1 not in contact with an anti-PD-L1 antibody, e.g., inhibits binding of PD1 by at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%. In one embodiment, the anti-PD-L1 antibody inhibits binding of PD1 by at least about 70%. In another embodiment, the anti-PD-L1 antibody inhibits binding of PD1 by at least 80%.

The term "cross-reacts," as used herein, refers to the ability of an anti-CD27 binding domain or an anti-PD-L1 binding domain of the invention to bind to CD27 or PD-L1, respectively, from a different species. For example, a CD27 binding domain of the invention that binds human CD27 may also bind another species of CD27. Similarly, an anti-PD-L1 binding domain of the invention that binds human PD-L1 may also bind another species of PD-L1. As used herein, cross-reactivity is measured by detecting a specific reactivity with purified antigen in binding assays (e.g., SPR, ELISA) or binding to, or otherwise functionally interacting with, cells physiologically expressing CD27. Methods for determining cross-reactivity include standard binding assays as described herein, for example, by Biacore™ surface plasmon resonance (SPR) analysis using a Biacore™ 2000 SPR instrument (Biacore AB, Uppsala, Sweden), or flow cytometric techniques.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The present invention also encompasses "conservative sequence modifications" of any of the sequences set forth in SEQ ID NOs: 1-160, i.e., nucleotide and amino acid sequence modifications which do not abrogate the binding of the VH and VL sequences encoded by the nucleotide sequence or containing the amino acid sequence, to the antigen. Such conservative sequence modifications include conservative nucleotide and amino acid substitutions, as well as, nucleotide and amino acid additions and deletions. For example, modifications can be introduced into SEQ ID NOs:1-160 by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an anti-CD27 antibody is preferably replaced with another amino acid residue from the same side chain family. Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997)).

In certain embodiments, conservative amino acid sequence modifications refer to at most 1, 2, 3, 4 or 5 conservative amino acid substitutions to the CDR sequences described herein. For example, each such CDR may contain up to 5 conservative amino acid substitutions, e.g., up to (i.e., not more than) 4 conservative amino acid substitutions, e.g., up to (i.e., not more than) 3 conservative amino acid substitutions, e.g., up to (i.e., not more than) 2 conservative amino acid substitutions, or no more than 1 conservative amino acid substitution.

Alternatively, in another embodiment, mutations can be introduced randomly along all or part of an anti-CD27 or anti-PD-L1 binding domain coding sequence, such as by saturation mutagenesis, and the resulting modified anti-CD27 or anti-PD-L1 antibodies can be screened for binding activity.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

For amino acids, the term "substantial homology" indicates that two amino acid sequences, or designated sequences thereof, when optimally aligned and compared, are identical, with appropriate amino acid insertions or deletions, in at least about 80% of the amino acids, usually at least about 90% to 95%, and more preferably at least about 98% to 99% or 99.5% of the amino acids.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences identical to the nucleic acid molecules of the invention. BLAST protein searches can be performed with the XBLAST program, score=50, wordlength=3 to obtain amino acid sequences identical to the protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. See www.ncbi.nlm-.nih.gov.

B. Anti-CD27 Antibodies and Binding Domains Thereof

Provided herein are novel anti-CD27 antibodies and binding domains thereof. The term "CD27" (also referred to as "CD27 molecule", "CD27L receptor", "S1521", "T cell activation antigen CD27", "TNFRSF7," "MGC20393," "tumor necrosis factor receptor superfamily, member 7", "T cell activation antigen S152" "Tp55", "Tumor necrosis factor receptor superfamily member 7", "CD27 antigen", and "T-cell activation antigen CD27") refers to a receptor that is a member of the TNF-receptor superfamily, which binds to ligand CD70. CD27 is required for generation and long-term maintenance of T cell immunity and plays a key role in regulating B-cell activation and immunoglobulin synthesis. The term "CD27" includes any variants or isoforms of CD27 which are naturally expressed by cells (e.g., human CD27 deposited with GENBANK® having accession no. AAH12160.1 as set forth in SEQ ID NO:173). Accordingly, CD27 binding domains of the invention may cross-react with CD27 from species other than human. Alternatively, the CD27 binding domains may be specific for human CD27 and may not exhibit any cross-reactivity with other species. CD27 or any variants and isoforms thereof, may either be isolated from cells or tissues that naturally express them or be recombinantly produced using well-known techniques in the art and/or those described herein. Preferably the CD27 binding domains are targeted to human CD27, which has a normal glycosylation pattern.

The term "CD70" (also referred to as "CD70 molecule", "CD27L", "CD27LG", "TNFSF7," "tumor necrosis factor (ligand) superfamily member 7," "CD27 ligand," "CD70 antigen," "surface antigen CD70," "tumor necrosis factor ligand superfamily, member 7," "Ki-24 antigen," and "CD27-L") refers to the ligand for CD27 (see, for example, Bowman M R et al., J. Immunol. 1994 Feb. 15; 152(4): 1756-61). CD70 is a type II transmembrane protein that belongs to the tumor necrosis factor (TNF) ligand family. It is a surface antigen on activated T and B lymphocytes that induces proliferation of co-stimulated T cells, enhances the generation of cytolytic T cells, and contributes to T cell activation. It has also been suggested that CD70 plays a role in regulating B-cell activation, cytotoxic function of natural killer cells, and immunoglobulin synthesis (Hintzen R Q et al., J. Immunol. 1994 Feb. 15; 152(4):1762-73). Genbank® Accession No. NP_001243 reports the amino acid sequence of human CD70 (SEQ ID NO:174).

An exemplary anti-CD27 antibody is antibody 3C2 as described herein. In one embodiment, the anti-CD27 antibody or binding domain thereof comprises the heavy and light chain CDRs or variable regions of antibody 3C2. In another embodiment, the antibody or binding domain thereof comprises the CDR1, CDR2, and CDR3 domains of the heavy chain variable region of antibody 3C2 having the sequence set forth in SEQ ID NO:17, and the CDR1, CDR2 and CDR3 domains of the light chain variable region of antibody 3C2 having the sequence set forth in SEQ ID NO:18. In another embodiment, the antibody or binding domain thereof comprises heavy chain CDR1, CDR2 and CDR3 domains having the sequences set forth in SEQ ID NOs:1, 2, and 3, respectively, or conservative sequence modifications thereof, and light chain CDR1, CDR2 and CDR3 domains having the sequences set forth in SEQ ID NOs:4, 5, and 6, respectively, or conservative sequence modifications thereof. In another embodiment, the antibody or binding domain thereof comprises a heavy chain variable region having the amino acid sequence set forth in SEQ ID NO:17. In another embodiment, the antibody or binding domain thereof comprises a light chain variable region having the amino acid sequence set forth in SEQ ID NO:18. In another embodiment, the antibody or binding domain thereof comprises heavy and light chain variable regions having the amino acid sequences set forth in SEQ ID NO:17 and SEQ ID NO:18, respectively.

Another exemplary anti-CD27 antibody is antibody 2B3 as described herein. In one embodiment, the anti-CD27 antibody or binding domain thereof comprises the heavy and light chain CDRs or variable regions of antibody 2B3. In another embodiment, the antibody or binding domain thereof comprises the CDR1, CDR2, and CDR3 domains of the heavy chain variable region of antibody 2B3 having the sequence set forth in SEQ ID NO:19, and the CDR1, CDR2 and CDR3 domains of the light chain variable region of antibody 3C2 having the sequence set forth in SEQ ID NO:20. In another embodiment, the antibody or binding domain thereof comprises heavy chain CDR1, CDR2 and CDR3 domains having the sequences set forth in SEQ ID NOs:7, 8, and 9, respectively, or conservative sequence modifications thereof, and light chain CDR1, CDR2 and CDR3 domains having the sequences set forth in SEQ ID NOs: 10, 11, and 12, respectively, or conservative sequence modifications thereof. In another embodiment, the antibody or binding domain thereof comprises a heavy chain variable region having the amino acid sequences set forth in SEQ ID NO:19. In another embodiment, the antibody or binding domain thereof comprises a light chain variable region having the amino acid sequences set forth in SEQ ID NO:20. In another embodiment, the antibody or binding domain thereof comprises heavy and light chain variable regions having the amino acid sequences set forth in SEQ ID NO:19 and SEQ ID NO:20, respectively.

Sequences substantially identical to the anti-C27 binding domains described herein (e.g., at least 80%, 85%, 90%, 91%, 92%, 93%, 94%, 95%, 96%, 97%, 98% or 99% identical (identical) to the aforementioned sequences), are also provided. In one embodiment, the anti-CD27 binding domain comprises a heavy chain variable region comprising SEQ ID NO:17, SEQ ID NO: 19 or a sequence at least 90% identical thereto (e.g., at least 90%, 91%, 92%, 93%, 94%, 95%, 96%, 97%, 98% or 99% identical to the aforementioned sequences). In another embodiment, the anti-CD27 binding domain comprises a light chain variable region comprising SEQ ID NO:18, SEQ ID NO:20, or a sequence at least 90% identical thereto (e.g., at least 90%, 91%, 92%, 93%, 94%, 95%, 96%, 97%, 98% or 99% identical to the aforementioned sequences). In another embodiment, the anti-CD27 binding domain comprises a heavy chain variable region comprising SEQ ID NO:17 and a light chain variable region comprising SEQ ID NO:18 or sequences at least 90% identical thereto (e.g., at least 90%, 91%, 92%, 93%, 94%, 95%, 96%, 97%, 98% or 99% identical to the aforementioned sequences). In another embodiment, the anti-CD27 binding domain comprises a heavy chain variable region comprising SEQ ID NO:19 and a light chain variable region comprising SEQ ID NO:20 or sequences at least 90% identical thereto (e.g., at least 90%, 91%, 92%, 93%, 94%, 95%, 96%, 97%, 98% or 99% identical to the aforementioned sequences).

Anti-CD27 antibodies and binding domains thereof that that compete for binding with any of the anti-CD27 antibody or binding domain thereof described herein or that bind the same epitope as any of the anti-CD27 antibody or binding domain thereof described herein are also suitable for use and provided herein. For example, in one embodiment, the anti-CD27 antibody or binding domain thereof competes for binding to CD27 with antibody 3C2 (or an antibody having the heavy and light chain CDRs and/or heavy and light chain variable region sequences corresponding to antibody 3C2). In another embodiment, the anti-CD27 antibody or binding domain thereof competes for binding to CD27 with antibody 2B3 (or an antibody having the heavy and light chain CDRs and/or heavy and light chain variable region sequences corresponding to antibody 2B3). In another embodiment, the antibody or anti-CD27 binding domain thereof binds to the same epitope on CD27 as antibody 3C2 (or an antibody having the heavy and light chain CDRs and/or heavy and light chain variable region sequences corresponding to antibody 3C2). In another embodiment, the anti-CD27 antibody or binding domain thereof binds to the same epitope on CD27 as antibody 2B3 (or an antibody having the heavy and light chain CDRs and/or heavy and light chain variable region sequences corresponding to antibody 2B3).

In one embodiment, the anti-CD27 antibody, or antigen-binding fragment thereof, comprises heavy chain variable region CDR1, CDR2 and CDR3 as set forth in SEQ ID NOs:1, 2, and 3, respectively, and light chain variable region CDR1, CDR2 and CDR3 as set forth in SEQ ID NOs:4, 5, and 6, respectively. In another embodiment, the anti-CD27 antibody, or antigen-binding fragment thereof, comprises a heavy chain variable region comprising SEQ ID NO:17 and a light chain variable region comprising SEQ ID NO:18 or sequences at least 90% identical thereto (e.g., at least 90%, 91%, 92%, 93%, 94%, 95%, 96%, 97%, 98% or 99% identical to the aforementioned sequences).

In another embodiment, the anti-CD27 antibody, or antigen-binding fragment thereof, comprises heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively. In another embodiment, the anti-CD27 antibody, or antigen-binding fragment thereof, comprises a heavy chain variable region comprising SEQ ID NO:19 and a light chain variable region comprising SEQ ID NO:20 or sequences at least 95% identical thereto.

In another embodiment, the anti-CD27 antibody, or antigen-binding fragment thereof, has one or more of the following functional features: induces or enhances a T cell-mediated immune response, blocks binding of sCD70 to CD27 (e.g., partially or completely), induces NFκB activation, increases T cell proliferation, binds to human CD27 with an equilibrium dissociation constant Kd of $10^{-9}$ M or less, or alternatively, an equilibrium association constant Ka of $10^{+9}$ $M^{-1}$ or greater, induces specific complement mediated cytotoxicity (CDC) of CD27 expressing cells, induces antibody dependent cell-mediated cytotoxicity (ADCC) specific lysis of CD27 expressing cells, induces or enhances antigen-specific immune responses in vivo in combination with a vaccine or endogenous antigen, induces or enhances antigen-specific TH1 immune responses in vivo in combination with a vaccine or endogenous antigen, induces or enhances antigen-specific T-cell proliferation or activation in vivo in combination with a vaccine or endogenous antigen; and/or induces or enhances T-cell activity when combined with simultaneous, separate or sequential TCR activation.

C. Anti-PD-L1 Antibodies and Binding Domains

Provided herein are novel anti-PD-L1 antibodies binding domains thereof. As used herein, the terms "Programmed cell death 1 ligand 1", "PD-L1", "PDCD1 ligand 1", "Programmed death ligand 1", "B7 homolog 1", "B7-H1" and "CD274" are used interchangeably, and include variants, isoforms, species homologs of human PD-L1, and analogs having at least one common epitope with PD-L1. The complete PD-L1 sequence can be found under GenBank Accession No. NP_001254635 as set forth in SEQ ID NO:176.

Programmed death-ligand 1 (PD-L1) is a 40 kDa type 1 transmembrane protein that has been speculated to play a major role in suppressing the immune system during particular events such as pregnancy, tissue allografts, autoimmune disease, and other disease states such as hepatitis. Normally the immune system reacts to foreign antigens that are associated with exogenous or endogenous danger signals, which triggers a proliferation of antigen-specific CD8+ T cells and/or CD4+ helper cells. The binding of PD-L1 to PD-1 transmits an inhibitory signal that reduces the proliferation of these T cells and can also induce apoptosis, which is further mediated by a lower regulation of the gene Bcl-2. As used herein, the terms "Programmed Death 1," "Programmed Cell Death 1," "Protein PD-1," "PD-1," PD1," "PDCD1," "hPD-1" and "hPD-I" are used interchangeably, and include variants, isoforms, species homologs of human PD-1, and analogs having at least one common epitope with PD-1. The complete PD-1 sequence can be found under GenBank Accession No. NP_005009 as set forth in SEQ ID NO:175.

PD-L1 is abundant in a variety of human cancers (Dong et al. (2002) *Nat. Med.* 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) *J. Mol. Med.* 81:281-7; Blank et al. (2005) *Cancer Immunol. Immunother.* 54:307-314; Konishi et al. (2004) *Clin. Cancer Res.* 10:5094-100). Immune suppression can be reversed by inhibiting the local interaction of PD-1 with PD-L1, and the effect is additive when the interaction of PD-1 with PD-L2 is blocked as well (Iwai et al. (2002) *Proc. Nat'l. Acad. Sci. USA* 99:12293-7; Brown et al. (2003) *J. Immunol.* 170:1257-66).

An exemplary anti-PD-L1 antibody is antibody 7H7 as described herein. In one embodiment, the anti-PD-L1 antibody or binding domain thereof comprises the heavy and light chain CDRs or variable regions of antibody 7H7. In another embodiment, the antibody or binding domain thereof comprises the CDR1, CDR2, and CDR3 domains of the heavy chain variable region of antibody 7H7 having the sequence set forth in SEQ ID NO:77, and the CDR1, CDR2 and CDR3 domains of the light chain variable region of antibody 7H7 having the sequence set forth in SEQ ID NO:78. In another embodiment, the antibody or binding domain thereof comprises heavy chain CDR1, CDR2 and CDR3 domains having the sequences set forth in SEQ ID NOs:29, 30, and 31, respectively, or conservative sequence modifications thereof, and light chain CDR1, CDR2 and CDR3 domains having the sequences set forth in SEQ ID NOs:32, 33, and 34, respectively, or conservative sequence modifications thereof. In another embodiment, the antibody or binding domain thereof comprises a heavy chain variable region having the amino acid sequence set forth in SEQ ID NO:77. In another embodiment, the antibody or binding domain thereof comprises a heavy chain variable region having the amino acid sequence set forth in SEQ ID NO:77. In another embodiment, the antibody or binding domain thereof comprises heavy and light chain variable regions having the amino acid sequences set forth in SEQ ID NO:77 and SEQ ID NO:78, respectively.

Another exemplary anti-PD-L1 antibody is antibody 1B3 as described herein. In one embodiment, the anti-PD-L1 antibody or binding domain thereof comprises the heavy and light chain CDRs or variable regions of antibody 1B3. In another embodiment, the antibody or binding domain thereof comprises the CDR1, CDR2, and CDR3 domains of the heavy chain variable region of antibody 1B3 having the sequence set forth in SEQ ID NO:79, and the CDR1, CDR2 and CDR3 domains of the light chain variable region of antibody 1B3 having the sequence set forth in SEQ ID NO:80. In another embodiment, the antibody or binding domain thereof comprises heavy chain CDR1, CDR2 and CDR3 domains having the sequences set forth in SEQ ID NOs:35, 36, and 37, respectively, or conservative sequence modifications thereof, and light chain CDR1, CDR2 and CDR3 domains having the sequences set forth in SEQ ID NOs:38, 39, and 40, respectively, or conservative sequence modifications thereof. In another embodiment, the antibody or binding domain thereof comprises a heavy chain variable region having the amino acid sequences set forth in SEQ ID NO:79. In another embodiment, the antibody or binding domain thereof comprises a light chain variable region having the amino acid sequences set forth in SEQ ID NO:80. In another embodiment, the antibody or binding domain thereof comprises heavy and light chain variable regions having the amino acid sequences set forth in SEQ ID NO:79 and SEQ ID NO:80, respectively.

Another exemplary anti-PD-L1 antibody is antibody 3B6 as described herein. In one embodiment, the anti-PD-L1 antibody or binding domain thereof comprises the heavy and light chain CDRs or variable regions of antibody 3B6. In another embodiment, the antibody or binding domain thereof comprises the CDR1, CDR2, and CDR3 domains of the heavy chain variable region of antibody 3B6 having the sequence set forth in SEQ ID NO:81, and the CDR1, CDR2 and CDR3 domains of the light chain variable region of antibody 3B6 having the sequence set forth in SEQ ID NO:82. In another embodiment, the antibody or binding domain thereof comprises heavy chain CDR1, CDR2 and CDR3 domains having the sequences set forth in SEQ ID NOs:41, 42, and 43, respectively, or conservative sequence modifications thereof, and light chain CDR1, CDR2 and CDR3 domains having the sequences set forth in SEQ ID NOs:44, 45, and 46, respectively, or conservative sequence modifications thereof. In another embodiment, the antibody or binding domain thereof comprises a heavy chain variable region having the amino acid sequence set forth in SEQ ID NO:81. In another embodiment, the antibody or binding domain thereof comprises a light chain variable region having the amino acid sequence set forth in SEQ ID NO:82. In another embodiment, the antibody or binding domain thereof comprises heavy and light chain variable regions having the amino acid sequences set forth in SEQ ID NO:81 and SEQ ID NO:82, respectively.

Another exemplary anti-PD-L1 antibody is antibody 8B1 as described herein. In one embodiment, the anti-PD-L1 antibody or binding domain thereof comprises the heavy and light chain CDRs or variable regions of antibody 8B1. In another embodiment, the antibody or binding domain thereof comprises the CDR1, CDR2, and CDR3 domains of the heavy chain variable region of antibody 8B1 having the sequence set forth in SEQ ID NO:83, and the CDR1, CDR2 and CDR3 domains of the light chain variable region of antibody 8B1 having the sequence set forth in SEQ ID NO:84. In another embodiment, the antibody or binding domain thereof comprises heavy chain CDR1, CDR2 and CDR3 domains having the sequences set forth in SEQ ID NOs:47, 48, and 49, respectively, or conservative sequence modifications thereof, and light chain CDR1, CDR2 and CDR3 domains having the sequences set forth in SEQ ID NOs:50, 51, and 52, respectively, or conservative sequence modifications thereof. In another embodiment, the antibody or binding domain thereof comprises a heavy chain variable region having the amino acid sequences set forth in SEQ ID NO:83. In another embodiment, the antibody or binding domain thereof comprises a light chain variable region having the amino acid sequences set forth in SEQ ID NO:84. In another embodiment, the antibody or binding domain thereof comprises heavy and light chain variable regions having the amino acid sequences set forth in SEQ ID NO:83 and SEQ ID NO:84, respectively.

Another exemplary anti-PD-L1 antibody is antibody 4A3 as described herein. In one embodiment, the anti-PD-L1 antibody or binding domain thereof comprises the heavy and light chain CDRs or variable regions of antibody 4A3. In another embodiment, the antibody or binding domain thereof comprises the CDR1, CDR2, and CDR3 domains of the heavy chain variable region of antibody 4A3 having the sequence set forth in SEQ ID NO:85, and the CDR1, CDR2 and CDR3 domains of the light chain variable region of antibody 4A3 having the sequence set forth in SEQ ID NO:86. In another embodiment, the antibody or binding domain thereof comprises heavy chain CDR1, CDR2 and CDR3 domains having the sequences set forth in SEQ ID NOs:53, 54, and 55, respectively, or conservative sequence modifications thereof, and light chain CDR1, CDR2 and CDR3 domains having the sequences set forth in SEQ ID NOs:56, 57, and 58, respectively, or conservative sequence modifications thereof. In another embodiment, the antibody or binding domain thereof comprises a heavy chain variable region having the amino acid sequence set forth in SEQ ID NO:85. In another embodiment, the antibody or binding domain thereof comprises a light chain variable region having the amino acid sequence set forth in SEQ ID NO:86. In another embodiment, the antibody or binding domain thereof comprises heavy and light chain variable regions having the amino acid sequences set forth in SEQ ID NO:85 and SEQ ID NO:86, respectively.

Another exemplary anti-PD-L1 antibody is antibody 9H9 as described herein. In one embodiment, the anti-PD-L1 antibody or binding domain thereof comprises the heavy and light chain CDRs or variable regions of antibody 9H9. In another embodiment, the antibody or binding domain thereof comprises the CDR1, CDR2, and CDR3 domains of the heavy chain variable region of antibody 9H9 having the sequence set forth in SEQ ID NO:87, and the CDR1, CDR2 and CDR3 domains of the light chain variable region of antibody 9H9 having the sequence set forth in SEQ ID NO:88. In another embodiment, the antibody or binding domain thereof comprises heavy chain CDR1, CDR2 and CDR3 domains having the sequences set forth in SEQ ID NOs:59, 60, and 61, respectively, or conservative sequence modifications thereof, and light chain CDR1, CDR2 and CDR3 domains having the sequences set forth in SEQ ID NOs:62, 63, and 64, respectively, or conservative sequence modifications thereof. In another embodiment, the antibody or binding domain thereof comprises a heavy chain variable region having the amino acid sequence set forth in SEQ ID NO:87. In another embodiment, the antibody or binding domain thereof comprises a light chain variable region having the amino acid sequence set forth in SEQ ID NO:88. In another embodiment, the antibody or binding domain thereof comprises heavy and light chain variable regions having the amino acid sequences set forth in SEQ ID NO:87 and SEQ ID NO:88, respectively.

The antibody sequences can also be consensus sequences of several antibodies. For example, in one embodiment, the anti-PD-L1 binding domain comprises a heavy chain variable region CDR1 comprising an amino acid sequence selected from the consensus sequence: (T,S)(S,Y,H)WMS (SEQ ID NO:167). In another embodiment, the anti-PD-L1 binding domain comprises a heavy chain variable region CDR2 comprising SEQ ID NO:168. In another embodiment, the anti-PD-L1 binding domain comprises a heavy chain variable region CDR3 comprising SEQ ID NO:169. In another embodiment, the anti-PD-L1 binding domain comprises a light chain variable region CDR1 comprising SEQ ID NO:170. In another embodiment, the anti-PD-L1 binding domain comprises a light chain variable region CDR2 comprising SEQ ID NO:171. In another embodiment, the anti-PD-L1 binding domain comprises a light chain variable region CDR3 comprising SEQ ID NO:172.

Sequences substantially identical to the anti-PD-L1 antibodies and binding domains thereof described herein (e.g., at least 80%, 85%, 90%, 91%, 92%, 93%, 94%, 95%, 96%, 97%, 98% or 99% identical to the aforementioned sequences), are also encompassed by the invention. In one embodiment, the anti-PD-L1 binding domain comprises a heavy chain variable region comprising SEQ ID NO:77, SEQ ID NO:79, SEQ ID NO:81, SEQ ID NO:83, SEQ ID NO:85, SEQ ID NO:87, or a sequence at least 90% identical thereto (e.g., at least 90%, 91%, 92%, 93%, 94%, 95%, 96%, 97%, 98% or 99% identical to the aforementioned sequences). In another embodiment, the anti-PD-L1 binding domain comprises a light chain variable region comprising SEQ ID NO:78, SEQ ID NO:80, SEQ ID NO:82, SEQ ID NO:84, SEQ ID NO:86, SEQ ID NO:88 or a sequence at least 90% identical thereto (e.g., at least 90%, 91%, 92%, 93%, 94%, 95%, 96%, 97%, 98% or 99% identical to the aforementioned sequences). In another embodiment, the anti-PD-L1 binding domain comprises a heavy chain variable region comprising SEQ ID NO:77 and a light chain variable region comprising SEQ ID NO:78 or sequences at least 90% identical thereto (e.g., at least 90%, 91%, 92%, 93%, 94%, 95%, 96%, 97%, 98% or 99% identical to the aforementioned sequences). In another embodiment, the anti-PD-L1 binding domain comprises a heavy chain variable region comprising SEQ ID NO:79 and a light chain variable region comprising SEQ ID NO:80 or sequences at least 90% identical thereto (e.g., at least 90%, 91%, 92%, 93%, 94%, 95%, 96%, 97%, 98% or 99% identical to the aforementioned sequences). In another embodiment, the anti-PD-L1 binding domain comprises a heavy chain variable region comprising SEQ ID NO:81 and a light chain variable region comprising SEQ ID NO:82 or sequences at least 90% identical thereto (e.g., at least 90%, 91%, 92%, 93%, 94%, 95%, 96%, 97%, 98% or 99% identical to the aforementioned sequences). In another embodiment, the anti-PD-L1 binding domain comprises a heavy chain variable region comprising SEQ ID NO:83 and a light chain variable region comprising SEQ ID NO:84 or sequences at least 90% identical thereto (e.g., at least 90%, 91%, 92%, 93%, 94%, 95%, 96%, 97%, 98% or 99% identical to the aforementioned sequences). In another embodiment, the anti-PD-L1 binding domain comprises a heavy chain variable region comprising SEQ ID NO:85 and a light chain variable region comprising SEQ ID NO:86 or sequences at least 90% identical thereto (e.g., at least 90%, 91%, 92%, 93%, 94%, 95%, 96%, 97%, 98% or 99% identical to the aforementioned sequences). In another embodiment, the anti-PD-L1 binding domain comprises a heavy chain variable region comprising SEQ ID NO:87 and a light chain variable region comprising SEQ ID NO:88 or sequences at least 90% identical thereto (e.g., at least 90%, 91%, 92%, 93%, 94%, 95%, 96%, 97%, 98% or 99% identical to the aforementioned sequences).

Anti-PD-L1 antibodies and binding domains thereof that compete for binding with any of the anti-PD-L1 antibodies or binding domains thereof as described herein or that bind the same epitope as any of the anti-PD-L1 antibodies or binding domains thereof as described herein are also suitable for use and provided herein. For example, in one embodiment, the anti-PD-L1 antibody or binding domain thereof competes for binding to PD-L1 with antibody 7H7 (or an antibody having the heavy and light chain CDRs and/or heavy and light chain variable region sequences corresponding to antibody 7H7). In another embodiment, the anti-PD-L1 antibody or binding domain thereof binds to the same epitope on PD-L1 as antibody 7H7 (or an antibody having the heavy and light chain CDRs and/or heavy and light chain variable region sequences corresponding to antibody 7H7).

In another embodiment, the anti-PD-L1 antibody or binding domain thereof competes for binding to PD-L1 with antibody 1B3 (or an antibody having the heavy and light chain CDRs and/or heavy and light chain variable region sequences corresponding to antibody 1B3). In another embodiment, the anti-PD-L1 antibody or binding domain thereof binds to the same epitope on PD-L1 as antibody 1B3 (or an antibody having the heavy and light chain CDRs and/or heavy and light chain variable region sequences corresponding to antibody 1B3).

In another embodiment, the anti-PD-L1 antibody or binding domain thereof competes for binding to PD-L1 with antibody 3B6 (or an antibody having the heavy and light chain CDRs and/or heavy and light chain variable region sequences corresponding to antibody 3B6). In another embodiment, the anti-PD-L1 antibody or binding domain thereof binds to the same epitope on PD-L1 as antibody 3B6 (or an antibody having the heavy and light chain CDRs and/or heavy and light chain variable region sequences corresponding to antibody 3B6).

In another embodiment, the anti-PD-L1 antibody or binding domain thereof competes for binding to PD-L1 with antibody 8B1 (or an antibody having the heavy and light chain CDRs and/or heavy and light chain variable region sequences corresponding to antibody 8B1). In another embodiment, the anti-PD-L1 antibody or binding domain thereof binds to the same epitope on PD-L1 as antibody 8B1 (or an antibody having the heavy and light chain CDRs and/or heavy and light chain variable region sequences corresponding to antibody 8B1).

In another embodiment, the anti-PD-L1 antibody or binding domain thereof competes for binding to PD-L1 with antibody 4A3 (or an antibody having the heavy and light chain CDRs and/or heavy and light chain variable region sequences corresponding to antibody 4A3). In another embodiment, the anti-PD-L1 antibody or binding domain thereof binds to the same epitope on PD-L1 as antibody 4A3 (or an antibody having the heavy and light chain CDRs and/or heavy and light chain variable region sequences corresponding to antibody 4A3).

In another embodiment, the anti-PD-L1 antibody or binding domain thereof competes for binding to PD-L1 with antibody 9H9 (or an antibody having the heavy and light chain CDRs and/or heavy and light chain variable region sequences corresponding to antibody 9H9). In another embodiment, the anti-PD-L1 antibody or binding domain thereof binds to the same epitope on PD-L1 as antibody 9H9 (or an antibody having the heavy and light chain CDRs and/or heavy and light chain variable region sequences corresponding to antibody 9H9).

In another embodiment, the anti-PD-L1 binding domain is an anti-PD-L1 antibody, or antigen-binding portion thereof. In one embodiment, the anti-PD-L1 antibody, or antigen-binding fragment thereof, comprises heavy chain variable region CDR1, CDR2 and CDR3 as set forth in SEQ ID NOs:29, 30, and 31, respectively, and light chain variable region CDR1, CDR2 and CDR3 as set forth in SEQ ID NOs:32, 33, and 34, respectively. In another embodiment, the anti-PD-L1 antibody, or antigen-binding fragment thereof, comprises a heavy chain variable region comprising SEQ ID NO:77 and a light chain variable region comprising SEQ ID NO:78 or sequences at least 90% identical thereto (e.g., at least 90%, 91%, 92%, 93%, 94%, 95%, 96%, 97%, 98% or 99% identical to the aforementioned sequences). In another embodiment, the anti-PD-L1 antibody, or antigen-binding fragment thereof, comprises heavy chain variable region CDR1, CDR2 and CDR3 as set forth in SEQ ID NOs:35, 36, and 37, respectively, and light chain variable region CDR1, CDR2 and CDR3 as set forth in SEQ ID NOs:38, 39, and 40, respectively. In another embodiment, the anti-PD-L1 antibody, or antigen-binding fragment thereof, comprises a heavy chain variable region comprising SEQ ID NO:79 and a light chain variable region comprising SEQ ID NO:80 or sequences at least 90% identical thereto (e.g., at least 90%, 91%, 92%, 93%, 94%, 95%, 96%, 97%, 98% or 99% identical to the aforementioned sequences). In another embodiment, the anti-PD-L1 antibody, or antigen-binding fragment thereof, comprises heavy chain variable region CDR1, CDR2 and CDR3 as set forth in SEQ ID NOs:41, 42, and 43, respectively, and light chain variable region CDR1, CDR2 and CDR3 as set forth in SEQ ID NOs:44, 45, and 46, respectively. In another embodiment, the anti-PD-L1 antibody, or antigen-binding fragment thereof, comprises a heavy chain variable region comprising SEQ ID NO:81 and a light chain variable region comprising SEQ ID NO:82 or sequences at least 90% identical thereto (e.g., at least 90%, 91%, 92%, 93%, 94%, 95%, 96%, 97%, 98% or 99% identical to the aforementioned sequences). In another embodiment, the anti-PD-L1 antibody, or antigen-binding fragment thereof, comprises heavy chain variable region CDR1, CDR2 and CDR3 as set forth in SEQ ID NOs:47, 48, and 49, respectively, and light chain variable region CDR1, CDR2 and CDR3 as set forth in SEQ ID NOs:50, 51, and 52, respectively. In another embodiment, the anti-PD-L1 antibody, or antigen-binding fragment thereof, comprises a heavy chain variable region comprising SEQ ID NO:83 and a light chain variable region comprising SEQ ID NO:84 or sequences at least 90% identical thereto (e.g., at least 90%, 91%, 92%, 93%, 94%, 95%, 96%, 97%, 98% or 99% identical to the aforementioned sequences). In another embodiment, the anti-PD-L1 antibody, or antigen-binding fragment thereof, comprises heavy chain variable region CDR1, CDR2 and CDR3 as set forth in SEQ ID NOs:53, 54, and 55, respectively, and light chain variable region CDR1, CDR2 and CDR3 as set forth in SEQ ID NOs:56, 57, and 58, respectively. In another embodiment, the anti-PD-L1 antibody, or antigen-binding fragment thereof, comprises a heavy chain variable region comprising SEQ ID NO:85 and a light chain variable region comprising SEQ ID NO:86 or sequences at least 90% identical thereto (e.g., at least 90%, 91%, 92%, 93%, 94%, 95%, 96%, 97%, 98% or 99% identical to the aforementioned sequences). In another embodiment, the anti-PD-L1 antibody, or antigen-binding fragment thereof, comprises heavy chain variable region CDR1, CDR2 and CDR3 as set forth in SEQ ID NOs:59, 60, and 61, respectively, and light chain variable region CDR1, CDR2 and CDR3 as set forth in SEQ ID NOs:62, 63, and 64, respectively. In another embodiment, the anti-PD-L1 antibody, or antigen-binding fragment thereof, comprises a heavy chain variable region comprising SEQ ID NO:87 and a light chain variable region comprising SEQ ID NO:88 or sequences at least 90% identical thereto (e.g., at least 90%, 91%, 92%, 93%, 94%, 95%, 96%, 97%, 98% or 99% identical to the aforementioned sequences).

In another embodiment, the anti-PD-L1 antibody, or antigen-binding fragment thereof, has one or more of the following functional features: (a) blocks binding of PD1 to PD-L1 (e.g., partially or completely), (b) induces NFAT pathway activation, and/or (c) induces a mixed lymphocyte reaction.

D. Bispecific Constructs

Provided herein are bispecific constructs comprising an anti-CD27 binding domain linked to an anti-PD-L1 binding domain. Such bispecific constructs linked to one or more additional binding agents to form multispecific constructs also are provided.

A "bispecific" or "bifunctional" construct is an artificial hybrid having two different binding domain (e.g., heavy/light chain) pairs and two different binding sites. Bispecific constructs can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

For chemical conjugation, suitable reagents and methods are known in the art for coupling two or more moieties, in particular two or more antibodies, or fragments thereof, together. A variety of coupling or crosslinking agents are commercially available and can be used to conjugate the anti-CD27 binding domain and anti-PD-L1 binding domain. Non-limiting examples include Sulfo-SMCC, protein A, carboiimide, dimaleimide, dithio-bis-nitrobenzoic acid (DTNB), and N-succinimidyl-3-(2-pyridyldithio) propionate (SPDP). Sulfo-SMCC, SPDP and DTNB are preferred agents, with Sulfo-SMCC being particularly preferred. Other suitable procedures for crosslinking components (e.g., binding domains) with cross-linking agents are known in the art. See e.g., Karpovsky, B. et al., (1984) *J. Exp. Med.* 160:1686; Liu, M. A. et al., (1985) *Proc. Natl. Acad. Sci USA* 82:8648; Segal, D. M. and Perez, P., U.S. Pat. No. 4,676,980; and Brennan, M. (1986) Biotechniques 4:424.

For genetic engineering, nucleic acid molecules encoding the anti-CD27 binding domain can be inserted into an appropriate expression vector using standard recombinant DNA techniques. A nucleic acid molecule(s) encoding the anti-PD-L1 binding domain also can be inserted into the same expression vector, such that it is operatively linked (e.g., in-frame cloning) to the CD27 binding domain, thereby resulting in an expression vector that encodes a fusion protein that is the bispecific construct. Preferably, the anti-PD-L1 binding domain is operatively linked to the C-terminal region of the heavy chain of the anti-CD27 binding domain. Other suitable expression vectors and cloning strategies for preparing the bispecific constructs described herein are known in the art.

For expression of the bispecific constructs in host cells, the coding regions of the binding domains are combined with cloned promoter, leader sequence, translation initiation, leader sequence, constant region, 3' untranslated, polyadenylation, and transcription termination, sequences to form expression vector constructs. These constructs can be used to express, for example, full length human IgG$_1$κ or IgG$_4$κ antibodies. Fully human, humanized and chimeric antibodies used in the bispecific constructs described herein also include IgG2, IgG3, IgE, IgA, IgM, and IgD antibodies. Similar plasmids can be constructed for expression of other heavy chain isotypes, or for expression of antibodies comprising lambda light chains.

Following preparation of an expression vector encoding the bispecific construct, the bispecific construct can be expressed recombinantly in a host cell using standard transfection methods. For example, in one embodiment, nucleic acid encoding the bispecific construct can be ligated into an expression vector, such as a eukaryotic expression plasmid, such as used by GS gene expression system disclosed in WO 87/04462, WO 89/01036 and EP 338 841 or other expression systems well known in the art. The purified plasmid with the cloned bispecific construct gene can be introduced in eukaryotic host cells, such as CHO-cells or NS0-cells or alternatively other eukaryotic cells like a plant derived cells, fungi or yeast cells. The method used to introduce these genes could be methods described in the art, such as electroporation, lipofectin, lipofectamine or other. After introducing the expression vector in the host cells, cells expressing the bispecific construct can be identified and selected. These cells represent the transfectomas that can then be amplified for their expression level and upscaled to produce bispecific constructs. Alternatively these cloned bispecific constructs can be expressed in other expression systems, such as *E. coli* or in complete organisms or can be synthetically expressed. Recombinant bispecific constructs can be isolated and purified from these culture supernatants and/or cells.

A bispecific construct of the invention, whether prepared by chemical conjugation or by genetic engineering, can be isolated and purified using one or more methodologies for protein purification well established in the art. Preferred methods for isolation and purification include, but are not limited to, gel filtration chromatography, affinity chromatography, anion-exchange chromatography and the like. A particularly preferred method is gel filtration chromatography, e.g., using a Superdex 200 column. Isolated and purified bispecific constructs can be evaluated using standard methods such as SDS-PAGE analysis.

Accordingly, in one embodiment, the anti-PD-L1 binding domain and the anti-CD27 binding domain are genetically fused. In another embodiment, the anti-PD-L1 binding domain and the anti-CD27 binding domain are chemically conjugated. In one embodiment, the anti-PD-L1 binding domain further comprises a human IgG1 constant domain. In another embodiment, the anti-CD27 binding domain is linked to the C-terminus of the heavy chain of the anti-PD-L1 binding domain. In another embodiment, the anti-CD27 binding domain is a scFv. In another embodiment, the anti-CD27 binding domain further comprises a human IgG1 constant domain. In another embodiment, the anti-PD-L1 binding domain is linked to the C-terminus of the heavy chain of the anti-CD27 binding domain. In another embodiment, the anti-PD-L1 binding domain is a scFv.

Exemplary bispecific constructs are set forth below in Tables 1-2, wherein the binding domains are defined by CDR sequences (Table 1) or variable region sequences (Table 2).

TABLE 1

Exemplary Bispecific Constructs (CDRs)

| Bispecific Construct | CD27 Heavy Chain Variable CDRs | CD27 Light Chain Variable CDRs | PD-L1 Heavy Chain Variable CDRs | PD-L1 Light Chain Variable CDRs |
| --- | --- | --- | --- | --- |
| 2B3x7H7 | CDR1: SEQ ID NO: 7 CDR2: SEQ ID NO: 8 CDR3: SEQ ID NO: 9 | CDR1: SEQ ID NO: 10 CDR2: SEQ ID NO: 11 CDR3: SEQ ID NO: 12 | CDR1: SEQ ID NO: 29 CDR2: SEQ ID NO: 30 CDR3: SEQ ID NO: 31 | CDR1: SEQ ID NO: 32 CDR2: SEQ ID NO: 33 CDR3: SEQ ID NO: 34 |

TABLE 1-continued

Exemplary Bispecific Constructs (CDRs)

| Bispecific Construct | CD27 Heavy Chain Variable CDRs | CD27 Light Chain Variable CDRs | PD-L1 Heavy Chain Variable CDRs | PD-L1 Light Chain Variable CDRs |
|---|---|---|---|---|
| 2B3x1B3 | CDR1: SEQ ID NO: 7<br>CDR2: SEQ ID NO: 8<br>CDR3: SEQ ID NO: 9 | CDR1: SEQ ID NO: 10<br>CDR2: SEQ ID NO: 11<br>CDR3: SEQ ID NO: 12 | CDR1: SEQ ID NO: 35<br>CDR2: SEQ ID NO: 36<br>CDR3: SEQ ID NO: 37 | CDR1: SEQ ID NO: 38<br>CDR2: SEQ ID NO: 39<br>CDR3: SEQ ID NO: 40 |
| 2B3x3B6 | CDR1: SEQ ID NO: 7<br>CDR2: SEQ ID NO: 8<br>CDR3: SEQ ID NO: 9 | CDR1: SEQ ID NO: 10<br>CDR2: SEQ ID NO: 11<br>CDR3: SEQ ID NO: 12 | CDR1: SEQ ID NO: 41<br>CDR2: SEQ ID NO: 42<br>CDR3: SEQ ID NO: 43 | CDR1: SEQ ID NO: 44<br>CDR2: SEQ ID NO: 45<br>CDR3: SEQ ID NO: 46 |
| 2B3x8B1 | CDR1: SEQ ID NO: 7<br>CDR2: SEQ ID NO: 8<br>CDR3: SEQ ID NO: 9 | CDR1: SEQ ID NO: 10<br>CDR2: SEQ ID NO: 11<br>CDR3: SEQ ID NO: 12 | CDR1: SEQ ID NO: 47<br>CDR2: SEQ ID NO: 48<br>CDR3: SEQ ID NO: 49 | CDR1: SEQ ID NO: 50<br>CDR2: SEQ ID NO: 51<br>CDR3: SEQ ID NO: 52 |
| 2B3x4A3 | CDR1: SEQ ID NO: 7<br>CDR2: SEQ ID NO: 8<br>CDR3: SEQ ID NO: 9 | CDR1: SEQ ID NO: 10<br>CDR2: SEQ ID NO: 11<br>CDR3: SEQ ID NO: 12 | CDR1: SEQ ID NO: 53<br>CDR2: SEQ ID NO: 54<br>CDR3: SEQ ID NO: 55 | CDR1: SEQ ID NO: 56<br>CDR2: SEQ ID NO: 57<br>CDR3: SEQ ID NO: 58 |
| 2B3x9H9 | CDR1: SEQ ID NO: 7<br>CDR2: SEQ ID NO: 8<br>CDR3: SEQ ID NO: 9 | CDR1: SEQ ID NO: 10<br>CDR2: SEQ ID NO: 11<br>CDR3: SEQ ID NO: 12 | CDR1: SEQ ID NO: 59<br>CDR2: SEQ ID NO: 60<br>CDR3: SEQ ID NO: 61 | CDR1: SEQ ID NO: 62<br>CDR2: SEQ ID NO: 63<br>CDR3: SEQ ID NO: 64 |
| 3C2x7H7 | CDR1: SEQ ID NO: 1<br>CDR2: SEQ ID NO: 2<br>CDR3: SEQ ID NO: 3 | CDR1: SEQ ID NO: 4<br>CDR2: SEQ ID NO: 5<br>CDR3: SEQ ID NO: 6 | CDR1: SEQ ID NO: 29<br>CDR2: SEQ ID NO: 30<br>CDR3: SEQ ID NO: 31 | CDR1: SEQ ID NO: 32<br>CDR2: SEQ ID NO: 33<br>CDR3: SEQ ID NO: 34 |
| 3C2x1B3 | CDR1: SEQ ID NO: 1<br>CDR2: SEQ ID NO: 2<br>CDR3: SEQ ID NO: 3 | CDR1: SEQ ID NO: 4<br>CDR2: SEQ ID NO: 5<br>CDR3: SEQ ID NO: 6 | CDR1: SEQ ID NO: 35<br>CDR2: SEQ ID NO: 36<br>CDR3: SEQ ID NO: 37 | CDR1: SEQ ID NO: 38<br>CDR2: SEQ ID NO: 39<br>CDR3: SEQ ID NO: 40 |
| 3C2x3B6 | CDR1: SEQ ID NO: 1<br>CDR2: SEQ ID NO: 2<br>CDR3: SEQ ID NO: 3 | CDR1: SEQ ID NO: 4<br>CDR2: SEQ ID NO: 5<br>CDR3: SEQ ID NO: 6 | CDR1: SEQ ID NO: 41<br>CDR2: SEQ ID NO: 42<br>CDR3: SEQ ID NO: 43 | CDR1: SEQ ID NO: 44<br>CDR2: SEQ ID NO: 45<br>CDR3: SEQ ID NO: 46 |
| 3C2x8B1 | CDR1: SEQ ID NO: 1<br>CDR2: SEQ ID NO: 2<br>CDR3: SEQ ID NO: 3 | CDR1: SEQ ID NO: 4<br>CDR2: SEQ ID NO: 5<br>CDR3: SEQ ID NO: 6 | CDR1: SEQ ID NO: 47<br>CDR2: SEQ ID NO: 48<br>CDR3: SEQ ID NO: 49 | CDR1: SEQ ID NO: 50<br>CDR2: SEQ ID NO: 51<br>CDR3: SEQ ID NO: 52 |
| 3C2x4A3 | CDR1: SEQ ID NO: 1<br>CDR2: SEQ ID NO: 2<br>CDR3: SEQ ID NO: 3 | CDR1: SEQ ID NO: 4<br>CDR2: SEQ ID NO: 5<br>CDR3: SEQ ID NO: 6 | CDR1: SEQ ID NO: 53<br>CDR2: SEQ ID NO: 54<br>CDR3: SEQ ID NO: 55 | CDR1: SEQ ID NO: 56<br>CDR2: SEQ ID NO: 57<br>CDR3: SEQ ID NO: 58 |
| 3C2x9H9 | CDR1: SEQ ID NO: 1<br>CDR2: SEQ ID NO: 2<br>CDR3: SEQ ID NO: 3 | CDR1: SEQ ID NO: 4<br>CDR2: SEQ ID NO: 5<br>CDR3: SEQ ID NO: 6 | CDR1: SEQ ID NO: 59<br>CDR2: SEQ ID NO: 60<br>CDR3: SEQ ID NO: 61 | CDR1: SEQ ID NO: 62<br>CDR2: SEQ ID NO: 63<br>CDR3: SEQ ID NO: 64 |

TABLE 2

Exemplary Bispecific Constructs (VRs)

| Bispecific Constructs | CD27 Heavy Chain Variable Region | CD27 Light Chain Variable Region | PD-L1 Heavy Chain Variable Region | PD-L1 Light Chain Variable Region |
|---|---|---|---|---|
| 2B3x7H7 | SEQ ID NO: 19 | SEQ ID NO: 20 | SEQ ID NO: 77 | SEQ ID NO: 78 |
| 2B3x1B3 | SEQ ID NO: 19 | SEQ ID NO: 20 | SEQ ID NO: 79 | SEQ ID NO: 80 |
| 2B3x3B6 | SEQ ID NO: 19 | SEQ ID NO: 20 | SEQ ID NO: 81 | SEQ ID NO: 82 |
| 2B3x8B1 | SEQ ID NO: 19 | SEQ ID NO: 20 | SEQ ID NO: 83 | SEQ ID NO: 84 |
| 2B3x4A3 | SEQ ID NO: 19 | SEQ ID NO: 20 | SEQ ID NO: 85 | SEQ ID NO: 86 |
| 2B3x9H9 | SEQ ID NO: 19 | SEQ ID NO: 20 | SEQ ID NO: 87 | SEQ ID NO: 88 |
| 3C2x7H7 | SEQ ID NO: 17 | SEQ ID NO: 18 | SEQ ID NO: 77 | SEQ ID NO: 78 |
| 3C2x1B3 | SEQ ID NO: 17 | SEQ ID NO: 18 | SEQ ID NO: 79 | SEQ ID NO: 80 |
| 3C2x3B6 | SEQ ID NO: 17 | SEQ ID NO: 18 | SEQ ID NO: 81 | SEQ ID NO: 82 |
| 3C2x8B1 | SEQ ID NO: 17 | SEQ ID NO: 18 | SEQ ID NO: 83 | SEQ ID NO: 84 |
| 3C2x4A3 | SEQ ID NO: 17 | SEQ ID NO: 18 | SEQ ID NO: 85 | SEQ ID NO: 86 |
| 3C2x9H9 | SEQ ID NO: 17 | SEQ ID NO: 18 | SEQ ID NO: 87 | SEQ ID NO: 88 |

In one embodiment, a bispecific construct comprising an anti-CD27 binding domain linked to an anti-PD-L1 binding domain is provided, wherein:

(i) the anti-CD27 binding domain comprises:
  a. heavy chain variable region CDR1, CDR2 and CDR3 as set forth in SEQ ID NOs:1, 2, and 3, respectively, and light chain variable region CDR1, CDR2 and CDR3 as set forth in SEQ ID NOs:4, 5, and 6, respectively, or
  b. heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively; and
(ii) the anti-PD-L1 binding domain comprises:
  a. a heavy chain variable region CDR1 comprising an amino acid sequence selected from the consensus sequence: (T,S)(S,Y,H)WMS (SEQ ID NO:167);
  b. a heavy chain variable region CDR2 comprising SEQ ID NO:168;
  c. a heavy chain variable region CDR3 comprising SEQ ID NO:169;
  d. a light chain variable region CDR1 comprising SEQ ID NO:170;
  e. a light chain variable region CDR2 comprising SEQ ID NO:171; and
  f. a light chain variable region CDR3 comprising SEQ ID NO:172.

In another embodiment, a bispecific construct comprising an anti-CD27 binding domain linked to an anti-PD-L1 binding domain is provided, wherein:

(i) the anti-CD27 binding domain comprises:
  a. heavy chain variable region CDR1, CDR2 and CDR3 as set forth in SEQ ID NOs:1, 2, and 3, respectively, and light chain variable region CDR1, CDR2 and CDR3 as set forth in SEQ ID NOs:4, 5, and 6, respectively, or b. heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively; and (ii) the anti-PD-L1 binding domain comprises:

a. a heavy chain variable region comprising SEQ ID NO:77 and a light chain variable region comprising SEQ ID NO:78 or sequences at least 95% identical thereto (e.g., at least 95%, 96%, 97%, 98% or 99% identical to the aforementioned sequences);

b. a heavy chain variable region comprising SEQ ID NO:79 and a light chain variable region comprising SEQ ID NO:80 or sequences at least 95% identical thereto (e.g., at least 95%, 96%, 97%, 98% or 99% identical to the aforementioned sequences);

c. a heavy chain variable region comprising SEQ ID NO:81 and a light chain variable region comprising SEQ ID NO:82 or sequences at least 95% identical thereto (e.g., at least 95%, 96%, 97%, 98% or 99% identical to the aforementioned sequences);

d. a heavy chain variable region comprising SEQ ID NO:83 and a light chain variable region comprising SEQ ID NO:84 or sequences at least 95% identical thereto (e.g., at least 95%, 96%, 97%, 98% or 99% identical to the aforementioned sequences);

e. a heavy chain variable region comprising SEQ ID NO:85 and a light chain variable region comprising SEQ ID NO:86 or sequences at least 95% identical thereto (e.g., at least 95%, 96%, 97%, 98% or 99% identical to the aforementioned sequences); or f. a heavy chain variable region comprising SEQ ID NO:87 and a light chain variable region comprising SEQ ID NO:88 or sequences at least 95% identical thereto (e.g., at least 95%, 96%, 97%, 98% or 99% identical to the aforementioned sequences).

In another embodiment, the bispecific construct comprises (a) an anti-CD27 binding domain comprising heavy chain variable region CDR1, CDR2 and CDR3 as set forth in SEQ ID NOs:1, 2, and 3, respectively, and light chain variable region CDR1, CDR2 and CDR3 as set forth in SEQ ID NOs:4, 5, and 6, respectively and (b) an anti-PD-L1 binding domain comprising heavy chain variable region CDR1, CDR2 and CDR3 as set forth in SEQ ID NOs:29, 30, and 31, respectively, and light chain variable region CDR1, CDR2 and CDR3 as set forth in SEQ ID NOs: 32, 33, and 34, respectively.

In another embodiment, the bispecific construct comprises (a) an anti-CD27 binding domain comprising a heavy chain variable region comprising SEQ ID NO:17 and a light chain variable region comprising SEQ ID NO:18 and (b) an anti-PD-L1 binding domain comprising a heavy chain variable region comprising SEQ ID NO:77 and a light chain variable region comprising SEQ ID NO:78.

In another embodiment, the bispecific construct comprises (a) an anti-CD27 binding domain comprising heavy chain variable region CDR1, CDR2 and CDR3 as set forth in SEQ ID NOs:1, 2, and 3, respectively, and light chain variable region CDR1, CDR2 and CDR3 as set forth in SEQ ID NOs:4, 5, and 6, respectively and (b) an anti-PD-L1 binding domain comprising heavy chain variable region CDR1, CDR2 and CDR3 as set forth in SEQ ID NOs:35, 36, and 37, respectively, and light chain variable region CDR1, CDR2 and CDR3 as set forth in SEQ ID NOs: 38, 39, and 40, respectively.

In another embodiment, the bispecific construct comprises (a) an anti-CD27 binding domain comprising a heavy chain variable region comprising SEQ ID NO:17 and a light chain variable region comprising SEQ ID NO:18 and (b) an anti-PD-L1 binding domain comprising a heavy chain variable region comprising SEQ ID NO:79 and a light chain variable region comprising SEQ ID NO:80.

In another embodiment, the bispecific construct comprises (a) an anti-CD27 binding domain comprising heavy chain variable region CDR1, CDR2 and CDR3 as set forth in SEQ ID NOs:1, 2, and 3, respectively, and light chain variable region CDR1, CDR2 and CDR3 as set forth in SEQ ID NOs:4, 5, and 6, respectively and (b) an anti-PD-L1 binding domain comprising heavy chain variable region CDR1, CDR2 and CDR3 as set forth in SEQ ID NOs:41, 42, and 43, respectively, and light chain variable region CDR1, CDR2 and CDR3 as set forth in SEQ ID NOs:44, 45, and 46, respectively.

In another embodiment, the bispecific construct comprises (a) an anti-CD27 binding domain comprising a heavy chain variable region comprising SEQ ID NO:17 and a light chain variable region comprising SEQ ID NO:18 and (b) an anti-PD-L1 binding domain comprising a heavy chain variable region comprising SEQ ID NO:81 and a light chain variable region comprising SEQ ID NO:82.

In another embodiment, the bispecific construct comprises (a) an the anti-CD27 binding domain comprising heavy chain variable region CDR1, CDR2 and CDR3 as set forth in SEQ ID NOs:1, 2, and 3, respectively, and light chain variable region CDR1, CDR2 and CDR3 as set forth in SEQ ID NOs:4, 5, and 6, respectively and (b) an anti-PD-L1 binding domain comprising heavy chain variable region CDR1, CDR2 and CDR3 as set forth in SEQ ID NOs:47, 48, and 49, respectively, and light chain variable region CDR1, CDR2 and CDR3 as set forth in SEQ ID NOs:50, 51, and 52, respectively.

In another embodiment, the bispecific construct comprises (a) an anti-CD27 binding domain comprising a heavy chain variable region comprising SEQ ID NO:17 and a light chain variable region comprising SEQ ID NO:18 and (b) an anti-PD-L1 binding domain comprising a heavy chain variable region comprising SEQ ID NO:83 and a light chain variable region comprising SEQ ID NO:84.

In another embodiment, the bispecific construct comprises (a) an anti-CD27 binding domain comprising heavy chain variable region CDR1, CDR2 and CDR3 as set forth in SEQ ID NOs:1, 2, and 3, respectively, and light chain variable region CDR1, CDR2 and CDR3 as set forth in SEQ ID NOs:4, 5, and 6, respectively; and (b) an anti-PD-L1 binding domain comprising heavy chain variable region CDR1, CDR2 and CDR3 as set forth in SEQ ID NOs:53, 54, and 55, respectively, and light chain variable region CDR1, CDR2 and CDR3 as set forth in SEQ ID NOs:56, 57, and 58, respectively.

In another embodiment, the bispecific construct comprises (a) an anti-CD27 binding domain comprising a heavy chain variable region comprising SEQ ID NO:17 and a light chain variable region comprising SEQ ID NO:18 and (b) an anti-PD-L1 binding domain comprising a heavy chain variable region comprising SEQ ID NO:85 and a light chain variable region comprising SEQ ID NO:86.

In another embodiment, the bispecific construct comprises (a) an anti-CD27 binding domain comprising heavy chain variable region CDR1, CDR2 and CDR3 as set forth in SEQ ID NOs:1, 2, and 3, respectively, and light chain variable region CDR1, CDR2 and CDR3 as set forth in SEQ ID NOs:4, 5, and 6, respectively and an anti-PD-L1 binding domain comprising heavy chain variable region CDR1, CDR2 and CDR3 as set forth in SEQ ID NOs:59, 60, and 61, respectively, and light chain variable region CDR1, CDR2 and CDR3 as set forth in SEQ ID NOs: 62, 63, and 64, respectively.

In another embodiment, the bispecific construct comprises (a) an anti-CD27 binding domain comprising a heavy chain variable region comprising SEQ ID NO:17 and a light chain variable region comprising SEQ ID NO:18 and (b) an anti-PD-L1 binding domain comprising a heavy chain variable region comprising SEQ ID NO:87 and a light chain variable region comprising SEQ ID NO:88.

In another embodiment, the bispecific construct comprises (a) an anti-CD27 binding domain comprising heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively and (b) an anti-PD-L1 binding domain comprising heavy chain variable region CDR1, CDR2 and CDR3 as set forth in SEQ ID NOs:29, 30, and 31, respectively, and light chain variable region CDR1, CDR2 and CDR3 as set forth in SEQ ID NOs:32, 33, and 34, respectively.

In another embodiment, the bispecific construct comprises (a) an anti-CD27 binding domain comprising a heavy chain variable region comprising SEQ ID NO:19 and a light chain variable region comprising SEQ ID NO:20 and (b) an anti-PD-L1 binding domain comprising a heavy chain variable region comprising SEQ ID NO:77 and a light chain variable region comprising SEQ ID NO:78.

In another embodiment, the bispecific construct comprises (a) an anti-CD27 binding domain comprising heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively and an anti-PD-L1 binding domain comprising heavy chain variable region CDR1, CDR2 and CDR3 as set forth in SEQ ID NOs:35, 36, and 37, respectively, and light chain variable region CDR1, CDR2 and CDR3 as set forth in SEQ ID NOs:38, 39, and 40, respectively.

In another embodiment, the bispecific construct comprises (a) an anti-CD27 binding domain comprising a heavy chain variable region comprising SEQ ID NO:19 and a light chain variable region comprising SEQ ID NO:20 and (b) and anti-PD-L1 binding domain comprising a heavy chain variable region comprising SEQ ID NO:79 and a light chain variable region comprising SEQ ID NO:80.

In another embodiment, the bispecific construct comprises (a) an anti-CD27 binding domain comprising heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively and an anti-PD-L1 binding domain comprising heavy chain variable region CDR1, CDR2 and CDR3 as set forth in SEQ ID NOs:41, 42, and 43, respectively, and light chain variable region CDR1, CDR2 and CDR3 as set forth in SEQ ID NOs:44, 45, and 46, respectively.

In another embodiment, the bispecific construct comprises (a) an anti-CD27 binding domain comprises a heavy chain variable region comprising SEQ ID NO:19 and a light chain variable region comprising SEQ ID NO:20 and an anti-PD-L1 binding domain comprising a heavy chain variable region comprising SEQ ID NO:81 and a light chain variable region comprising SEQ ID NO:82.

In another embodiment, the bispecific construct comprises (a) an anti-CD27 binding domain comprising heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively and (b) an anti-PD-L1 binding domain comprising heavy chain variable region CDR1, CDR2 and CDR3 as set forth in SEQ ID NOs:47, 48, and 49, respectively, and light chain variable region CDR1, CDR2 and CDR3 as set forth in SEQ ID NOs:50, 51, and 52, respectively.

In another embodiment, the bispecific construct comprises (a) an anti-CD27 binding domain comprising a heavy chain variable region comprising SEQ ID NO:19 and a light chain variable region comprising SEQ ID NO:20 and (b) an anti-PD-L1 binding domain comprises a heavy chain variable region comprising SEQ ID NO:83 and a light chain variable region comprising SEQ ID NO:84.

In another embodiment, the bispecific construct comprises (a) an anti-CD27 binding domain comprising a heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively and (b) an anti-PD-L1 binding domain comprising a heavy chain variable region CDR1, CDR2 and CDR3 as set forth in SEQ ID NOs:53, 54, and 55, respectively, and light chain variable region CDR1, CDR2 and CDR3 as set forth in SEQ ID NOs:56, 57, and 58, respectively.

In another embodiment, the bispecific construct comprises (a) an anti-CD27 binding domain comprising a heavy chain variable region comprising SEQ ID NO:19 and a light chain variable region comprising SEQ ID NO:20 and (b) an anti-PD-L1 binding domain comprising a heavy chain variable region comprising SEQ ID NO:85 and a light chain variable region comprising SEQ ID NO:86.

In another embodiment, the bispecific construct comprises (a) an anti-CD27 binding domain comprising a heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively and (b) an anti-PD-L1 binding domain comprising a heavy chain variable region CDR1, CDR2 and CDR3 as set forth in SEQ ID NOs:59, 60, and 61, respectively, and light chain variable region CDR1, CDR2 and CDR3 as set forth in SEQ ID NOs:62, 63, and 64, respectively.

In another embodiment, the bispecific construct comprises (a) an anti-CD27 binding domain comprising a heavy chain variable region comprising SEQ ID NO:19 and a light chain variable region comprising SEQ ID NO:20 and (b) an anti-PD-L1 binding domain comprises a heavy chain variable region comprising SEQ ID NO:87 and a light chain variable region comprising SEQ ID NO:88.

In a particular embodiment, the bispecific construct comprises an anti-PD-L1 antibody linked to an anti-CD27 scFv, wherein:
  (i) the anti-CD27 scFv comprises:
    a. heavy chain variable region CDR1, CDR2 and CDR3 as set forth in SEQ ID NOs:1, 2, and 3, respectively, and light chain variable region CDR1, CDR2 and CDR3 as set forth in SEQ ID NOs:4, 5, and 6, respectively, or
    b. heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively; and (ii) the anti-PD-L1 antibody comprises:
  a. heavy chain variable region CDR1, CDR2 and CDR3 as set forth in SEQ ID NOs: 29, 30, and 31, respectively, and light chain variable region CDR1, CDR2 and CDR3 as set forth in SEQ ID NOs:32, 33, and 34, respectively;
  b. heavy chain variable region CDR1, CDR2 and CDR3 as set forth in SEQ ID NOs: 35, 36, and 37, respectively, and light chain variable region CDR1, CDR2 and CDR3 as set forth in SEQ ID NOs:38, 39, and 40, respectively;
  c. heavy chain variable region CDR1, CDR2 and CDR3 as set forth in SEQ ID NOs: 41, 42, and 43, respectively, and light chain variable region CDR1, CDR2 and CDR3 as set forth in SEQ ID NOs:44, 45, and 46, respectively;
  d. heavy chain variable region CDR1, CDR2 and CDR3 as set forth in SEQ ID NOs: 47, 48, and 49, respectively, and light chain variable region CDR1, CDR2 and CDR3 as set forth in SEQ ID NOs:50, 51, and 52, respectively;
  e. heavy chain variable region CDR1, CDR2 and CDR3 as set forth in SEQ ID NOs: 53, 54, and 55, respectively, and light chain variable region CDR1, CDR2 and CDR3 as set forth in SEQ ID NOs:56, 57, and 58, respectively; or
  f. heavy chain variable region CDR1, CDR2 and CDR3 as set forth in SEQ ID NOs: 59, 60, and 61, respectively, and light chain variable region CDR1, CDR2 and CDR3 as set forth in SEQ ID NOs:62, 63, and 64, respectively; and
  g. a human IgG1 constant domain.

In another particular embodiment, the bispecific construct comprises an anti-CD27 antibody linked to an anti-PD-L1 scFv, wherein:
(i) the anti-CD27 antibody comprises:
  a. heavy chain variable region CDR1, CDR2 and CDR3 as set forth in SEQ ID NOs:1, 2, and 3, respectively, and light chain variable region CDR1, CDR2 and CDR3 as set forth in SEQ ID NOs:4, 5, and 6, respectively, or
  b. heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively; and
  c. a human IgG1 constant domain; and
(ii) the anti-PD-L1 scFv comprises:
  a. heavy chain variable region CDR1, CDR2 and CDR3 as set forth in SEQ ID NOs: 29, 30, and 31, respectively, and light chain variable region CDR1, CDR2 and CDR3 as set forth in SEQ ID NOs:32, 33, and 34, respectively;
  b. heavy chain variable region CDR1, CDR2 and CDR3 as set forth in SEQ ID NOs: 35, 36, and 37, respectively, and light chain variable region CDR1, CDR2 and CDR3 as set forth in SEQ ID NOs:38, 39, and 40, respectively;
  c. heavy chain variable region CDR1, CDR2 and CDR3 as set forth in SEQ ID NOs: 41, 42, and 43, respectively, and light chain variable region CDR1, CDR2 and CDR3 as set forth in SEQ ID NOs:44, 45, and 46, respectively;
  d. heavy chain variable region CDR1, CDR2 and CDR3 as set forth in SEQ ID NOs: 47, 48, and 49, respectively, and light chain variable region CDR1, CDR2 and CDR3 as set forth in SEQ ID NOs:50, 51, and 52, respectively;
  e. heavy chain variable region CDR1, CDR2 and CDR3 as set forth in SEQ ID NOs: 53, 54, and 55, respectively, and light chain variable region CDR1, CDR2 and CDR3 as set forth in SEQ ID NOs:56, 57, and 58, respectively; or
  f. heavy chain variable region CDR1, CDR2 and CDR3 as set forth in SEQ ID NOs: 59, 60, and 61, respectively, and light chain variable region CDR1, CDR2 and CDR3 as set forth in SEQ ID NOs:62, 63, and 64, respectively.

In another embodiment, the bispecific construct comprises an anti-PD-L1 antibody linked to an anti-CD27 scFv, wherein:
(i) the anti-CD27 scFv comprises:
  a. a heavy chain variable region comprising SEQ ID NO:17 and a light chain variable region comprising SEQ ID NO:18; or
  b. a heavy chain variable region comprising SEQ ID NO:19 and a light chain variable region comprising SEQ ID NO:20; and
(ii) the anti-PD-L1 antibody comprises:
  a. a heavy chain variable region comprising SEQ ID NO:77 and a light chain variable region comprising SEQ ID NO:78;
  b. a heavy chain variable region comprising SEQ ID NO:79 and a light chain variable region comprising SEQ ID NO:80;
  c. a heavy chain variable region comprising SEQ ID NO:81 and a light chain variable region comprising SEQ ID NO:82;
  d. a heavy chain variable region comprising SEQ ID NO:83 and a light chain variable region comprising SEQ ID NO:84;
  e. a heavy chain variable region comprising SEQ ID NO:85 and a light chain variable region comprising SEQ ID NO:86; or
  f. a heavy chain variable region comprising SEQ ID NO:87 and a light chain variable region comprising SEQ ID NO:88; and
  g. a human IgG1 constant domain.

In another embodiment, the bispecific construct comprises an anti-CD27 antibody linked to an anti-PD-L1 scFv, wherein:
(i) the anti-CD27 antibody comprises:
  a. a heavy chain variable region comprising SEQ ID NO:17 and a light chain variable region comprising SEQ ID NO:18; or
  b. a heavy chain variable region comprising SEQ ID NO:19 and a light chain variable region comprising SEQ ID NO:20; and
  c. a human IgG1 constant domain; and
(ii) the anti-PD-L1 scFv comprises:
  a. a heavy chain variable region comprising SEQ ID NO:77 and a light chain variable region comprising SEQ ID NO:78;
  b. a heavy chain variable region comprising SEQ ID NO:79 and a light chain variable region comprising SEQ ID NO:80;
  c. a heavy chain variable region comprising SEQ ID NO:81 and a light chain variable region comprising SEQ ID NO:82;

d. a heavy chain variable region comprising SEQ ID NO:83 and a light chain variable region comprising SEQ ID NO:84;
e. a heavy chain variable region comprising SEQ ID NO:85 and a light chain variable region comprising SEQ ID NO:86; or
f. a heavy chain variable region comprising SEQ ID NO:87 and a light chain variable region comprising SEQ ID NO:88.

In another embodiment, the bispecific construct comprises an anti-PD-L1 antibody linked to an anti-CD27 scFv, wherein:
(i) the anti-CD27 scFv comprises heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and
12, respectively; and
(ii) the anti-PD-L1 antibody comprises a heavy chain variable region CDR1, CDR2 and CDR3 as set forth in SEQ ID NOs: 47, 48, and 49, respectively, and light chain variable region CDR1, CDR2 and CDR3 as set forth in SEQ ID NOs:50, 51, and 52, respectively, and a human IgG1 constant domain.

In another embodiment, the bispecific construct comprises an anti-CD27 antibody linked to an anti-PD-L1 scFv, wherein:
(i) the anti-CD27 antibody comprises heavy chain variable region CDR1, CDR2 and
CDR3 as set forth in SEQ ID NOs:7, 8, and 9, respectively, and light chain variable region CDR1, CDR2 and CDR3 as set forth in SEQ ID NOs:10, 11, and
12, respectively, and a human IgG1 constant domain; and
(ii) the anti-PD-L1 scFv comprises a heavy chain variable region CDR1, CDR2 and
CDR3 as set forth in SEQ ID NOs: 47, 48, and 49, respectively, and light chain
variable region CDR1, CDR2 and CDR3 as set forth in SEQ ID NOs:50, 51, and
52, respectively.

In another embodiment, the bispecific construct comprises an anti-PD-L1 antibody linked to an anti-CD27 scFv, wherein:
(i) the anti-CD27 scFv comprises a heavy chain variable region comprising SEQ ID NO:19, a light chain variable region comprising SEQ ID NO:20; and
(ii) the anti-PD-L1 antibody comprises a heavy chain variable region comprising SEQ ID NO:83 and a light chain variable region comprising SEQ ID NO:84, and a human IgG1 constant domain.

In another embodiment, the bispecific construct comprises an anti-CD27 antibody linked to an anti-PD-L1 scFv, wherein:
(i) the anti-CD27 antibody comprises a heavy chain variable region comprising SEQ
ID NO:19, a light chain variable region comprising SEQ ID NO:20, and a human
IgG1 constant domain; and
(ii) the anti-PD-L1 scFv comprises a heavy chain variable region comprising SEQ ID
NO:83 and a light chain variable region comprising SEQ ID NO:84.

In another embodiment, the bispecific construct comprises an anti-PD-L1 antibody linked to an anti-CD27 scFv, wherein:
(i) the anti-CD27 scFv comprises heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and
12, respectively; and
(ii) the anti-PD-L1 antibody comprises heavy chain variable region CDR1, CDR2 and
CDR3 as set forth in SEQ ID NOs:59, 60, and 61, respectively, and light chain variable region CDR1, CDR2 and CDR3 as set forth in SEQ ID NOs:62, 63, and 64, respectively, and a human IgG1 constant domain.

In another embodiment, the bispecific construct comprises an anti-CD27 antibody linked to an anti-PD-L1 scFv, wherein:
(i) the anti-CD27 antibody comprises heavy chain variable region CDR1, CDR2 and
CDR3 as set forth in SEQ ID NOs:7, 8, and 9, respectively, and light chain variable region CDR1, CDR2 and CDR3 as set forth in SEQ ID NOs:10, 11, and
12, respectively, and a human IgG1 constant domain; and
(ii) the anti-PD-L1 scFv comprises heavy chain variable region CDR1, CDR2 and CDR3 as set forth in SEQ ID NOs:59, 60, and 61, respectively, and light chain variable region CDR1, CDR2 and CDR3 as set forth in SEQ ID NOs:62, 63, and 64, respectively.

In another embodiment, the bispecific construct comprises an anti-PD-L1 antibody linked to an anti-CD27 scFv, wherein:
(i) the anti-CD27 scFv comprises a heavy chain variable region comprising SEQ ID NO:19, a light chain variable region comprising SEQ ID NO:20; and
(ii) the anti-PD-L1 antibody comprises a heavy chain variable region comprising SEQ ID NO:87 and a light chain variable region comprising SEQ ID NO:88, and a human IgG1 constant domain.

In another embodiment, the bispecific construct comprises an anti-CD27 antibody linked to an anti-PD-L1 scFv, wherein:
(i) the anti-CD27 antibody comprises a heavy chain variable region comprising SEQ
ID NO:19, a light chain variable region comprising SEQ ID NO:20, and a human IgG1 constant domain; and
(ii) the anti-PD-L1 scFv comprises a heavy chain variable region comprising SEQ ID
NO:87 and a light chain variable region comprising SEQ ID NO:88.

In another aspect, the bispecific construct is provided, wherein the bispecific construct comprises any one of the anti-CD27 antibodies, or antigen binding fragments thereof, described herein linked to an anti-PD-L1 binding domain. In one embodiment, the anti-PD-L1 binding domain is selected from the group consisting of:
a. an anti-PD-L1 antibody, or antigen binding fragment thereof, comprising heavy chain variable region CDR1, CDR2 and CDR3 as set forth in SEQ ID NOs: 29, 30, and 31, respectively, and light chain variable region CDR1, CDR2 and CDR3 as set forth in SEQ ID NOs:32, 33, and 34, respectively;
b. an anti-PD-L1 antibody, or antigen binding fragment thereof, comprising heavy chain variable region CDR1, CDR2 and CDR3 as set forth in SEQ ID NOs: 35, 36, and 37, respectively, and light chain variable region CDR1, CDR2 and CDR3 as set forth in SEQ ID NOs:38, 39, and 40, respectively;

c. an anti-PD-L1 antibody, or antigen binding fragment thereof, comprising heavy chain variable region CDR1, CDR2 and CDR3 as set forth in SEQ ID NOs: 41, 42, and 43, respectively, and light chain variable region CDR1, CDR2 and CDR3 as set forth in SEQ ID NOs:44, 45, and 46, respectively;

d. an anti-PD-L1 antibody, or antigen binding fragment thereof, comprising heavy chain variable region CDR1, CDR2 and CDR3 as set forth in SEQ ID NOs: 47, 48, and 49, respectively, and light chain variable region CDR1, CDR2 and CDR3 as set forth in SEQ ID NOs:50, 51, and 52, respectively;

e. anti-PD-L1 antibody, or antigen binding fragment thereof, comprising heavy chain variable region CDR1, CDR2 and CDR3 as set forth in SEQ ID NOs: 53, 54, and 55, respectively, and light chain variable region CDR1, CDR2 and CDR3 as set forth in SEQ ID NOs:56, 57, and 58, respectively; and f. anti-PD-L1 antibody, or antigen binding fragment thereof, comprising heavy chain variable region CDR1, CDR2 and CDR3 as set forth in SEQ ID NOs: 59, 60, and 61, respectively, and light chain variable region CDR1, CDR2 and CDR3 as set forth in SEQ ID NOs:62, 63, and 64, respectively.

In another embodiment, the anti-PD-L1 binding domain is selected from the group consisting of: (a) a heavy chain variable region comprising SEQ ID NO:77 and a light chain variable region comprising SEQ ID NO:78; (b) a heavy chain variable region comprising SEQ ID NO:79 and a light chain variable region comprising SEQ ID NO:80; (c) a heavy chain variable region comprising SEQ ID NO:81 and a light chain variable region comprising SEQ ID NO:82; (d) a heavy chain variable region comprising SEQ ID NO:83 and a light chain variable region comprising SEQ ID NO:84; (e) a heavy chain variable region comprising SEQ ID NO:85 and a light chain variable region comprising SEQ ID NO:86; and (f) a heavy chain variable region comprising SEQ ID NO:87 and a light chain variable region comprising SEQ ID NO:88. In a particular embodiment, the anti-PD-L1 binding domain further comprises a human IgG1 constant domain. In another embodiment, the anti-PD-L1 binding domain is an scFv.

In another aspect, a bispecific construct is provided, wherein the bispecific construct comprises any one of the anti-PD-L1 antibodies, or antigen binding fragments thereof, described herein, linked to an anti-CD27 binding domain. In one embodiment, the anti-C27 binding domain comprises an anti-CD27 antibody comprising heavy chain variable region CDR1, CDR2 and CDR3 as set forth in SEQ ID NOs:1, 2, and 3, respectively, and light chain variable region CDR1, CDR2 and CDR3 as set forth in SEQ ID NOs:4, 5, and 6, respectively. In another embodiment, the anti-CD27 binding domain comprises an antibody comprising a heavy chain variable region comprising SEQ ID NO:17 and a light chain variable region comprising SEQ ID NO:18, or sequences at least 90% identical thereto (e.g., at least 90%, 91%, 92%, 93%, 94%, 95%, 96%, 97%, 98% or 99% identical to the aforementioned sequences). In another embodiment, the anti-C27 binding domain comprises an anti-CD27 antibody comprising heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively. In another embodiment, the anti-C27 binding domain comprises an anti-CD27 antibody comprising a heavy chain variable region comprising SEQ ID NO:19 and a light chain variable region comprising SEQ ID NO:20, or sequences at least 90% identical thereto (e.g., at least 90%, 91%, 92%, 93%, 94%, 95%, 96%, 97%, 98% or 99% identical to the aforementioned sequences). In one embodiment, the anti-CD27 binding domain is an scFv. In another embodiment, the anti-CD27 binding domain further comprises a human IgG1 constant domain.

In another embodiment, the bispecific construct has one or more of the following functional features: induces NFκB activation, increases T cell proliferation, induces a CD8 T cell response, and/or increases IL-2 production. In another embodiment, the bispecific construct increases IL-2 production by at least about 1.5-fold (e.g., at least 2-fold, 2.5 fold, 3-fold, 3.5 fold, or 4-fold) compared to an anti-CD27 monoclonal antibody or anti-PD-L1 monoclonal antibody alone. In another embodiment, the bispecific construct induces a CD8 T cell response by at least about 2-fold greater (e.g., at least 2-fold, 2.5 fold, 3-fold, 3.5 fold, 4-fold, 4.5-fold, 5-fold, 5.5-fold, 6-fold, 6.5-fold, 7-fold, 7.5-fold, 8.0-fold, 8.5-fold, or 9-fold) than an anti-CD27 monoclonal antibody alone. In another embodiment, the bispecific construct increases survival by at least about 1.5-fold longer (e.g., at least 1.5-fold, 2.0-fold, 2.5 fold, 3-fold, 3.5 fold, 4-fold, 4.5-fold, or 5-fold) compared to an anti-CD27 monoclonal antibody or anti-PD-L1 monoclonal antibody alone. In another embodiment, the bispecific construct decreases tumor weight by at least about 1.5-fold (e.g., at least 1.5-fold, 2.0-fold, 2.5 fold, 3-fold, 3.5 fold, 4-fold, 4.5-fold, or 5-fold) compared to anti-CD27 monoclonal antibodies or anti-PD-L1 monoclonal antibodies alone or in combination. In another embodiment, the bispecific construct increases T cell production by at least about 1.5-fold (e.g., at least 1.5-fold, 2.0-fold, 2.5 fold, 3-fold, 3.5 fold, 4-fold, 4.5-fold, 5-fold, 5.5-fold, 6-fold, 6.5-fold, 7-fold, 7.5-fold, 8.0-fold, 8.5-fold, or 9-fold) compared to anti-CD27 monoclonal antibodies or anti-PD-L1 monoclonal antibodies alone or in combination.

In certain embodiments, the bispecific constructs described herein exhibit synergistic effects (e.g., in enhancing immune responses in vivo) as compared to use of anti-CD27 binding domains and anti-PD-L1 binding domains in combination (i.e., co-administration of unlinked antibodies).

E. Compositions

Also provided herein are compositions, e.g., a composition comprising one or a combination of any of the binding domains, antibodies, or antigen binding fragments thereof, the bispecific constructs, or the multispecific constructs described herein, formulated together with a carrier (e.g., a pharmaceutically acceptable carrier).

As used herein, the terms "carrier" and "pharmaceutically acceptable carrier" includes any and all solvents, salts, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound (i.e., any of the binding domains, antibodies, or antigen binding fragments thereof, the bispecific constructs, or the multispecific constructs described herein), may be coated in a material to protect the compound from the action of acids and other natural conditions that may inactivate the compound.

Examples of adjuvants which may be used with the binding domains, antibodies, or antigen binding fragments thereof, the bispecific constructs, or the multispecific constructs described here include, but are not limited to: Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatised polysaccharides; polyphosphazenes; biodegradable microspheres; cytokines, such as GM-CSF, interleukin-2, -7, -12, and other like factors; 3D-MPL; CpG oligonucleotide; and monophosphoryl lipid A, for example 3-de-O-acylated monophosphoryl lipid A.

MPL adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996.

Further alternative adjuvants include, for example, saponins, such as Quil A™ adjuvant, or derivatives thereof, including QS21 and QS7 (Aquila Biopharmaceuticals Inc., Framingham, Mass.); Escin; Digitonin; or Gypsophila or Chenopodium quinoa saponins; Montanide ISA 720 (Seppic, France); SAF (Chiron, Calif., United States); ISCOMS (CSL), MF-59 (Chiron); the SBAS series of adjuvants (e.g., SBAS-2 or SBAS-4, available from SmithKline Beecham, Rixensart, Belgium); Detox (Enhanzyn™) (Corixa, Hamilton, Mont.); RC-529 (Corixa, Hamilton, Mont.) and other aminoalkyl glucosaminide 4-phosphates (AGPs); polyoxyethylene ether adjuvants such as those described in WO 99/52549A1; synthetic imidazoquinolines such as imiquimod [S-26308, R-837], (Harrison, et al., Vaccine 19: 1820-1826, 2001; and resiquimod [S-28463, R-848] (Vasilakos, et al., Cellular immunology 204: 64-74, 2000; Schiff bases of carbonyls and amines that are constitutively expressed on antigen presenting cell and T-cell surfaces, such as tucaresol (Rhodes, J. et al., Nature 377: 71-75, 1995); cytokine, chemokine and co-stimulatory molecules as either protein or peptide, including for example pro-inflammatory cytokines such as Interferon, GM-CSF, IL-1 alpha, IL-1 beta, TGF-alpha and TGF-beta, Th1 inducers such as interferon gamma, IL-2, IL-12, IL-15, IL-18 and IL-21, Th2 inducers such as IL-4, IL-5, IL-6, IL-10 and IL-13 and other chemokine and co-stimulatory genes such as MCP-1, MIP-1 alpha, MIP-1 beta, RANTES, TCA-3, CD80, CD86 and CD40L; immunostimulatory agents targeting ligands such as CTLA-4 and L-selectin, apoptosis stimulating proteins and peptides such as Fas; synthetic lipid based adjuvants, such as vaxfectin, (Reyes et al., *Vaccine* 19: 3778-3786, 2001) squalene, alpha-tocopherol, polysorbate 80, DOPC and cholesterol; endotoxin, [LPS], (Beutler, B., *Current Opinion in Microbiology* 3: 23-30, 2000); ligands that trigger Toll receptors to produce Th1-inducing cytokines, such as synthetic Mycobacterial lipoproteins, Mycobacterial protein p19, peptidoglycan, teichoic acid and lipid A; and CT (cholera toxin, subunits A and B) and LT (heat labile enterotoxin from *E. coli*, subunits A and B), heat shock protein family (HSPs), and LLO (listeriolysin O; WO 01/72329). These and various further Toll-like Receptor (TLR) agonists are described for example in Kanzler et al, *Nature Medicine*, May 2007, Vol 13, No 5.

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Acceptable diluents include saline and aqueous buffer solutions. Liposomes include water-in-oil-in-water CGF emulsions as well as conventional liposomes (Strejan et al. (1984) *J. Neuroimmunol.* 7:27).

Carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the antibodies of the invention may be administered once or twice weekly by subcutaneous or intramuscular injection or once or twice monthly by subcutaneous or intramuscular injection.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

When the compounds of the present invention are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient that is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound that is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties that are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134), different species of which may comprise the formulations of the inventions, as well as components of the invented molecules; p120 (Schreier et al. (1994) J. Biol. Chem. 269: 9090); see also K. Keinanen; M. L. Laukkanen (1994) FEBS Lett. 346:123; J. J. Killion; I. J. Fidler (1994) Immunomethods 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

The ability of a compound to inhibit cancer can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

F. Nucleic Acids

The term "nucleic acid molecule," as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding binding domains, antibodies, or antibody portions (e.g., $V_H$, $V_L$, CDR3) that bind to CD27 and/or PD-L1, is intended to refer to a nucleic acid molecule in which the nucleotide sequences encoding the binding domain, antibodies, or antibody portions are free of other nucleotide sequences encoding the binding domain, antibodies, or antibody portions that bind antigens other than CD27 and/or PD-L1, which other sequences may naturally flank the nucleic acid in human genomic DNA.

The nucleic acids may be present in whole cells, in a cell lysate, or in a partially purified or substantially pure form. A nucleic acid is "isolated" or "rendered substantially pure"

when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid molecules of the present invention, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially identical to or derived from native V, D, J, constant, switches and other such sequences described herein are contemplated (where "derived" indicates that a sequence is identical or modified from another sequence).

A nucleic acid is "operably linked" or "operatively linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

Isolated nucleic acid molecules encoding the binding domains, antibodies, or antigen-binding portions thereof, bispecific constructs, and multispecific constructs described herein are also provided, as well as expression vectors comprising such nucleic acids and host cells comprising such expression vectors. In another embodiment, a nucleic acid molecule coding for any of the binding domains, antibodies, or antigen-binding portions thereof, bispecific constructs, or multispecific constructs described herein is provided. In another embodiment, the nucleic acid molecule is in the form of an expression vector. In another embodiment, the nucleic acid molecule is in the form of an expression vector which expresses the binding domain, antibody, or antigen-binding portion thereof, bispecific construct, or the multispecific construct when administered to a subject in vivo.

In one embodiment, the nucleic acid molecule comprises a nucleotide sequence encoding an antibody variable region, wherein the antibody variable region comprises the amino acid sequence depicted in SEQ ID NO:17, 18, 19, 20, 77, 78, 79, 80, 81, 82, 83, 84, 85, 86, 87, 88, or an amino acid sequence at least 90% identical thereto (e.g., at least 90%, 91%, 92%, 93%, 94%, 95%, 96%, 97%, 98% or 99% identical to one or more of the aforementioned sequences). In another embodiment, the nucleic acid molecule comprises a nucleotide sequence as set forth in SEQ ID NO:25, 26, 27, 28, 101, 102, 103, 104, 105, 106, 107, 108, 109, 110, 111, 112, or a nucleotide sequence at least 90% identical thereto (e.g., at least 90%, 91%, 92%, 93%, 94%, 95%, 96%, 97%, 98% or 99% identical to one or more of the aforementioned sequences).

In another embodiment, the nucleic acid molecule comprises a nucleotide sequence encoding heavy and light chain variable regions of an antibody, wherein the heavy and light chain variable regions comprise the amino acid sequences depicted in SEQ ID NOs:17 and 18, SEQ ID NOs:19 and 20, SEQ ID NOs:77 and 78, SEQ ID NOs:79 and 80, SEQ ID NOs:81 and 82, SEQ ID NOs: 83 and 84, SEQ ID NOs:85 and 86, or SEQ ID NOs:87 and 88, respectively, or amino acids sequences at least 90% identical thereto (e.g., at least 90%, 91%, 92%, 93%, 94%, 95%, 96%, 97%, 98% or 99% identical the aforementioned sequences).

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

G. Combination Therapies

Any of the binding domains, antibodies, antigen binding fragments thereof, bispecific constructs, and/or multispecific constructs described herein, can be administered in combination with an additional therapy, i.e., combined with other agents. The term "coadministered" as used herein includes any or all of simultaneous, separate, or sequential administration of the binding domains, antibodies, antigen binding fragments thereof, bispecific constructs, or multispecific constructs described herein with adjuvants and other agents, including administration as part of a dosing regimen. For example, the combination therapy can include administering any of the binding domains, antibodies, antigen binding fragments thereof, bispecific constructs, and/or multispecific constructs described herein with at least one or more additional therapeutic agents, such as anti-inflammatory agents, DMARDs (disease-modifying anti-rheumatic drugs), immunosuppressive agents, chemotherapeutics, radiation therapy, other antibodies, cytotoxins and/or drugs, as well as adjuvants, immunostimulatory agents and/or immunosuppressive agents.

Chemotherapeutic agents suitable for coadministration with the binding domains, antibodies, antigen binding fragments thereof, bispecific constructs, and/or multispecific constructs described herein in the treatment of tumors include, for example: taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Further agents include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine) and temozolomide.

Agents that delete or inhibit immunosuppressive activities, for example, by immune cells (for example regulatory T-cells, NKT cells, macrophages, myeloid-derived suppressor cells, immature or suppressive dendritic cells) or suppressive factors produced by the tumor or host cells in the local microenvironment of the tumor (for example, TGFβ, indoleamine 2,3 dioxygenase—IDO), may also be administered with the binding domains, antibodies, antigen binding fragments thereof, bispecific constructs, and/or multispecific constructs described herein. Such agents include antibodies and small molecule drugs such as IDO inhibitors such as 1 methyl tryptophan or derivatives.

Suitable agents for coadministration with the binding domains, antibodies, antigen binding fragments thereof, bispecific constructs, and/or multispecific constructs described herein for treatment of such immune disorders include for example, immunosuppressive agents such as rapamycin, cyclosporin and FK506; anti-TNF agents such as etanercept, adalimumab and infliximab; and steroids. Examples of specific natural and synthetic steroids include, for example: aldosterone, beclomethasone, betamethasone, budesonide, cloprednol, cortisone, cortivazol, deoxycortone, desonide, desoximetasone, dexamethasone, difluorocortolone, fluclorolone, flumethasone, flunisolide, fluocinolone, fluocinonide, fluocortin butyl, fluorocortisone, fluorocortolone, fluorometholone, flurandrenolone, fluticasone, halcinonide, hydrocortisone, icomethasone, meprednisone, methylprednisolone, paramethasone, prednisolone, prednisone, tixocortol and triamcinolone.

Suitable agents for coadministration with the binding domains, antibodies, antigen binding fragments thereof, bispecific constructs, and/or multispecific constructs described herein for inducement or enhancement of an immune response include, for example, adjuvants and/or immunostimulatory agents, non-limiting examples of which have been disclosed hereinbefore. In one embodiment, the immunostimulatory agent is a TLR3 agonist, such as Poly IC.

As used herein, the term "immunostimulatory agent" includes, but is not limited to, compounds capable of stimulating antigen presenting cells (APCs), such as dendritic cells (DCs) and macrophages. For example, suitable immunostimulatory agents for use in the present invention are capable of stimulating APCs, so that the maturation process of the APCs is accelerated, the proliferation of APCs is increased, and/or the recruitment or release of co-stimulatory molecules (e.g., CD80, CD86, ICAM-1, MHC molecules and CCR7) and pro-inflammatory cytokines (e.g., IL-1β, IL-6, IL-12, IL-15, and IFN-γ) is upregulated. Suitable immunostimulatory agents are also capable of increasing T cell proliferation. Such immunostimulatory agents include, but are not be limited to, CD40 ligand; FLT 3 ligand; cytokines, such as IFN-α, IFN-β, IFN-γ and IL-2; colony-stimulating factors, such as G-CSF (granulocyte colony-stimulating factor) and GM-CSF (granulocyte-macrophage colony-stimulating factor); an anti-CTLA-4 antibody, anti-PD1 antibody, anti-41BB antibody, or anti-OX-40 antibody; LPS (endotoxin); ssRNA; dsRNA; Bacille Calmette-Guerin (BCG); Levamisole hydrochloride; and intravenous immune globulins. In one embodiment an immunostimulatory agant may be a Toll-like Receptor (TLR) agonist. For example the immunostimulatory agent may be a TLR3 agonist such as double-stranded inosine:cytosine polynucleotide (Poly I:C, for example available as Ampligen™ from Hemispherx Bipharma, PA, US or Poly IC:LC from Oncovir) or Poly A:U; a TLR4 agonist such as monophosphoryl lipid A (MPL) or RC-529 (for example as available from GSK, UK); a TLR5 agonist such as flagellin; a TLR7 or TLR8 agonist such as an imidazoquinoline TLR7 or TLR 8 agonist, for example imiquimod (eg Aldara™) or resiquimod and related imidazoquinoline agents (for example as available from 3M Corporation); or a TLR 9 agonist such as a deoxynucleotide with unmethylated CpG motifs (so-called "CpGs", for example as available from Coley Pharmaceutical). Such immunostimulatory agents may be administered simultaneously, separately or sequentially with the binding domains, antibodies, antigen binding fragments thereof, bispecific constructs, and/or multispecific constructs described herein.

H. Uses and Methods of the Invention

Provided herein are methods of stimulating T cell activity, methods of inducing or enhancing an immune response, and methods of treating a disease or condition (e.g., cancer) by administering the bispecific constructs, multispecific constructs, antibodies, or antigen binding fragments thereof, or compositions described herein to a patient in need thereof.

As used herein, the term "T cell-mediated response" or "T cell activity" refers to any response mediated by T cells, including effector T cells (e.g., CD8$^+$ cells) and helper T cells (e.g., CD4$^+$ cells). T cell mediated responses include, for example, T cell cytotoxicity and proliferation. Stimulation of T cell activity can be evaluated using any of a number of indicators of T cell activity known in the art. For example, enhancement of interferon-gamma production by OKT3-stimulated T cells can be used as a measure of T cell activation. Stimulation of T cell activity also can be evaluated using an NFκB-driven reporter gene system in a CD27-expressing cell. Other suitable assays of T cell activation are well established in the art.

The terms "inducing an immune response" and "enhancing an immune response" are used interchangeably and refer the stimulation of an immune response (i.e., either passive or adaptive) to a particular antigen.

The terms "treat," "treating," and "treatment," as used herein, refer to therapeutic or preventative measures described herein. The methods of "treatment" employ administration to a subject, in need of such treatment, a bispecific construct, multispecific construct, antibody, antigen binding fragment thereof, or composition as described herein, for example, a subject in need of an enhanced immune response against a particular antigen or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

The term "patient" includes human and other mammalian subjects that receive either prophylactic or therapeutic treatment.

As used herein, the term "inhibits growth" (e.g., referring to cells) is intended to include any measurable decrease in the growth of a cell, e.g., the inhibition of growth of a cell by at least about 10%, 20%, 30%, 40%, 50%, 60%, 70%, 80%, 90%, 99%, or 100%.

In one aspect, methods of stimulating T cell activity are provided, which comprise contacting T cells with any one of the antibodies, or antigen binding fragments thereof, bispecific constructs, multispecific constructs, or the compositions of described herein. Stimulating T cell activity can comprise, for example, stimulating IFN-gamma production.

In another aspect, methods for inducing or enhancing an immune response (e.g., against an antigen) in a subject comprising administering to the subject any one of the antibodies, or antigen binding fragments thereof, bispecific constructs, multispecific constructs, or the compositions described herein, in an amount effective to induce or enhance an immune response in the subject (e.g., against an antigen).

In another aspect, methods of for treating a condition or disease in a subject are provided, the method comprising administering to the subject any one of the antibodies, or antigen binding fragments thereof, bispecific constructs, multispecific constructs, or the compositions described herein, in an amount effective to treat the condition or disease.

In another aspect, methods for treating a condition or disease in a subject are provided, wherein the method comprises administering to the subject any one of the anti-CD27 antibodies, or antigen binding fragments thereof, described herein in combination with any one of the anti-PD-L1 antibodies, or antigen binding fragments thereof, described herein.

For example, in one embodiment:
(i) the anti-CD27 antibody, or antigen binding fragment thereof, is selected from the group consisting of: (a) an anti-CD27 antibody, or antigen binding fragment thereof, comprising heavy chain variable region CDR1, CDR2 and CDR3 as set forth in SEQ ID NOs:1, 2, and 3, respectively, and light chain variable region CDR1, CDR2 and CDR3 as set forth in SEQ ID NOs:4, 5, and 6, respectively, and (b) an anti-CD27 antibody, or antigen binding fragment thereof, comprising heavy chain variable region CDR1, CDR2 and CDR3 as set forth in SEQ ID NOs:7, 8, and 9, respectively, and light chain variable region CDR1, CDR2 and CDR3 as set forth in SEQ ID NOs:10, 11, and 12, respectively; and
(ii) the anti-PD-L1 antibody, or antigen binding fragment thereof, is selected from the group consisting of: (a) an anti-PD-L1 antibody, or antigen binding fragment thereof, comprising heavy chain variable region CDR1, CDR2 and CDR3 as set forth in SEQ ID NOs: 29, 30, and 31, respectively, and light chain variable region CDR1, CDR2 and CDR3 as set forth in SEQ ID NOs:32, 33, and 34, respectively; (b) an anti-PD-L1 antibody, or antigen binding fragment thereof, comprising heavy chain variable region CDR1, CDR2 and CDR3 as set forth in SEQ ID NOs: 35, 36, and 37, respectively, and light chain variable region CDR1, CDR2 and CDR3 as set forth in SEQ ID NOs:38, 39, and 40, respectively; (c) an anti-PD-L1 antibody, or antigen binding fragment thereof, comprising heavy chain variable region CDR1, CDR2 and CDR3 as set forth in SEQ ID NOs: 41, 42, and 43, respectively, and light chain variable region CDR1, CDR2 and CDR3 as set forth in SEQ ID NOs:44, 45, and 46, respectively; (d) an anti-PD-L1 antibody, or antigen binding fragment thereof, comprising heavy chain variable region CDR1, CDR2 and CDR3 as set forth in SEQ ID NOs: 47, 48, and 49, respectively, and light chain variable region CDR1, CDR2 and CDR3 as set forth in SEQ ID NOs:50, 51, and 52, respectively; (e) anti-PD-L1 antibody, or antigen binding fragment thereof, comprising heavy chain variable region CDR1, CDR2 and CDR3 as set forth in SEQ ID NOs: 53, 54, and 55, respectively, and light chain variable region CDR1, CDR2 and CDR3 as set forth in SEQ ID NOs:56, 57, and 58, respectively; and (f) anti-PD-L1 antibody, or antigen binding fragment thereof, comprising heavy chain variable region CDR1, CDR2 and CDR3 as set forth in SEQ ID NOs: 59, 60, and 61, respectively, and light chain variable region CDR1, CDR2 and CDR3 as set forth in SEQ ID NOs:62, 63, and 64, respectively.

In another embodiment,
(i) the anti-CD27 antibody, or antigen binding fragment thereof, is selected from the group consisting of: (a) an anti-CD27 antibody, or antigen-binding fragment thereof, comprising a heavy chain variable region comprising SEQ ID NO:17 and a light chain variable region comprising SEQ ID NO:18 and (b) an anti-CD27 antibody, or antigen-binding fragment thereof, comprising SEQ ID NO:19 and a light chain variable region comprising SEQ ID NO:20 or sequences; and
(ii) the anti-PD-L1 antibody, or antigen binding fragment thereof, is selected from the group consisting of: (a) an anti-PD-L1 antibody, or antigen binding fragment thereof, comprising a heavy chain variable region comprising SEQ ID NO:77 and a light chain variable region comprising SEQ ID NO:78; (b) an anti-PD-L1 antibody, or antigen binding fragment thereof, comprising a heavy chain variable region comprising SEQ ID NO:79 and a light chain variable region comprising SEQ ID NO:80; (c) an anti-PD-L1 antibody, or antigen binding fragment thereof, comprising a heavy chain variable region comprising SEQ ID NO:81 and a light chain variable region comprising SEQ ID NO:82; (d) an anti-PD-L1 antibody, or antigen binding fragment thereof, comprising a heavy chain variable region comprising SEQ ID NO:83 and a light chain variable region comprising SEQ ID NO:84; (e) an anti-PD-L1 antibody, or antigen binding fragment thereof, comprising a heavy chain variable region comprising SEQ ID NO:85 and a light chain variable region comprising SEQ ID NO:86; and (f) an anti-PD-L1 antibody, or antigen binding fragment thereof, comprising a heavy chain variable region comprising SEQ ID NO:87 and a light chain variable region comprising SEQ ID NO:88.

In one embodiment, the anti-CD27 antibody, or antigen binding fragment thereof, and the anti-PD-L1 antibody, or antigen binding fragment thereof, are administered separately. In one embodiment, the anti-CD27 antibody, or antigen binding fragment thereof, and the anti-PD-L1 antibody, or antigen binding fragment thereof, are administered sequentially. For example, the anti-CD27 antibody, or antigen binding fragment thereof, can be administered first followed by (e.g., immediately followed by) administration of the anti-PD-L1 antibody, or antigen binding fragment thereof, or vice versa. In another embodiment, the anti-CD27 antibody, or antigen binding fragment thereof, and the anti-PD-L1 antibody, or antigen binding fragment thereof, are administered together. In another embodiment, the anti-CD27 antibody, or antigen binding fragment thereof, and the anti-PD-L1 antibody, or antigen binding fragment thereof, are administered simultaneously. In another embodiment, the anti-CD27 antibody, or antigen binding fragment thereof, and the anti-PD-L1 antibody, or antigen binding fragment thereof, are simultaneously administered in a single formulation. Alternatively, the anti-CD27 antibody, or antigen binding fragment thereof, and the anti-PD-L1 antibody, or antigen binding fragment thereof, are formulated for separate administration and are administered concurrently or sequentially. Such concurrent or sequential administration preferably results in both antibodies being simultaneously present in treated patients.

In certain embodiments, administration of any of the anti-CD27 antibodies, or antigen binding fragment thereof, described herein in combination with any of the anti-PD-L1 antibodies, or antigen binding fragments thereof, described herein results in synergistic effects (e.g., in enhancing immune responses in vivo) as compared to use of either antibody alone.

The subject can be, for example, one who suffers from a condition or disease in which stimulation of an immune response is desired. In one embodiment, the condition or disease is cancer. Types of cancers include, but are not limited to, leukemia, acute lymphocytic leukemia, acute myelocytic leukemia, myeloblasts promyelocyte myelomonocytic monocytic erythroleukemia, chronic leukemia, chronic myelocytic (granulocytic) leukemia, chronic lymphocytic leukemia, mantle cell lymphoma, primary central nervous system lymphoma, Burkitt's lymphoma and marginal zone B cell lymphoma, Polycythemia vera Lymphoma, Hodgkin's disease, non-Hodgkin's disease, multiple myeloma, Waldenstrom's macroglobulinemia, heavy chain disease, solid tumors, sarcomas, and carcinomas, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, esophageal carcinoma, basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), melanoma, neuroblastoma; oral cavity cancer (for example lip, tongue, mouth and pharynx), ovarian cancer, pancreatic cancer, retinoblastoma, rhabdomyosarcoma, rectal cancer; cancer of the respiratory system, sarcoma, skin cancer, stomach cancer, testicular cancer, thyroid cancer, uterine cancer, and cancer of the urinary system. Particular cancers include CD27-expressing tumors selected from the group consisting of chronic lymphocytic leukemia, mantle cell lymphoma, primary central nervous system lymphoma, Burkitt's lymphoma and marginal zone B cell lymphoma.

Other disease indications include bacterial, fungal, viral and parasitic infectious diseases.

The methods of inducing or enhancing an immune response (e.g., against an antigen) in a subject described herein can further comprise administering the antigen to the subject. As used herein, the term "antigen" refers to any natural or synthetic immunogenic substance, such as a protein, peptide, hapten, polysaccharide and/or lipid. The bispecific construct, multispecific construct, antibody, antigen binding fragment thereof, or composition described herein and antigen can be administered at the same time or, alternatively, the bispecific construct, multispecific construct, antibody, antigen binding fragment thereof, or composition can be administered before or after the antigen is administered.

In one embodiment, a bispecific construct, multispecific construct, antibody, antigen binding fragment thereof, or composition described herein is administered in combination with a vaccine, to enhance the immune response against the vaccine antigen, for example a tumor antigen (to thereby enhance the immune response against the tumor) or an antigen from an infectious disease pathogen (to thereby enhance the immune response against the infectious disease pathogen). Accordingly, in one embodiment, a vaccine antigen can comprise, for example, an antigen or antigenic composition capable of eliciting an immune response against a tumor or against an infectious disease pathogen such as a virus, a bacteria, a parasite or a fungus. The antigen or antigens be derived from tumors, such as the various tumor antigens previously disclosed herein. Alternatively, the antigen or antigens can be derived from pathogens such as viruses, bacteria, parasites and/or fungi.

Preferred antigens to be co-administered with the antibodies, or antigen binding fragments thereof, bispecific constructs, multispecific constructs, or the compositions of described herein include tumor antigens and vaccine antigens (e.g., bacterial, viral or other pathogen antigens against which protective immunity is desired to be raised in a subject for purposes of vaccination). Additional examples of suitable pathogen antigens include tumor-associated antigens (TAAs), including but not limited to, sequences comprising all or part of the sequences of EGFR, EGFRvIII, gp100 or Pme117, HER2/neu, mesothelin, CEA, MART1, MAGE-A1, MAGE-A2, MAGE-A3, MAGE-A4, MUC-1, GPNMB, HMW-MAA, TIM1, ROR1, CD19 and germ cell derived tumor antigens.

Other suitable antigens include viral antigens for the prevention or treatment of viral diseases. Examples of viral antigens include, but are not limited to, HIV-1 env, HBsAg, HPV, FAS, HSV-1, HSV-2, p17, ORF2 and ORFS antigens.

In addition, viral antigens or antigenic determinants can be derived from, for example: Cytomegalovirus (especially Human, such as gB or derivatives thereof); Epstein Barr virus (such as gp350); flaviviruses (e.g. Yellow Fever Virus, Dengue Virus, Tick-borne encephalitis virus, Japanese Encephalitis Virus); hepatitis virus such as hepatitis B virus (for example Hepatitis B Surface antigen such as the PreS1, PreS2 and S antigens described in EP-A-414 374; EP-A-0304 578, and EP-A-198474), hepatitis A virus, hepatitis C virus and hepatitis E virus; HIV-1, (such as tat, nef, gp120 or gp160); human herpes viruses, such as gD or derivatives thereof or Immediate Early protein such as ICP27 from HSV1 or HSV2; human papilloma viruses (for example HPV6, 11, 16, 18); Influenza virus (whole live or inactivated virus, split influenza virus, grown in eggs or MDCK cells, or Vero cells or whole flu virosomes (as described by Gluck, *Vaccine,* 1992, 10, 915-920) or purified or recombinant proteins thereof, such as NP, NA, HA, or M proteins); measles virus; mumps virus; parainfluenza virus; rabies virus; Respiratory Syncytial virus (such as F and G proteins); rotavirus (including live attenuated viruses); smallpox virus; Varicella Zoster Virus (such as gp1, II and 1E63); and the HPV viruses responsible for cervical cancer (for example the early proteins E6 or E7 in fusion with a protein D carrier to form Protein D-E6 or E7 fusions from HPV 16, or combinations thereof; or combinations of E6 or E7 with L2 (see for example WO 96/26277).

Examples of bacterial antigens include, but are not limited to, *Toxoplasma gondii* or *Treponema pallidum.* The bacterial antigens can be in the treatment or prevention of various bacterial diseases such as Anthrax, Botulism, Tetanus, Chlamydia, Cholera, Diphtheria, Lyme Disease, Syphilis and Tuberculosis. Bacterial antigens or antigenic determinants can be derived from, for example: *Bacillus* spp., including *B. anthracis* (e.g., botulinum toxin); *Bordetella* spp, including *B. pertussis* (for example pertactin, pertussis toxin, filamenteous hemagglutinin, adenylate cyclase, fimbriae); *Borrelia* spp., including *B. burgdorferi* (eg OspA, OspC, DbpA, DbpB), *B. garinii* (eg OspA, OspC, DbpA, DbpB), *B. afzelii* (eg OspA, OspC, DbpA, DbpB), *B. andersonii* (eg OspA, OspC, DbpA, DbpB), *B. hermsii; Campylobacter* spp, including *C. jejuni* (for example toxins, adhesins and invasins) and *C. coli; Chlamydia* spp., including *C. trachomatis* (eg MOMP, heparin-binding proteins), *C. pneumonie* (eg MOMP, heparin-binding proteins), *C. psittaci; Clostridium* spp., including *C. tetani* (such as tetanus toxin), *C. botulinum* (for example botulinum toxin), *C. difficile* (eg *clostridium* toxins A or B); *Corynebacterium* spp., including *C. diphtheriae* (eg diphtheria toxin); *Ehrlichia* spp., including *E. equi* and the agent of the Human Granulocytic Ehrlichiosis; *Rickettsia* spp, including *R. rickettsii; Enterococcus* spp., including *E. faecalis, E. faecium; Escherichia* spp, including enterotoxic *E. coli* (for example colonization factors, heat-labile toxin or derivatives thereof, or heat-stable toxin), enterohemorragic *E. coli,* enteropathogenic *E. coli* (for example shiga toxin-like toxin); *Haemophilus* spp., including *H. influenzae* type B (eg PRP), non-typable *H. influenzae,* for example OMP26, high molecular weight adhesins, P5, P6, protein D and lipoprotein D, and fimbrin and fimbrin derived peptides (see for example U.S. Pat. No. 5,843,464); *Helicobacter* spp., including *H. pylori* (for example urease, catalase, vacuolating toxin); *Pseudomonas* spp, including *P. aeruginosa; Legionella* spp, including *L. pneumophila;* Leptospira spp., including *L. interrogans; Listeria* spp., including *L. monocytogenes; Moraxella* spp., including *M. catarrhalis,* also known as *Branhamella catarrhalis* (for example high and low molecular weight adhesins and invasins); *Morexella Catarrhalis* (including outer membrane vesicles thereof, and OMP106 (see for example WO97/41731)); *Mycobacterium* spp., including *M. tuberculosis* (for example ESAT6, Antigen 85A, —B or —C), *M. bovis, M. leprae, M. avium, M. paratuberculosis, M. smegmatis; Neisseria* spp, including N. gonorrhea and *N. meningitidis* (for example capsular polysaccharides and conjugates thereof, transferrin-binding proteins, lactoferrin binding proteins, Pi1C, adhesins); *Neisseria mengitidis* B (including outer membrane vesicles thereof, and NspA (see for example WO 96/29412); *Salmonella* spp, including *S. typhi, S. paratyphi, S. choleraesuis, S. enteritidis; Shigella* spp, including *S. sonnei, S. dysenteriae, S. flexnerii; Staphylococcus* spp., including *S. aureus, S. epidermidis; Streptococcus* spp, including *S. pneumonie* (e.g., capsular polysaccharides and conjugates thereof, PsaA, PspA, streptolysin, choline-binding proteins) and the protein antigen Pneumolysin (*Biochem Biophys Acta,* 1989, 67,1007; Rubins et al., *Microbial Pathogenesis,* 25, 337-342), and mutant detoxified derivatives thereof (see for example WO 90/06951; WO 99/03884); *Treponema* spp., including *T. pallidum* (eg the outer membrane proteins), *T. denticola, T. hyodysenteriae; Vibrio* spp, including *V. cholera* (for example cholera toxin); and *Yersinia* spp, including *Y. enterocolitica* (for example a Yop protein), *Y. pestis, Y. pseudotuberculosis.*

Parasitic/fungal antigens or antigenic determinants can be derived from, for example: *Babesia* spp., including *B. microti; Candida* spp., including *C. albicans; Cryptococcus* spp., including *C. neoformans; Entamoeba* spp., including *E. histolytica;* Giardia spp., including; *G. lamblia; Leshmania* spp., including *L. major; Plasmodium. faciparum* (MSP1, AMA1, MSPS, EBA, GLURP, RAP1, RAP2, Sequestrin, PfEMP1, Pf332, LSA1, LSA3, STARP, SALSA, PfEXP1, Pfs25, Pfs28, PFS27/25, Pfs16, Pfs48/45, Pfs230 and their analogues in *Plasmodium* spp.); *Pneumocystis* spp., including *P. carinii; Schisostoma* spp., including *S. mansoni; Trichomonas* spp., including *T. vaginalis; Toxoplasma* spp., including *T. gondii* (for example SAG2, SAGS, Tg34); *Trypanosoma* spp., including *T. cruzi.*

It will be appreciated that in accordance with this aspect of the present invention antigens and antigenic determinants can be used in many different forms. For example, antigens or antigenic determinants can be present as isolated proteins or peptides (for example in so-called "subunit vaccines") or, for example, as cell-associated or virus-associated antigens or antigenic determinants (for example in either live or killed pathogen strains). Live pathogens will preferably be attenuated in known manner. Alternatively, antigens or antigenic determinants may be generated in situ in the subject by use of a polynucleotide coding for an antigen or antigenic determinant (as in so-called "DNA vaccination"), although it will be appreciated that the polynucleotides which can be used with this approach are not limited to DNA, and may also include RNA and modified polynucleotides as discussed above.

In one embodiment, a vaccine antigen can also be targeted, for example to particular cell types or to particular tissues. For example, the vaccine antigen can be targeted to Antigen Presenting Cells (APCs), for example by use of agents such as antibodies targeted to APC-surface receptors such as DEC-205, for example as discussed in WO 2009/061996 (Celldex Therapeutics, Inc), or the Mannose Receptor (CD206) for example as discussed in WO 03040169 (Medarex, Inc.).

I. Kits

Also provided are kits (e.g., diagnostic kits) comprising one or more anti-CD27 binding domains, anti-PD-L1 binding domains, bispecific constructs, multispecific constructs, or compositions as described herein, optionally with instructions for use. Kits may also include informative pamphlets, for example, pamphlets informing one how to use reagents to practice a method disclosed herein. The term "pamphlet" includes any writing, marketing materials or recorded material supplied on or with the kit, or which otherwise accompanies the kit.

The present invention is further illustrated by the following examples, which should not be construed as further limiting. The contents of figures and all references, patents and published patent applications cited throughout this application are expressly incorporated herein by reference.

V. EXAMPLES

Example 1: Generation of CD27-Specific Human Monoclonal Antibodies

Human anti-CD27 monoclonal antibodies were generated by immunizing the H2L2 strain of Harbour® transgenic mice with a soluble human CD27 antigen. Harbour® transgenic mice have had the endogenous mouse heavy chain (HC) and kappa light chain (κ-chain) DNA sequences knocked out and have had sequences for the human variable (V) regions and rat constant (C) regions stably incorporated into the mouse genome.

Antigen and Immunization: The antigen was a soluble fusion protein comprising a CD27 extracellular domain with an Fc tag (R&D Systems). The antigen was mixed with MPL™ plus TDM adjuvant system (Sigma) for immunizations. 5-25 micrograms soluble recombinant CD27 antigen in PBS were mixed 1:1 with the adjuvant. Mice were injected with 200 microliters of the prepared antigen into the peritoneal cavity every 14 days. Animals that developed anti-CD27 titers were given an i.v. injection of 5-10 micrograms soluble recombinant CD27 antigen three to four days prior to fusion. Mouse spleens were harvested, and the isolated splenocytes used for hybridoma preparation.

Hybridoma Preparation: The P3x63Ag8.653 murine myeloma cell line (ATCC CRL 1580) was used for the fusions. RPMI 1640 (Invitrogen) containing 10% FBS was used to culture the myeloma cells. Additional media supplements were added to the Hybridoma growth media, which included: up to 10% Hybridoma Enhancing Supplement (Sigma), 10% FBS (Sigma), L-glutamine (Gibco), 0.1% gentamycin (Gibco), 2-mercaptoethanol (Gibco), with HAT (Sigma; $1.0 \times 10^4$ M hypoxanthine, $4.0 \times 10^{-7}$ M aminopterin, $1.6 \times 10^{-5}$ M thymidine media).

Spleen cells were mixed with the P3x63Ag8.653 myeloma cells in a 6:1 ratio and pelleted by centrifugation. Polyethylene glycol was added dropwise with careful mixing to facilitate fusion. Hybridomas were allowed to grow out for one to two weeks until visible colonies become established. Supernatant was harvested and used for initial screening for rat IgG via ELISA using a human soluble CD27 fusion protein and a rat Fc specific detection. IgG positive supernatants were then assayed for CD27 specificity via flow cytometry. The hybridomas were also screened for cross-reactivity with cynomolgus macaque CD27 and all were positive for binding.

Hybridoma cells were expanded and cell pellets were frozen for RNA isolation and sequencing. The $V_H$ and $V_L$ coding regions of human monoclonal antibodies were identified using RNA from the corresponding hybridomas. RNA was reverse transcribed to cDNA, the V coding regions were amplified by PCR and the PCR products were sequenced, inserted into a human IgG1kappa vector, transiently expressed and purified by protein A column chromatography which led to the isolation of antibodies of particular interest, which were designated as 2B3 and 3C2.

Example 2: Assays to Determine Human Monoclonal Antibody Binding Characteristics to CD27

Figure 1:
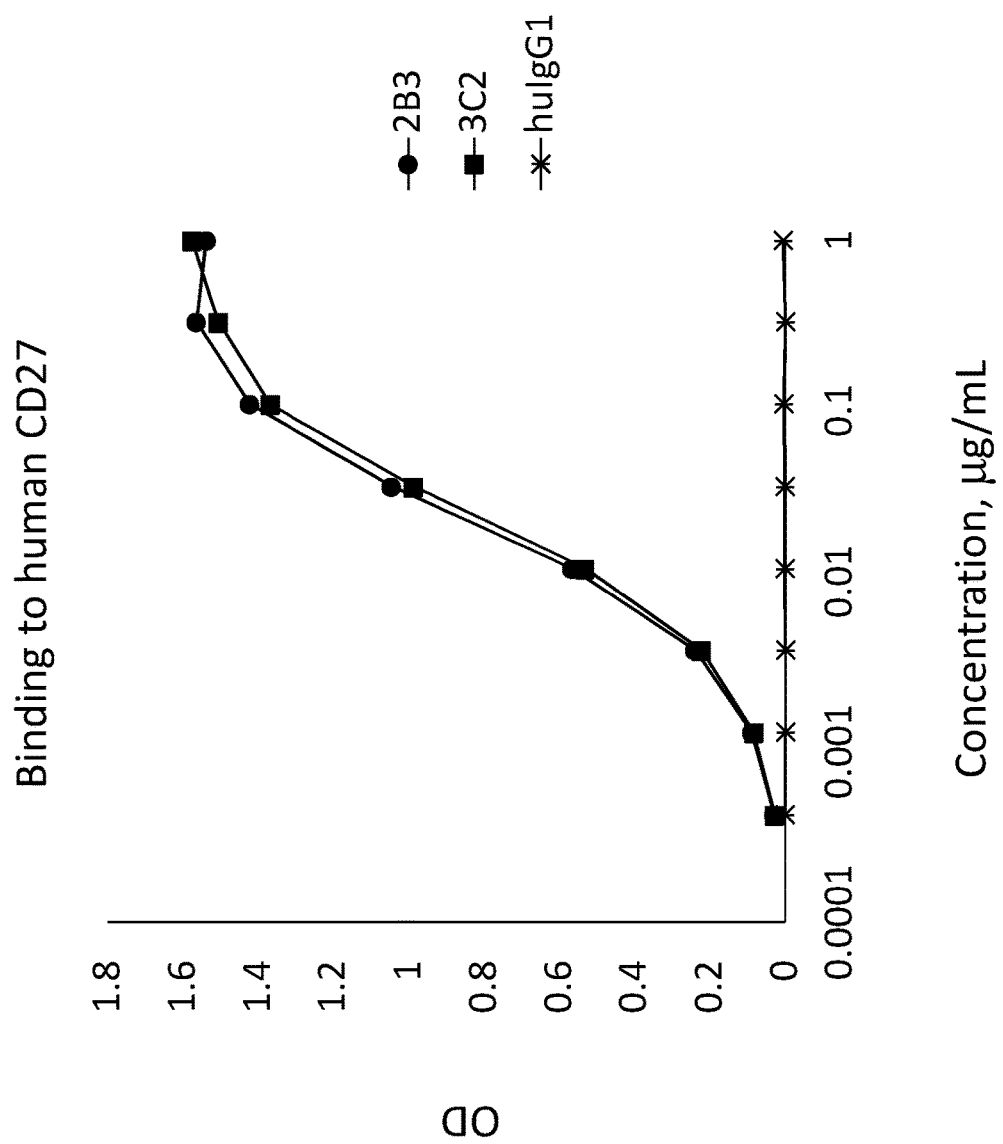
FIG. 1 is a graph showing binding of CD27 antibodies 2B3 and 3C2 to recombinant human CD27, as a function of antibody concentration.

Microtiter plates were coated with recombinant human CD27-FLAG-HIS in PBS, and then blocked with 5% bovine serum albumin in PBS. Protein A purified human monoclonal antibodies were added at various concentrations and incubated at 37° C. The plates were washed with PBS/Tween™ detergent and then incubated with a goat-anti-human IgG Fc-specific polyclonal reagent conjugated to horseradish peroxidase at 37° C. After washing, the plates were developed with HRP substrate, and analyzed at OD 450-650 nm using a microtiter plate reader. FIG. 1 shows that anti-CD27 antibodies 2B3 and 3C2 bind human CD27.

Figure 2:
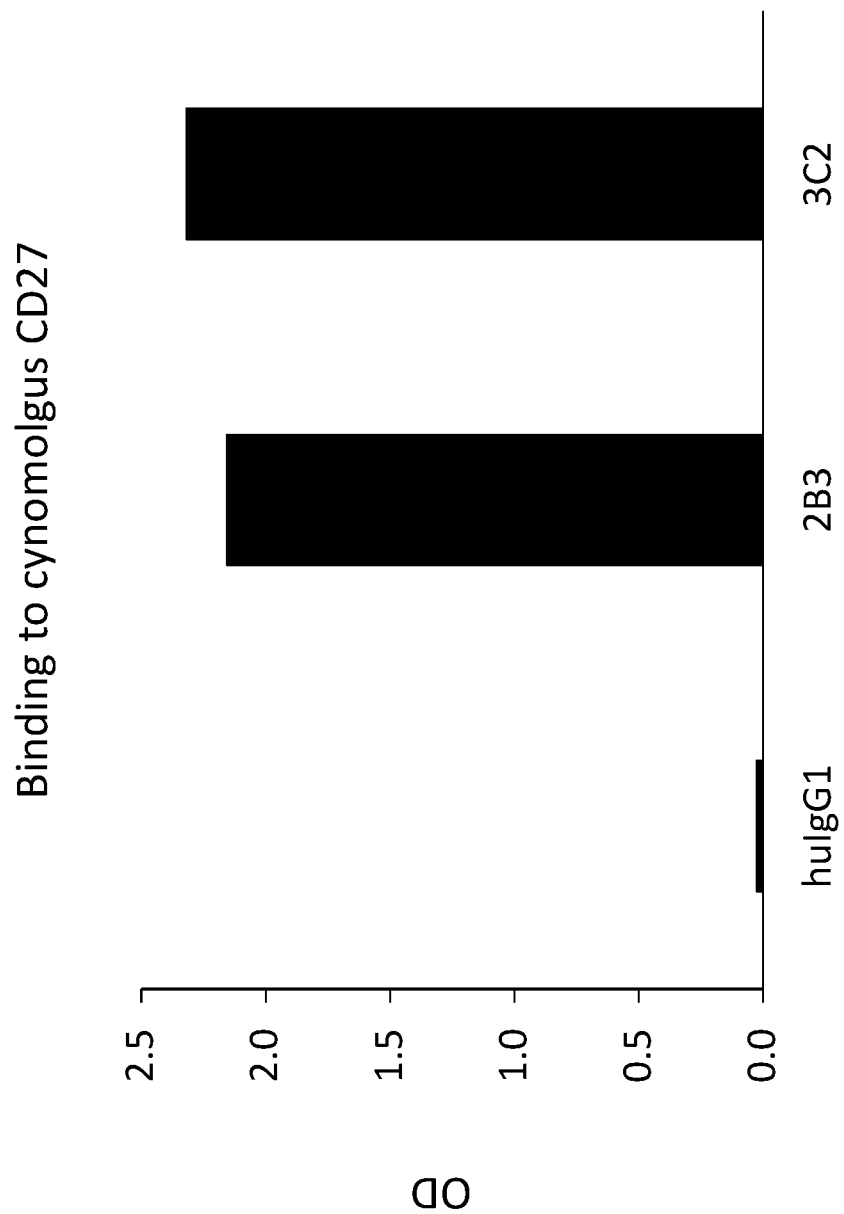
FIG. 2 is a graph showing binding of CD27 antibodies 2B3 and 3C2 to recombinant cynomolgus CD27.

To establish that cynomolgus macaques are a relevant model for testing anti-CD27 monoclonal antibodies, microtiter plates were coated with recombinant cynomolgus CD27-FLAG-HIS in PBS, and then blocked with 5% bovine serum albumin in PBS. Hybridoma supernatants or rat IgG control were added and incubated at 37° C. The plates were washed with PBS/Tween detergent and then incubated with a mouse-anti-rat IgG Fc-specific polyclonal reagent conjugated to horseradish peroxidase at 37° C. After washing, the plates were developed with HRP substrate, and analyzed at OD 450-650 nm using a microtiter plate reader. FIG. 2 shows that anti-CD27 antibodies 2B3 and 3C2 bind cynomolgus CD27.

Example 3: Binding to CD27 Cells

The ability of anti-CD27 human monoclonal antibodies to bind to CD27 on cells expressing human CD27 on their surface was investigated by flow cytometry as follows:

Antibodies were tested for binding to a human cell line expressing human CD27 on their surface. Protein A purified human monoclonal antibodies (3 μg/ml) were incubated with Ramos cells expressing human CD27 at room temperature on a plate shaker. After 20 minutes, the cells were washed with PBS containing 0.1% BSA and 0.05% $NaN_3$ (PBA) and the bound antibodies were detected by incubating the cells with a PE labeled goat anti-human IgG Fc-specific probe. The excess probe was washed from the cells with PBA and the cell associated fluorescence was determined by analysis using a FACSCanto II™ instrument (BD Biosciences, NJ, USA) according to the manufacturer's directions.

Figure 3:
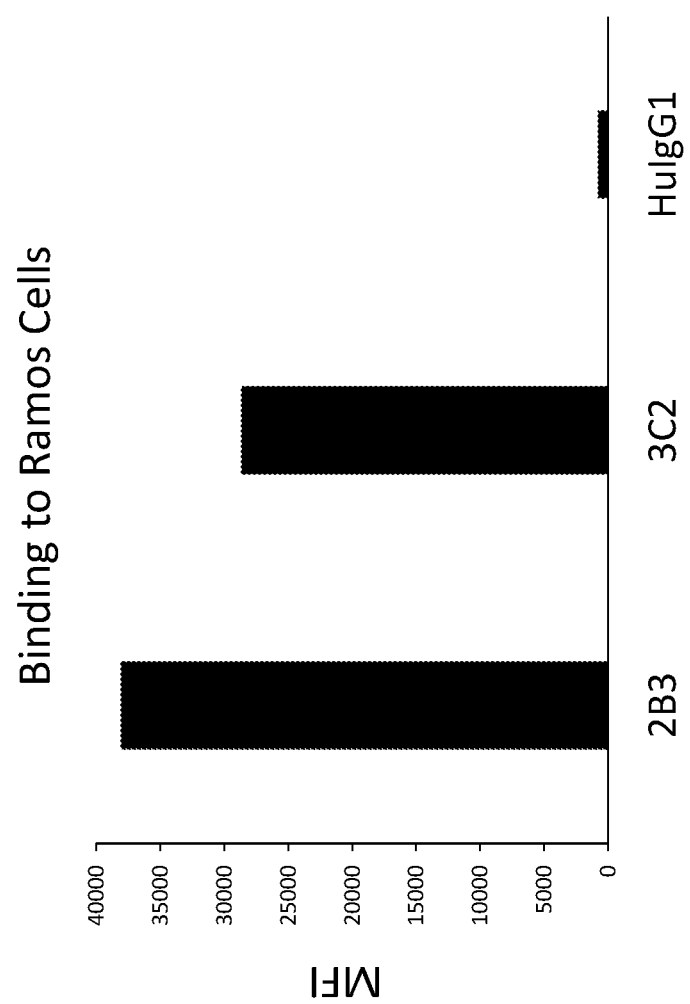
FIG. 3 is a graph showing high level binding of CD27 antibodies 2B3 and 3C2 to Ramos cells expressing CD27 on their surface.

As shown in FIG. 3, the anti-CD27 human monoclonal antibodies demonstrated high levels of binding to cells expressing human CD27.

Example 4: Binding to Human T Cells

The ability of anti-CD27 human monoclonal antibodies to bind to CD27 on human T cells was investigated by flow cytometry as follows:

Antibodies were tested for binding to human CD3$^+$ T cells which express human CD27 on their surface. Human peripheral blood mononuclear cells were isolated from buffy coats using Ficoll separation, and CD3$^+$ cells were further isolated from the PBMC's using magnetic bead separation technology from Miltenyi Biotec. Protein A purified human monoclonal antibodies (3 μg/ml) were incubated with the T cells at room temperature on a plate shaker. After 20 minutes, the cells were washed with PBS containing 0.1% BSA and 0.05% $NaN_3$ (PBA) and the bound antibodies were detected by incubating the cells with a PE labeled goat anti-human IgG Fc-specific probe. The excess probe was washed from the cells with PBA and the cell associated fluorescence was determined by analysis using a FACSCanto II™ instrument (BD Biosciences, NJ, USA) according to the manufacturer's directions.

Figure 4:
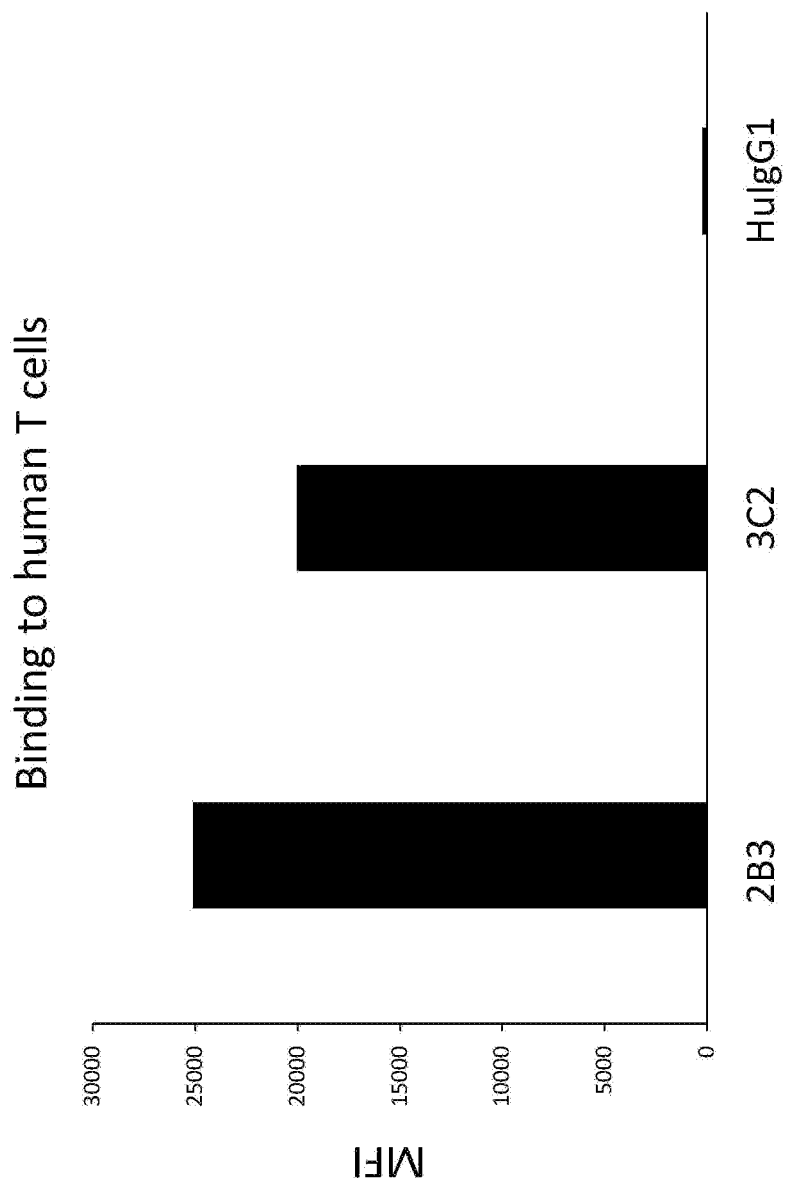
FIG. 4 is a graph showing high level binding of CD27 antibodies 2B3 and 3C2 to T cells.

As shown in FIG. 4, the anti-CD27 human monoclonal antibodies demonstrated high levels of binding to human T cells.

Example 5: Blocking of CD70 Binding

Figure 5:
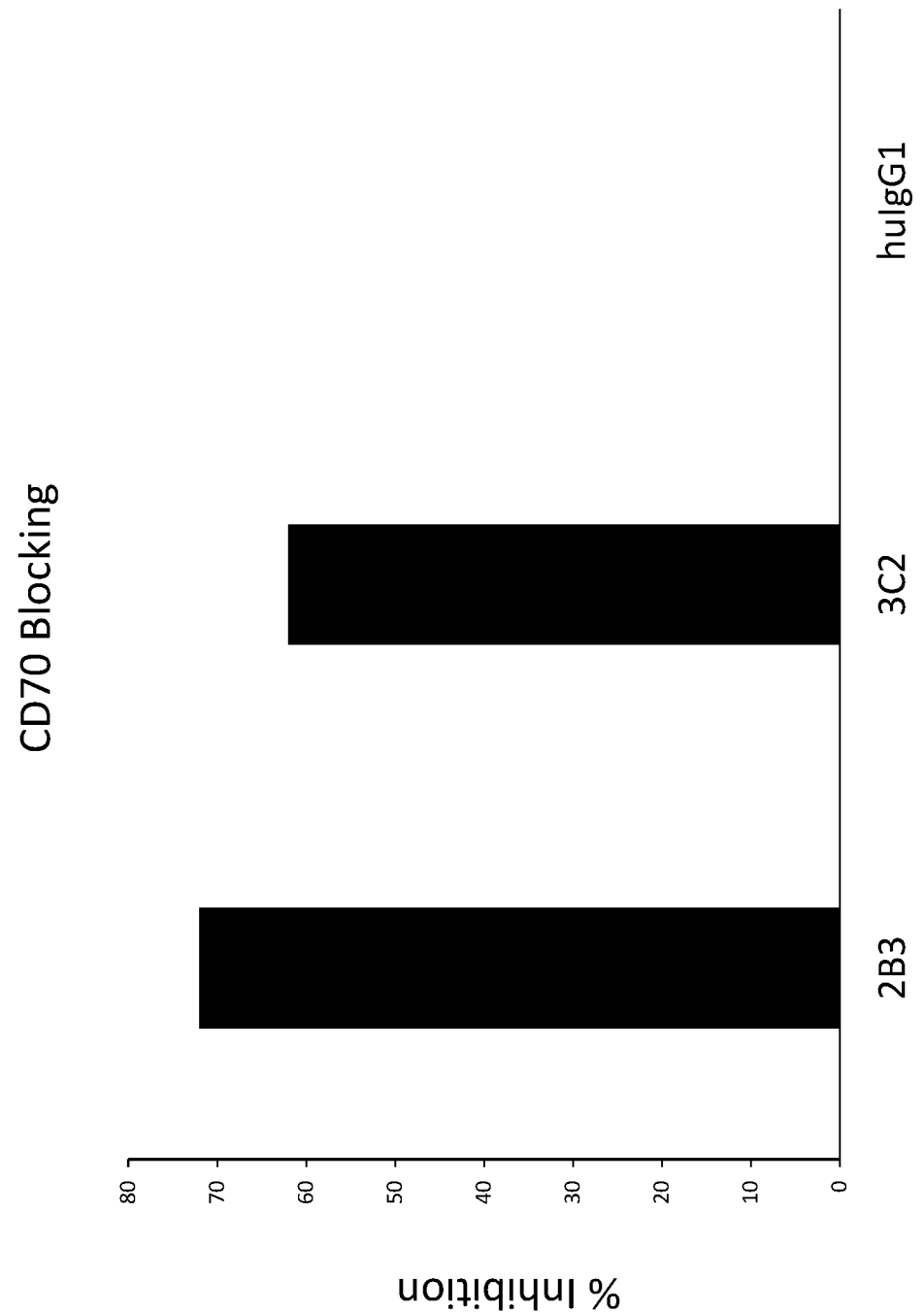
FIG. 5 is a graph showing antibodies 2B3 and 3C2 significantly block CD70 binding to CD27.

The effect of the human monoclonal antibodies on the binding of soluble CD70 to CD27 on the cell surface was measured by flow cytometry. Ramos cells expressing CD27 were incubated for 5 minutes at room temperature with the antibodies (50 µg/ml), followed by the addition of human CD70-biotin ([final]=0.5 µg/mL) for 20 minutes at room temperature on a plate shaker. CD27 captured CD70 was detected with streptavidin PE and analyzed on a FACSCanto II™ instrument (BD Biosciences, NJ, USA). FIG. 5 shows that anti-CD27 antibodies 2B3 and 3C2 block CD70 binding to CD27 on cells.

Example 6: NFκB Activation

Figure 6:
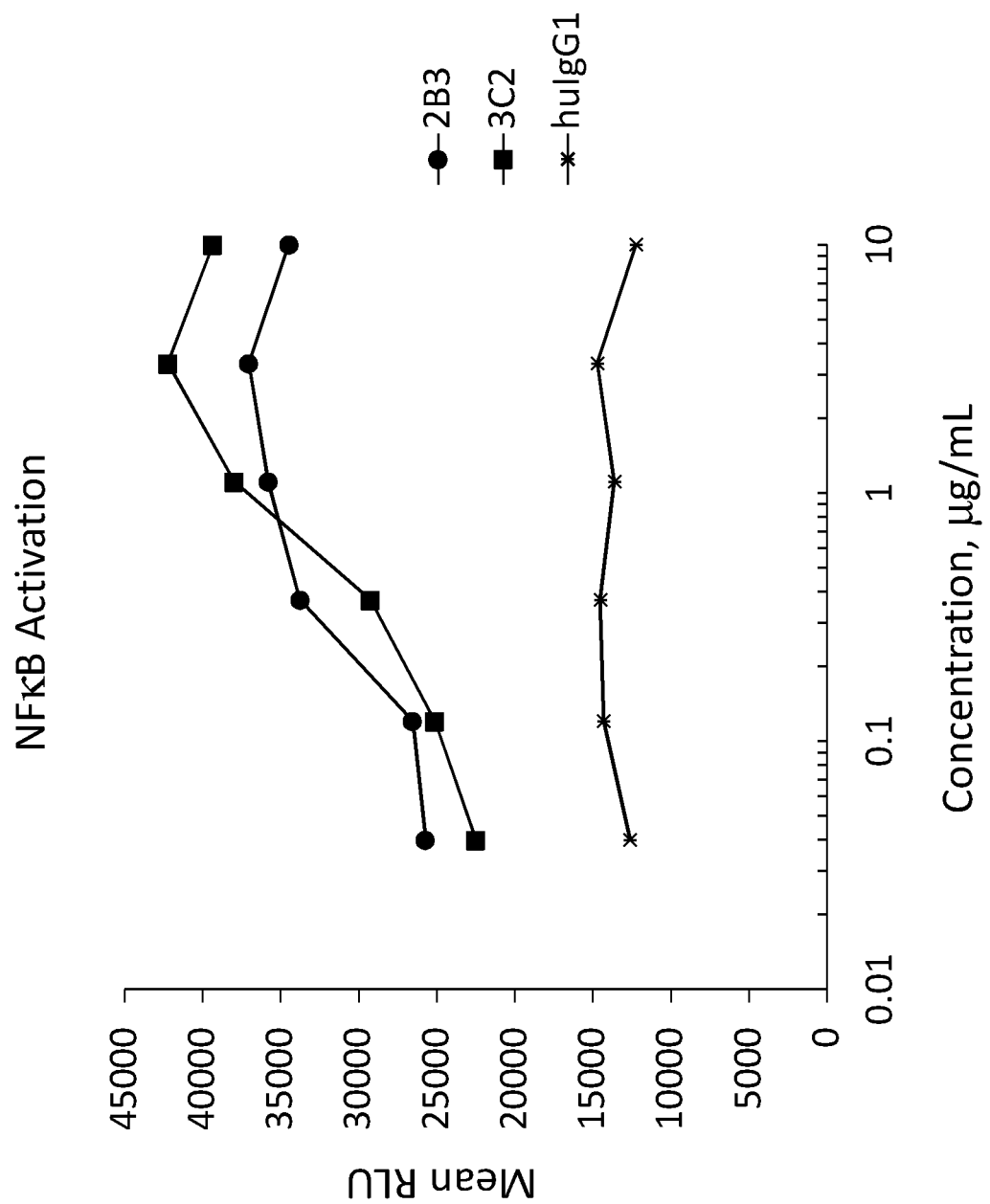
FIG. 6 is a graph showing antibodies 2B3 and 3C2 induced significant NFκB activation, as a function of antibody concentration.

A luciferase reporter cell line expressing CD27 was incubated for 6 hours at 37° C., 6% $CO_2$ with various concentrations of the human anti-CD27 antibodies. Luciferase is expressed upon activation and was detected with the Luciferase Assay System by Promega according to the manufacturer's guidelines. FIG. 6 shows the high level of NFκB activation induced by 2B3 and 3C2 antibodies as a function of antibody concentration.

Example 7: T Cell Proliferation

Figure 7:
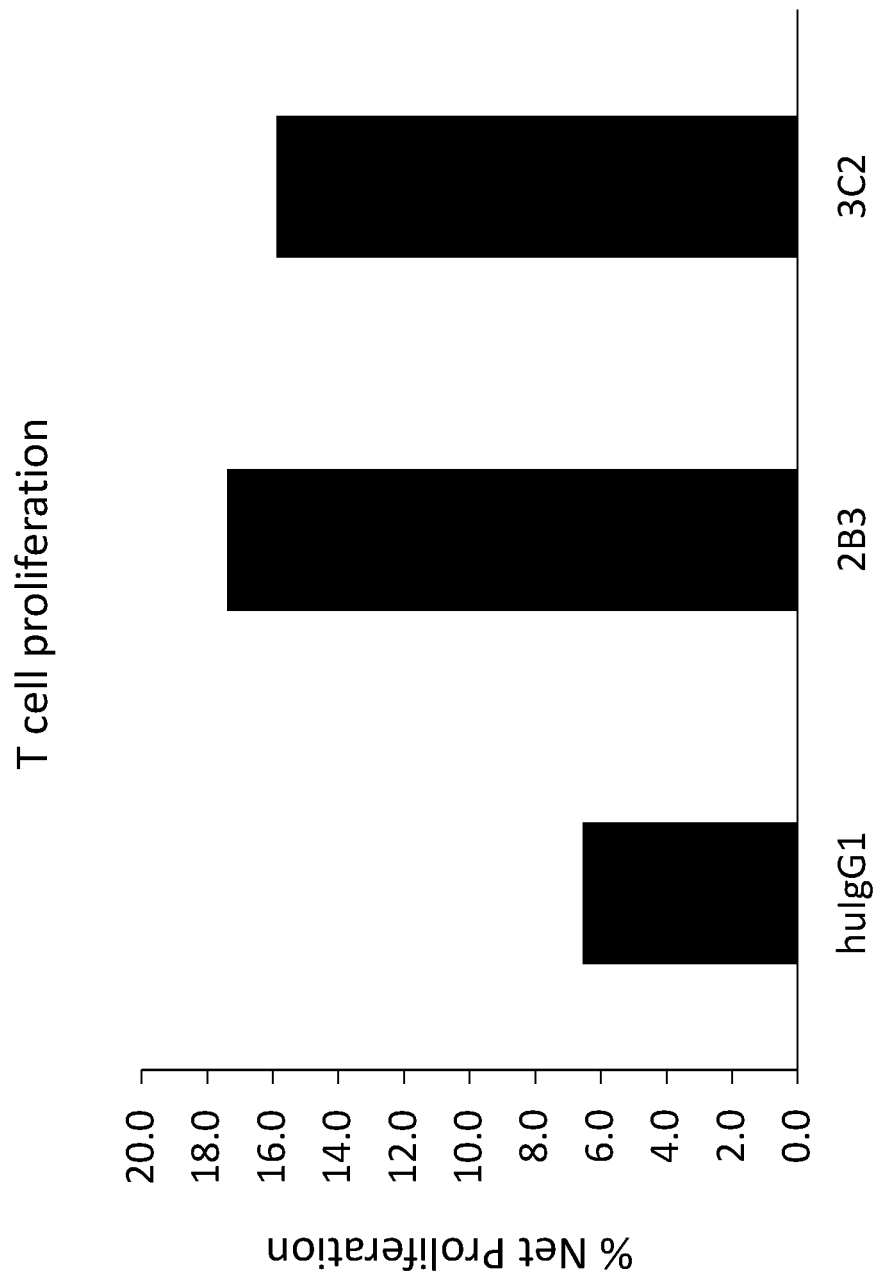
FIG. 7 is a graph showing antibodies 2B3 and 3C2 increase T cell proliferation.

Human Peripheral Blood Mononuclear Cells (PBMCs) isolated from buffy coat preparations and $CD3^+$ cells were further isolated from the PBMCs using magnetic bead separation technology from Miltenyi Biotec. The T cells were labeled with 1 mM carboxyfluorescein succinimidyl ester (CFSE) at room temperature while rotating for 5 minutes. The CFSE labeled PBMCs ($1\times10^6$) were dispensed into wells dry coated with anti-CD3 antibody (OKT3, eBioscience) at 1 µg/mL and the anti-CD27 antibodies or human IgG1 control at 10 µg/mL. The plates were incubated at 37° C., 5% $CO_2$ for 72 hours. The cells were harvested and analyzed by flow cytometry on a FACSCanto II™ instrument (BD Biosciences, NJ, USA) according to the manufacturer's directions. FIG. 7 shows that antibodies 2B3 and 3C2 significantly increase T cell proliferation.

Example 8: Generation of PD-L1-Specific Human Monoclonal Antibodies

Human anti-PD-L1 monoclonal antibodies were generated by immunizing the H2L2 strain of Harbour® transgenic mice with a soluble human PD-L1 antigen. Harbour® transgenic mice have had the endogenous mouse heavy chain (HC) and kappa light chain (κ-chain) DNA sequences knocked out and have had sequences for the human variable (V) regions and rat constant (C) regions stably incorporated into the mouse genome.

Antigen and Immunization: The antigen was a soluble fusion protein comprising a PD-L1 extracellular domain with a HIS tag (R&D Systems), or a recombinant human PD-L1-msG2a chimeric protein (made in-house). The antigen was mixed with MPL plus TDM adjuvant system (Sigma) for immunizations. 5-25 micrograms soluble recombinant PD-L1 antigen in PBS were mixed 1:1 with the adjuvant. Mice were injected with 200 microliters of the prepared antigen into the peritoneal cavity every 14 days. Animals that developed anti-PD-L1 titers were given an iv injection of 5-10 micrograms soluble recombinant PD-L1 antigen three to four days prior to fusion. Mouse spleens were harvested, and the isolated splenocytes used for hybridoma preparation.

Hybridoma Preparation: The P3x63Ag8.653 murine myeloma cell line (ATCC CRL 1580) was used for the fusions. RPMI 1640 (Invitrogen) containing 10% FBS was used to culture the myeloma cells. Additional media supplements were added to the Hybridoma growth media, which included: up to 10% Hybridoma Enhancing Supplement (Sigma), 10% FBS (Sigma), L-glutamine (Gibco), 0.1% gentamycin (Gibco), 2-mercaptoethanol (Gibco), with HAT (Sigma; $1.0\times10^4$ M hypoxanthine, $4.0\times10^{-7}$ M aminopterin, $1.6\times10^{-5}$ M thymidine media).

Spleen cells were mixed with the P3x63Ag8.653 myeloma cells in a 6:1 ratio and pelleted by centrifugation. Polyethylene glycol was added dropwise with careful mixing to facilitate fusion. Hybridomas were allowed to grow out for one to two weeks until visible colonies become established. Supernatant was harvested and used for initial screening for rat IgG via ELISA using a human soluble PD-L1 fusion protein and a rat Fc specific detection. IgG positive supernatants were then assayed for PD-L1 specificity via flow cytometry. The hybridomas were also screened for cross-reactivity with cynomolgus macaque PD-L1 and all were positive for binding.

Hybridoma cells were expanded and cell pellets were frozen for RNA isolation and sequencing. The $V_H$ and $V_L$ coding regions of human monoclonal antibodies were identified using RNA from the corresponding hybridomas. RNA was reverse transcribed to cDNA, the V coding regions were amplified by PCR and the PCR products were sequenced, inserted into human IgG1kappa vector, transiently expressed and purified by protein A column chromatography which led to the isolation of a number of antibodies of particular interest, which were designated as 1B3, 3B6, 4A3, 7H7, 8B1 and 9H9.

Example 9: Assays to Determine Human Monoclonal Antibody Binding Characteristics to PD-L1

Microtiter plates were coated with recombinant human PD-L1-msFc in PBS, and then blocked with 5% bovine serum albumin in PBS. Protein A purified human monoclonal antibodies were added at various concentrations and incubated at 37° C. The plates were washed with PBS/Tween and then incubated with a goat-anti-human IgG Fc-specific polyclonal reagent conjugated to horseradish peroxidase at 37° C. After washing, the plates were developed with HRP substrate, and analyzed at OD 450-650 nm using a microtiter plate Microtiter plates were coated with recombinant human PD-L1-msFc in PBS, and then blocked with 5% bovine serum albumin in PBS. Protein A purified human monoclonal antibodies were added at various concentrations and incubated at 37° C. The plates were washed with PBS/

Figure 8:
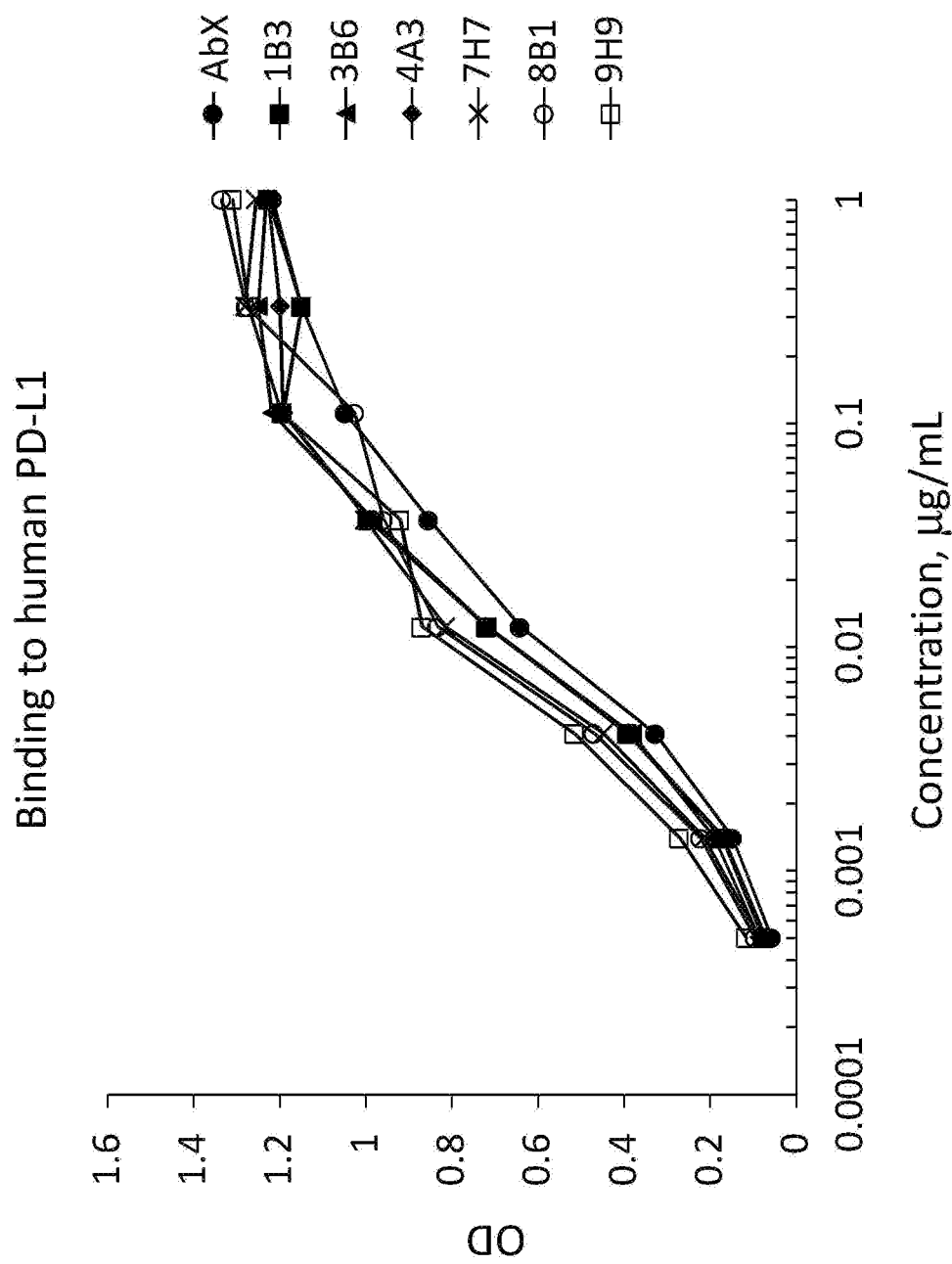
FIG. 8 is a graph showing anti-PD-L1 antibodies bind human PD-L1 as a function of antibody concentration with anti-PD-L1 antibody AbX as a comparator.

Tween detergent and then incubated with a goat-anti-human IgG Fc-specific polyclonal reagent conjugated to horseradish peroxidase at 37° C. After washing, the plates were developed with HRP substrate, and analyzed at OD 450-650 nm using a microtiter plate reader. FIG. 8 shows that the anti-PD-L1 antibodies strongly bind human PD-L1 as a function of antibody concentration.

Figure 9:
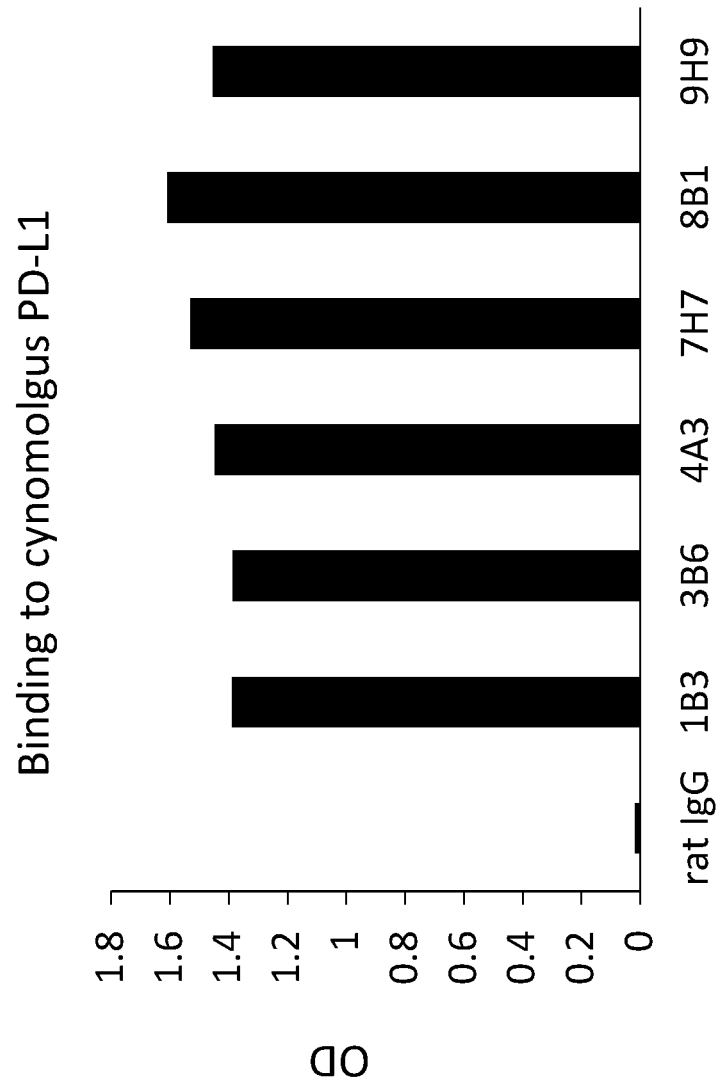
FIG. 9 is a graph showing binding of anti-PD-L1 antibodies to recombinant cynomolgus PD-L1.

To establish that cynomolgus macaques are a relevant model for testing anti-PD-L1 monoclonal antibodies, microtiter plates were coated with recombinant cynomolgus PD-L1-FLAG-HIS in PBS, and then blocked with 5% bovine serum albumin in PBS. Hybridoma supernatants or rat IgG control were added and incubated at 37° C. The plates were washed with PBS/Tween detergent and then incubated with a mouse-anti-rat IgG Fc-specific polyclonal reagent conjugated to horseradish peroxidase at 37° C. After washing, the plates were developed with HRP substrate, and analyzed at OD 450-650 nm using a microtiter plate reader. FIG. 9 shows that the anti-PD-L1 antibodies bind cynomolgus PD-L1.

Example 10: Blocking of PD1 Binding

Figure 10:
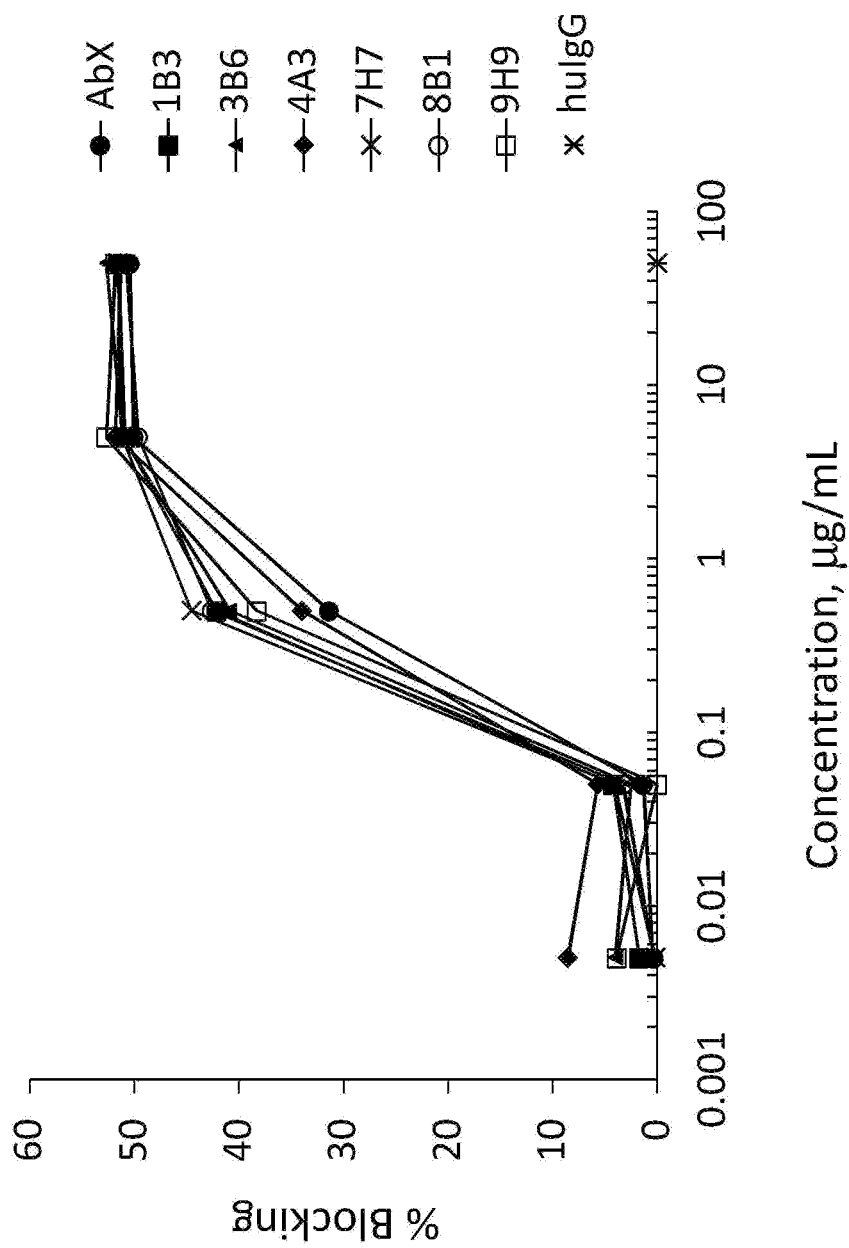
FIG. 10 is a graph showing anti-PD-L1 antibodies significantly block PD-L1 binding to PD1 as a function of antibody concentration with anti-PD-L1 antibody AbX as a comparator.

The effect of the human monoclonal antibodies on the binding of soluble PD1 to PD-L1 on the cell surface was measured by flow cytometry. 293 cells expressing PD-L1 were incubated for 5 minutes at room temperature with the antibodies, followed by the addition of human PD1-biotin ([final]=0.5 mg/mL). PD-L1 captured PD1 was detected with streptavidin PE and analyzed on a FACSCanto II™ instrument (BD Biosciences, NJ, USA). FIG. 10 shows that the anti-PD-L1 antibodies block PD-L1 binding to PD1 as a function of antibody concentration.

Example 11: Binding to PD-L1 Cells

The ability of anti-PD-L1 human monoclonal antibodies to bind to PD-L1 on cells expressing human PD-L1 on their surface was investigated by flow cytometry as follows:

Antibodies were tested for binding to a human cell line expressing human PD-L1 on their surface. Protein A purified human monoclonal antibodies were incubated with 293 cells expressing human PD-L1 at room temperature on a plate shaker. After 20 minutes, the cells were washed with PBS containing 0.1% BSA and 0.05% $NaN_3$ (PBA) and the bound antibodies were detected by incubating the cells with a PE labeled goat anti-human IgG Fc-specific probe. The excess probe was washed from the cells with PBA and the cell associated fluorescence was determined by analysis using a FACSCanto II™ instrument (BD Biosciences, NJ, USA) according to the manufacturer's directions.

Figure 11:
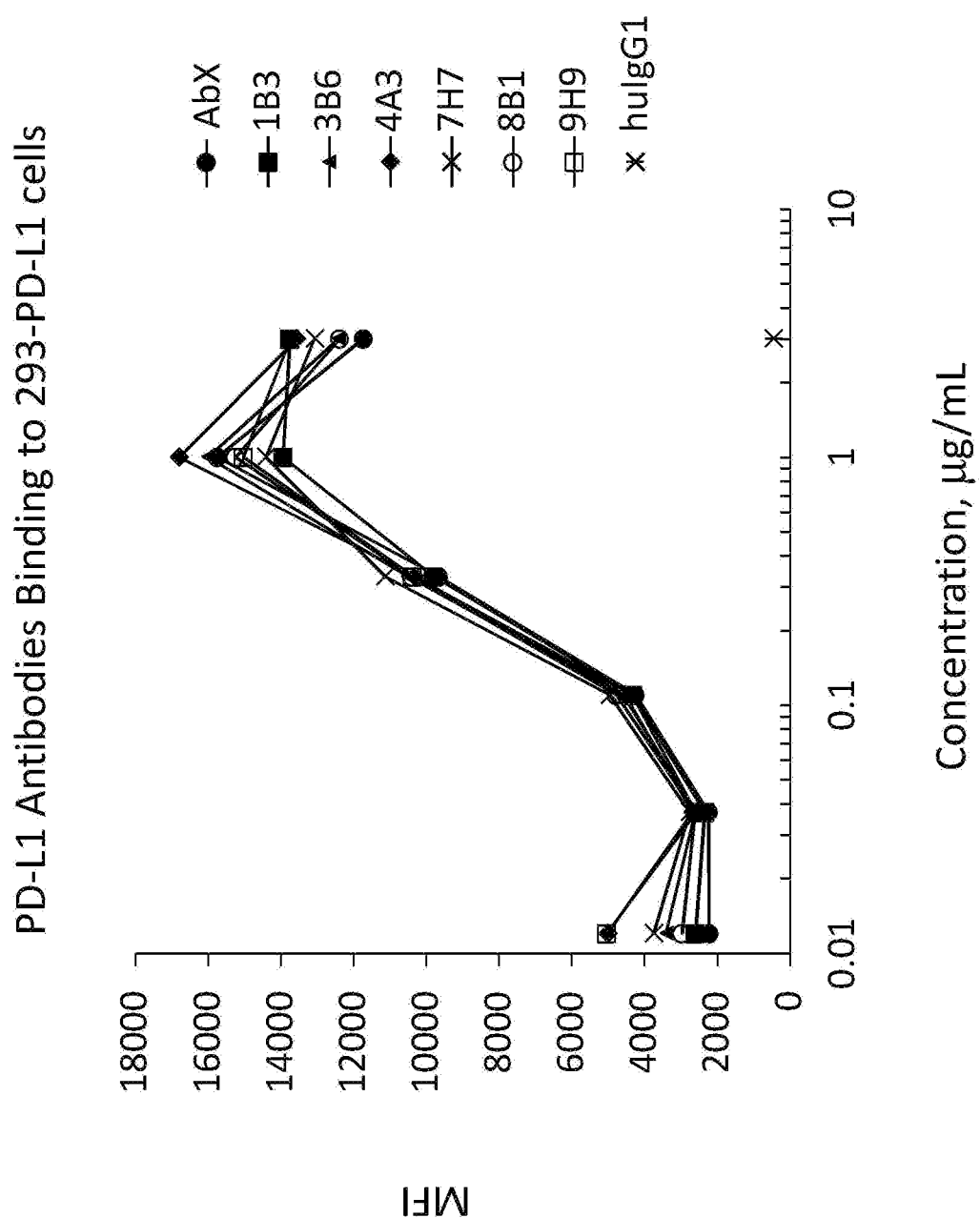
FIG. 11 is a graph showing high level of binding of anti-PD-L1 antibodies to cells that express human PD-L1 as a function of antibody concentration with anti-PD-L1 antibody AbX as a comparator.

As shown in FIG. 11, the anti-PD-L1 human monoclonal antibodies demonstrated high levels of binding to cells expressing human PD-L1 as a function of antibody concentration.

Example 12: Binding to Human Dendritic Cells

The ability of anti-PD-L1 human monoclonal antibodies to bind to PD-L1 on human dendritic cells was investigated by flow cytometry as follows:

Antibodies were tested for binding to human dendritic cells which express human PD-L1 on their surface. Dendritic cells were generated as follows: PMBC's were added to a T175 $cm^2$ flasks and monocytes allowed to adhere for ~2 hours at 37° C., 6% $CO_2$. The non-adherent cells were removed and the monocytes cultured for 7 days in RPMI containing 10% FBS, 10 ng/mL IL-4 (R&D Systems) and 100 ng/mL GM-CSF (R&D Systems). Non-adherent cells were harvested and confirmed to be dendritic cells by expression of CD11c (not shown). Protein A purified human monoclonal antibodies were incubated with the dendritic cells at room temperature on a plate shaker. After 20 minutes, the cells were washed with PBS containing 0.1% BSA and 0.05% $NaN_3$ (PBA) and the bound antibodies were detected by incubating the cells with a PE labeled goat anti-human IgG Fc-specific probe. The excess probe was washed from the cells with PBA and the cell associated fluorescence was determined by analysis using a FACSCanto II™ instrument (BD Biosciences, NJ, USA) according to the manufacturer's directions.

Figure 12:
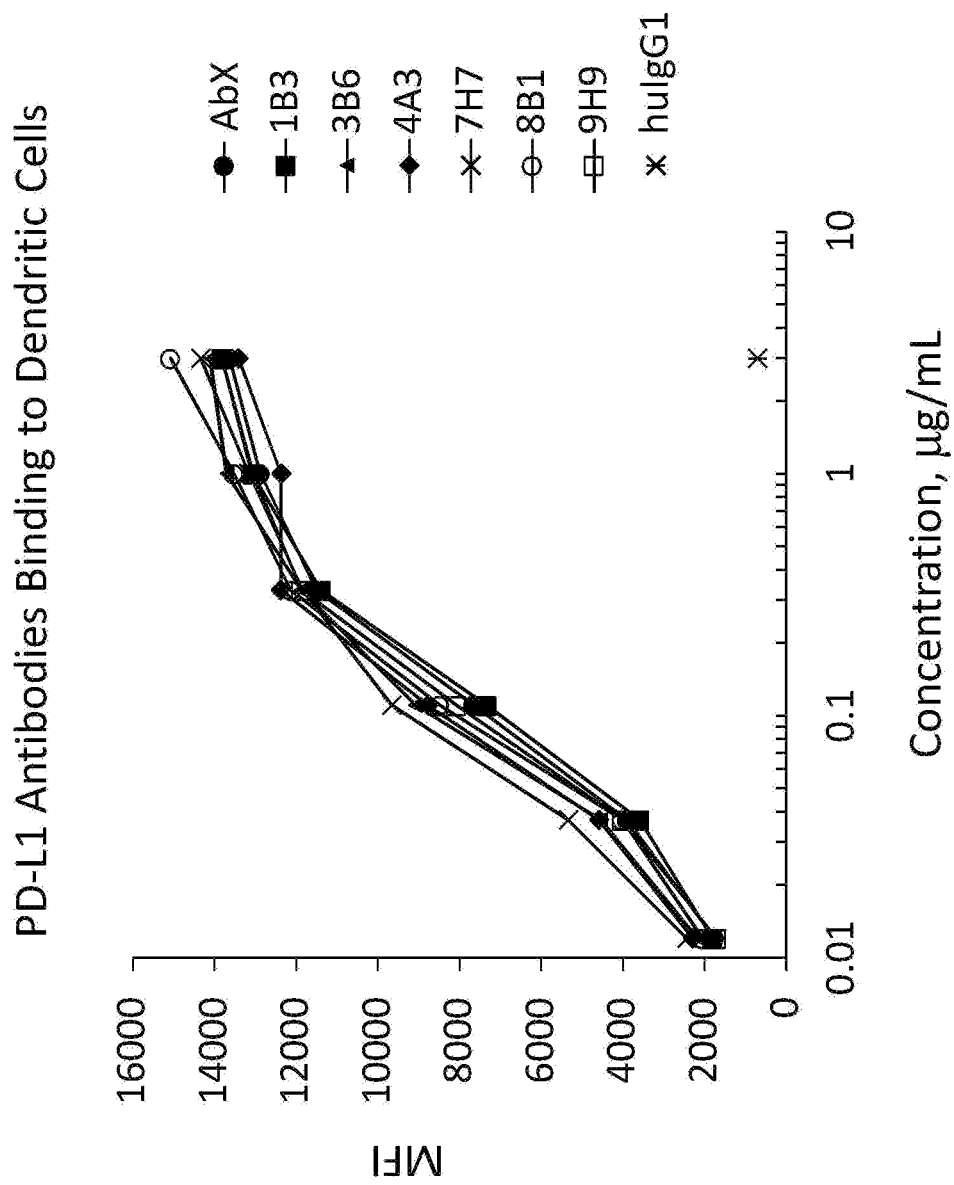
FIG. 12 is a graph showing high level of binding of anti-PD-L1 antibodies to human dendritic cells as a function of antibody concentration with anti-PD-L1 antibody AbX as a comparator.

As shown in FIG. 12, the anti-PD-L1 human monoclonal antibodies demonstrated high levels of binding to human dendritic cells as a function of antibody concentration.

Example 13: T Cell PD1/PD-L1 Blockade Bioassay

Figure 13:
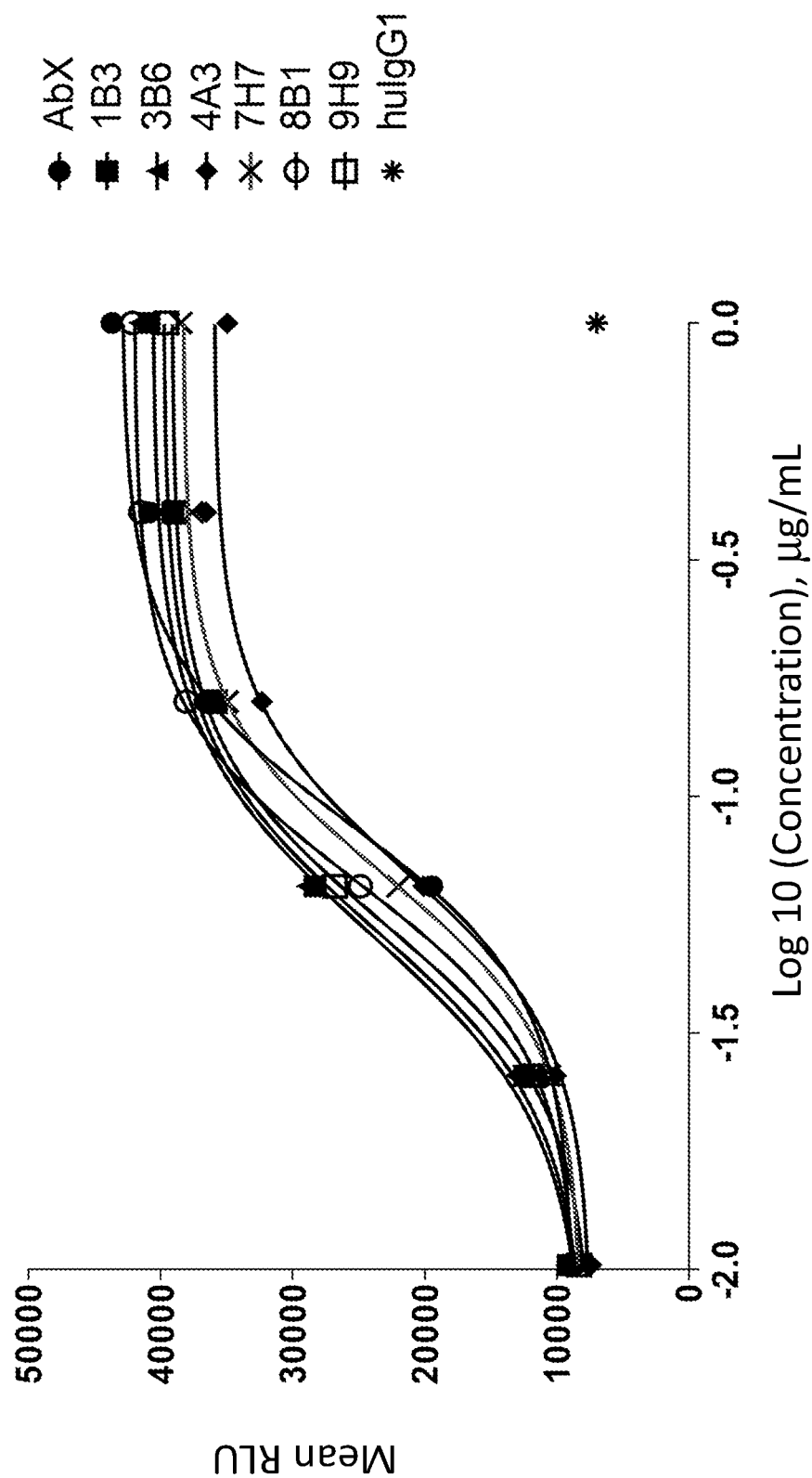
FIG. 13 is a graph showing anti-PD-L1 antibodies block PD1/PD-L1 interaction between cells resulting in NFAT pathway activation.

The effect of the PD-L1 antibodies on blockade of the PD1/PD-L1 interaction was determined using the PD1/PD-L1 Blockade Assay from Promega. Two engineered cell lines, PD1 Effector cells and PD-L1 aAPC/CHO-K1 cells were co-cultured in the presence of the antibodies for 6 hours. Blocking of the PD1/PD-L1 interaction results in TCR activation and induces luminescence via the NFAT pathway. Luminescence was detected by the addition of Bio-Glo™ reagent and quantitated on a Perkin Elmer Victor X luminometer. As shown on FIG. 13, the anti-PD-L1 antibodies effectively block the PD1/PD-L1 interaction between cells leading to activation of the NFAT pathway.

Example 14: Mixed Lymphocyte Reaction

Figure 14:
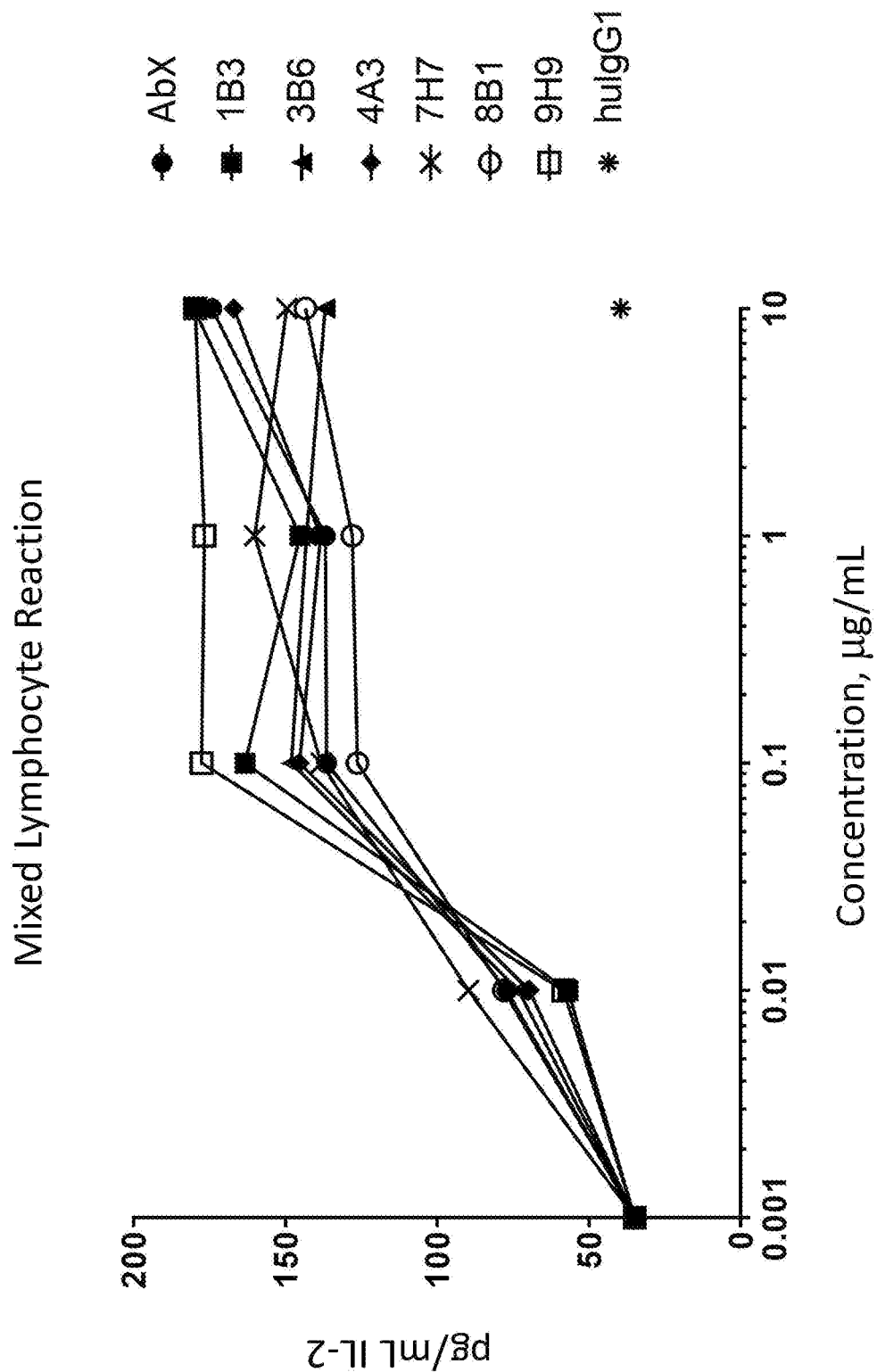
FIG. 14 is a graph showing anti-PD-L1 antibodies induce a mixed lymphocyte response as a function of antibody concentration with anti-PD-L1 antibody AbX as a comparator.

Human peripheral blood mononuclear cells were isolated from buffy coats using Ficoll separation, and $CD4^+$ cells were further isolated from the PBMC's using magnetic bead separation technology from Miltenyi Biotec. Allogeneic dendritic cells were generated as follows: PMBC's were added to a T175 $cm^2$ flasks and monocytes allowed to adhere for ~2 hours at 37° C., 6% $CO_2$. The non-adherent cells were removed and the monocytes cultured for 7 days in RPMI containing 10% FBS, 10 ng/mL IL-4 (R&D Systems) and 100 ng/mL GM-CSF (R&D Systems). Non-adherent cells were harvested and confirmed to be dendritic cells by expression of CD11c (not shown). The CD4+ cells and DC's were co-incubated at a 10:1 ratio in the presence of the antibody dilutions for 3 days. Supernatants were harvested and analyzed for IL-2 production by ELISA (R&D Systems). As shown on FIG. 14, the anti-PD-L1 antibodies were able to induce a significant mixed lymphocyte response.

Example 15: Development and Functional Testing of Bispecific Constructs

Figure 15A:
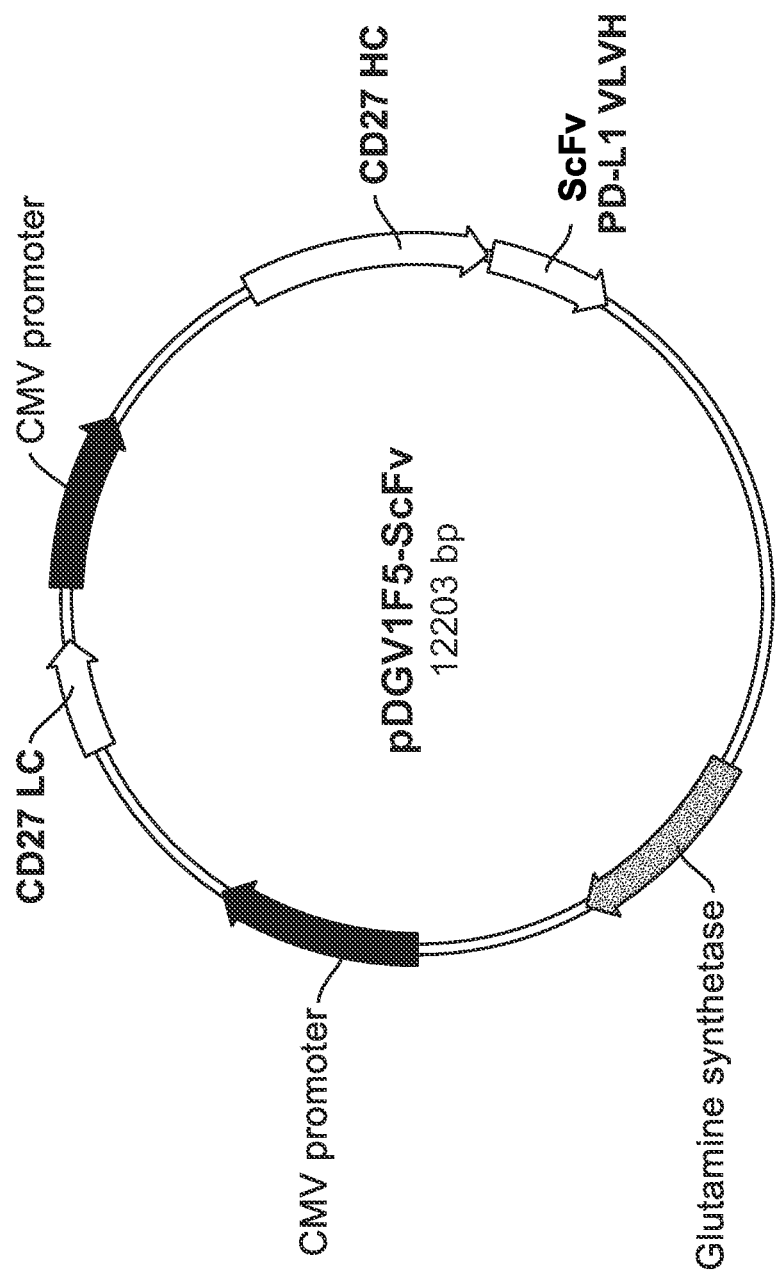
FIG. 15A is a representative DNA expression vector containing the anti-CD27 light chain, anti-CD27 heavy chain, and the c-terminal anti-PD-L1 single chain (VL+VH) peptide.
Figures 15B, 15C:
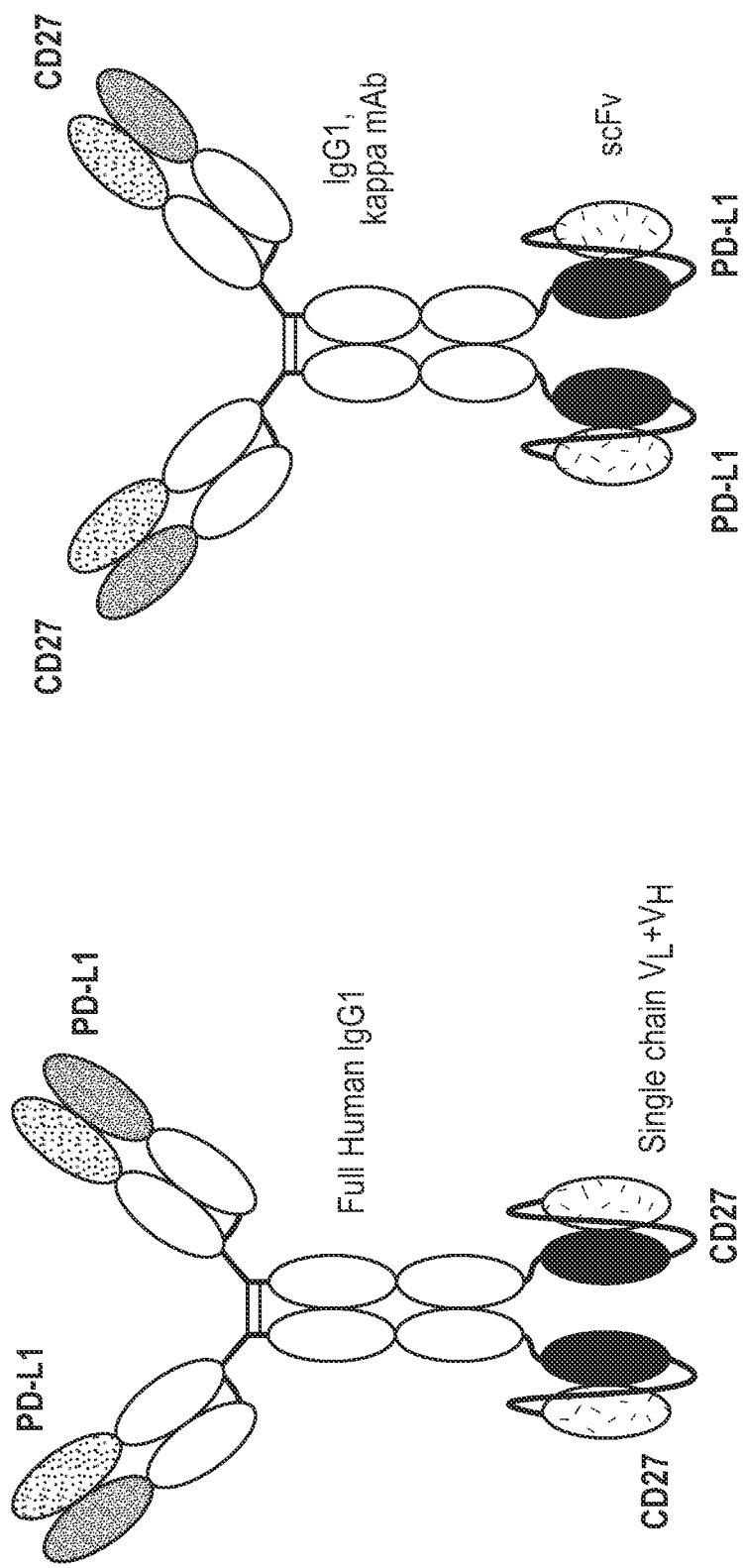
FIG. 15B is a drawing of the CD27/PD-L1 bispecific antibody protein wherein an anti-PD-L1 antibody is linked to an anti-CD27 scFv.
FIG. 15C is a drawing of the CD27/PD-L1 bispecific antibody protein wherein an anti-CD27 antibody is linked to an anti-PD-L1 scFv.

Tetravalent bispecific constructs were developed using a fully human IgG1 backbone for the PD-L1 monoclonal antibody and the scFv of the CD27 monoclonal antibody genetically linked to the c-terminus of the heavy chain. Alternative bispecific constructs also were developed using a fully human IgG1 backbone for the CD27 monoclonal antibody and the scFv of the PD-L1 monoclonal antibody. FIG. 15A shows a representative vector containing the CD27 light chain, CD27 heavy chain, and the c-terminal PD-L1 single chain Fv (VL+VH) polypeptide. FIGS. 15B and 15C are two alternative depictions of the CD27/PD-L1 bispecific format. FIG. 15B shows the CD27/PD-L1 bispecific antibody protein wherein an anti-PD-L1 antibody is linked to an anti-CD27 scFv (referred to herein as "CDX-527" when the anti-PD-L1 antibody is 9H9 and the anti-CD27 scFv is derived from 2B3. Otherwise AbXx2B3) and FIG. 15C shows the CD27/PD-L1 bispecific antibody protein wherein an anti-CD27 antibody is linked to an anti-PD-L1 scFv. FIG. 15D is a table of representative anti-CD27/anti-PD-L1 bispecific constructs generated.

The full 9H9x2B3 (CDX-527) heavy chain sequence was as follows (with the IgG1 constant region sequence shown in bold):

(SEQ ID NO: 179)
EVQLVESGGGLVQPGGSLRLSCAASGGIISTYWMSWVRQAPGKGLEWVAN

IKQDGSEKYYVDSVKGRFTISRDNAKNSLYLQMNSLRVEDTAMYYCARDR

PVAGASALWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGKG

SSGGGGSEIVMTQSPATLSVSPGERATLSCRASQSIRSNLAWYQQKPGQA

PRLLIYGASTRATGIPARFSGSGSGTEFTLTISSLQSENFAVYYCQQYNN

WPLTFGCGTKVEIKGGGGSGGGGSGGGGSGGGGSQVQLVQSGAEVKKPGA

SVKVSCKASGYTFTGYYIHWVRQAPGQCLEWMGWINPNSGGTNSAQKFQD

RVTITRVTSINTAYMELSRLRSDDTAVYFCARDRLVLPWFGEIFPDAFDI

WGQGTLVTVSS

The 9H9x2B3 (CDX-527) light chain sequence was as follows (with the constant region sequence shown in bold):

(SEQ ID NO: 180)
DIQMTQSPSTLSASVGDRVTITCRASQSISGWLAWYQQKPGKAPKLLIYK

ASSLESGVPSRFSGSGSGTEFTLTISSLQPDDFATYYCQQYYGSSRTFGQ

GTNVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Figure 16:
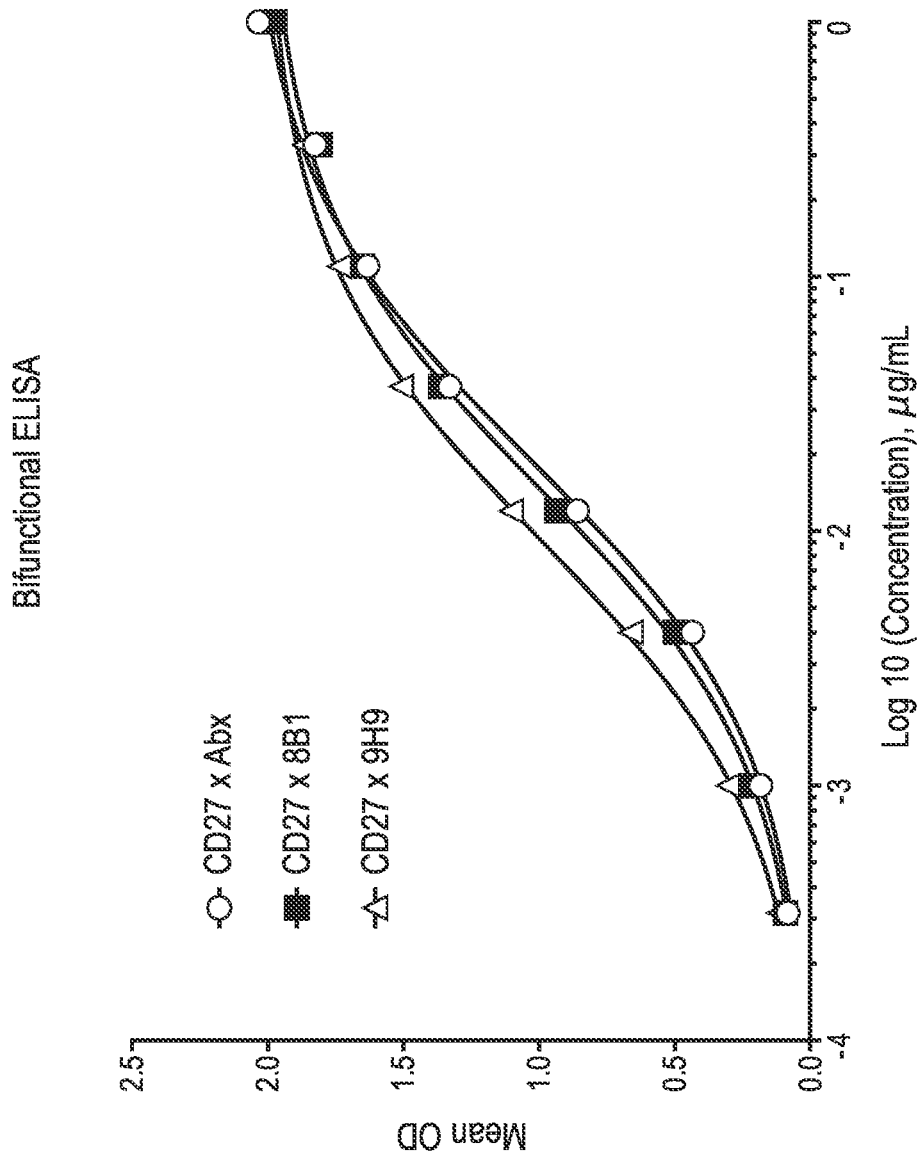
FIG. 16 is a graph showing binding of anti-CD27/antiPD-L1 bispecific constructs (BsAbs) to CD27 and PD-L1 using a bifunctional ELISA.

Example 16: Assays to Determine Bispecific Monoclonal Antibody Binding Characteristics and Functional Activity Binding of bispecific constructs to CD27 and PD-L1 was assessed using a bifunctional ELISA. Antibody AbX is a known anti-PD-L1 monoclonal antibody. In brief, a microtiter plate was coated with human CD27-FLAG-HIS. Dilutions of the bispecific constructs were allowed to bind before adding human PD-L1-msFc that was detected with an HRP labeled goat anti-mouse IgG (Fc specific) antibody. Representative binding curves for three bispecific constructs (CD27xAbX, CD27x8B1, and CD27x9H9) are shown in FIG. 16. All three antibodies demonstrated significant binding to CD27 and PD-L1.

Figure 17:
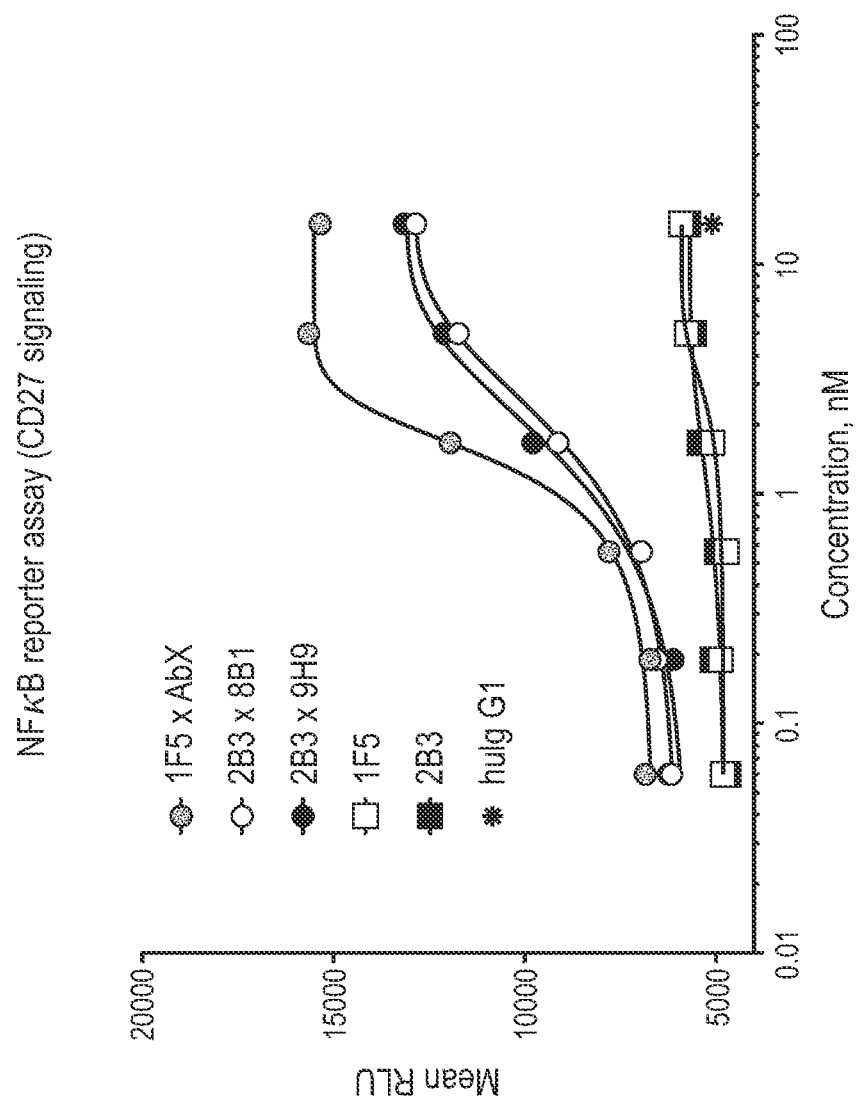
FIG. 17 is a graph showing increased NFκB activation induced by anti-CD27/anti-PD-L1 bispecific constructs as compared to antibodies 1F5 or 2B3 alone.

CD27 pathway activation was assessed by measuring NFκB activation. In brief, CD27 was transfected into a NFκB-luciferase reporter cell line (Signosis). The cells were incubated for 6 hours with each bispecific construct or antibody (1F5xAbX, 2B3x8B1, 2B3x9H9, 1F5, 2B3, or huIgG1) and luciferase expression was detected with the Brite-Glo™ system (Promega). Note: the reporter cell line is positive for human PD-L1. FIG. 17 shows the level of NFκB activation induced by the antibodies as a function of concentration. Additionally, the bispecific constructs 1F5xAbX, 2B3x8B1, and 2B3x9H9 showed significantly higher NFκB activation than 1F5 or 2B3 alone.

Figure 18:
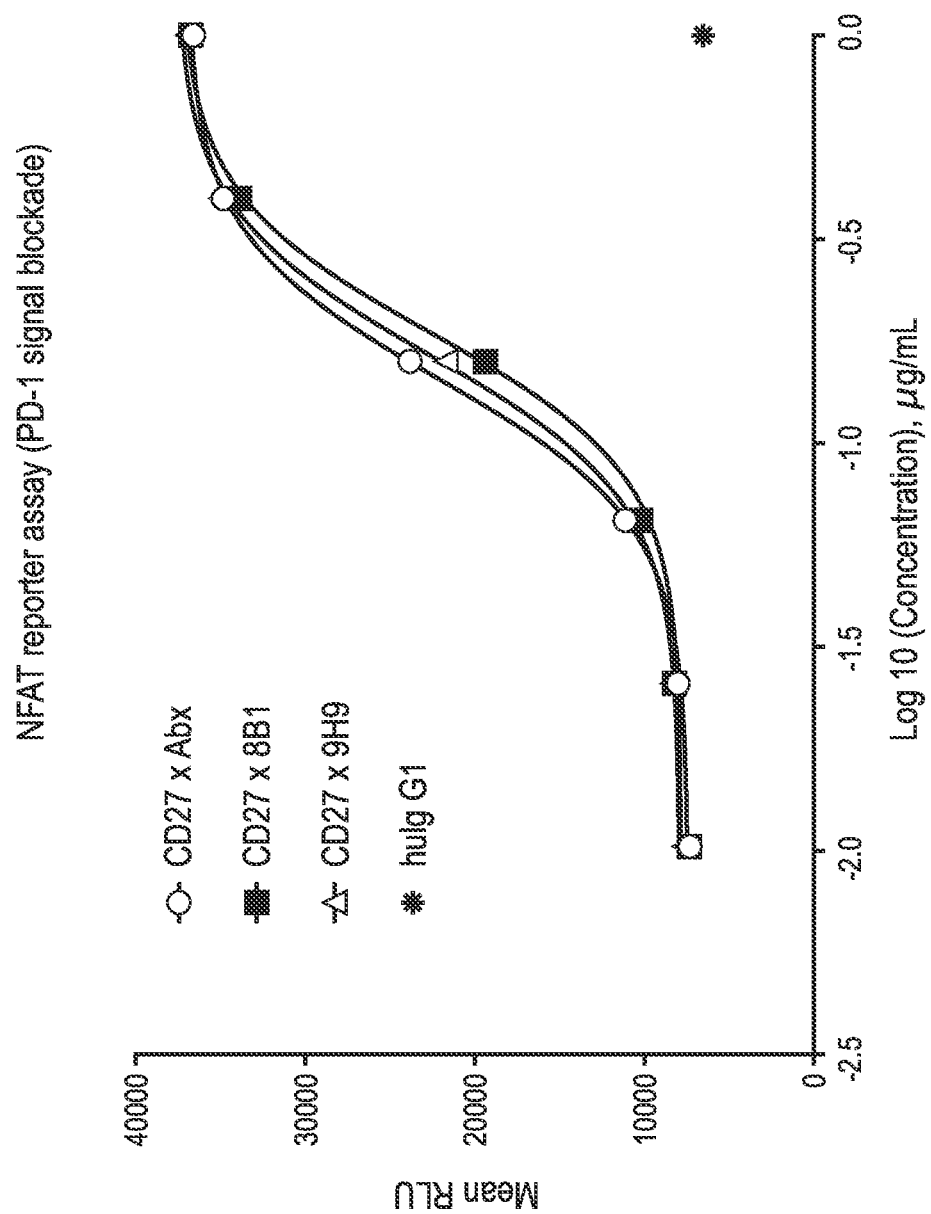
FIG. 18 is a graph showing anti-CD27/anti-PD-L1 bispecific constructs block PD1/PD-L1 interaction and induce NFAT pathway activation as a function of antibody concentration.

PD-1 signaling blockade was assessed by measuring NFAT pathway activation. In brief, PD-1 Effector cells and PD-L1 aAPC cells were co-cultured in the presence of dilutions of each bispecific construct or the control antibody (CD27xAbX, CD27x8B1, CD27x9H9, or huIgG1). Activation of the NFAT pathway via PD-L1/PD-1 blockade is detected by addition of Bio-Glo™ reagent. (Commercially available kit from Promega). As shown in FIG. 18, the bispecific constructs induced strong NFAT pathway activation as a function of antibody concentration.

Figure 19:
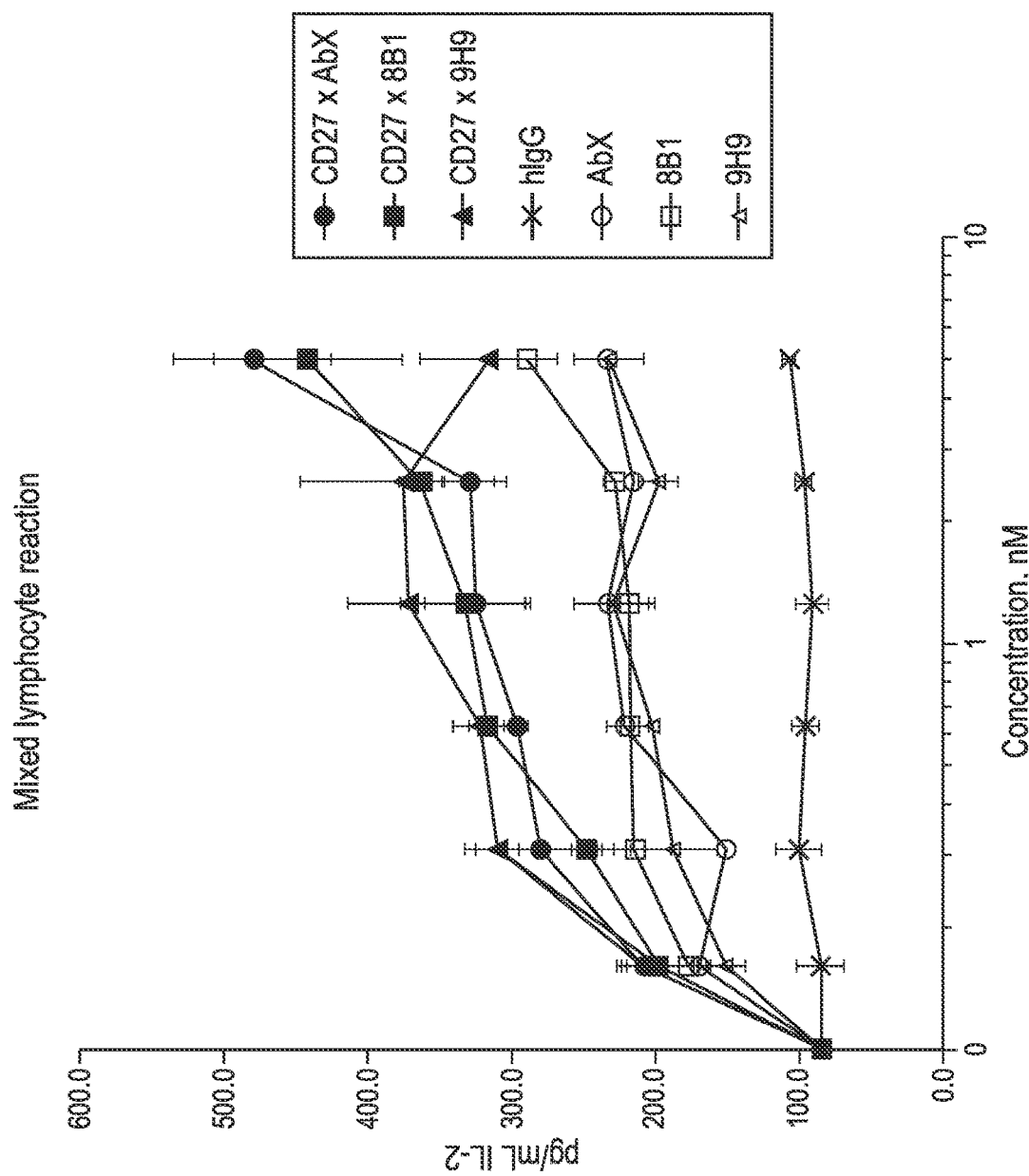
FIG. 19 is a graph showing anti-CD27/anti-PD-L1 bispecific constructs increase IL-2 production/secretion in a mixed lymphocyte reaction as compared to antibodies AbX (a known anti-PD-L1 monoclonal antibody), 8B1, or 9H9 alone.

IL-2 production/secretion was also measured in a mixed lymphocyte reaction. In brief, CD4 cells were incubated in the presence of allogeneic dendritic cells and dilutions of each bispecific constructs or antibody (CD27xAbX, CD27x8B1, CD27x9H9, huIgG1, AbX, 8B1, or 9H9) for 3 days. Supernatants were harvest and IL-2 levels were assessed by ELISA (R&D Systems). Representative IL-2 concentration curves are shown in FIG. 19. The bispecific constructs CD27xAbX, CD27x8B1 and CD27x9H9 showed significantly higher IL-2 production/secretion than AbX (a known anti-PD-L1 monoclonal antibody), 8B1, or 9H9 alone (e.g., about 2× higher IL-2 production).

Figures 20A, 20B:
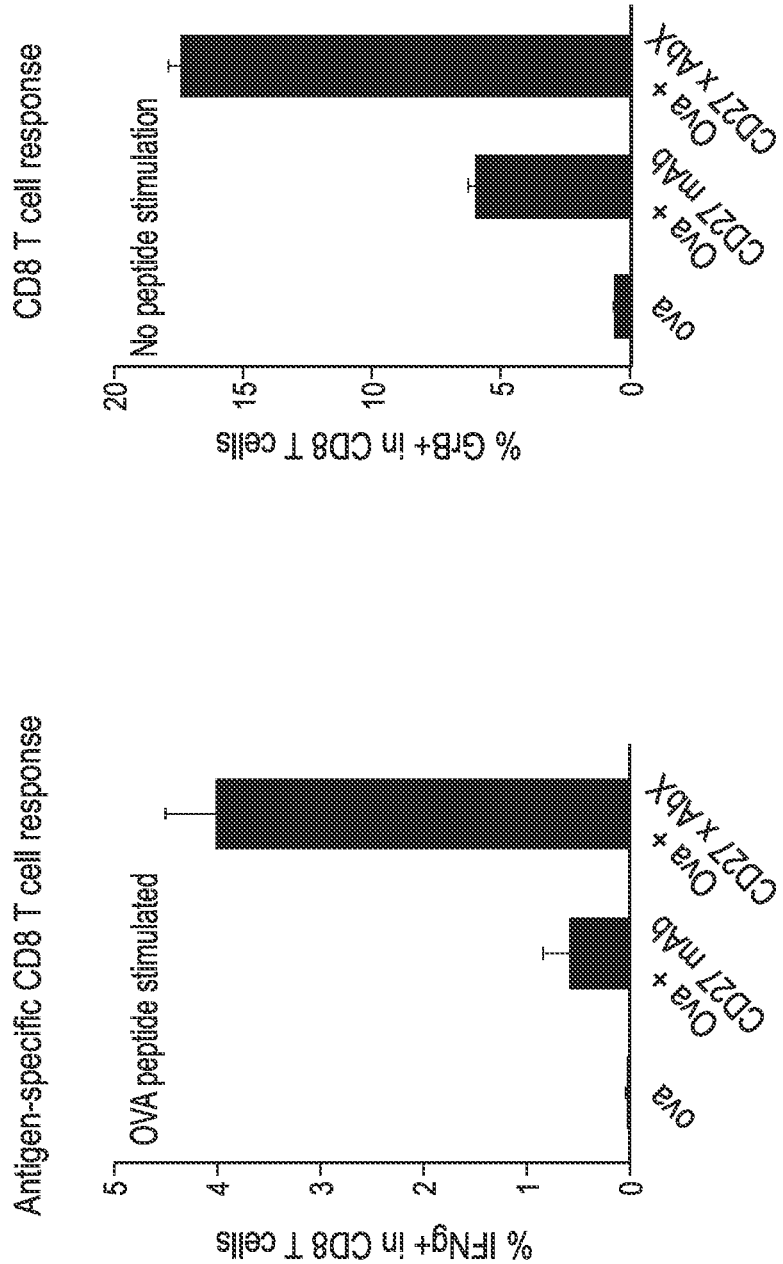
FIGS. 20A and 20B are graphs showing an anti-CD27/anti-PD-L1 bispecific construct (e.g., CD27xAbX) induces a higher CD8 T cell response as compared to CD27 monoclonal antibody alone.

Example 17: Assays to Determine In Vivo Activity of CD27/PD-L1 Bispecific Constructs HuCD27-Tg mice were injected with 0.1 mg of bispecific CD27xAbX construct (BsAb) or CD27 monospecific antibody (mAb), and 5 mg of Ovalbumin on day 0, as indicated in the x-axis of each graph. On Day 7 spleen cells were harvested and intracellular cytokine IFNγ and IL2, and cytolysis enzyme granzyme B (GrB) were detected by flow cytometry analysis with and without ex-vivo stimulation of SIINFEKL peptide (SEQ ID NO: 188). Percentage of SIINFEKL(SEQ ID NO: 188)-specific IFN-γ$^+$ and IL2$^+$ in CD8 T cells (FIG. 20A), and percentage of GrB+ in CD8 T cells without SIINFEKL (SEQ ID NO: 188) stimulation (FIG. 20B) are shown, indicating the CD27xAbX bispecific construct induces a significant CD8 T cell response as compared to CD27 monoclonal antibody alone (e.g., about 2.5× to about 8× higher response).

Figure 21:
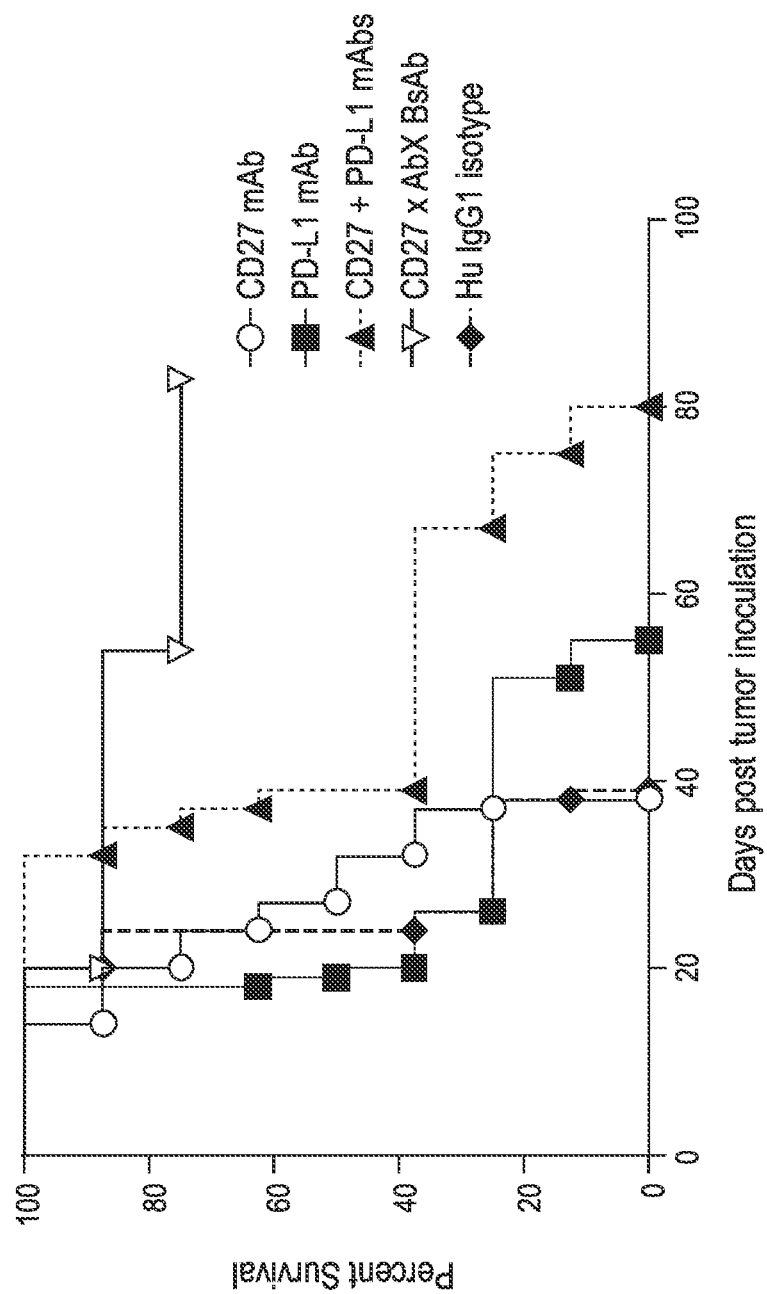
FIG. 21 is a Kaplan-Meier curve showing improved survival of mice treated with a bispecific construct (e.g., CD27xAbX) compared to CD27 and PD-L1 antibodies administered alone or in combination in a mouse tumor model.

Tumor growth, survival, and tumor infiltrate numbers were also measured in mice treated with the BsAb or mAbs. HuCD27-Tg mice were injected i.v. with BCL1 cells (5×10$^6$) on day 0. Antibodies or the bispecific construct were injected i.p (0.2 mg) on day 5. Mice were divided into two groups. One group was used to measure survival (n=8). FIG. 21 shows percent survival over time of mice treated with either CD27 monoclonal antibody, PD-L1 monoclonal antibody, combination of CD27+PD-L1 monoclonal antibodies, and CD27xAbX BsAb. Mice treated with CD27+PD-L1 antibodies survived significantly longer than mice treated with either CD27 monoclonal antibody, PD-L1 monoclonal antibody, or Hu IgG1 alone (e.g., 1.5×-2× longer). Moreover, mice treated with the CD27xAbX BsAb survived significantly longer than mice treated with any of the other antibodies tested either alone or in combination. In fact, 70% to 80% of mice treated with CD27xAbX BsAb were still alive after 80 days post tumor inoculation whereas mice in other groups had all died. Three surviving mice were re-challenged with same number of BCL1 cells after 180 days follow-up, and they were protected from the re-challenge.

The second group of mice was used to measure tumor weight and T cell levels on day 11. FIGS. 22A-22D show tumor weight, percent CD8 T cells, percent CD4 T cells, and IFNγ and GrB double positive CD8 T cells, respectively. Similar to the survival data, CD27xAbX BsAb significantly reduced tumor weight (e.g., 1.5× to 3× less), and significantly increased T cell numbers and activity (e.g., 1.5× to 4× more), as compared to any of the other antibodies tested either alone or in combination. FIGS. 23A and 23B show the upregulation of PD-L1 expression level on the surface of BCL1 lymphoma cells (FIG. 23A) and tumor microenvironment infiltrated cells (FIG. 23B) upon CD27 mAb treatment (CDX-1127), providing rationale for the combination or BsAb of anti-CD27 and anti-PD-L1.

Example 18: Bifunctional ELISA

Figure 15E:
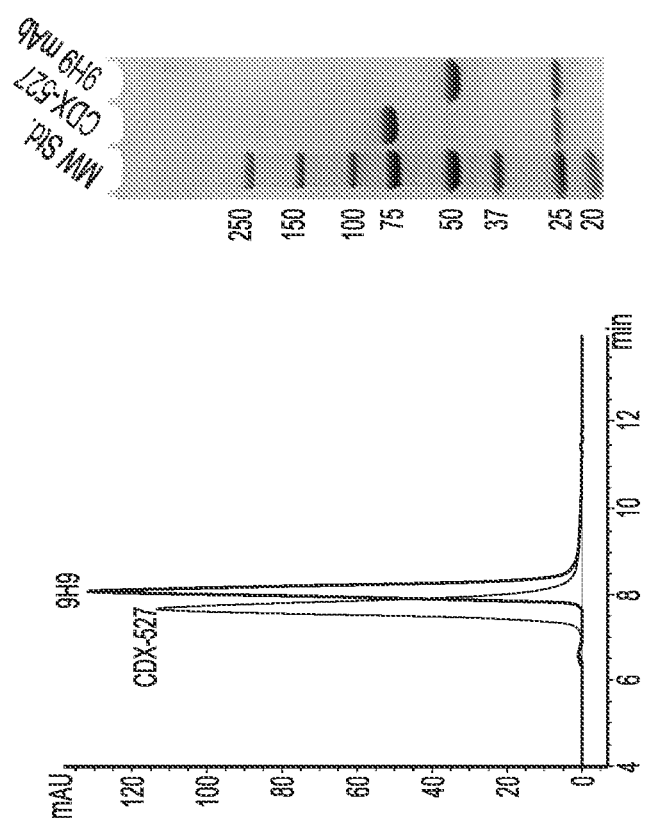
FIG. 15E shows characterization of the bispecific antibody CDX-527 by HPLC and gel electrophoresis.

Characterization and binding of the bispecific construct CDX-527 (prepared as in Example 15) was analyzed. FIG. 15E shows characterization of the bispecific antibody CDX-527 by HPLC and gel electrophoresis (reducing conditions). Binding to both CD27 and PD-L1 was determined using a bifunctional ELISA generally as described in Example 16. Results are shown in FIG. 24 from which it can be seen that CDX-527 demonstrated significant binding to CD27 and PD-L1.

Example 19: Activation of NFκB by Bispecific Construct CDX-527

Activation of NFκB by the bispecific construct CDX-527 (prepared as in Example 15) was determined generally as described in Example 16 except that SteadyGlo™ reagent from Promega was used instead of BriteGlo™.

Results are shown in FIG. 25, which shows the higher level of activation by CDX-527 compared to the monospecific anti-CD27 antibodies 1F5 and 2B3 alone. Activation was also measured in the presence of soluble FcγR1, which further increased NFκB activation as shown.

Example 20: Mixed Lymphocyte Reaction

The ability of the bispecific construct CDX-527 (prepared as in Example 15) to induce a mixed lymphocyte response was determined by the method described generally in Example 14, with testing for IL-2.

Results are shown in FIG. 26, from which it can be seen that CDX-527 was able to induce a significant mixed lymphocyte response which was also significantly greater than that of the monospecific antibodies 2B3 and 9H9 when used either alone or in combination.

Example 21: T-Cell Activation

Human Peripheral Blood Mononuclear Cells (PBMCs) were isolated from buffy coat preparations and CD3+ cells were further isolated from the PBMCs using magnetic bead separation technology from Miltenyi Biotec. CD3+ cells ($1×10^5$) were dispensed into wells coated with anti-CD3 antibody (OKT3, eBioscience) and soluble human PD-L1. Antibodies 2B3 and 9H9 or CDX-527 (prepared as in Example 15) were added to the cells at concentrations between 0.1 nM and 10 nM. The plates were incubated at 37° C., 5% $CO_2$ for 72 hours at which time IL-2 levels in the supernatants were measured.

Results are shown in FIG. 27 from which it can be seen that CDX-527 significantly activated T-cells and did so to a significantly greater extent than the monospecific antibodies 2B3 and 9H9 when used in combination.

Example 22: Pharmacokinetics

Pharmacokinetics of CDX-527 was studied in non-human primates (NHPs) at a dose level of 7.0 mg/kg and volume of 3.0 ml/kg i.v. No significant change was observed in any clinical parameters during the 21 day study. Serum levels of CDX-527 were determined by ELISA.

Results are shown in FIG. 28. Pharmacokinetic analysis resulted in T1/2 of approximately 110 hours.

Example 23: Cell Based PD1/PDL1 Blockade Assay

Bispecific antibodies 9H9x2B3 and the opposite configuration 2B3x9H9 were compared in a cell based PD1/PDL1 blockade assay generally as described in Example 13.

Results are shown in FIG. 29 from which it can be seen that the 9H9x2B3 configuration was more potent at blockade of PD-1 signaling than the 2B3x9H9 configuration.

Example 24: Mixed Lymphocyte Reaction

Bispecific antibodies 9H9x2B3 and the opposite configuration 2B3x9H9 were compared in a mixed lymphocyte reaction generally as described in Example 14.

Results are shown in FIG. 30 from which it can be seen that the 9H9x2B3 configuration was more potent at T-cell activation than the 2B3x9H9 configuration.

Example 25: Vaccine Induced CD8 T Cell Response

Bispecific antibodies AbXx2B3 and the opposite configuration 2B3xAbX were compared in a vaccine model of T-cell response generally as described in Example 17.

Results are shown in FIG. 31 from which it can be seen that AbXx2B3 was more potent than 2B3xAbX in stimulating a vaccine induced CD8+ T-cell response.

Example 26: BCL1 Tumor Model

Bispecific antibodies AbXx2B3 and the opposite configuration 2B3xAbX were compared in a BCL1 Tumor Model generally as described in Example 17.

Results are shown in FIG. 32 from which it can be seen that AbXx2B3 had greater anti-tumor activity than 2B3xAbX.

Example 27: Blocking of PD-L1 Binding to CD80

A microtiter plate was coated with recombinant human CD80, then blocked. Biotinylated huPD-L1 was pre-incubated for 1 hour at room temperature with 50 ug/mL of the huIgG1 control or the anti-PD-L1 antibodies (AbX or 9H9), then added to the plate. Streptavidin-HRP was used to detect the binding of the PD-L1 to CD80.

Results are shown in FIG. 33 from which it can be seen that the anti-PD-L1 antibodies completely blocked PD-L1 binding to CD80.

Example 28: 2B3 Binding to huCD27

The full length wild type extracellular domain (ECD) of human CD27 or human CD27 with mutated amino acids 85, 87, 88, and 89 (A85S, R87A, N88A and G89A; see FIG. 34) were coated to a plate, then blocked. Supernatant from transiently transfected cells expressing mAb 2B3 was added and binding was detected with an HRP conjugated goat anti-human IgG Fc polyclonal antibody.

Results are shown in FIG. 35 from which it can be seen that the anti-CD27 antibody 2B3 did not bind to the mutated CD27 ECD. Accordingly, this indicates that antibody 2B3 binds to an epitope on human CD27 involving or including one or more residues within amino acids 80-95, e.g., one or more residues within amino acids 85-89, of the extracellular domain (ECD) of human CD27 (SEQ ID NO: 183), e.g., amino acids 85, 87, 88, and/or 89 of the ECD of human CD27 (SEQ ID NO: 183).

Example 29: Increasing 9H9x2B3 Expression Through Protein Engineering: 9H9-2B3 (DD)

To increase expression of the bispecific product the rare valine (V) residue at H72 in FR3 of the 2B3 heavy chain and the rare asparagine (N) residue at L82 in FR3 of the 2B3 light chain were each changed to aspartic acid (D) residues (ie V72D and N82D respectively).

The modified 2B3 heavy chain sequence was as follows (the CDRs are underlined and the modified residue in FR3 is double underlined):

(SEQ ID NO: 177)
QVQLVQSGAEVKKPGASVKVSCKASGYTFTGYYIHWVRQAPGQGLEWMGW
INPNSGGTNSAQKFQDRVTITRDTSINTAYMELSRLRSDDTAVYFCARDR
LVLPWFGEIFPDAFDIWGQGTLVTVSS

The modified 2B3 light chain sequence was as follows (the CDRs are underlined and the modified residue in FR3 is double underlined):

(SEQ ID NO: 178)
EIVMTQSPATLSVSPGERATLSCRASQSIRSNLAWYQQKPGQAPRLLIYG
ASTRATGIPARFSGSGSGTEFTLTISSLQSEDFAVYYCQQYNNWPLTFGG
GTKVEIK

These sequences (designated 2B3(DD)) were used in an scFv format which was genetically linked to the C-terminus of the heavy chains of the 9H9 antibody. The resulting 9H9x2B3(DD) bispecific antibody was designated 9H9x2B3(DD).

The full 9H9x2B3(DD) heavy chain sequence was as follows (with the IgG1 constant "backbone" sequence shown in bold):

(SEQ ID NO: 181)
EVQLVESGGGLVQPGGSLRLSCAASGGIISTYWMSWVRQAPGKGLEWVAN
IKQDGSEKYYVDSVKGRFTISRDNAKNSLYLQMNSLRVEDTAMYYCARDR

PVAGASALWGQGTLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGKG
SSGGGGSEIVMTQSPATLSVSPGERATLSCRASQSIRSNLAWYQQKPGQA
PRLLIYGASTRATGIPARFSGSGSGTEFTLTISSLQSEDFAVYYCQQYNN
WPLTFGCGTKVEIKGGGGSGGGGSGGGGSGGGGSQVQLVQSGAEVKKPGA
SVKVSCKASGYTFTGYYIHWVRQAPGQCLEWMGWINPNSGGTNSAQKFQD
RVTITRDTSINTAYMELSRLRSDDTAVYFCARDRLVLPWFGEIFPDAFDI
WGQGTLVTVSS

The 9H9x2B3(DD) light chain sequence was as follows (with the constant region shown in bold):

(SEQ ID NO: 182)
DIQMTQSPSTLSASVGDRVTITCRASQSISGWLAWYQQKPGKAPKLLIYK
ASSLESGVPSRFSGSGSGTEFTLTISSLQPDDFATYYCQQYYGSSRTFGQ
GTNVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

The DNA sequence of the 9H9x2B3(DD) variable domain sequence was as follows:

(SEQ ID NO: 185)
GAAGTGCAACTGGTGGAGTCGGGTGGTGGACTCGTGCAGCCCGGCGGATC
CCTGAGACTCTCTTGTGCCGCATCGGGCGGCATTATTAGCACTTACTGGA
TGTCATGGGTCAGACAGGCACCGGGAAAGGGCTTGGAATGGGTGGCGAAT
ATCAAGCAGGATGGATCCGAGAAGTACTACGTGGACTCCGTGAAGGGCAG
ATTCACCATTTCCCGGGACAACGCCAAGAACTCGCTCTATCTGCAAATGA
ACTCGTTGCGGGTGGAAGATACTGCCATGTACTACTGCGCCCGGGACCGG
CCTGTGGCCGGGGCGTCGGCCCTCTGGGGCCAGGGCACTCTGGTCACCGT
GTCCTCT

The DNA sequence of the 9H9x2B3(DD) scFv domain sequence was as follows (connector and linker sequences are shown in bold):

(SEQ ID NO: 186)
GGCTCCAGCGGGGGTGGCGGTTCCGAGATCGTGATGACTCAGAGCCCGGC
AACCCTGTCCGTGTCTCCGGGGGAGCGGGCTACTCTTTCCTGCCGGGCAT
CCCAGTCCATCCGGTCGAACCTTGCGTGGTACCAACAGAAGCCTGGACAG
GCGCCCCGCCTGCTGATCTACGGGGCGTCGACTAGGGCCACCGGCATCCC
GGCCCGCTTCTCCGGGTCCGGATCCGGCACCGAATTCACCCTCACCATCT
CGAGCCTGCAGTCCGAAAACTTCGCCGTCTACTACTGCCAGCAGTACAAC

-continued

```
AACTGGCCGCTGACATTCGGATGCGGAACCAAAGTGGAAATCAAGGGCGG

CGGCGGATCCGGCGGTGGCGGCAGCGGCGGTGGAGGATCCGGTGGCGGCG

GTTCACAAGTGCAGCTGGTGCAGTCAGGCGCCGAAGTCAAGAAGCCCGGG

GCCAGCGTGAAAGTCAGCTGCAAGGCTTCCGGATACACCTTCACGGGTTA

CTACATTCACTGGGTTCGCCAAGCGCCCGGGCAGTGTCTGGAGTGGATGG

GATGGATCAACCCTAACTCGGGGGGAACCAACTCGGCCCAAAAGTTCCAG

GACCGGGTCACCATTACAAGAGTCACGTCCATCAACACTGCCTACATGGA

GTTGAGCCGGCTGCGATCAGACGACACCGCCGTGTACTTCTGCGCGAGGG

ACCGCCTCGTCCTCCCGTGGTTTGGAGAGATCTTCCCGGATGCCTTCGAC

ATTTGGGGACAGGGGACCCTCGTGACTGTGTCCAGC
```

The DNA sequence of the 9H9x2B3(DD) light chain variable sequence was as follows:

(SEQ ID NO: 187)
```
GATATCCAGATGACCCAGAGCCCGTCCACCCTTTCCGCGAGCGTCGGCGA

CAGAGTGACCATTACTTGTCGGGCCTCGCAAAGCATCTCCGGCTGGCTGG

CTTGGTACCAGCAAAAGCCTGGAAAGGCCCCTAAGCTGCTGATCTACAAG

GCCTCATCCCTGGAGTCCGGAGTGCCTTCACGCTTTTCGGGGAGCGGATC

GGGGACTGAGTTCACCCTCACCATTTCCTCCCTGCAACCCGACGATTTCG

CGACATACTACTGCCAGCAGTACTACGGTTCCTCGCGCACGTTCGGACAG

GGCACTAACGTCGAGATCAAG
```

As can be seen from FIG. 36 transient transfections showed improved production (expression) of the 9H9-2B3(DD) modified construct compared to the original (unmodified) 9H9-2B3 construct.

SUMMARY OF SEQUENCE LISTING

| | |
|---|---|
| SEQ ID NO: 1<br>3C2 $V_H$ CDR1 | GYYWS |
| SEQ ID NO: 2<br>3C2 $V_H$ CDR2 | YNYYSGSTNYNPSLKS |
| SEQ ID NO: 3<br>3C2 $V_H$ CDR3 | YPLIRGAFDY |
| SEQ ID NO: 4<br>3C2 $V_L$ CDR1 | RSSQNLLHTNGYNYLD |
| SEQ ID NO: 5<br>3C2 $V_L$ CDR2 | LGSNRAS |
| SEQ ID NO: 6<br>3C2 $V_L$ CDR3 | MQALQTPLT |
| SEQ ID NO: 7<br>2B3 $V_H$ CDR1 | GYYIH |
| SEQ ID NO: 8<br>2B3 $V_H$ CDR2 | WINPNSGGTNSAQKFQD |
| SEQ ID NO: 9<br>2B3 $V_H$ CDR3 | DRLVLPWFGEIFPDAFDI |
| SEQ ID NO: 10<br>2B3 $V_L$ CDR1 | RASQSIRSNLA |
| SEQ ID NO: 11<br>2B3 $V_L$ CDR2 | GASTRAT |
| SEQ ID NO: 12<br>2B3 $V_L$ CDR3 | QQYNNWPLT |
| SEQ ID NO: 13<br>3C2 $V_H$ - with<br>signal sequence | MKHLWFCLLLVAAPRWVLSQAQLQESGPGLVKPSETLSLTCTVSTGSIS<br>GYYWSWIRQPPGKGLEWIGYNYYSGSTNYNPSLKSRVTISIDTSKNQFS<br>LKLNSVTAADTAVYYCARYPLIRGAFDYWGQGTLVTVSS |
| SEQ ID NO: 14<br>3C2 $V_L$ - with<br>signal sequence | MRLPAQLLGLLMLWVSGSSGDIVMTQSPLSLPVTPGEPASISCRSSQNL<br>LHTNGYNYLDWYLQKPGQSPQLLIYLGSNRASGVPDRFSGSGSGTDFTL<br>KISRVEAEDVGVYYCMQALQTPLTFGGGTKVEIK |
| SEQ ID NO: 15<br>2B3 $V_H$ - with<br>signal sequence | MDWTWRILFLVAAATGAHSQVQLVQSGAEVKKPGASVKVSCKASGYTFT<br>GYYIHWVRQAPGQGLEWMGWINPNSGGTNSAQKFQDRVTITRVTSINTA<br>YMELSRLRSDDTAVYFCARDRLVLPWFGEIFPDAFDIWGQGTLVTVSS |
| SEQ ID NO: 16<br>2B3 $V_L$ - with<br>signal sequence | MEAPAQLLFLLLLWLPDSTGEIVMTQSPATLSVSPGERATLSCRASQSI<br>RSNLAWYQQKPGQAPRLLIYGASTRATGIPARFSGSGSGTEFTLTISSL<br>QSENFAVYYCQQYNNWPLTFGGGTKVEIK |

| SUMMARY OF SEQUENCE LISTING | |
|---|---|
| SEQ ID NO: 17<br>3C2 V_H -<br>without signal<br>sequence | QAQLQESGPGLVKPSETLSLTCTVSTGSISGYYWSWIRQPPGKGLEWIG<br>YNYYSGSTNYNPSLKSRVTISIDTSKNQFSLKLNSVTAADTAVYYCARY<br>PLIRGAFDYWGQGTLVTVSS |
| SEQ ID NO: 18<br>3C2 V_L -<br>without signal<br>sequence | DIVMTQSPLSLPVTPGEPASISCRSSQNLLHTNGYNYLDWYLQKPGQSP<br>QLLIYLGSNRASGVPDRFSGSGSGTDFTLKISRVEAEDVGVYYCMQALQ<br>TPLTFGGGTKVEIK |
| SEQ ID NO: 19<br>2B3 V_H -<br>without signal<br>sequence | QVQLVQSGAEVKKPGASVKVSCKASGYTFTGYYIHWVRQAPGQGLEWMG<br>WINPNSGGTNSAQKFQDRVTITRVTSINTAYMELSRLRSDDTAVYFCAR<br>DRLVLPWFGEIFPDAFDIWGQGTLVTVSS |
| SEQ ID NO: 20<br>2B3 V_L -<br>without signal<br>sequence | EIVMTQSPATLSVSPGERATLSCRASQSIRSNLAWYQQKPGQAPRLLIY<br>GASTRATGIPARFSGSGSGTEFTLTISSLQSENFAVYYCQQYNNWPLTF<br>GGGTKVEIK |
| SEQ ID NO: 21<br>3C2 V_H DNA<br>Sequence - with<br>signal sequence | ATGAAACATCTGTGGTTCTGCCTTCTCCTGGTGGCAGCTCCCAGATGGG<br>TCCTGTCCCAGGCGCAGCTGCAGGAGTCGGGCCCAGGACTGGTGAAGCC<br>TTCGGAGACCCTGTCCCTCACCTGCACTGTCTCTACTGGCTCCATCAGT<br>GGTTACTACTGGAGCTGGATCCGGCAGCCCCAGGGAAGGGACTGGAGT<br>GGATTGGGTATAATTATTACAGTGGGAGCACCAACTACAACCCCTCCCT<br>CAAGAGTCGAGTCACCATATCAATAGACACGTCCAAGAACCAGTTCTCC<br>CTGAAGCTGAATTCTGTGACCGCTGCGGACACGGCCGTATATTACTGTG<br>CGAGATATCCTCTGATTCGGGGAGCTTTTGACTACTGGGGCCAGGGAAC<br>CCTGGTCACCGTCTCCTCA |
| SEQ ID NO: 22<br>3C2 V_L DNA<br>Sequence - with<br>signal sequence | ATGAGGCTCCCTGCTCAGCTCCTGGGGCTGCTAATGCTCTGGGTCTCTG<br>GATCCAGTGGGGATATTGTGATGACTCAGTCTCCACTCTCCCTGCCCGT<br>CACCCCTGGAGAGCCGGCCTCCATCTCCTGTAGGTCTAGTCAGAACCTC<br>CTGCATACTAATGGCTACAACTATTTGGATTGGTACCTGCAGAAGCCAG<br>GGCAGTCTCCACAGCTCCTGATCTATTTGGGTTCTAATCGGGCCTCCGG<br>GGTCCCTGACAGGTTCAGTGGCAGTGGATCAGGCACAGATTTTACACTG<br>AAAATCAGCAGAGTGGAGGCTGAGGATGTTGGGGTTTATTACTGCATGC<br>AAGCTCTACAAACTCCGCTCACTTTCGGCGGAGGGACCAAGGTGGAGAT<br>CAAA |
| SEQ ID NO: 23<br>2B3 V_H DNA<br>Sequence - with<br>signal sequence | ATGGACTGGACCTGGAGGATCCTCTTCTTGGTGGCAGCAGCCACAGGAG<br>CCCACTCCCAGGTGCAGCTGGTGCAGTCTGGGGCTGAGGTGAAGAAGCC<br>TGGGGCCTCAGTGAAGGTCTCCTGCAAGGCTTCTGGATACACCTTCACC<br>GGCTACTATATACACTGGGTGCGACAGGCCCCTGGACAAGGGCTTGAGT<br>GGATGGGATGGATCAACCCTAACAGTGGTGGCACAAACTCTGCACAGAA<br>GTTTCAGGACAGGGTCACCATCACCAGGGTCACGTCCATCAACACAGCC<br>TACATGGAGCTGAGCAGACTGAGATCTGACGACACGGCCGTGTATTTCT<br>GTGCGAGAGATCGGCTCGTATTACCATGGTTCGGGGAAATATTCCCAGA<br>TGCTTTTGATATCTGGGGCCAAGGGACATTGGTCACCGTCTCTTCA |
| SEQ ID NO: 24<br>2B3 V_L DNA<br>Sequence - with<br>signal sequence | ATGGAAGCCCCAGCGCAGCTTCTCTTCCTCCTGCTACTCTGGCTCCCAG<br>ATTCCACTGGAGAAATAGTGATGACGCAGTCTCCAGCCACCCTGTCTGT<br>GTCTCCAGGGGAAAGAGCCACCCTCTCCTGCAGGGCCAGTCAGAGTATT<br>AGGAGCAACTTAGCCTGGTATCAGCAGAAACCTGGCCAGGCTCCCAGGC<br>TCCTCATCTATGGTGCATCCACCAGGGCCACTGGTATCCCAGCCAGGTT<br>CAGTGGCAGTGGGTCTGGGACAGAGTTCACTCTCACCATCAGCAGCCTG<br>CAGTCTGAAAATTTTGCAGTTTATTACTGTCAGCAGTATAATAACTGGC<br>CTCTCACTTTCGGCGGAGGGACCAAGGTGGAGATCAAA |
| SEQ ID NO: 25<br>3C2 V_H DNA<br>Sequence -<br>without signal<br>sequence | CAGGCGCAGCTGCAGGAGTCGGGCCCAGGACTGGTGAAGCCTTCGGAGA<br>CCCTGTCCCTCACCTGCACTGTCTCTACTGGCTCCATCAGTGGTTACTA<br>CTGGAGCTGGATCCGGCAGCCCCAGGGAAGGGACTGGAGTGGATTGGG<br>TATAATTATTACAGTGGGAGCACCAACTACAACCCCTCCCTCAAGAGTC<br>GAGTCACCATATCAATAGACACGTCCAAGAACCAGTTCTCCCTGAAGCT<br>GAATTCTGTGACCGCTGCGGACACGGCCGTATATTACTGTGCGAGATAT<br>CCTCTGATTCGGGGAGCTTTTGACTACTGGGGCCAGGGAACCCTGGTCA<br>CCGTCTCCTCA |
| SEQ ID NO: 26<br>3C2 V_L DNA<br>Sequence -<br>without signal<br>sequence | GATATTGTGATGACTCAGTCTCCACTCTCCCTGCCCGTCACCCCTGGAG<br>AGCCGGCCTCCATCTCCTGTAGGTCTAGTCAGAACCTCCTGCATACTAA<br>TGGCTACAACTATTTGGATTGGTACCTGCAGAAGCCAGGGCAGTCTCCA<br>CAGCTCCTGATCTATTTGGGTTCTAATCGGGCCTCCGGGGTCCCTGACA<br>GGTTCAGTGGCAGTGGATCAGGCACAGATTTTACACTGAAAATCAGCAG<br>AGTGGAGGCTGAGGATGTTGGGGTTTATTACTGCATGCAAGCTCTACAA<br>ACTCCGCTCACTTTCGGCGGAGGGACCAAGGTGGAGATCAAA |

| SUMMARY OF SEQUENCE LISTING | |
|---|---|
| SEQ ID NO: 27<br>2B3 $V_H$ DNA<br>Sequence -<br>without signal<br>sequence | CAGGTGCAGCTGGTGCAGTCTGGGGCTGAGGTGAAGAAGCCTGGGGCCT<br>CAGTGAAGGTCTCCTGCAAGGCTTCTGGATACACCTTCACCGGCTACTA<br>TATACACTGGGTGCGACAGGCCCCTGGACAAGGGCTTGAGTGGATGGGA<br>TGGATCAACCCTAACAGTGGTGGCACAAACTCTGCACAGAAGTTTCAGG<br>ACAGGGTCACCATCACCAGGGTCACGTCCATCAACACAGCCTACATGGA<br>GCTGAGCAGACTGAGATCTGACGACACGGCCGTGTATTTCTGTGCGAGA<br>GATCGGCTCGTATTACCATGGTTCGGGGAAATATTCCCAGATGCTTTTG<br>ATATCTGGGGCCAAGGGACATTGGTCACCGTCTCTTCA |
| SEQ ID NO: 28<br>2B3 $V_L$ DNA<br>Sequence -<br>without signal<br>sequence | GAAATAGTGATGACGCAGTCTCCAGCCACCCTGTCTGTGTCTCCAGGGG<br>AAAGAGCCACCCTCTCCTGCAGGGCCAGTCAGAGTATTAGGAGCAACTT<br>AGCCTGGTATCAGCAGAAACCTGGCCAGGCTCCCAGGCTCCTCATCTAT<br>GGTGCATCCACCAGGGCCACTGGTATCCCAGCCAGGTTCAGTGGCAGTG<br>GGTCTGGGACAGAGTTCACTCTCACCATCAGCAGCCTGCAGTCTGAAAA<br>TTTTGCAGTTTATTACTGTCAGCAGTATAATAACTGGCCTCTCACTTTC<br>GGCGGAGGGACCAAGGTGGAGATCAAA |
| SEQ ID NO: 29<br>7H7 $V_H$ CDR1 | TSWMS |
| SEQ ID NO: 30<br>7H7 $V_H$ CDR2 | NIKQDGSEKYYVDSVKG |
| SEQ ID NO: 31<br>7H7 $V_H$ CDR3 | DRPVAGASAL |
| SEQ ID NO: 32<br>7H7 $V_L$ CDR1 | RASQSISGWLA |
| SEQ ID NO: 33<br>7H7 $V_L$ CDR2 | KASSLES |
| SEQ ID NO: 34<br>7H7 $V_L$ CDR3 | QQYYGSSRT |
| SEQ ID NO: 35<br>1B3 $V_H$ CDR1 | TSWMS |
| SEQ ID NO: 36<br>1B3 $V_H$ CDR2 | NIKQDGSEKYYVDSVKG |
| SEQ ID NO: 37<br>1B3 $V_H$ CDR3 | DRPVAGASAL |
| SEQ ID NO: 38<br>1B3 $V_L$ CDR1 | RASQSISGWLA |
| SEQ ID NO: 39<br>1B3 $V_L$ CDR2 | KASSLES |
| SEQ ID NO: 40<br>1B3 $V_L$ CDR3 | QQYYGSSRT |
| SEQ ID NO: 41<br>3B6 $V_H$ CDR 1 | TYWMS |
| SEQ ID NO: 42<br>3B6 $V_H$ CDR2 | NIKQDGSEKYYVDSVKG |
| SEQ ID NO: 43<br>3B6 $V_H$ CDR3 | DRPVAGASAL |
| SEQ ID NO: 44<br>3B6 $V_L$ CDR1 | RASQSISGWLA |
| SEQ ID NO: 45<br>3B6 $V_L$ CDR2 | KASSLES |
| SEQ ID NO: 46<br>3B6 $V_L$ CDR3 | QQYYGSSRT |
| SEQ ID NO: 47<br>8B1 $V_H$ CDR1 | THWMS |
| SEQ ID NO: 48<br>8B1 $V_H$ CDR2 | NIKQDGSEKYYVDSVKG |

-continued

| SUMMARY OF SEQUENCE LISTING |
|---|

SEQ ID NO: 49　　　DRPVAGASAL
8B1 V_H CDR3

SEQ ID NO: 50　　　RASQSISGWLA
8B1 V_L CDR1

SEQ ID NO: 51　　　KASSLES
8B1 V_L CDR2

SEQ ID NO: 52　　　QQYYGSSRT
8B1 V_L CDR3

SEQ ID NO: 53　　　SSWMS
4A3 V_H CDR1

SEQ ID NO: 54　　　NIKQDGSEKYYVDSVKG
4A3 V_H CDR2

SEQ ID NO: 55　　　DRPVAGASAL
4A3 V_H CDR3

SEQ ID NO: 56　　　RASQSISGWLA
4A3 V_L CDR1

SEQ ID NO: 57　　　KASSLES
4A3 V_L CDR2

SEQ ID NO: 58　　　QQYYGSSRT
4A3 V_L CDR3

SEQ ID NO: 59　　　TYWMS
9H9 V_H CDR1

SEQ ID NO: 60　　　NIKQDGSEKYYVDSVKG
9H9 V_H CDR2

SEQ ID NO: 61　　　DRPVAGASAL
9H9 V_H CDR3

SEQ ID NO: 62　　　RASQSISGWLA
9H9 V_L CDR1

SEQ ID NO: 63　　　KASSLES
9H9 V_L CDR2

SEQ ID NO: 64　　　QQYYGSSRT
9H9 V_L CDR3

SEQ ID NO: 65　　　MELGLSXVFLVAILEGVQCEVQLVESGGGLVQPGGSLRLSCAASGGTIS
7H7 V_H - with　　TSWMSWVRQAPGKGLEWVANIKQDGSEKYYVDSVKGRFTISRDNAKNSL
signal sequence　YLQMNSLRVEDTAIYYCARDRPVAGASALWGQGTLVTVSS SEQ ID NO: 66　　　MRVPAQLLGLLLLWLPGAKCDIQMTQSPSTLSASVGDRVTITCRASQSI
7H7 V_L - with　　SGWLAWYQQKQGKAPKLLIYKASSLESGVPSRFSGSGSGTEFTLTISSL
signal sequence　QPDDFATYYCQQYYGSSRTFGQGTNVEIK SEQ ID NO: 67　　　MELGLSWVFLVAILEGVQCEVQLVESGGGLVQPGGSLRLSCAASGGTIS
1B3 V_H - with　　TSWMSWVRQAPGKGLEWVANIKQDGSEKYYVDSVKGRFTISRDNAKNSL
signal sequence　YLQMNSLRVEDTAMYYCARDRPVAGASALWGQGTLVTVSS SEQ ID NO: 68　　　MRVPAQLLGLLLLWLPGAKCDIQMTQSPSTLSASVGDRVTITCRASQSI
1B3 V_L - with　　SGWLAWYQQKPGKAPKLLIYKASSLESGVPSRFSGSGSGTEFTLTISSL
signal sequence　QPDDFATYYCQQYYGSSRTFGQGTNVEIK SEQ ID NO: 69　　　MELGLSWVFLVAILEGVQCEVQLVESGGGLVQPGGSLRLSCAASGGTTS
3B6 V_H - with　　TYWMSWVRQAPGKGLEWVANIKQDGSEKYYVDSVKGRFTISRDNAKNSL
signal sequence　NLQMNSLRVEDTAIYYCARDRPVAGASALWGQGTLVTVSS SEQ ID NO: 70　　　MRVPAQLLGLLLLWLPGAKCDIQMTQSPSTLSASVGDRVTITCRASQSI
3B6 V_L - with　　SGWLAWYQQKPGKAPKLLIYKASSLESGVPSRFSGSGSGTEFTLTISSL
signal sequence　QPDDFATYYCQQYYGSSRTFGQGTNVEIK SEQ ID NO: 71　　　MELGLSWVFLVAILEGVKCEVRLVESGGGLVQPGGSLRLSCAASGDIIS
8B1 V_H - with　　THWMSWVRQAPGKGLEWVANIKQDGSEKYYVDSVKGRFTISRDNAKNSL
signal sequence　YLQMNTLRVEDTAIYYCTRDRPVAGASALWGQGTLVTVSS

SUMMARY OF SEQUENCE LISTING

SEQ ID NO: 72
8B1 V$_L$ - with signal sequence
MRVPAQLLGLLLLWLPGAKCDIQMTQSPSTLSASVGDRVTITCRASQSISGWLAWYQQKPGKAPKLLIYKASSLESGVPLRFSGSGSGTEFTLTISSLQPDDFATYYCQQYYGSSRTFGQGTNVEIK SEQ ID NO: 73
4A3 V$_H$ - with signal sequence
MELGLSWVFLVAILEGVQCEVQLVESGGGLVQPGGSLRLSCAASGGIISSSWMSWVRQAPGKGLEWVANIKQDGSEKYYVDSVKGRFTISRDNAKDLLYLQMNSLRVEDTALYYCARDRPVAGASALWGQGTLVTVSS SEQ ID NO: 74
4A3 V$_L$ - with signal sequence
MRVPAQLLGLLLLWLPGAKCDIQMTQSPSTLSASVGDRVTITCRASQSISGWLAWYQQKPGKAPKLLIYKASSLESGVPSRFSGSGSGTEFTLTISSLQPDDFATYYCQQYYGSSRTFGQGTNVEIK SEQ ID NO: 75
9H9 V$_H$ - with signal sequence
MELGLSWVFLVAILEGVQCEVQLVESGGGLVQPGGSLRLSCAASGGIISTYWMSWVRQAPGKGLEWVANIKQDGSEKYYVDSVKGRFTISRDNAKNSLYLQMNSLRVEDTAMYYCARDRPVAGASALWGQGTLVTVSS SEQ ID NO: 76
9H9 V$_L$ - with signal sequence
MRVPAQLLGLLLLWLPGAKCDIQMTQSPSTLSASVGDRVTITCRASQSISGWLAWYQQKPGKAPKLLIYKASSLESGVPSRFSGSGSGTEFTLTISSLQPDDFATYYCQQYYGSSRTFGQGTNVEIK SEQ ID NO: 77
7H7 V$_H$ - without signal sequence
EVQLVESGGGLVQPGGSLRLSCAASGGTISTSWMSWVRQAPGKGLEWVANIKQDGSEKYYVDSVKGRFTISRDNAKNSLYLQMNSLRVEDTAIYYCARDRPVAGASALWGQGTLVTVSS SEQ ID NO: 78
7H7 V$_L$ - without signal sequence
DIQMTQSPSTLSASVGDRVTITCRASQSISGWLAWYQQKQGKAPKLLIYKASSLESGVPSRFSGSGSGTEFTLTISSLQPDDFATYYCQQYYGSSRTFGQGTNVEIK SEQ ID NO: 79
1B3 V$_H$ - without signal sequence
EVQLVESGGGLVQPGGSLRLSCAASGGTISTSWMSWVRQAPGKGLEWVANIKQDGSEKYYVDSVKGRFTISRDNAKNSLYLQMNSLRVEDTAMYYCARDRPVAGASALWGQGTLVTVSS SEQ ID NO: 80
1B3 V$_L$ - without signal sequence
DIQMTQSPSTLSASVGDRVTITCRASQSISGWLAWYQQKPGKAPKLLIYKASSLESGVPSRFSGSGSGTEFTLTISSLQPDDFATYYCQQYYGSSRTFGQGTNVEIK SEQ ID NO: 81
3B6 V$_H$ - without signal sequence
EVQLVESGGGLVQPGGSLRLSCAASGGTTSTYWMSWVRQAPGKGLEWVANIKQDGSEKYYVDSVKGRFTISRDNAKNSLNLQMNSLRVEDTAIYYCARDRPVAGASALWGQGTLVTVSS SEQ ID NO: 82
3B6 V$_L$ - without signal sequence
DIQMTQSPSTLSASVGDRVTITCRASQSISGWLAWYQQKPGKAPKLLIYKASSLESGVPSRFSGSGSGTEFTLTISSLQPDDFATYYCQQYYGSSRTFGQGTNVEIK SEQ ID NO: 83
8B1 V$_H$ - without signal sequence
EVRLVESGGGLVQPGGSLRLSCAASGDIISTHWMSWVRQAPGKGLEWVANIKQDGSEKYYVDSVKGRFTISRDNAKNSLYLQMNTLRVEDTAIYYCTRDRPVAGASALWGQGTLVTVSS SEQ ID NO: 84
8B1 V$_L$ - without signal sequence
DIQMTQSPSTLSASVGDRVTITCRASQSISGWLAWYQQKPGKAPKLLIYKASSLESGVPLRFSGSGSGTEFTLTISSLQPDDFATYYCQQYYGSSRTFGQGTNVEIK SEQ ID NO: 85
4A3 V$_H$ - without signal sequence
EVQLVESGGGLVQPGGSLRLSCAASGGIISSSWMSWVRQAPGKGLEWVANIKQDGSEKYYVDSVKGRFTISRDNAKDLLYLQMNSLRVEDTALYYCARDRPVAGASALWGQGTLVTVSS SEQ ID NO: 86
4A3 V$_L$ - without signal sequence
DIQMTQSPSTLSASVGDRVTITCRASQSISGWLAWYQQKPGKAPKLLIYKASSLESGVPSRFSGSGSGTEFTLTISSLQPDDFATYYCQQYYGSSRTFGQGTNVEIK SEQ ID NO: 87
9H9 V$_H$ - without signal sequence
EVQLVESGGGLVQPGGSLRLSCAASGGIISTYWMSWVRQAPGKGLEWVANIKQDGSEKYYVDSVKGRFTISRDNAKNSLYLQMNSLRVEDTAMYYCARDRPVAGASALWGQGTLVTVSS

| SUMMARY OF SEQUENCE LISTING | |
|---|---|
| SEQ ID NO: 88<br>9H9 V$_L$ -<br>without signal<br>sequence | DIQMTQSPSTLSASVGDRVTITCRASQSISGWLAWYQQKPGKAPKLLIY<br>KASSLESGVPSRFSGSGSGTEFTLTISSLQPDDFATYYCQQYYGSSRTF<br>GQGTNVEIK |
| SEQ ID NO: 89<br>7H7 V$_H$ DNA<br>Sequence - with<br>signal sequence | ATGGAATTGGGGCTGAGCTGNGTTTTCCTTGTTGCTATTTTAGAAGGTG<br>TCCAGTGTGAGGTGCAACTGGTGGAGTCTGGGGGAGGCTTGGTCCAGCC<br>TGGGGGGTCCCTGAGACTCTCCTGTGCAGCCTCTGGAGGCACCATTAGT<br>ACCTCTTGGATGAGCTGGGTCCGCCAGGCTCCAGGGAAGGGGCTGGAAT<br>GGGTGGCCAACATAAAGCAAGATGGAAGTGAGAAATATTATGTGGACTC<br>TGTGAAGGGCCGATTCACCATCTCCAGAGACAACGCCAAGAACTCACTG<br>TATTTGCAAATGAACAGCCTGAGAGTCGAGGACACGGCTATATATTACT<br>GTGCGAGAGATCGTCCAGTGGCTGGTGCGTCGGCCCTCTGGGGCCAGGG<br>AACCCTGGTCACCGTCTCCTCA |
| SEQ ID NO: 90<br>7H7 V$_L$ DNA<br>Sequence - with<br>signal sequence | ATGAGGGTCCCCGCTCAGCTCCTGGGGCTCCTGCTGCTCTGGCTCCCAG<br>GTGCCAAATGTGACATCCAGATGACCCAGTCTCCTTCCACCCTGTCTGC<br>ATCTGTAGGAGACAGAGTCACCATCACTTGCCGGGCCAGTCAGAGTATA<br>AGTGGCTGGTTGGCCTGGTATCAGCAGAAACAAGGGAAAGCCCCTAAGC<br>TCCTGATCTATAAGGCGTCTAGTTTAGAAAGTGGGGTCCCATCAAGGTT<br>CAGCGGCAGTGGATCTGGGACAGAATTCACTCTCACCATCAGCAGCCTG<br>CAGCCTGATGATTTTGCAACTTATTACTGCCAACAGTATTATGGTTCTT<br>CTCGGACGTTCGGCCAAGGGACCAATGTGGAAATCAAA |
| SEQ ID NO: 91<br>1B3 V$_H$ DNA<br>Sequence - with<br>signal sequence | ATGGAATTGGGGCTGAGCTGGGTTTTCCTTGTTGCTATTTTAGAAGGTG<br>TCCAGTGTGAGGTGCAACTGGTGGAGTCTGGGGGAGGCTTGGTCCAGCC<br>TGGGGGGTCCCTGAGACTCTCCTGTGCAGCCTCTGGAGGCACCATTAGT<br>ACCTCTTGGATGAGCTGGGTCCGCCAGGCTCCAGGGAAGGGGCTGGAAT<br>GGGTGGCCAACATAAAGCAAGATGGAAGTGAGAAATATTATGTGGACTC<br>TGTGAAGGGCCGATTCACCATCTCCAGAGACAACGCCAAGAACTCACTG<br>TATTTGCAAATGAACAGCCTGAGAGTCGAAGACACGGCTATGTATTACT<br>GTGCGAGAGATCGTCCAGTGGCTGGTGCGTCGGCCCTCTGGGGCCAGGG<br>AACCCTGGTCACCGTCTCCTCA |
| SEQ ID NO: 92<br>1B3 V$_L$ DNA<br>Sequence - with<br>signal sequence | ATGAGGGTCCCCGCTCAGCTCCTGGGGCTCCTGCTGCTCTGGCTCCCAG<br>GTGCCAAATGTGACATCCAGATGACCCAGTCTCCTTCCACCCTGTCTGC<br>ATCTGTAGGAGACAGAGTCACCATCACTTGCCGGGCCAGTCAGAGTATT<br>AGTGGCTGGTTGGCCTGGTATCAGCAGAAACCAGGGAAAGCCCCTAAGC<br>TCCTGATCTATAAGGCGTCTAGTTTAGAAAGTGGGGTCCCATCAAGGTT<br>CAGCGGCAGTGGATCTGGGACAGAATTCACTCTCACCATCAGCAGCCTG<br>CAGCCTGATGATTTTGCAACTTATTACTGCCAACAGTATTATGGTTCTT<br>CTCGGACGTTCGGCCAAGGGACCAATGTGGAAATCAAA |
| SEQ ID NO: 93<br>3B6 V$_H$ DNA<br>Sequence - with<br>signal sequence | ATGGAATTGGGGCTGAGCTGGGTTTTCCTTGTTGCTATTTTAGAAGGTG<br>TCCAGTGTGAGGTGCAACTGGTGGAGTCTGGGGGAGGCTTGGTCCAGCC<br>TGGGGGGTCCCTGAGACTCTCCTGTGCAGCCTCTGGAGGCACAACCAGT<br>ACCTATTGGATGAGCTGGGTCCGCCAGGCTCCAGGGAAGGGGCTGGAAT<br>GGGTGGCCAACATAAAGCAAGATGGAAGTGAGAAATATTATGTGGACTC<br>TGTGAAGGGCCGATTCACCATCTCCAGAGACAACGCCAAGAACTCACTG<br>AATTTGCAAATGAACAGCCTGAGAGTCGAGGACACGGCTATATATTACT<br>GTGCGAGAGATCGTCCAGTGGCTGGTGCGTCGGCCCTCTGGGGCCAGGG<br>AACCCTGGTCACCGTCTCCTCA |
| SEQ ID NO: 94<br>3B6 V$_L$ DNA<br>Sequence - with<br>signal sequence | ATGAGGGTCCCCGCTCAGCTCCTGGGGCTCCTGCTGCTCTGGCTCCCAG<br>GTGCCAAATGTGACATCCAGATGACCCAGTCTCCTTCCACCCTGTCTGC<br>ATCTGTAGGAGACAGAGTCACCATCACTTGCCGGGCCAGTCAGAGTATT<br>AGTGGCTGGTTGGCCTGGTATCAGCAGAAACAGGGAAAGCCCCTAAGC<br>TCCTGATCTATAAGGCGTCTAGTTTAGAAAGTGGGGTCCCATCAAGGTT<br>CAGCGGCAGTGGATCTGGGACAGAATTCACTCTCACCATCAGCAGCCTG<br>CAGCCTGATGATTTTGCAACTTATTACTGCCAACAGTATTATGGTTCTT<br>CTCGGACGTTCGGCCAAGGGACCAATGTGGAAATCAAA |
| SEQ ID NO: 95<br>8B1 V$_H$ DNA<br>Sequence - with<br>signal sequence | ATGGAATTGGGGCTGAGCTGGGTTTTCCTTGTTGCTATTTTAGAAGGTG<br>TCAAGTGTGAGGTGCGACTGGTGGAGTCTGGGGGAGGCTTGGTCCAGCC<br>TGGGGGGTCCCTGAGACTCTCCTGTGCAGCCTCTGGAGACATAATTAGT<br>ACCCATTGGATGAGCTGGGTCCGCCAGGCTCCAGGGAAGGGGCTGGAAT<br>GGGTGGCCAACATAAAACAAGATGGAAGTGAGAAGTATTATGTGGACTC<br>TGTGAAGGGCCGATTCACCATCTCCAGAGACAACGCCAAGAACTCACTG<br>TATTTGCAAATGAACACCCTGAGAGTCGAGGACACGGCTATATATTACT<br>GTACGAGAGATCGTCCAGTGGCTGGTGCGTCGGCCCTCTGGGGCCAGGG<br>AACCCTGGTCACCGTCTCCTCA |
| SEQ ID NO: 96<br>8B1 V$_L$ DNA<br>Sequence - with<br>signal sequence | ATGAGGGTCCCCGCTCAGCTCCTGGGGCTCCTGCTGCTCTGGCTCCCAG<br>GTGCCAAATGTGACATCCAGATGACCCAGTCTCCTTCCACCCTGTCTGC<br>ATCTGTAGGAGACAGAGTCACCATCACTTGCCGGGCCAGTCAGAGTATT<br>AGTGGCTGGTTGGCCTGGTATCAGCAGAAACCAGGGAAAGCCCCTAAGC |

| | SUMMARY OF SEQUENCE LISTING |
|---|---|
| | TCCTGATCTATAAGGCGTCTAGTTTAGAAAGTGGGGTCCCATTAAGGTT<br>CAGCGGCAGTGGATCTGGGACAGAATTCACTCTCACCATCAGCAGCCTG<br>CAGCCTGATGATTTTGCAACTTATTACTGCCAACAGTATTATGGTTCTT<br>CTCGGACGTTCGGCCAAGGGACCAATGTGGAAATCAAA |
| SEQ ID NO: 97<br>4A3 $V_H$ DNA<br>Sequence - with<br>signal sequence | ATGGAATTGGGGCTGAGCTGGGTTTTCCTTGTTGCTATTTTAGAAGGTG<br>TCCAGTGTGAGGTGCAACTGGTGGAGTCTGGGGGAGGCTTGGTCCAGCC<br>GGGGGGGTCCCTGAGACTCTCCTGTGCAGCCTCTGGAGGCATCATTAGT<br>TCCTCTTGGATGAGCTGGGTCCGCCAGGCTCCAGGGAAGGGGCTGGAAT<br>GGGTGGCCAACATAAAGCAAGATGGAAGTGAGAAATATTATGTGGACTC<br>TGTGAAGGGCCGATTCACCATCTCCAGAGACAACGCCAAGAACTTACTG<br>TATTTGCAAATGAACAGCCTGAGAGTCGAGGACACGGCTTTATATTACT<br>GTGCGAGAGATCGTCCAGTGGCTGGTGCGTCGGCCCTCTGGGGCCAGGG<br>AACCCTGGTCACCGTCTCCTCT |
| SEQ ID NO: 98<br>4A3 $V_L$ DNA<br>Sequence - with<br>signal sequence | ATGAGGGTCCCCGCTCAGCTCCTGGGGCTCCTGCTGCTCTGGCTCCCAG<br>GTGCCAAATGTGACATCCAGATGACCCAGTCTCCTTCCACCCTGTCTGC<br>ATCTGTAGGAGACAGAGTCACCATCACTTGCCGGGCCAGTCAGAGTATT<br>AGTGGCTGGTTGGCCTGGTATCAGCAGAAACCAGGGAAAGCCCCTAAGC<br>TCCTGATCTATAAGGCGTCTAGTTTAGAAAGTGGGGTCCCATCAAGGTT<br>CAGCGGCAGTGGATCTGGGACAGAATTCACTCTCACCATCAGCAGCCTG<br>CAGCCTGATGATTTTGCAACTTATTACTGCCAACAGTATTATGGTTCTT<br>CTCGGACGTTCGGCCAAGGGACCAATGTGGAAATCAAA |
| SEQ ID NO: 99<br>9H9 $V_H$ DNA<br>Sequence - with<br>signal sequence | ATGGAATTGGGGCTGAGCTGGGTTTTCCTTGTTGCTATTTTAGAAGGTG<br>TCCAGTGTGAGGTGCAACTGGTGGAGTCTGGGGGAGGCTTGGTCCAGCC<br>TGGGGGGTCCCTGAGACTCTCCTGTGCAGCCTCTGGAGGCATCATTAGT<br>ACCTATTGGATGAGCTGGGTCCGCCAGGCTCCAGGGAAGGGGCTGGAAT<br>GGGTGGCCAACATAAAGCAAGATGGAAGTGAGAAATATTATGTGGACTC<br>TGTGAAGGGCCGATTCACCATCTCCAGAGACAACGCCAAGAACTCACTG<br>TATTTGCAAATGAACAGCCTGAGAGTCGAGGACACGGCTATGTATTACT<br>GTGCGAGAGATCGTCCAGTGGCTGGTGCGTCGGCCCTCTGGGGCCAGGG<br>AACCCTGGTCACCGTCTCCTCA |
| SEQ ID NO: 100<br>9H9 $V_L$ DNA<br>Sequence - with<br>signal sequence | ATGAGGGTCCCCGCTCAGCTCCTGGGGCTCCTGCTGCTCTGGCTCCCAG<br>GTGCCAAATGTGACATCCAGATGACCCAGTCTCCTTCCACCCTGTCTGC<br>ATCTGTAGGAGACAGAGTCACCATCACTTGCCGGGCCAGTCAGAGTATT<br>AGTGGCTGGTTGGCCTGGTATCAGCAGAAACCAGGGAAAGCCCCTAAGC<br>TCCTGATCTATAAGGCGTCTAGTTTAGAAAGTGGGGTCCCATCAAGGTT<br>CAGCGGCAGTGGATCTGGGACAGAATTCACTCTCACCATCAGCAGCCTG<br>CAGCCTGATGATTTTGCAACTTATTACTGCCAACAGTATTATGGTTCTT<br>CTCGGACGTTCGGCCAAGGGACCAATGTGGAAATCAAA |
| SEQ ID NO: 101<br>7H7 $V_H$ DNA<br>Sequence -<br>without signal<br>sequence | GAGGTGCAACTGGTGGAGTCTGGGGGAGGCTTGGTCCAGCCTGGGGGGT<br>CCCTGAGACTCTCCTGTGCAGCCTCTGGAGGCACCATTAGTACCTCTTG<br>GATGAGCTGGGTCCGCCAGGCTCCAGGGAAGGGGCTGGAATGGGTGGCC<br>AACATAAAGCAAGATGGAAGTGAGAAATATTATGTGGACTCTGTGAAGG<br>GCCGATTCACCATCTCCAGAGACAACGCCAAGAACTCACTGTATTTGCA<br>AATGAACAGCCTGAGAGTCGAGGACACGGCTATATATTCTGTGCGAGA<br>GATCGTCCAGTGGCTGGTGCGTCGGCCCTCTGGGGCCAGGGAACCCTGG<br>TCACCGTCTCCTCA |
| SEQ ID NO: 102<br>7H7 $V_L$ DNA<br>Sequence -<br>without signal<br>sequence | GACATCCAGATGACCCAGTCTCCTTCCACCCTGTCTGCATCTGTAGGAG<br>ACAGAGTCACCATCACTTGCCGGGCCAGTCAGAGTATAAGTGGCTGGTT<br>GGCCTGGTATCAGCAGAAACAAGGGAAAGCCCCTAAGCTCCTGATCTAT<br>AAGGCGTCTAGTTTAGAAAGTGGGGTCCCATCAAGGTTCAGCGGCAGTG<br>GATCTGGGACAGAATTCACTCTCACCATCAGCAGCCTGCAGCCTGATGA<br>TTTTGCAACTTATTACTGCCAACAGTATTATGGTTCTTCTCGGACGTTC<br>GGCCAAGGGACCAATGTGGAAATCAAA |
| SEQ ID NO: 103<br>1B3 $V_H$ DNA<br>Sequence -<br>without signal<br>sequence | GAGGTGCAACTGGTGGAGTCTGGGGGAGGCTTGGTCCAGCCTGGGGGGT<br>CCCTGAGACTCTCCTGTGCAGCCTCTGGAGGCACCATTAGTACCTCTTG<br>GATGAGCTGGGTCCGCCAGGCTCCAGGGAAGGGGCTGGAATGGGTGGCC<br>AACATAAAGCAAGATGGAAGTGAGAAATATTATGTGGACTCTGTGAAGG<br>GCCGATTCACCATCTCCAGAGACAACGCCAAGAACTCACTGTATTTGCA<br>AATGAACAGCCTGAGAGTCGAAGACACGGCTATGTATTACTGTGCGAGA<br>GATCGTCCAGTGGCTGGTGCGTCGGCCCTCTGGGGCCAGGGAACCCTGG<br>TCACCGTCTCCTCA |
| SEQ ID NO: 104<br>1B3 $V_L$ DNA<br>Sequence -<br>without signal<br>sequence | GACATCCAGATGACCCAGTCTCCTTCCACCCTGTCTGCATCTGTAGGAG<br>ACAGAGTCACCATCACTTGCCGGGCCAGTCAGAGTATTAGTGGCTGGTT<br>GGCCTGGTATCAGCAGAAACCAGGGAAAGCCCCTAAGCTCCTGATCTAT<br>AAGGCGTCTAGTTTAGAAAGTGGGGTCCCATCAAGGTTCAGCGGCAGTG<br>GATCTGGGACAGAATTCACTCTCACCATCAGCAGCCTGCAGCCTGATGA<br>TTTTGCAACTTATTACTGCCAACAGTATTATGGTTCTTCTCGGACGTTC<br>GGCCAAGGGACCAATGTGGAAATCAAA |

| SUMMARY OF SEQUENCE LISTING | |
|---|---|
| SEQ ID NO: 105<br>3B6 $V_H$ DNA<br>Sequence -<br>without signal<br>sequence | GAGGTGCAACTGGTGGAGTCTGGGGGAGGCTTGGTCCAGCCTGGGGGT<br>CCCTGAGACTCTCCTGTGCAGCCTCTGGAGGCACAACCAGTACCTATTG<br>GATGAGCTGGGTCCGCCAGGCTCCAGGGAAGGGGCTGGAATGGGTGGCC<br>AACATAAAGCAAGATGGAAGTGAGAAATATTATGTGGACTCTGTGAAGG<br>GCCGATTCACCATCTCCAGAGACAACGCCAAGAACTCACTGAATTTGCA<br>AATGAACAGCCTGAGAGTCGAGGACACGGCTATATATTACTGTGCGAGA<br>GATCGTCCAGTGGCTGGTGCGTCGGCCCTCTGGGGCCAGGGAACCCTGG<br>TCACCGTCTCCTCA |
| SEQ ID NO: 106<br>3B6 $V_L$ DNA<br>Sequence -<br>without signal<br>sequence | GACATCCAGATGACCCAGTCTCCTTCCACCCTGTCTGCATCTGTAGGAG<br>ACAGAGTCACCATCACTTGCCGGGCCAGTCAGAGTATTAGTGGCTGGTT<br>GGCCTGGTATCAGCAGAAACCAGGGAAAGCCCCTAAGCTCCTGATCTAT<br>AAGGCGTCTAGTTTAGAAAGTGGGGTCCCATCAAGGTTCAGCGGCAGTG<br>GATCTGGGACAGAATTCACTCTCACCATCAGCAGCCTGCAGCCTGATGA<br>TTTTGCAACTTATTACTGCCAACAGTATTATGGTTCTTCTCGGACGTTC<br>GGCCAAGGGACCAATGTGGAAATCAAA |
| SEQ ID NO: 107<br>8B1 $V_H$ DNA<br>Sequence -<br>without signal<br>sequence | GAGGTGCGACTGGTGGAGTCTGGGGGAGGCTTGGTCCAGCCTGGGGGT<br>CCCTGAGACTCTCCTGTGCAGCCTCTGGAGACATAATTAGTACCCATTG<br>GATGAGCTGGGTCCGCCAGGCTCCAGGGAAGGGGCTGGAATGGGTGGCC<br>AACATAAAACAAGATGGAAGTGAAGTATTATGTGGACTCTGTGAAGG<br>GCCGATTCACCATCTCCAGAGACAACGCCAAGAACTCACTGTATTTGCA<br>AATGAACACCCTGAGAGTCGAGGACACGGCTATATATTACTGTACGAGA<br>GATCGTCCAGTGGCTGGTGCGTCGGCCCTCTGGGGCCAGGGAACCCTGG<br>TCACCGTCTCCTCA |
| SEQ ID NO: 108<br>8B1 $V_L$ DNA<br>Sequence -<br>without signal<br>sequence | GACATCCAGATGACCCAGTCTCCTTCCACCCTGTCTGCATCTGTAGGAG<br>ACAGAGTCACCATCACTTGCCGGGCCAGTCAGAGTATTAGTGGCTGGTT<br>GGCCTGGTATCAGCAGAAACCAGGGAAAGCCCCTAAGCTCCTGATCTAT<br>AAGGCGTCTAGTTTAGAAAGTGGGGTCCCATTAAGGTTCAGCGGCAGTG<br>GATCTGGGACAGAATTCACTCTCACCATCAGCAGCCTGCAGCCTGATGA<br>TTTTGCAACTTATTACTGCCAACAGTATTATGGTTCTTCTCGGACGTTC<br>GGCCAAGGGACCAATGTGGAAATCAAA |
| SEQ ID NO: 109<br>4A3 $V_H$ DNA<br>Sequence -<br>without signal<br>sequence | GAGGTGCAACTGGTGGAGTCTGGGGGAGGCTTGGTCCAGCCGGGGGGT<br>CCCTGAGACTCTCCTGTGCAGCCTCTGGAGGCATCATTAGTTCCTCTTG<br>GATGAGCTGGGTCCGCCAGGCTCCAGGGAAGGGGCTGGAATGGGTGGCC<br>AACATAAAGCAAGATGGAAGTGAGAAATATTATGTGGACTCTGTGAAGG<br>GCCGATTCACCATCTCCAGAGACAACGCCAAAGACTTACTGTATTTGCA<br>AATGAACAGCCTGAGAGTCGAGGACACGGCTTTATATTACTGTGCGAGA<br>GATCGTCCAGTGGCTGGTGCGTCGGCCCTCTGGGGCCAGGGAACCCTGG<br>TCACCGTCTCCTCT |
| SEQ ID NO: 110<br>4A3 $V_L$ DNA<br>Sequence -<br>without signal<br>sequence | GACATCCAGATGACCCAGTCTCCTTCCACCCTGTCTGCATCTGTAGGAG<br>ACAGAGTCACCATCACTTGCCGGGCCAGTCAGAGTATTAGTGGCTGGTT<br>GGCCTGGTATCAGCAGAAACCAGGGAAAGCCCCTAAGCTCCTGATCTAT<br>AAGGCGTCTAGTTTAGAAAGTGGGGTCCCATCAAGGTTCAGCGGCAGTG<br>GATCTGGGACAGAATTCACTCTCACCATCAGCAGCCTGCAGCCTGATGA<br>TTTTGCAACTTATTACTGCCAACAGTATTATGGTTCTTCTCGGACGTTC<br>GGCCAAGGGACCAATGTGGAAATCAAA |
| SEQ ID NO: 111<br>9H9 $V_H$ DNA<br>Sequence -<br>without signal<br>sequence | GAGGTGCAACTGGTGGAGTCTGGGGGAGGCTTGGTCCAGCCTGGGGGT<br>CCCTGAGACTCTCCTGTGCAGCCTCTGGAGGCATCATTAGTACCTATTG<br>GATGAGCTGGGTCCGCCAGGCTCCAGGGAAGGGGCTGGAATGGGTGGCC<br>AACATAAAGCAAGATGGAAGTGAGAAATATTATGTGGACTCTGTGAAGG<br>GCCGATTCACCATCTCCAGAGACAACGCCAAGAACTCACTGTATTTGCA<br>AATGAACAGCCTGAGAGTCGAGGACACGGCTATGTATTACTGTGCGAGA<br>GATCGTCCAGTGGCTGGTGCGTCGGCCCTCTGGGGCCAGGGAACCCTGG<br>TCACCGTCTCCTCA |
| SEQ ID NO: 112<br>9H9 $V_L$ DNA<br>Sequence -<br>without signal<br>sequence | GACATCCAGATGACCCAGTCTCCTTCCACCCTGTCTGCATCTGTAGGAG<br>ACAGAGTCACCATCACTTGCCGGGCCAGTCAGAGTATTAGTGGCTGGTT<br>GGCCTGGTATCAGCAGAAACCAGGGAAAGCCCCTAAGCTCCTGATCTAT<br>AAGGCGTCTAGTTTAGAAAGTGGGGTCCCATCAAGGTTCAGCGGCAGTG<br>GATCTGGGACAGAATTCACTCTCACCATCAGCAGCCTGCAGCCTGATGA<br>TTTTGCAACTTATTACTGCCAACAGTATTATGGTTCTTCTCGGACGTTC<br>GGCCAAGGGACCAATGTGGAAATCAAA |
| SEQ ID NO: 113<br>3C2 $V_H$ CDR1<br>(Chothia) | TGSISGY |
| SEQ ID NO: 114<br>3C2 $V_H$ CDR2<br>(Chothia) | YYSGS |

-continued

| SUMMARY OF SEQUENCE LISTING |
| --- |

SEQ ID NO: 115  YPLIRGAFDY
3C2 V<sub>H</sub> CDR3
(Chothia)

SEQ ID NO: 116  RSSQNLLHTNGYNYLD
3C2 V<sub>L</sub> CDR1
(Chothia)

SEQ ID NO: 117  LGSNRAS
3C2 V<sub>L</sub> CDR2
(Chothia)

SEQ ID NO: 118  MQALQTPLT
3C2 V<sub>L</sub> CDR3
(Chothia)

SEQ ID NO: 119  GYTFTGY
2B3 V<sub>H</sub> CDR1
(Chothia)

SEQ ID NO: 120  NPNSGG
2B3 V<sub>H</sub> CDR2
(Chothia)

SEQ ID NO: 121  DRLVLPWFGEIFPDAFDI
2B3 V<sub>H</sub> CDR3
(Chothia)

SEQ ID NO: 122  RASQSIRSNLA
2B3 V<sub>L</sub> CDR1
(Chothia)

SEQ ID NO: 123  GASTRAT
2B3 V<sub>L</sub> CDR2
(Chothia)

SEQ ID NO: 124  QQYNNWPLT
2B3 V<sub>L</sub> CDR3
(Chothia)

SEQ ID NO: 125  GGTISTS
7H7 V<sub>H</sub> CDR1
(Chothia)

SEQ ID NO: 126  KQDGSE
7H7 V<sub>H</sub> CDR2
(Chothia)

SEQ ID NO: 127  DRPVAGASAL
7H7 V<sub>H</sub> CDR3
(Chothia)

SEQ ID NO: 128  RASQSISGWLA
7H7 V<sub>L</sub> CDR1
(Chothia)

SEQ ID NO: 129  KASSLES
7H7 V<sub>L</sub> CDR2
(Chothia)

SEQ ID NO: 130  QQYYGSSRT
7H7 V<sub>L</sub> CDR3
(Chothia)

SEQ ID NO: 131  GGTISTS
1B3 V<sub>H</sub> CDR1
(Chothia)

SEQ ID NO: 132  KQDGSE
1B3 V<sub>H</sub> CDR2
(Chothia)

SEQ ID NO: 133  DRPVAGASAL
1B3 V<sub>H</sub> CDR3
(Chothia)

-continued

| SUMMARY OF SEQUENCE LISTING |  |
| --- | --- |
| SEQ ID NO: 134<br>1B3 $V_L$ CDR1<br>(Chothia) | RASQSISGWLA |
| SEQ ID NO: 135<br>1B3 $V_L$ CDR2<br>(Chothia) | KASSLES |
| SEQ ID NO: 136<br>1B3 $V_L$ CDR3<br>(Chothia) | QQYYGSSRT |
| SEQ ID NO: 137<br>3B6 $V_H$ CDR1<br>(Chothia) | GGTTSTY |
| SEQ ID NO: 138<br>3B6 $V_H$ CDR2<br>(Chothia) | KQDGSE |
| SEQ ID NO: 139<br>3B6 $V_H$ CDR3<br>(Chothia) | DRPVAGASAL |
| SEQ ID NO: 140<br>3B6 $V_L$ CDR1<br>(Chothia) | RASQSISGWLA |
| SEQ ID NO: 141<br>3B6 $V_L$ CDR2<br>(Chothia) | KASSLES |
| SEQ ID NO: 142<br>3B6 $V_L$ CDR3<br>(Chothia) | QQYYGSSRT |
| SEQ ID NO: 143<br>8B1 $V_H$ CDR1<br>(Chothia) | GDIISTH |
| SEQ ID NO: 144<br>8B1 $V_H$ CDR2<br>(Chothia) | KQDGSE |
| SEQ ID NO: 145<br>8B1 $V_H$ CDR3<br>(Chothia) | DRPVAGASAL |
| SEQ ID NO: 146<br>8B1 $V_L$ CDR1<br>(Chothia) | RASQSISGWLA |
| SEQ ID NO: 147<br>8B1 $V_L$ CDR2<br>(Chothia) | KASSLES |
| SEQ ID NO: 148<br>8B1 $V_L$ CDR3<br>(Chothia) | QQYYGSSRT |
| SEQ ID NO: 149<br>4A3 $V_H$ CDR1<br>(Chothia) | GGIISSS |
| SEQ ID NO: 150<br>4A3 $V_H$ CDR2<br>(Chothia) | KQDGSE |
| SEQ ID NO: 151<br>4A3 $V_H$ CDR3<br>(Chothia) | DRPVAGASAL |
| SEQ ID NO: 152<br>4A3 $V_L$ CDR1<br>(Chothia) | RASQSISGWLA |

-continued

| SUMMARY OF SEQUENCE LISTING |  |
|---|---|
| SEQ ID NO: 153<br>4A3 $V_L$ CDR2<br>(Chothia) | KASSLES |
| SEQ ID NO: 154<br>4A3 $V_L$ CDR3<br>(Chothia) | QQYYGSSRT |
| SEQ ID NO: 155<br>9H9 $V_H$ CDR1<br>(Chothia) | GGIISTY |
| SEQ ID NO: 156<br>9H9 $V_H$ CDR2<br>(Chothia) | KQDGSE |
| SEQ ID NO: 157<br>9H9 $V_H$ CDR3<br>(Chothia) | DRPVAGASAL |
| SEQ ID NO: 158<br>9H9 $V_L$ CDR1<br>(Chothia) | RASQSISGWLA |
| SEQ ID NO: 159<br>9H9 $V_L$ CDR2<br>(Chothia) | KASSLES |
| SEQ ID NO: 160<br>9H9 $V_L$ CDR3<br>(Chothia) | QQYYGSSRT |
| SEQ ID NO: 161<br>CD27 antibody<br>$V_H$ CDR1<br>consensus<br>sequence<br>(Kabat) | GYY(W,I)(S,H) |
| SEQ ID NO: 162<br>CD27 antibody<br>$V_H$ CDR2<br>consensus<br>sequence<br>(Kabat) | (—,W)(Y,I)N(Y,P)(Y,N)SG(S,G)TN(Y,S)(N,A)(P,Q)<br>(S,K)(L,F)(K,Q)(S,D) |
| SEQ ID NO: 163<br>CD27 antibody<br>$V_H$ CDR3<br>consensus<br>sequence<br>(Kabat) | (—,D)(—,R)(—,L)(—,V)(—,L)(—,P)(—,W)(—,F)(—,G)<br>(—,E)(—,I)(-Y,F)P(L,—)(I,—)(R,—)(G,D)AFD(Y,I) |
| SEQ ID NO: 164<br>CD27 antibody<br>$V_L$ CDR1<br>consensus<br>sequence<br>(Kabat) | R(S,A)SQ(—,S)(—,I)(—,R)(—,S)NL(L,A)(H,—)(T,—)<br>(N,—)(G,—)(Y,—)(N,—)(Y,—)(L,—)(D,—) |
| SEQ ID NO: 165<br>CD27 antibody<br>$V_L$ CDR2<br>consensus<br>sequence<br>(Kabat) | (L,G)(G,A)S(N,T)RA(S,T) |
| SEQ ID NO: 166<br>CD27 antibody<br>$V_L$ CDR3<br>consensus<br>sequence<br>(Kabat) | (M,Q)Q(A,Y)(L,N)(Q,N)(T,W)PLT |

SUMMARY OF SEQUENCE LISTING

| | |
|---|---|
| SEQ ID NO: 167<br>PD-L1 antibody<br>V$_H$ CDR1<br>consensus<br>sequence<br>(Kabat) | (T,S)(S,Y,H)WMS |
| SEQ ID NO: 168<br>PD-L1 antibody<br>V$_H$ CDR2<br>consensus<br>sequence<br>(Kabat) | NIKQDGSEKYYVDSVKG |
| SEQ ID NO: 169<br>PD-L1 antibody<br>V$_H$ CDR3<br>consensus<br>sequence<br>(Kabat) | DRPVAGASAL |
| SEQ ID NO: 170<br>PD-L1 antibody<br>V$_L$ CDR1<br>consensus<br>sequence<br>(Kabat) | RASQSISGWLA |
| SEQ ID NO: 171<br>PD-L1 antibody<br>V$_L$ CDR2<br>consensus<br>sequence<br>(Kabat) | KASSLES |
| SEQ ID NO: 172<br>PD-L1 antibody<br>V$_L$ CDR3<br>consensus<br>sequence<br>(Kabat) | QQYYGSSRT |
| SEQ ID NO: 173<br>CD27 amino<br>acid sequence<br>(Accession No.<br>AAH12160.1) | MARPHPWWLCVLGTLVGLSATPAPKSCPERHYWAQGKLCCQMCEPGTFL<br>VKDCDQHRKAAQCDPCIPGVSFSPDHHTRPHCESCRHCNSGLLVRNCTI<br>TANAECACRNGWQCRDKECTECDPLPNPSLTARSSQALSPHPQPTHLPY<br>VSEMLEARTAGHMQTLADFRQLPARTLSTHWPPQRSLCSSDFIRILVIF<br>SGMFLVFTLAGALFLHQRRKYRSNKGESPVEPAEPCRYSCPREEEGSTI<br>PIQEDYRKPEPACSP |
| SEQ ID NO: 174<br>CD70 amino<br>acid sequence<br>(Accession No.<br>NP_001243) | MPEEGSGCSVRRRPYGCVLRAALVPLVAGLVICLVVCIQRFAQAQQQLP<br>LESLGWDVAELQLNHTGPQQDPRLYWQGGPALGRSFLHGPELDKGQLRI<br>HRDGIYMVHIQVTLAICSSTTASRHHPTTLAVGICSPASRSISLLRLSF<br>HQGCTIASQRLTPLARGDTLCTNLTGTLLPSRNTDETFFGVQWVRP |
| SEQ ID NO: 175<br>PD1 amino acid<br>sequence<br>(Accession No.<br>NP_005009) | MQIPQAPWPVVWAVLQLGWRPGWFLDSPDRPWNPPTFSPALLVVTEGDN<br>ATFTCSFSNTSESFVLNWYRMSPSNQTDKLAAFPEDRSQPGQDCRFRVT<br>QLPNGRDFHMSVVRARRNDSGTYLCGAISLAPKAQIKESLRAELRVTER<br>RAEVPTAHPSPSPRPAGQFQTLVVGVVGGLLGSLVLLVWVLAVICSRAA<br>RGTIGARRTGQPLKEDPSAVPVFSVDYGELDFQWREKTPEPPVPCVPEQ<br>TEYATIVFPSGMGTSSPARRGSADGPRSAQPLRPEDGHCSWPL |
| SEQ ID NO: 176<br>PD-L1 amino<br>acid sequence<br>(isoform b<br>precursor)<br>(Accession No.<br>NP_001254635) | MRIFAVFIFMTYWHLLNAPYNKINQRILVVDPVTSEHELTCQAEGYPKA<br>EVIWTSSDHQVLSGKTTTTNSKREEKLFNVTSTLRINTTTNEIFYCTFR<br>RLDPEENHTAELVIPELPLAHPPNERTHLVILGAILLCLGVALTFIFRL<br>RKGRMMDVKKCGIQDTNSKKQSDTHLEET |
| SEQ ID NO: 177<br>2B3 V$_H$<br>(modified) | QVQLVQSGAEVKKPGASVKVSCKASGYTFTGYYIHWVRQAPGQGLEWMG<br>WINPNSGGTNSACIKFQDRVTITRDTSINTAYMELSRLSDDTAVYFCA<br>RDRLVLPWFGEIFPDAFDIWGQGTLVTVSS |

| SUMMARY OF SEQUENCE LISTING | |
|---|---|
| SEQ ID NO: 178<br>2B3 V_L<br>(modified) | EIVMTQSPATLSVSPGERATLSCRASQSIRSNLAWYQQKPGQAPRLLIY<br>GASTRATGIPARFSGSGSGTEFTLTISSLQSEDFAVYYCQQYNNWPLTF<br>GGGTKVEIK |
| SEQ ID NO: 179<br>Full 9H9-2B3<br>(CDX-527)<br>heavy chain<br>sequence was as<br>follows (with the<br>IgG1 constant<br>region sequence<br>shown in bold) | EVQLVESGGGLVQPGGSLRLSCAASGGIISTYWMSWVRQAPGKGLEWVA<br>NIKQDGSEKYYVDSVKGRFTISRDNAKNSLYLQMNSLRVEDTAMYYCAR<br>DRPVAGASALWGQGTLVTVSSASTKGPSVFPLAPSSKSTSGGTAALGCL<br>VKDYFPEPVTVSWNSGALTSGVHTFPAVLQSSGLYSLSSVVTVPSSSLG<br>TQTYICNVNHKPSNTKVDKKVEPKSCDKTHTCPPCPAPELLGGPSVFLF<br>PPKPKDTLMISRTPEVTCVVVDVSHEDPEVKFNWYVDGVEVHNAKTKPR<br>EEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENN<br>YKTTPPVLDSDGSFFLYSKLTVDKSRWQQGNVFSCSVMHEALHNHYTQK<br>SLSLSPGK<u>GSSGGGGS</u>EIVMTQSPATLSVSPGERATLSCRASQSIRSNL<br>AWYQQKPGQAPRLLIYGASTRATGIPARFSGSGSGTEFTLTISSLQSEN<br>FAVYYCQQYNNWPLTFGCGTKVEIK<u>GGGGSGGGGSGGGGSGGGGS</u>QVQL<br>VQSGAEVKKPGASVKVSCKASGYTFTGYYIHWVRQAPGQCLEWMGWINP<br>NSGGTNSAQKFQDRVTITRVTSINTAYMELSRLRSDDTAVYFCARDRLV<br>LPWFGEIFPDAFDIWGQGTLVTVSS |
| SEQ ID NO: 180<br>9H9-2B3 (CDX-527)<br>light chain<br>sequence was as<br>follows (with the<br>constant region<br>sequence shown<br>in bold) | DIQMTQSPSTLSASVGDRVTITCRASQSISGWLAWYQQKPGKAPKLLIY<br>KASSLESGVPSRFSGSGSGTEFTLTISSLQPDDFATYYCQQYYGSSRTF<br>GQGTNVEIKRTVAAPSVFIFPPSDEQLKSGTASVVCLLNNFYPREAKVQ<br>WKVDNALQSGNSQESVTEQDSKDSTYSLSSTLTLSKADYEKHKVYACEV<br>THQGLSSPVTKSFNRGEC |
| SEQ ID NO: 181<br>Full 9H9-2B3(DD)<br>heavy chain<br>sequence was as<br>follows (with the<br>IgG1 constant<br>"backbone"<br>sequence shown<br>in bold) | EVQLVESGGGLVQPGGSLRLSCAASGGIISTYWMSWVRQAPGKGLEWVA<br>NIKQDGSEKYYVDSVKGRFTISRDNAKNSLYLQMNSLRVEDTAMYYCAR<br>DRPVAGASALWGQGTLVTVSSASTKGPSVFPLAPSSKSTSGGTAALGCL<br>VKDYFPEPVTVSWNSGALTSGVHTFPAVLQSSGLYSLSSVVTVPSSSLG<br>TQTYICNVNHKPSNTKVDKKVEPKSCDKTHTCPPCPAPELLGGPSVFLF<br>PPKPKDTLMISRTPEVTCVVVDVSHEDPEVKFNWYVDGVEVHNAKTKPR<br>EEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENN<br>YKTTPPVLDSDGSFFLYSKLTVDKSRWQQGNVFSCSVMHEALHNHYTQK<br>SLSLSPGK<u>GSSGGGGS</u>EIVMTQSPATLSVSPGERATLSCRASQSIRSNL<br>AWYQQKPGQAPRLLIYGASTRATGIPARFSGSGSGTEFTLTISSLQSED<br>FAVYYCQQYNNWPLTFGCGTKVEIK<u>GGGGSGGGGSGGGGSGGGGS</u>QVQL<br>VQSGAEVKKPGASVKVSCKASGYTFTGYYIHWVRQAPGQ<u>C</u>LEWMGWINP<br>NSGGTNSAQKFQDRVTITRDTSINTAYMELSRLRSDDTAVYFCARDRLV<br>LPWFGEIFPDAFDIWGQGTLVTVSS |
| SEQ ID NO: 182<br>9H9-2B3(DD)<br>light chain<br>sequence was as<br>follows (with the<br>constant region<br>shown in bold) | DIQMTQSPSTLSASVGDRVTITCRASQSISGWLAWYQQKPGKAPKLLIY<br>KASSLESGVPSRFSGSGSGTEFTLTISSLQPDDFATYYCQQYYGSSRTF<br>GQGTNVEIKRTVAAPSVFIFPPSDEQLKSGTASVVCLLNNFYPREAKVQ<br>WKVDNALQSGNSQESVTEQDSKDSTYSLSSTLTLSKADYEKHKVYACEV<br>THQGLSSPVTKSFNRGEC |
| SEQ ID NO: 183<br>ECD of huCD27 | TPAPKSCPERHYWAQGKLCCQMCEPGTFLVKDCDQHRKAAQCDPCIPGV<br>SFSPDHHTRPHCESCRHCNSGLLVRNCTITANAEC<u>ACRNG</u>WQCRDKECT<br>ECDPLPNPSLTARSSQALSPHPQPTHLPYVSEMLEARTAGHMQTLADFR<br>QLPARTLSTHWPPQRSLCSSD |
| SEQ ID NO: 184<br>ECD of huCD27<br>mutated | TPAPKSCPERHYWAQGKLCCQMCEPGTFLVKDCDQHRKAAQCDPCIPGV<br>SFSPDHHTRPHCESCRHCNSGLLVRNCTITANAEC<u>SCAAA</u>WQCRDKECT<br>ECDPLPNPSLTARSSQALSPHPQPTHLPYVSEMLEARTAGHMQTLADFR<br>QLPARTLSTHWPPQRSLCSSD |
| SEQ ID NO: 185<br>NA sequence of<br>9H9x2B3(DD)<br>variable domain | GAAGTGCAACTGGTGGAGTCGGGTGGTGGACTCGTGCAGCCCGGCGGAT<br>CCCTGAGACTCTCTTGTGCCGCATCGGGCGGCATTATTAGCACTTACTG<br>GATGTCATGGGTCAGACAGGCACCGGGAAAGGGCTTGGAATGGGTGGCG<br>AATATCAAGCAGGATGGATCCGAGAAGTACTACGTGGACTCCGTGAAGG<br>GCAGATTCACCATTTCCCGGGACAACGCCAAGAACTCGCTCTATCTGCA<br>AATGAACTCGTTGCGGGTGGAAGATACTGCCATGTACTACTGCGCCCGG<br>GACCGGCCTGTGGCCGGGGCGTCGGCCCTCTGGGGCCAGGGCACTCTGG<br>TCACCGTGTCCTCT |
| SEQ ID NO: 186<br>NA sequence of<br>9H9x2B3(DD)<br>scFv domain | <u>GGCTCCAGCGGGGGTGGCGGTTCC</u>GAGATCGTGATGACTCAGAGCCCGG<br>CAACCCTGTCCGTGTCTCCGGGGGAGCGGGCTACTCTTTCCTGCCGGGC<br>ATCCCAGTCCATCCGGTCGAACCTTGCTGGTACCAACAGAAGCCTGGA<br>CAGGCGCCCCGCCTGCTGATCTACGGGGCGTCGACTAGGGCCACCGGCA |

SUMMARY OF SEQUENCE LISTING

| | |
|---|---|
| (connector and linker sequences are shown in bold) | TCCCGGCCCGCTTCTCCGGGTCCGGATCCGGCACCGAATTCACCCTCAC CATCTCGAGCCTGCAGTCCGAAAACTTCGCCGTCTACTACTGCCAGCAG TACAACAACTGGCCGCTGACATTCGGATGCGGAACCAAAGTGGAAATCA AGGGCGGCGGCGGATCCGGCGGTGGCGGCAGCGGCGGTGGAGGATCCGG TGGCGGCGGTTCACAAGTGCAGCTGGTGCAGTCAGGCGCCGAAGTCAAG AAGCCCGGGGCCAGCGTGAAAGTCAGCTGCAAGGCTTCCGGATACACCT TCACGGGTTACTACATTCACTGGGTTCGCCAAGCGCCCGGGCAGTGTCT GGAGTGGATGGGATGGATCAACCCTAACTCGGGGGGAACCAACTCGGCC CAAAAGTTCCAGGACCGGGTCACCATTACAAGAGTCACGTCCATCAACA CTGCCTACATGGAGTTGAGCCGGCTGCGATCAGACGACACCGCCGTGTA CTTCTGCGCGAGGGACCGCCTCGTCCTCCCGTGGTTTGGAGAGATCTTC CCGGATGCCTTCGACATTTGGGGACAGGGGACCCTCGTGACTGTGTCCA GC |
| SEQ ID NO: 187 NA sequence of the 9H9x2B3(DD) light chain variable domain | GATATCCAGATGACCCAGAGCCCGTCCACCCTTTCCGCGAGCGTCGGCG ACAGAGTGACCATTACTTGTCGGGCCTCGCAAAGCATCTCCGGCTGGCT GGCTTGGTACCAGCAAAAGCCTGGAAAGGCCCCTAAGCTGCTGATCTAC AAGGCCTCATCCCTGGAGTCCGGAGTGCCTTCACGCTTTTCGGGGAGCG GATCGGGGACTGAGTTCACCCTCACCATTTCCTCCCTGCAACCCGACGA TTTCGCGACATACTACTGCCAGCAGTACTACGGTTCCTCGCGCACGTTC GGACAGGGCACTAACGTCGAGATCAAG (SEQ ID NO: 187) |

EQUIVALENTS

Those skilled in the art will recognize, or be able to ascertain using no more than routine experimentation, many equivalents of the specific embodiments of the invention described herein. Such equivalents are intended to be encompassed by the following claims.

The invention claimed is:

1. A bispecific construct comprising an anti-CD27 antibody binding domain which binds to human CD27 linked to an anti-PD-L1 antibody binding domain which binds to human PD-L1, wherein:
(a) the anti-CD27 antibody binding domain comprises heavy chain CDR1, CDR2 and CDR3 regions comprising the amino acid sequences set forth in SEQ ID NOs:7, 8, and 9, respectively, and light chain CDR1, CDR2 and CDR3 regions comprising the amino acid sequences set forth in SEQ ID NOs:10, 11, and 12, respectively; and
(ii) the anti-PD-L1 antibody binding domain comprises heavy chain CDR1, CDR2 and CDR3 regions comprising the amino acid sequences set forth in SEQ ID NOs:59, 60, and 61, respectively, and light chain CDR1, CDR2 and CDR3 regions comprising the amino acid sequences set forth in SEQ ID NOs:62, 63, and 64, respectively, and
wherein the anti-CD27 antibody binding domain and the anti-PD-L1 antibody binding domain are linked by a peptide or a synthetic linker.

2. The bispecific construct of claim 1, wherein the anti-CD27 antibody binding domain comprises a heavy chain variable region comprising the amino acid sequence set forth in SEQ ID NO:27 and a light chain variable region comprising the amino acid sequence set forth in SEQ ID NO:28.

3. The bispecific construct of claim 1, wherein the anti-PD-L1 antibody binding domain comprises a heavy chain variable region comprising the amino acid sequence set forth in SEQ ID NO:87 and a light chain variable region comprising the amino acid sequence set forth in SEQ ID NO:88.

4. The bispecific construct of claim 1, wherein (a) the anti-PD-L1 antibody binding domain further comprises a human IgG1 constant domain or (b) the anti-CD27 antibody binding domain further comprises a human IgG1 constant domain or (c) the anti-PD-L1 antibody binding domain comprises a heavy chain and the anti-CD27 antibody binding domain is linked to the C-terminus of the heavy chain of the anti-PD-L1 antibody binding domain or (d) the anti-CD27 antibody binding domain comprises a heavy chain and the anti-PD-L1 antibody binding domain is linked to the C-terminus of the heavy chain of the anti-CD27 antibody binding domain.

5. The bispecific construct of claim 1, wherein the anti-CD27 antibody binding domain is a scFv or (b) the anti-PD-L1 antibody binding domain is a scFv.

6. The bispecific construct of claim 1, wherein the construct is encoded by the nucleotide sequence set forth in SEQ ID NO: 186.

7. A composition comprising the bispecific construct of claim 1 and a pharmaceutically acceptable carrier.

8. A kit comprising the bispecific construct of claim 1 and instructions for use.

9. A bispecific construct comprising a full-length anti-PD-L1 antibody which binds to human PD-L1 linked to an anti-CD27 scFv which binds to human CD27, wherein:
(a) the anti-CD27 scFv comprises heavy chain CDR1, CDR2 and CDR3 regions comprising the amino acid sequences set forth in SEQ ID NOs:7, 8, and 9, respectively, and light chain CDR1, CDR2 and CDR3 regions comprising the amino acid sequences set forth in SEQ ID NOs:10, 11, and 12, respectively; and
(b) the anti-PD-L1 antibody comprises heavy chain CDR1, CDR2 and CDR3 regions comprising the amino acid sequences set forth in SEQ ID NOs: 59, 60, and 61, respectively, and light chain CDR1, CDR2 and CDR3 regions comprising the amino acid sequences set forth in SEQ ID NOs:62, 63, and 64, respectively, and a human IgG1 constant domain, and
wherein the anti-PD-L1 antibody and the anti-CD27 scFv are linked by a peptide or a synthetic linker.

10. The bispecific construct of claim 9, wherein the anti-PD-L1 antibody comprises a heavy chain variable region comprising the amino acid sequence set forth in SEQ ID NO:87 and a light chain variable region comprising the amino acid sequence set forth in SEQ ID NO:88.

11. The bispecific construct of claim 9, comprising:
   (a) a heavy chain comprising the amino acid sequence set forth in SEQ ID NO:179 and a light chain comprising the amino acid sequence set forth in SEQ ID NO: 180; or
   (b) a heavy chain comprising the amino acid sequence set forth in SEQ ID NO:181 and a light chain comprising the amino acid sequence set forth in SEQ ID NO: 182.

12. A composition comprising the bispecific construct of claim 9 and a pharmaceutically acceptable carrier.

13. A composition comprising the bispecific construct of claim 10 and a pharmaceutically acceptable carrier.

14. A composition comprising the bispecific construct of claim 11 and a pharmaceutically acceptable carrier.

15. A kit comprising the bispecific construct of claim 9 and instructions for use.

16. A kit comprising the bispecific construct of claim 10 and instructions for use.

17. A kit comprising the bispecific construct of claim 11 and instructions for use.

18. A bispecific construct comprising a full-length anti-CD27 antibody which binds to human CD27 linked to an anti-PD-L1 scFv which binds to human PD-L1, wherein:
   (a) the anti-CD27 antibody comprises heavy chain CDR1, CDR2 and CDR3 regions comprising the amino acid sequences set forth in SEQ ID NOs:7, 8, and 9, respectively, and light chain CDR1, CDR2 and CDR3 regions comprising the amino acid sequences set forth in SEQ ID NOs:10, 11, and 12, respectively and a human IgG1 constant domain; and
   (b) the anti-PD-L1 scFv comprises heavy chain CDR1, CDR2 and CDR3 regions comprising the amino acid sequences set forth in SEQ ID NOs: 59, 60, and 61, respectively, and light chain CDR1, CDR2 and CDR3 regions comprising the amino acid sequences set forth in SEQ ID NOs:62, 63, and 64, respectively, and wherein the anti-CD27 antibody and the anti-PD-L1 scFv are linked by a peptide or a synthetic linker.

19. The bispecific construct of claim 18, wherein the anti-CD27 antibody comprises a heavy chain variable region comprising the amino acid sequence set forth in SEQ ID NO:27 and a light chain variable region comprising the amino acid sequence set forth in SEQ ID NO:28.

20. A composition comprising the bispecific construct of claim 18 and a pharmaceutically acceptable carrier.

21. A composition comprising the bispecific construct of claim 19 and a pharmaceutically acceptable carrier.

22. A kit comprising the bispecific construct of claim 18 and instructions for use.

23. A kit comprising the bispecific construct of claim 19 and instructions for use.

24. A bispecific construct comprising a full-length anti-PD-L1 antibody which binds to human PD-L1 linked to an anti-CD27 scFv which binds to human CD27, wherein:
   (a) the anti-CD27 scFv comprises heavy chain CDR1, CDR2 and CDR3 regions comprising the amino acid sequences set forth in SEQ ID NOs:7, 8, and 9, respectively, and light chain CDR1, CDR2 and CDR3 regions comprising the amino acid sequences set forth in SEQ ID NOs:10, 11, and 12, respectively; and
   (b) the anti-PD-L1 antibody comprises heavy chain CDR1, CDR2 and CDR3 regions comprising the amino acid sequences set forth in SEQ ID NOs: 59, 60, and 61, respectively, and light chain CDR1, CDR2 and CDR3 regions comprising the amino acid sequences set forth in SEQ ID NOs:62, 63, and 64, respectively; and
   (c) the anti-PD-L1 antibody further comprises a human IgG1 constant domain; and
   (d) the anti-PD-L1 antibody and the anti-CD27 scFv comprise a fusion protein.

25. A composition comprising the bispecific construct of claim 24 and a pharmaceutically acceptable carrier.

26. A kit comprising the bispecific construct of claim 24 and instructions for use.

* * * * *

SEQUENCE LISTING

```
<160> NUMBER OF SEQ ID NOS: 188

<210> SEQ ID NO 1
<211> LENGTH: 5
<212> TYPE: PRT
<213> ORGANISM: Artificial Sequence
<220> FEATURE:
<223> OTHER INFORMATION: Synthetic: 3C2 VH CDR1

<400> SEQUENCE: 1

Gly Tyr Tyr Trp Ser
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic: 3C2 VH CDR2

<400> SEQUENCE: 2

Tyr Asn Tyr Tyr Ser Gly Ser Thr Asn Tyr Asn Pro Ser Leu Lys Ser
1               5                   10                  15

<210> SEQ ID NO 3
<211> LENGTH: 10
<212> TYPE: PRT
<213> ORGANISM: Artificial Sequence
<220> FEATURE:
<223> OTHER INFORMATION: Synthetic: 3C2 VH CDR3

<400> SEQUENCE: 3

Tyr Pro Leu Ile Arg Gly Ala Phe Asp Tyr
1               5                   10
```

```
<210> SEQ ID NO 4
<211> LENGTH: 16
<212> TYPE: PRT
<213> ORGANISM: Artificial Sequence
<220> FEATURE:
<223> OTHER INFORMATION: Synthetic: 3C2 VL CDR1

<400> SEQUENCE: 4

Arg Ser Ser Gln Asn Leu Leu His Thr Asn Gly Tyr Asn Tyr Leu Asp
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Synthetic: 3C2 VL CDR2

<400> SEQUENCE: 5

Leu Gly Ser Asn Arg Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic: 3C2 VL CDR3

<400> SEQUENCE: 6

Met Gln Ala Leu Gln Thr Pro Leu Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic: 2B3 VH CDR1

<400> SEQUENCE: 7

Gly Tyr Tyr Ile His
1               5

<210> SEQ ID NO 8
<211> LENGTH: 17
<212> TYPE: PRT
<213> ORGANISM: Artificial Sequence
<220> FEATURE:
<223> OTHER INFORMATION: Synthetic: 2B3 VH CDR2

<400> SEQUENCE: 8

Trp Ile Asn Pro Asn Ser Gly Gly Thr Asn Ser Ala Gln Lys Phe Gln
1               5                   10                  15

Asp

<210> SEQ ID NO 9
<211> LENGTH: 18
<212> TYPE: PRT
<213> ORGANISM: Artificial Sequence
<220> FEATURE:
<223> OTHER INFORMATION: Synthetic: 2B3 VH CDR3

<400> SEQUENCE: 9

Asp Arg Leu Val Leu Pro Trp Phe Gly Glu Ile Phe Pro Asp Ala Phe
1               5                   10                  15
```

-continued

Asp Ile

<210> SEQ ID NO 10
<211> LENGTH: 11
<212> TYPE: PRT
<213> ORGANISM: Artificial Sequence
<220> FEATURE:
<223> OTHER INFORMATION: Synthetic: 2B3 VL CDR1

<400> SEQUENCE: 10

Arg Ala Ser Gln Ser Ile Arg Ser Asn Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Synthetic: 2B3 VL CDR2

<400> SEQUENCE: 11

Gly Ala Ser Thr Arg Ala Thr
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic: 2B3 VL CDR3

<400> SEQUENCE: 12

Gln Gln Tyr Asn Asn Trp Pro Leu Thr
1               5

<210> SEQ ID NO 13
<211> LENGTH: 137
<212> TYPE: PRT
<213> ORGANISM: Artificial Sequence
<220> FEATURE:
<223> OTHER INFORMATION: Synthetic: 3C2 VH  with signal sequence

<400> SEQUENCE: 13

Met Lys His Leu Trp Phe Cys Leu Leu Leu Val Ala Ala Pro Arg Trp
1               5                   10                  15

Val Leu Ser Gln Ala Gln Leu Gln Glu Ser Gly Pro Gly Leu Val Lys
                20                  25                  30

Pro Ser Glu Thr Leu Ser Leu Thr Cys Thr Val Ser Thr Gly Ser Ile
            35                  40                  45

Ser Gly Tyr Tyr Trp Ser Trp Ile Arg Gln Pro Pro Gly Lys Gly Leu
        50                  55                  60

Glu Trp Ile Gly Tyr Asn Tyr Tyr Ser Gly Ser Thr Asn Tyr Asn Pro
65                  70                  75                  80

Ser Leu Lys Ser Arg Val Thr Ile Ser Ile Asp Thr Ser Lys Asn Gln
                85                  90                  95

Phe Ser Leu Lys Leu Asn Ser Val Thr Ala Ala Asp Thr Ala Val Tyr
            100                 105                 110

Tyr Cys Ala Arg Tyr Pro Leu Ile Arg Gly Ala Phe Asp Tyr Trp Gly
        115                 120                 125

Gln Gly Thr Leu Val Thr Val Ser Ser
    130                 135

<210> SEQ ID NO 14
<211> LENGTH: 132
<212> TYPE: PRT
<213> ORGANISM: Artificial Sequence
<220> FEATURE:
<223> OTHER INFORMATION: Synthetic: 3C2 VL with signal sequence

<400> SEQUENCE: 14

```
Met Arg Leu Pro Ala Gln Leu Leu Gly Leu Leu Met Leu Trp Val Ser
1               5                   10                  15

Gly Ser Ser Gly Asp Ile Val Met Thr Gln Ser Pro Leu Ser Leu Pro
                20                  25                  30

Val Thr Pro Gly Glu Pro Ala Ser Ile Ser Cys Arg Ser Ser Gln Asn
            35                  40                  45

Leu Leu His Thr Asn Gly Tyr Asn Tyr Leu Asp Trp Tyr Leu Gln Lys
        50                  55                  60

Pro Gly Gln Ser Pro Gln Leu Leu Ile Tyr Leu Gly Ser Asn Arg Ala
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Ala Leu Gln Thr Pro Leu Thr Phe Gly Gly Gly Thr Lys
        115                 120                 125

Val Glu Ile Lys
    130
```

<210> SEQ ID NO 15
<211> LENGTH: 146
<212> TYPE: PRT
<213> ORGANISM: Artificial Sequence
<220> FEATURE:
<223> OTHER INFORMATION: Synthetic: 2B3 VH with signal sequence

<400> SEQUENCE: 15

```
Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Gly Tyr Tyr Ile His Trp Val Arg Gln Ala Pro Gly Gln Gly Leu
        50                  55                  60

Glu Trp Met Gly Trp Ile Asn Pro Asn Ser Gly Gly Thr Asn Ser Ala
65                  70                  75                  80

Gln Lys Phe Gln Asp Arg Val Thr Ile Thr Arg Val Thr Ser Ile Asn
                85                  90                  95

Thr Ala Tyr Met Glu Leu Ser Arg Leu Arg Ser Asp Asp Thr Ala Val
            100                 105                 110

Tyr Phe Cys Ala Arg Asp Arg Leu Val Leu Pro Trp Phe Gly Glu Ile
        115                 120                 125

Phe Pro Asp Ala Phe Asp Ile Trp Gly Gln Gly Thr Leu Val Thr Val
    130                 135                 140

Ser Ser
145
```

<210> SEQ ID NO 16

```
<211> LENGTH: 127
<212> TYPE: PRT
<213> ORGANISM: Artificial Sequence
<220> FEATURE:
<223> OTHER INFORMATION: Synthetic: 2B3 VL  with signal sequence

<400> SEQUENCE: 16

Met Glu Ala Pro Ala Gln Leu Leu Phe Leu Leu Leu Leu Trp Leu Pro
1               5                   10                  15

Asp Ser Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Ile Arg Ser Asn Leu Ala Trp Tyr Gln Gln Lys Pro Gly Gln Ala Pro
    50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asn Phe Ala Val Tyr Tyr Cys Gln Gln Tyr Asn
            100                 105                 110

Asn Trp Pro Leu Thr Phe Gly Gly Gly Thr Lys Val Glu Ile Lys
        115                 120                 125

<210> SEQ ID NO 17
<211> LENGTH: 118
<212> TYPE: PRT
<213> ORGANISM: Artificial Sequence
<220> FEATURE:
<223> OTHER INFORMATION: Synthetic: 3C2 VH  without signal sequence

<400> SEQUENCE: 17

Gln Ala Gln Leu Gln Glu Ser Gly Pro Gly Leu Val Lys Pro Ser Glu
1               5                   10                  15

Thr Leu Ser Leu Thr Cys Thr Val Ser Thr Gly Ser Ile Ser Gly Tyr
            20                  25                  30

Tyr Trp Ser Trp Ile Arg Gln Pro Pro Gly Lys Gly Leu Glu Trp Ile
        35                  40                  45

Gly Tyr Asn Tyr Tyr Ser Gly Ser Thr Asn Tyr Asn Pro Ser Leu Lys
    50                  55                  60

Ser Arg Val Thr Ile Ser Ile Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Tyr Pro Leu Ile Arg Gly Ala Phe Asp Tyr Trp Gly Gln Gly Thr
            100                 105                 110

Leu Val Thr Val Ser Ser
        115

<210> SEQ ID NO 18
<211> LENGTH: 112
<212> TYPE: PRT
<213> ORGANISM: Artificial Sequence
<220> FEATURE:
<223> OTHER INFORMATION: Synthetic: 3C2 VL  without signal sequence

<400> SEQUENCE: 18

Asp Ile Val Met Thr Gln Ser Pro Leu Ser Leu Pro Val Thr Pro Gly
1               5                   10                  15
```

```
Glu Pro Ala Ser Ile Ser Cys Arg Ser Ser Gln Asn Leu Leu His Thr
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                 85                  90                  95

Leu Gln Thr Pro Leu Thr Phe Gly Gly Gly Thr Lys Val Glu Ile Lys
            100                 105                 110

<210> SEQ ID NO 19
<211> LENGTH: 127
<212> TYPE: PRT
<213> ORGANISM: Artificial Sequence
<220> FEATURE:
<223> OTHER INFORMATION: Synthetic: 2B3 VH without signal sequence

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
             20                  25                  30

Tyr Ile His Trp Val Arg Gln Ala Pro Gly Gln Gly Leu Glu Trp Met
         35                  40                  45

Gly Trp Ile Asn Pro Asn Ser Gly Gly Thr Asn Ser Ala Gln Lys Phe
     50                  55                  60

Gln Asp Arg Val Thr Ile Thr Arg Val Thr Ser Ile Asn Thr Ala Tyr
65                  70                  75                  80

Met Glu Leu Ser Arg Leu Arg Ser Asp Asp Thr Ala Val Tyr Phe Cys
                 85                  90                  95

Ala Arg Asp Arg Leu Val Leu Pro Trp Phe Gly Glu Ile Phe Pro Asp
            100                 105                 110

Ala Phe Asp Ile Trp Gly Gln Gly Thr Leu Val Thr Val Ser Ser
            115                 120                 125

<210> SEQ ID NO 20
<211> LENGTH: 107
<212> TYPE: PRT
<213> ORGANISM: Artificial Sequence
<220> FEATURE:
<223> OTHER INFORMATION: Synthetic: 2B3 VL without signal sequence

<400> SEQUENCE: 20

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Arg Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
     50                  55                  60

Ser Gly Ser Gly Thr Glu Phe Thr Leu Thr Ile Ser Ser Leu Gln Ser
65                  70                  75                  80

Glu Asn Phe Ala Val Tyr Tyr Cys Gln Gln Tyr Asn Asn Trp Pro Leu
                 85                  90                  95
```

<210> SEQ ID NO 21
<211> LENGTH: 411
<212> TYPE: DNA
<213> ORGANISM: Artificial Sequence
<220> FEATURE:
<223> OTHER INFORMATION: Synthetic: 3C2 VH DNA Sequence with signal
      sequence

<400> SEQUENCE: 21

| | | | | | |
|---|---|---|---|---|---|
| atgaaacatc | tgtggttctg | ccttctcctg | gtggcagctc | ccagatgggt | cctgtcccag | 60 |
| gcgcagctgc | aggagtcggg | cccaggactg | gtgaagcctt | cggagaccct | gtccctcacc | 120 |
| tgcactgtct | ctactggctc | catcagtggt | tactactgga | gctggatccg | gcagccccca | 180 |
| gggaagggac | tggagtggat | tgggtataat | tattacagtg | ggagcaccaa | ctacaacccc | 240 |
| tccctcaaga | gtcgagtcac | catatcaata | gacacgtcca | agaaccagtt | ctccctgaag | 300 |
| ctgaattctg | tgaccgctgc | ggacacggcc | gtatattact | gtgcgagata | tcctctgatt | 360 |
| cggggagctt | ttgactactg | gggccaggga | accctggtca | ccgtctcctc | a | 411 |

<210> SEQ ID NO 22
<211> LENGTH: 396
<212> TYPE: DNA
<213> ORGANISM: Artificial Sequence
<220> FEATURE:
<223> OTHER INFORMATION: Synthetic: 3C2 VL DNA Sequence with signal
      sequence

<400> SEQUENCE: 22

| | | | | | |
|---|---|---|---|---|---|
| atgaggctcc | ctgctcagct | cctggggctg | ctaatgctct | gggtctctgg | atccagtggg | 60 |
| gatattgtga | tgactcagtc | tccactctcc | ctgcccgtca | cccctggaga | gccggcctcc | 120 |
| atctcctgta | ggtctagtca | gaacctcctg | catactaatg | gctacaacta | tttggattgg | 180 |
| tacctgcaga | agccagggca | gtctccacag | ctcctgatct | atttgggttc | taatcgggcc | 240 |
| tccggggtcc | ctgacaggtt | cagtggcagt | ggatcaggca | cagattttac | actgaaaatc | 300 |
| agcagagtgg | aggctgagga | tgttggggtt | tattactgca | tgcaagctct | acaaactccg | 360 |
| ctcactttcg | gcggagggac | caaggtggag | atcaaa | | | 396 |

<210> SEQ ID NO 23
<211> LENGTH: 438
<212> TYPE: DNA
<213> ORGANISM: Artificial Sequence
<220> FEATURE:
<223> OTHER INFORMATION: Synthetic: 2B3 VH DNA Sequence with signal
      sequence

<400> SEQUENCE: 23

| | | | | | |
|---|---|---|---|---|---|
| atggactgga | cctggaggat | cctcttcttg | gtggcagcag | ccacaggagc | ccactcccag | 60 |
| gtgcagctgg | tgcagtctgg | ggctgaggtg | aagaagcctg | ggcctcagt | gaaggtctcc | 120 |
| tgcaaggctt | ctggatacac | cttcaccggc | tactatatac | actgggtgcg | acaggcccct | 180 |
| ggacaagggc | ttgagtggat | gggatggatc | aaccctaaca | gtggtggcac | aaactctgca | 240 |
| cagaagtttc | aggacagggt | caccatcacc | agggtcacgt | ccatcaacac | agcctacatg | 300 |
| gagctgagca | gactgagatc | tgacgacacg | gccgtgtatt | tctgtgcgag | agatcggctc | 360 |
| gtattaccat | ggttcgggga | aatattccca | gatgcttttg | atatctgggg | ccaagggaca | 420 | ttggtcaccg tctcttca                                           438

<210> SEQ ID NO 24
<211> LENGTH: 381
<212> TYPE: DNA
<213> ORGANISM: Artificial Sequence
<220> FEATURE:
<223> OTHER INFORMATION: Synthetic: 2B3 VL DNA Sequence with signal
      sequence

<400> SEQUENCE: 24
atggaagccc cagcgcagct tctcttcctc ctgctactct ggctcccaga ttccactgga    60
gaaatagtga tgacgcagtc tccagccacc ctgtctgtgt ctccagggga aagagccacc   120
ctctcctgca gggccagtca gagtattagg agcaacttag cctggtatca gcagaaacct   180
ggccaggctc ccaggctcct catctatggt gcatccacca gggccactgg tatcccagcc   240
aggttcagtg gcagtgggtc tgggacagag ttcactctca ccatcagcag cctgcagtct   300 gaaattttg cagtttatta ctgtcagcag tataataact ggcctctcac tttcggcgga   360
gggaccaagg tggagatcaa a                                            381

<210> SEQ ID NO 25
<211> LENGTH: 354
<212> TYPE: DNA
<213> ORGANISM: Artificial Sequence
<220> FEATURE:
<223> OTHER INFORMATION: Synthetic: 3C2 VH DNA Sequence without signal
      sequence

<400> SEQUENCE: 25
caggcgcagc tgcaggagtc gggcccagga ctggtgaagc cttcggagac cctgtccctc    60
acctgcactg tctctactgg ctccatcagt ggttactact ggagctggat ccggcagccc   120
ccagggaagg gactggagtg gattgggtat aattattaca gtgggagcac caactacaac   180
ccctccctca gagtcgagt caccatatca atagacacgt ccaagaacca gttctccctg   240
aagctgaatt ctgtgaccgc tgcggacacg gccgtatatt actgtgcgag atatcctctg   300
attcggggag cttttgacta ctggggccag ggaaccctgg tcaccgtctc ctca         354

<210> SEQ ID NO 26
<211> LENGTH: 336
<212> TYPE: DNA
<213> ORGANISM: Artificial Sequence
<220> FEATURE:
<223> OTHER INFORMATION: Synthetic: 3C2 VL DNA Sequence without signal
      sequence

<400> SEQUENCE: 26
gatattgtga tgactcagtc tccactctcc ctgcccgtca cccctggaga gccggcctcc    60
atctcctgta ggtctagtca gaacctcctg catactaatg gctacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactccg   300
ctcactttcg gcggagggac caaggtggag atcaaa                             336

<210> SEQ ID NO 27
<211> LENGTH: 381
<212> TYPE: DNA
<213> ORGANISM: Artificial Sequence
<220> FEATURE:

<223> OTHER INFORMATION: Synthetic: 2B3 VH DNA Sequence without signal
      sequence

<400> SEQUENCE: 27
caggtgcagc tggtgcagtc tggggctgag gtgaagaagc ctggggcctc agtgaaggtc     60
tcctgcaagg cttctggata caccttcacc ggctactata tacactgggt gcgacaggcc    120
cctggacaag gcttgagtg gatgggatgg atcaaccctca acagtggtgg cacaaactct    180
gcacagaagt tcaggacag gtcaccatc accaggtca cgtccatcaa cacagcctac       240
atggagctga gcagactgag atctgacgac acggccgtgt atttctgtgc gagagatcgg    300
ctcgtattac catggttcgg ggaaatattc ccagatgctt ttgatatctg gggccaaggg    360
acattggtca ccgtctcttc a                                              381

<210> SEQ ID NO 28
<211> LENGTH: 321
<212> TYPE: DNA
<213> ORGANISM: Artificial Sequence
<220> FEATURE:
<223> OTHER INFORMATION: Synthetic: 2B3 VL DNA Sequence without signal
      sequence

<400> SEQUENCE: 28
gaaatagtga tgacgcagtc tccagccacc ctgtctgtgt ctccagggga aagagccacc     60
ctctcctgca gggccagtca gagtattagg agcaacttag cctggtatca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaaaattttg cagtttatta ctgtcagcag tataataact ggcctctcac tttcggcgga    300
gggaccaagg tggagatcaa a                                              321

<210> SEQ ID NO 29
<211> LENGTH: 5
<212> TYPE: PRT
<213> ORGANISM: Artificial Sequence
<220> FEATURE:
<223> OTHER INFORMATION: Synthetic: 7H7 VH CDR1

<400> SEQUENCE: 29

Thr Ser Trp Met Ser
1               5

<210> SEQ ID NO 30
<211> LENGTH: 17
<212> TYPE: PRT
<213> ORGANISM: Artificial Sequence
<220> FEATURE:
<223> OTHER INFORMATION: Synthetic: 7H7 VH CDR2

<400> SEQUENCE: 30

Asn Ile Lys Gln Asp Gly Ser Glu Lys Tyr Tyr Val Asp Ser Val Lys
1               5                   10                  15

Gly

<210> SEQ ID NO 31
<211> LENGTH: 10
<212> TYPE: PRT
<213> ORGANISM: Artificial Sequence
<220> FEATURE:
<223> OTHER INFORMATION: Synthetic: 7H7 VH CDR3

<400> SEQUENCE: 31

```
Asp Arg Pro Val Ala Gly Ala Ser Ala Leu
1               5                   10
```

<210> SEQ ID NO 32
<211> LENGTH: 11
<212> TYPE: PRT
<213> ORGANISM: Artificial Sequence
<220> FEATURE:
<223> OTHER INFORMATION: Synthetic: 7H7 VL CDR1

<400> SEQUENCE: 32

```
Arg Ala Ser Gln Ser Ile Ser Gly Trp Leu Ala
1               5                   10
```

<210> SEQ ID NO 33
<211> LENGTH: 7
<212> TYPE: PRT
<213> ORGANISM: Artificial Sequence
<220> FEATURE:
<223> OTHER INFORMATION: Synthetic: 7H7 VL CDR2

<400> SEQUENCE: 33

```
Lys Ala Ser Ser Leu Glu Ser
1               5
```

<210> SEQ ID NO 34
<211> LENGTH: 9
<212> TYPE: PRT
<213> ORGANISM: Artificial Sequence
<220> FEATURE:
<223> OTHER INFORMATION: Synthetic: 7H7 VL CDR3

<400> SEQUENCE: 34

```
Gln Gln Tyr Tyr Gly Ser Ser Arg Thr
1               5
```

<210> SEQ ID NO 35
<211> LENGTH: 5
<212> TYPE: PRT
<213> ORGANISM: Artificial Sequence
<220> FEATURE:
<223> OTHER INFORMATION: Synthetic: 1B3 VH CDR1

<400> SEQUENCE: 35

```
Thr Ser Trp Met Ser
1               5
```

<210> SEQ ID NO 36
<211> LENGTH: 17
<212> TYPE: PRT
<213> ORGANISM: Artificial Sequence
<220> FEATURE:
<223> OTHER INFORMATION: Synthetic: 1B3 VH CDR2

<400> SEQUENCE: 36

```
Asn Ile Lys Gln Asp Gly Ser Glu Lys Tyr Tyr Val Asp Ser Val Lys
1               5                   10                  15
Gly
```

<210> SEQ ID NO 37
<211> LENGTH: 10
<212> TYPE: PRT
<213> ORGANISM: Artificial Sequence
<220> FEATURE:
<223> OTHER INFORMATION: Synthetic: 1B3 VH CDR3

```
<400> SEQUENCE: 37

Asp Arg Pro Val Ala Gly Ala Ser Ala Leu
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic: 1B3 VL CDR1

<400> SEQUENCE: 38

Arg Ala Ser Gln Ser Ile Ser Gly Trp Leu Ala
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Synthetic: 1B3 VL CDR2

<400> SEQUENCE: 39

Lys Ala Ser Ser Leu Glu Ser
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic: 1B3 VL CDR3

<400> SEQUENCE: 40

Gln Gln Tyr Tyr Gly Ser Ser Arg Thr
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic: 3B6 VH CDR1

<400> SEQUENCE: 41

Thr Tyr Trp Met Ser
1               5

<210> SEQ ID NO 42
<211> LENGTH: 17
<212> TYPE: PRT
<213> ORGANISM: Artificial Sequence
<220> FEATURE:
<223> OTHER INFORMATION: Synthetic: 3B6 VH CDR2

<400> SEQUENCE: 42

Asn Ile Lys Gln Asp Gly Ser Glu Lys Tyr Tyr Val Asp Ser Val Lys
1               5                   10                  15

Gly

<210> SEQ ID NO 43
<211> LENGTH: 10
<212> TYPE: PRT
<213> ORGANISM: Artificial Sequence
<220> FEATURE:
<223> OTHER INFORMATION: Synthetic: 3B6 VH CDR3
```

```
<400> SEQUENCE: 43

Asp Arg Pro Val Ala Gly Ala Ser Ala Leu
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic: 3B6 VL CDR1

<400> SEQUENCE: 44

Arg Ala Ser Gln Ser Ile Ser Gly Trp Leu Ala
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Synthetic: 3B6 VL CDR2

<400> SEQUENCE: 45

Lys Ala Ser Ser Leu Glu Ser
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic: 3B6 VL CDR3

<400> SEQUENCE: 46

Gln Gln Tyr Tyr Gly Ser Ser Arg Thr
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic: 8B1 VH CDR1

<400> SEQUENCE: 47

Thr His Trp Met Ser
1               5

<210> SEQ ID NO 48
<211> LENGTH: 17
<212> TYPE: PRT
<213> ORGANISM: Artificial Sequence
<220> FEATURE:
<223> OTHER INFORMATION: Synthetic: 8B1 VH CDR2

<400> SEQUENCE: 48

Asn Ile Lys Gln Asp Gly Ser Glu Lys Tyr Tyr Val Asp Ser Val Lys
1               5                   10                  15

Gly

<210> SEQ ID NO 49
<211> LENGTH: 10
<212> TYPE: PRT
<213> ORGANISM: Artificial Sequence
<220> FEATURE:
```

```
<223> OTHER INFORMATION: Synthetic: 8B1 VH CDR3

<400> SEQUENCE: 49

Asp Arg Pro Val Ala Gly Ala Ser Ala Leu
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic: 8B1 VL CDR1

<400> SEQUENCE: 50

Arg Ala Ser Gln Ser Ile Ser Gly Trp Leu Ala
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Synthetic: 8B1 VL CDR2

<400> SEQUENCE: 51

Lys Ala Ser Ser Leu Glu Ser
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic: 8B1 VL CDR3

<400> SEQUENCE: 52

Gln Gln Tyr Tyr Gly Ser Ser Arg Thr
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic: 4A3 VH CDR1

<400> SEQUENCE: 53

Ser Ser Trp Met Ser
1               5

<210> SEQ ID NO 54
<211> LENGTH: 17
<212> TYPE: PRT
<213> ORGANISM: Artificial Sequence
<220> FEATURE:
<223> OTHER INFORMATION: Synthetic: 4A3 VH CDR2

<400> SEQUENCE: 54

Asn Ile Lys Gln Asp Gly Ser Glu Lys Tyr Tyr Val Asp Ser Val Lys
1               5                   10                  15

Gly

<210> SEQ ID NO 55
<211> LENGTH: 10
<212> TYPE: PRT
<213> ORGANISM: Artificial Sequence
```

```
<220> FEATURE:
<223> OTHER INFORMATION: Synthetic: 4A3 VH CDR3

<400> SEQUENCE: 55

Asp Arg Pro Val Ala Gly Ala Ser Ala Leu
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Synthetic: 4A3 VL CDR1

<400> SEQUENCE: 56

Arg Ala Ser Gln Ser Ile Ser Gly Trp Leu Ala
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Synthetic: 4A3 VL CDR2

<400> SEQUENCE: 57

Lys Ala Ser Ser Leu Glu Ser
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic: 4A3 VL CDR3

<400> SEQUENCE: 58

Gln Gln Tyr Tyr Gly Ser Ser Arg Thr
1               5

<210> SEQ ID NO 59
<211> LENGTH: 5
<212> TYPE: PRT
<213> ORGANISM: Artificial Sequence
<220> FEATURE:
<223> OTHER INFORMATION: Synthetic: 9H9 VH CDR1

<400> SEQUENCE: 59

Thr Tyr Trp Met Ser
1               5

<210> SEQ ID NO 60
<211> LENGTH: 17
<212> TYPE: PRT
<213> ORGANISM: Artificial Sequence
<220> FEATURE:
<223> OTHER INFORMATION: Synthetic: 9H9 VH CDR2

<400> SEQUENCE: 60

Asn Ile Lys Gln Asp Gly Ser Glu Lys Tyr Tyr Val Asp Ser Val Lys
1               5                   10                  15

Gly

<210> SEQ ID NO 61
<211> LENGTH: 10
<212> TYPE: PRT
```

<210> SEQ ID NO 62
<211> LENGTH: 11
<212> TYPE: PRT
<213> ORGANISM: Artificial Sequence
<220> FEATURE:
<223> OTHER INFORMATION: Synthetic: 9H9 VH CDR3

<400> SEQUENCE: 61

Asp Arg Pro Val Ala Gly Ala Ser Ala Leu
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Synthetic: 9H9 VL CDR1

<400> SEQUENCE: 62

Arg Ala Ser Gln Ser Ile Ser Gly Trp Leu Ala
1               5                   10

<210> SEQ ID NO 63
<211> LENGTH: 7
<212> TYPE: PRT
<213> ORGANISM: Artificial Sequence
<220> FEATURE:
<223> OTHER INFORMATION: Synthetic: 9H9 VL CDR2

<400> SEQUENCE: 63

Lys Ala Ser Ser Leu Glu Ser
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic: 9H9 VL CDR3

<400> SEQUENCE: 64

Gln Gln Tyr Tyr Gly Ser Ser Arg Thr
1               5

<210> SEQ ID NO 65
<211> LENGTH: 138
<212> TYPE: PRT
<213> ORGANISM: Artificial Sequence
<220> FEATURE:
<223> OTHER INFORMATION: Synthetic: 7H7 VH  with signal sequence
<220> FEATURE:
<221> NAME/KEY: misc_feature
<222> LOCATION: (7)..(7)
<223> OTHER INFORMATION: Xaa can be any naturally occurring amino acid

<400> SEQUENCE: 65

Met Glu Leu Gly Leu Ser Xaa Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Gly Thr Ile
        35                  40                  45

Ser Thr Ser Trp Met Ser Trp Val Arg Gln Ala Pro Gly Lys Gly Leu
    50                  55                  60

Glu Trp Val Ala Asn Ile Lys Gln Asp Gly Ser Glu Lys Tyr Tyr Val
65                  70                  75                  80

Asp Ser Val Lys Gly Arg Phe Thr Ile Ser Arg Asp Asn Ala Lys Asn
                85                  90                  95

```
Ser Leu Tyr Leu Gln Met Asn Ser Leu Arg Val Glu Asp Thr Ala Ile
            100                 105                 110

Tyr Tyr Cys Ala Arg Asp Arg Pro Val Ala Gly Ala Ser Ala Leu Trp
        115                 120                 125

Gly Gln Gly Thr Leu Val Thr Val Ser Ser
        130                 135

<210> SEQ ID NO 66
<211> LENGTH: 127
<212> TYPE: PRT
<213> ORGANISM: Artificial Sequence
<220> FEATURE:
<223> OTHER INFORMATION: Synthetic: 7H7 VL  with signal sequence

<400> SEQUENCE: 66

Met Arg Val Pro Ala Gln Leu Leu Gly Leu Leu Leu Leu Trp Leu Pro
1               5                   10                  15

Gly Ala Lys Cys Asp Ile Gln Met Thr Gln Ser Pro Ser Thr Leu Ser
            20                  25                  30

Ala Ser Val Gly Asp Arg Val Thr Ile Thr Cys Arg Ala Ser Gln Ser
        35                  40                  45

Ile Ser Gly Trp Leu Ala Trp Tyr Gln Gln Lys Gln Gly Lys Ala Pro
    50                  55                  60

Lys Leu Leu Ile Tyr Lys Ala Ser Ser Leu Glu Ser Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Asp Asp Phe Ala Thr Tyr Tyr Cys Gln Gln Tyr Tyr
            100                 105                 110

Gly Ser Ser Arg Thr Phe Gly Gln Gly Thr Asn Val Glu Ile Lys
        115                 120                 125

<210> SEQ ID NO 67
<211> LENGTH: 138
<212> TYPE: PRT
<213> ORGANISM: Artificial Sequence
<220> FEATURE:
<223> OTHER INFORMATION: Synthetic: 1B3 VH  with signal sequence

<400> SEQUENCE: 67

Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Gly Thr Ile
        35                  40                  45

Ser Thr Ser Trp Met Ser Trp Val Arg Gln Ala Pro Gly Lys Gly Leu
    50                  55                  60

Glu Trp Val Ala Asn Ile Lys Gln Asp Gly Ser Glu Lys Tyr Tyr Val
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Val Glu Asp Thr Ala Met
            100                 105                 110

Tyr Tyr Cys Ala Arg Asp Arg Pro Val Ala Gly Ala Ser Ala Leu Trp
        115                 120                 125

Gly Gln Gly Thr Leu Val Thr Val Ser Ser
        130                 135
```

<210> SEQ ID NO 68
<211> LENGTH: 127
<212> TYPE: PRT
<213> ORGANISM: Artificial Sequence
<220> FEATURE:
<223> OTHER INFORMATION: Synthetic: 1B3 VL with signal sequence

<400> SEQUENCE: 68

```
Met Arg Val Pro Ala Gln Leu Leu Gly Leu Leu Leu Trp Leu Pro
 1               5                  10                  15

Gly Ala Lys Cys Asp Ile Gln Met Thr Gln Ser Pro Ser Thr Leu Ser
            20                  25                  30

Ala Ser Val Gly Asp Arg Val Thr Ile Thr Cys Arg Ala Ser Gln Ser
        35                  40                  45

Ile Ser Gly Trp Leu Ala Trp Tyr Gln Gln Lys Pro Gly Lys Ala Pro
    50                  55                  60

Lys Leu Leu Ile Tyr Lys Ala Ser Ser Leu Glu Ser Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Asp Asp Phe Ala Thr Tyr Tyr Cys Gln Gln Tyr Tyr
            100                 105                 110

Gly Ser Ser Arg Thr Phe Gly Gln Gly Thr Asn Val Glu Ile Lys
        115                 120                 125
```

<210> SEQ ID NO 69
<211> LENGTH: 138
<212> TYPE: PRT
<213> ORGANISM: Artificial Sequence
<220> FEATURE:
<223> OTHER INFORMATION: Synthetic: 3B6 VH with signal sequence

<400> SEQUENCE: 69

```
Met Glu Leu Gly Leu Ser Trp Val Phe Leu Val Ala Ile Leu Glu Gly
 1               5                  10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Gly Thr Thr
        35                  40                  45

Ser Thr Tyr Trp Met Ser Trp Val Arg Gln Ala Pro Gly Lys Gly Leu
    50                  55                  60

Glu Trp Val Ala Asn Ile Lys Gln Asp Gly Ser Glu Lys Tyr Tyr Val
65                  70                  75                  80

Asp Ser Val Lys Gly Arg Phe Thr Ile Ser Arg Asp Asn Ala Lys Asn
                85                  90                  95

Ser Leu Asn Leu Gln Met Asn Ser Leu Arg Val Glu Asp Thr Ala Ile
            100                 105                 110

Tyr Tyr Cys Ala Arg Asp Arg Pro Val Ala Gly Ala Ser Ala Leu Trp
        115                 120                 125

Gly Gln Gly Thr Leu Val Thr Val Ser Ser
    130                 135
```

<210> SEQ ID NO 70
<211> LENGTH: 127
<212> TYPE: PRT
<213> ORGANISM: Artificial Sequence
<220> FEATURE:

<223> OTHER INFORMATION: Synthetic: 3B6 VL with signal sequence

<400> SEQUENCE: 70

Met Arg Val Pro Ala Gln Leu Leu Gly Leu Leu Leu Trp Leu Pro
1               5                   10                  15

Gly Ala Lys Cys Asp Ile Gln Met Thr Gln Ser Pro Ser Thr Leu Ser
            20                  25                  30

Ala Ser Val Gly Asp Arg Val Thr Ile Thr Cys Arg Ala Ser Gln Ser
        35                  40                  45

Ile Ser Gly Trp Leu Ala Trp Tyr Gln Gln Lys Pro Gly Lys Ala Pro
    50                  55                  60

Lys Leu Leu Ile Tyr Lys Ala Ser Ser Leu Glu Ser Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Asp Asp Phe Ala Thr Tyr Tyr Cys Gln Gln Tyr Tyr
            100                 105                 110

Gly Ser Ser Arg Thr Phe Gly Gln Gly Thr Asn Val Glu Ile Lys
        115                 120                 125

<210> SEQ ID NO 71
<211> LENGTH: 138
<212> TYPE: PRT
<213> ORGANISM: Artificial Sequence
<220> FEATURE:
<223> OTHER INFORMATION: Synthetic: 8B1 VH with signal sequence

<400> SEQUENCE: 71

Met Glu Leu Gly Leu Ser Trp Val Phe Leu Val Ala Ile Leu Glu Gly
1               5                   10                  15

Val Lys Cys Glu Val Arg Leu Val Glu Ser Gly Gly Gly Leu Val Gln
            20                  25                  30

Pro Gly Gly Ser Leu Arg Leu Ser Cys Ala Ala Ser Gly Asp Ile Ile
        35                  40                  45

Ser Thr His Trp Met Ser Trp Val Arg Gln Ala Pro Gly Lys Gly Leu
    50                  55                  60

Glu Trp Val Ala Asn Ile Lys Gln Asp Gly Ser Glu Lys Tyr Tyr Val
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Thr Leu Arg Val Glu Asp Thr Ala Ile
            100                 105                 110

Tyr Tyr Cys Thr Arg Asp Arg Pro Val Ala Gly Ala Ser Ala Leu Trp
        115                 120                 125

Gly Gln Gly Thr Leu Val Thr Val Ser Ser
    130                 135

<210> SEQ ID NO 72
<211> LENGTH: 127
<212> TYPE: PRT
<213> ORGANISM: Artificial Sequence
<220> FEATURE:
<223> OTHER INFORMATION: Synthetic: 8B1 VL with signal sequence

<400> SEQUENCE: 72

Met Arg Val Pro Ala Gln Leu Leu Gly Leu Leu Leu Trp Leu Pro
1               5                   10                  15

Gly Ala Lys Cys Asp Ile Gln Met Thr Gln Ser Pro Ser Thr Leu Ser

```
                    20                  25                  30
Ala Ser Val Gly Asp Arg Val Thr Ile Thr Cys Arg Ala Ser Gln Ser
                35                  40                  45

Ile Ser Gly Trp Leu Ala Trp Tyr Gln Gln Lys Pro Gly Lys Ala Pro
     50                  55                  60

Lys Leu Leu Ile Tyr Lys Ala Ser Ser Leu Glu Ser Gly Val Pro Leu
 65                  70                  75                  80

Arg Phe Ser Gly Ser Gly Ser Gly Thr Glu Phe Thr Leu Thr Ile Ser
                85                  90                  95

Ser Leu Gln Pro Asp Asp Phe Ala Thr Tyr Tyr Cys Gln Gln Tyr Tyr
                100                 105                 110

Gly Ser Ser Arg Thr Phe Gly Gln Gly Thr Asn Val Glu Ile Lys
            115                 120                 125

<210> SEQ ID NO 73
<211> LENGTH: 138
<212> TYPE: PRT
<213> ORGANISM: Artificial Sequence
<220> FEATURE:
<223> OTHER INFORMATION: Synthetic: 4A3 VH  with signal sequence

<400> SEQUENCE: 73

Met Glu Leu Gly Leu Ser Trp Val Phe Leu Val Ala Ile Leu Glu Gly
  1               5                  10                  15

Val Gln Cys Glu Val Gln Leu Val Glu Ser Gly Gly Gly Leu Val Gln
                20                  25                  30

Pro Gly Gly Ser Leu Arg Leu Ser Cys Ala Ala Ser Gly Gly Ile Ile
            35                  40                  45

Ser Ser Ser Trp Met Ser Trp Val Arg Gln Ala Pro Gly Lys Gly Leu
     50                  55                  60

Glu Trp Val Ala Asn Ile Lys Gln Asp Gly Ser Glu Lys Tyr Tyr Val
 65                  70                  75                  80

Asp Ser Val Lys Gly Arg Phe Thr Ile Ser Arg Asp Asn Ala Lys Asp
                85                  90                  95

Leu Leu Tyr Leu Gln Met Asn Ser Leu Arg Val Glu Asp Thr Ala Leu
                100                 105                 110

Tyr Tyr Cys Ala Arg Asp Arg Pro Val Ala Gly Ala Ser Ala Leu Trp
            115                 120                 125

Gly Gln Gly Thr Leu Val Thr Val Ser Ser
        130                 135

<210> SEQ ID NO 74
<211> LENGTH: 127
<212> TYPE: PRT
<213> ORGANISM: Artificial Sequence
<220> FEATURE:
<223> OTHER INFORMATION: Synthetic: 4A3 VL  with signal sequence

<400> SEQUENCE: 74

Met Arg Val Pro Ala Gln Leu Leu Gly Leu Leu Leu Leu Trp Leu Pro
  1               5                  10                  15

Gly Ala Lys Cys Asp Ile Gln Met Thr Gln Ser Pro Ser Thr Leu Ser
                20                  25                  30

Ala Ser Val Gly Asp Arg Val Thr Ile Thr Cys Arg Ala Ser Gln Ser
            35                  40                  45

Ile Ser Gly Trp Leu Ala Trp Tyr Gln Gln Lys Pro Gly Lys Ala Pro
     50                  55                  60
```

```
Lys Leu Leu Ile Tyr Lys Ala Ser Ser Leu Glu Ser Gly Val Pro Ser
 65                  70                  75                  80

Arg Phe Ser Gly Ser Gly Ser Gly Thr Glu Phe Thr Leu Thr Ile Ser
                 85                  90                  95

Ser Leu Gln Pro Asp Asp Phe Ala Thr Tyr Tyr Cys Gln Gln Tyr Tyr
            100                 105                 110

Gly Ser Ser Arg Thr Phe Gly Gln Gly Thr Asn Val Glu Ile Lys
        115                 120                 125
```

<210> SEQ ID NO 75
<211> LENGTH: 138
<212> TYPE: PRT
<213> ORGANISM: Artificial Sequence
<220> FEATURE:
<223> OTHER INFORMATION: Synthetic: 9H9 VH with signal sequence

<400> SEQUENCE: 75

```
Met Glu Leu Gly Leu Ser Trp Val Phe Leu Val Ala Ile Leu Glu Gly
  1               5                  10                  15

Val Gln Cys Glu Val Gln Leu Val Glu Ser Gly Gly Gly Leu Val Gln
             20                  25                  30

Pro Gly Gly Ser Leu Arg Leu Ser Cys Ala Ala Ser Gly Gly Ile Ile
         35                  40                  45

Ser Thr Tyr Trp Met Ser Trp Val Arg Gln Ala Pro Gly Lys Gly Leu
 50                  55                  60

Glu Trp Val Ala Asn Ile Lys Gln Asp Gly Ser Glu Lys Tyr Tyr Val
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Val Glu Asp Thr Ala Met
            100                 105                 110

Tyr Tyr Cys Ala Arg Asp Arg Pro Val Ala Gly Ala Ser Ala Leu Trp
        115                 120                 125

Gly Gln Gly Thr Leu Val Thr Val Ser Ser
    130                 135
```

<210> SEQ ID NO 76
<211> LENGTH: 127
<212> TYPE: PRT
<213> ORGANISM: Artificial Sequence
<220> FEATURE:
<223> OTHER INFORMATION: Synthetic: 9H9 VL with signal sequence

<400> SEQUENCE: 76

```
Met Arg Val Pro Ala Gln Leu Leu Gly Leu Leu Leu Leu Trp Leu Pro
  1               5                  10                  15

Gly Ala Lys Cys Asp Ile Gln Met Thr Gln Ser Pro Ser Thr Leu Ser
             20                  25                  30

Ala Ser Val Gly Asp Arg Val Thr Ile Thr Cys Arg Ala Ser Gln Ser
         35                  40                  45

Ile Ser Gly Trp Leu Ala Trp Tyr Gln Gln Lys Pro Gly Lys Ala Pro
 50                  55                  60

Lys Leu Leu Ile Tyr Lys Ala Ser Ser Leu Glu Ser Gly Val Pro Ser
 65                  70                  75                  80

Arg Phe Ser Gly Ser Gly Ser Gly Thr Glu Phe Thr Leu Thr Ile Ser
                 85                  90                  95

Ser Leu Gln Pro Asp Asp Phe Ala Thr Tyr Tyr Cys Gln Gln Tyr Tyr
            100                 105                 110
```

-continued

Gly Ser Ser Arg Thr Phe Gly Gln Gly Thr Asn Val Glu Ile Lys
        115                 120                 125

<210> SEQ ID NO 77
<211> LENGTH: 119
<212> TYPE: PRT
<213> ORGANISM: Artificial Sequence
<220> FEATURE:
<223> OTHER INFORMATION: Synthetic: 7H7 VH  without signal sequence

<400> SEQUENCE: 77

Glu Val Gln Leu Val Glu Ser Gly Gly Leu Val Gln Pro Gly Gly
1               5                   10                  15

Ser Leu Arg Leu Ser Cys Ala Ala Ser Gly Gly Thr Ile Ser Thr Ser
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Ile Tyr Tyr Cys
                85                  90                  95

Ala Arg Asp Arg Pro Val Ala Gly Ala Ser Ala Leu Trp Gly Gln Gly
            100                 105                 110

Thr Leu Val Thr Val Ser Ser
        115

<210> SEQ ID NO 78
<211> LENGTH: 107
<212> TYPE: PRT
<213> ORGANISM: Artificial Sequence
<220> FEATURE:
<223> OTHER INFORMATION: Synthetic: 7H7 VL  without signal sequence

<400> SEQUENCE: 78

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Trp
            20                  25                  30

Leu Ala Trp Tyr Gln Gln Lys Gln Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Gly Ser Ser Arg
                85                  90                  95

Thr Phe Gly Gln Gly Thr Asn Val Glu Ile Lys
            100                 105

<210> SEQ ID NO 79
<211> LENGTH: 119
<212> TYPE: PRT
<213> ORGANISM: Artificial Sequence
<220> FEATURE:
<223> OTHER INFORMATION: Synthetic: 1B3 VH  without signal sequence

<400> SEQUENCE: 79

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Thr Ile Ser Thr Ser
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Met Tyr Tyr Cys
                85                  90                  95

Ala Arg Asp Arg Pro Val Ala Gly Ala Ser Ala Leu Trp Gly Gln Gly
            100                 105                 110

Thr Leu Val Thr Val Ser Ser
            115
```

<210> SEQ ID NO 80
<211> LENGTH: 107
<212> TYPE: PRT
<213> ORGANISM: Artificial Sequence
<220> FEATURE:
<223> OTHER INFORMATION: Synthetic: 1B3 VL without signal sequence

<400> SEQUENCE: 80

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Ser Ser Ser Arg
                85                  90                  95

Thr Phe Gly Gln Gly Thr Asn Val Glu Ile Lys
            100                 105
```

<210> SEQ ID NO 81
<211> LENGTH: 119
<212> TYPE: PRT
<213> ORGANISM: Artificial Sequence
<220> FEATURE:
<223> OTHER INFORMATION: Synthetic: 3B6 VH without signal sequence

<400> SEQUENCE: 81

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Thr Ser Thr Thr Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Asn
65                  70                  75                  80
```

```
Leu Gln Met Asn Ser Leu Arg Val Glu Asp Thr Ala Ile Tyr Tyr Cys
                85                  90                  95

Ala Arg Asp Arg Pro Val Ala Gly Ala Ser Ala Leu Trp Gly Gln Gly
            100                 105                 110

Thr Leu Val Thr Val Ser Ser
        115

<210> SEQ ID NO 82
<211> LENGTH: 107
<212> TYPE: PRT
<213> ORGANISM: Artificial Sequence
<220> FEATURE:
<223> OTHER INFORMATION: Synthetic: 3B6 VL  without signal sequence

<400> SEQUENCE: 82

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Gly Ser Ser Arg
                85                  90                  95

Thr Phe Gly Gln Gly Thr Asn Val Glu Ile Lys
            100                 105

<210> SEQ ID NO 83
<211> LENGTH: 119
<212> TYPE: PRT
<213> ORGANISM: Artificial Sequence
<220> FEATURE:
<223> OTHER INFORMATION: Synthetic: 8B1 VH  without signal sequence

<400> SEQUENCE: 83

Glu Val Arg Leu Val Glu Ser Gly Gly Gly Leu Val Gln Pro Gly Gly
1               5                   10                  15

Ser Leu Arg Leu Ser Cys Ala Ala Ser Gly Asp Ile Ile Ser Thr His
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Thr Leu Arg Val Glu Asp Thr Ala Ile Tyr Tyr Cys
                85                  90                  95

Thr Arg Asp Arg Pro Val Ala Gly Ala Ser Ala Leu Trp Gly Gln Gly
            100                 105                 110

Thr Leu Val Thr Val Ser Ser
        115

<210> SEQ ID NO 84
<211> LENGTH: 107
<212> TYPE: PRT
```

<213> ORGANISM: Artificial Sequence
<220> FEATURE:
<223> OTHER INFORMATION: Synthetic: 8B1 VL  without signal sequence

<400> SEQUENCE: 84

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Gly Ser Ser Arg
                85                  90                  95

Thr Phe Gly Gln Gly Thr Asn Val Glu Ile Lys
            100                 105

<210> SEQ ID NO 85
<211> LENGTH: 119
<212> TYPE: PRT
<213> ORGANISM: Artificial Sequence
<220> FEATURE:
<223> OTHER INFORMATION: Synthetic: 4A3 VH  without signal sequence

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ile Ile Ser Ser Ser
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asp Leu Leu Tyr
65                  70                  75                  80

Leu Gln Met Asn Ser Leu Arg Val Glu Asp Thr Ala Leu Tyr Tyr Cys
                85                  90                  95

Ala Arg Asp Arg Pro Val Ala Gly Ala Ser Ala Leu Trp Gly Gln Gly
            100                 105                 110

Thr Leu Val Thr Val Ser Ser
        115

<210> SEQ ID NO 86
<211> LENGTH: 107
<212> TYPE: PRT
<213> ORGANISM: Artificial Sequence
<220> FEATURE:
<223> OTHER INFORMATION: Synthetic: 4A3 VL  without signal sequence

<400> SEQUENCE: 86

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Trp
            20                  25                  30

Leu Ala Trp Tyr Gln Gln Lys Pro Gly Lys Ala Pro Lys Leu Leu Ile
        35                  40                  45

```
Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Tyr Gly Ser Ser Arg
                85                  90                  95

Thr Phe Gly Gln Gly Thr Asn Val Glu Ile Lys
            100                 105

<210> SEQ ID NO 87
<211> LENGTH: 119
<212> TYPE: PRT
<213> ORGANISM: Artificial Sequence
<220> FEATURE:
<223> OTHER INFORMATION: Synthetic: 9H9 VH  without signal sequence

<400> SEQUENCE: 87

Glu Val Gln Leu Val Glu Ser Gly Gly Gly Leu Val Gln Pro Gly Gly
 1               5                  10                  15

Ser Leu Arg Leu Ser Cys Ala Ala Ser Gly Gly Ile Ile Ser Thr Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Met Tyr Tyr Cys
                85                  90                  95

Ala Arg Asp Arg Pro Val Ala Gly Ala Ser Ala Leu Trp Gly Gln Gly
                100                 105                 110

Thr Leu Val Thr Val Ser Ser
        115

<210> SEQ ID NO 88
<211> LENGTH: 107
<212> TYPE: PRT
<213> ORGANISM: Artificial Sequence
<220> FEATURE:
<223> OTHER INFORMATION: Synthetic: 9H9 VL  without signal sequence

<400> SEQUENCE: 88

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Gly Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Tyr Gly Ser Ser Arg
                85                  90                  95

Thr Phe Gly Gln Gly Thr Asn Val Glu Ile Lys
            100                 105
```

```
<210> SEQ ID NO 89
<211> LENGTH: 414
<212> TYPE: DNA
<213> ORGANISM: Artificial Sequence
<220> FEATURE:
<223> OTHER INFORMATION: Synthetic: 7H7 VH DNA Sequence with signal
      sequence
<220> FEATURE:
<221> NAME/KEY: misc_feature
<222> LOCATION: (21)..(21)
<223> OTHER INFORMATION: n is a, c, g, or t

<400> SEQUENCE: 89
atggaattgg ggctgagctg ngttttcctt gttgctattt tagaaggtgt ccagtgtgag      60
gtgcaactgg tggagtctgg gggaggcttg gtccagcctg gggggtccct gagactctcc     120
tgtgcagcct ctggaggcac cattagtacc tcttggatga gctgggtccg ccaggctcca     180
gggaaggggc tggaatgggt ggccaacata aagcaagatg aagtgagaa atattatgtg      240 gactctgtga agggccgatt caccatctcc agagacaacg ccaagaactc actgtatttg     300
caaatgaaca gcctgagagt cgaggacacg gctatatatt actgtgcgag agatcgtcca     360
gtggctggtg cgtcggccct ctggggccag ggaaccctgg tcaccgtctc ctca           414

<210> SEQ ID NO 90
<211> LENGTH: 381
<212> TYPE: DNA
<213> ORGANISM: Artificial Sequence
<220> FEATURE:
<223> OTHER INFORMATION: Synthetic: 7H7 VL DNA Sequence with signal
      sequence

<400> SEQUENCE: 90
atgagggtcc ccgctcagct cctggggctc ctgctgctct ggctcccagg tgccaaatgt      60
gacatccaga tgacccagtc tccttccacc ctgtctgcat ctgtaggaga cagagtcacc     120
atcacttgcc gggccagtca gagtataagt ggctggttgg cctggtatca gcagaaacaa     180
gggaaagccc ctaagctcct gatctataag gcgtctagtt tagaaagtgg ggtcccatca     240
aggttcagcg gcagtggatc tgggacagaa ttcactctca ccatcagcag cctgcagcct     300
gatgattttg caacttatta ctgccaacag tattatggtt cttctcggac gttcggccaa     360
gggaccaatg tggaaatcaa a                                                381

<210> SEQ ID NO 91
<211> LENGTH: 414
<212> TYPE: DNA
<213> ORGANISM: Artificial Sequence
<220> FEATURE:
<223> OTHER INFORMATION: Synthetic: 1B3 VH DNA Sequence with signal
      sequence

<400> SEQUENCE: 91
atggaattgg ggctgagctg ggttttcctt gttgctattt tagaaggtgt ccagtgtgag      60
gtgcaactgg tggagtctgg gggaggcttg gtccagcctg gggggtccct gagactctcc     120
tgtgcagcct ctggaggcac cattagtacc tcttggatga gctgggtccg ccaggctcca     180
gggaaggggc tggaatgggt ggccaacata aagcaagatg aagtgagaa atattatgtg      240 gactctgtga agggccgatt caccatctcc agagacaacg ccaagaactc actgtatttg     300
caaatgaaca gcctgagagt cgaagacacg gctatgtatt actgtgcgag agatcgtcca     360
gtggctggtg cgtcggccct ctggggccag ggaaccctgg tcaccgtctc ctca           414
```

<210> SEQ ID NO 92
<211> LENGTH: 381
<212> TYPE: DNA
<213> ORGANISM: Artificial Sequence
<220> FEATURE:
<223> OTHER INFORMATION: Synthetic: 1B3 VL DNA Sequence with signal
      sequence

<400> SEQUENCE: 92

```
atgagggtcc cgctcagct cctggggctc ctgctgctct ggctcccagg tgccaaatgt      60
gacatccaga tgacccagtc tccttccacc ctgtctgcat ctgtaggaga cagagtcacc     120
atcacttgcc gggccagtca gagtattagt ggctggttgg cctggtatca gcagaaacca    180
gggaaagccc ctaagctcct gatctataag gcgtctagtt tagaaagtgg ggtcccatca    240
aggttcagcg gcagtggatc tgggacagaa ttcactctca ccatcagcag cctgcagcct    300
gatgattttg caacttatta ctgccaacag tattatggtt cttctcggac gttcggccaa    360
gggaccaatg tggaaatcaa a                                               381
```

<210> SEQ ID NO 93
<211> LENGTH: 414
<212> TYPE: DNA
<213> ORGANISM: Artificial Sequence
<220> FEATURE:
<223> OTHER INFORMATION: Synthetic: 3B6 VH DNA Sequence with signal
      sequence

<400> SEQUENCE: 93

```
atggaattgg gctgagctg ggttttcctt gttgctattt tagaaggtgt ccagtgtgag      60
gtgcaactgg tggagtctgg gggaggcttg gtccagcctg gggggtccct gagactctcc    120
tgtgcagcct ctggaggcac aaccagtacc tattggatga gctgggtccg ccaggctcca    180
gggaaggggc tggaatgggt ggccaacata aagcaagatg gaagtgagaa atattatgtg    240
gactctgtga agggccgatt caccatctcc agagacaacg ccaagaactc actgaatttg    300
caaatgaaca gcctgagagt cgaggacacg gctatatatt actgtgcgag agatcgtcca    360
gtggctggtg cgtcggccct ctggggccag ggaaccctgg tcaccgtctc ctca          414
```

<210> SEQ ID NO 94
<211> LENGTH: 381
<212> TYPE: DNA
<213> ORGANISM: Artificial Sequence
<220> FEATURE:
<223> OTHER INFORMATION: Synthetic: 3B6 VL DNA Sequence with signal
      sequence

<400> SEQUENCE: 94

```
atgagggtcc cgctcagct cctggggctc ctgctgctct ggctcccagg tgccaaatgt      60
gacatccaga tgacccagtc tccttccacc ctgtctgcat ctgtaggaga cagagtcacc    120
atcacttgcc gggccagtca gagtattagt ggctggttgg cctggtatca gcagaaacca    180
gggaaagccc ctaagctcct gatctataag gcgtctagtt tagaaagtgg ggtcccatca    240
aggttcagcg gcagtggatc tgggacagaa ttcactctca ccatcagcag cctgcagcct    300
gatgattttg caacttatta ctgccaacag tattatggtt cttctcggac gttcggccaa    360
gggaccaatg tggaaatcaa a                                               381
```

<210> SEQ ID NO 95
<211> LENGTH: 414
<212> TYPE: DNA
<213> ORGANISM: Artificial Sequence
<220> FEATURE:
<223> OTHER INFORMATION: Synthetic: 8B1 VH DNA Sequence with signal
sequence

<400> SEQUENCE: 95

| atggaattgg ggctgagctg ggttttcctt gttgctattt tagaaggtgt caagtgtgag | 60 |
| gtgcgactgg tggagtctgg gggaggcttg gtccagcctg gggggtccct gagactctcc | 120 |
| tgtgcagcct ctggagacat aattagtacc cattggatga gctgggtccg ccaggctcca | 180 |
| gggaaggggc tggaatgggt ggccaacata aacaagatg gaagtgagaa gtattatgtg | 240 |
| gactctgtga agggccgatt caccatctcc agagacaacg ccaagaactc actgtatttg | 300 |
| caaatgaaca ccctgagagt cgaggacacg gctatatatt actgtacgag agatcgtcca | 360 |
| gtggctggtg cgtcggccct ctggggccag ggaaccctgg tcaccgtctc ctca | 414 |

<210> SEQ ID NO 96
<211> LENGTH: 381
<212> TYPE: DNA
<213> ORGANISM: Artificial Sequence
<220> FEATURE:
<223> OTHER INFORMATION: Synthetic: 8B1 VL DNA Sequence with signal
sequence

<400> SEQUENCE: 96

| atgagggtcc ccgctcagct cctggggctc ctgctgctct ggctcccagg tgccaaatgt | 60 |
| gacatccaga tgacccagtc tccttccacc ctgtctgcat ctgtaggaga cagagtcacc | 120 |
| atcacttgcc gggccagtca gagtattagt ggctggttgg cctggtatca gcagaaacca | 180 |
| gggaaagccc ctaagctcct gatctataag gcgtctagtt tagaaagtgg ggtcccatta | 240 |
| aggttcagcg gcagtggatc tgggacagaa ttcactctca ccatcagcag cctgcagcct | 300 |
| gatgattttg caacttatta ctgccaacag tattatggtt cttctcggac gttcggccaa | 360 |
| gggaccaatg tggaaatcaa a | 381 |

<210> SEQ ID NO 97
<211> LENGTH: 414
<212> TYPE: DNA
<213> ORGANISM: Artificial Sequence
<220> FEATURE:
<223> OTHER INFORMATION: Synthetic: 4A3 VH DNA Sequence with signal
sequence

<400> SEQUENCE: 97

| atggaattgg ggctgagctg ggttttcctt gttgctattt tagaaggtgt ccagtgtgag | 60 |
| gtgcaactgg tggagtctgg gggaggcttg gtccagccgg gggggtccct gagactctcc | 120 |
| tgtgcagcct ctggaggcat cattagttcc tcttggatga gctgggtccg ccaggctcca | 180 |
| gggaaggggc tggaatgggt ggccaacata aagcaagatg gaagtgagaa atattatgtg | 240 |
| gactctgtga agggccgatt caccatctcc agagacaacg ccaaagactt actgtatttg | 300 |
| caaatgaaca gcctgagagt cgaggacacg gctttatatt actgtgcgag agatcgtcca | 360 |
| gtggctggtg cgtcggccct ctggggccag ggaaccctgg tcaccgtctc ctct | 414 |

<210> SEQ ID NO 98
<211> LENGTH: 381
<212> TYPE: DNA
<213> ORGANISM: Artificial Sequence
<220> FEATURE:
<223> OTHER INFORMATION: Synthetic: 4A3 VL DNA Sequence with signal
sequence

<400> SEQUENCE: 98

```
atgagggtcc ccgctcagct cctggggctc ctgctgctct ggctcccagg tgccaaatgt      60
gacatccaga tgacccagtc tccttccacc ctgtctgcat ctgtaggaga cagagtcacc     120
atcacttgcc gggccagtca gagtattagt ggctggttgg cctggtatca gcagaaacca     180
gggaaagccc ctaagctcct gatctataag gcgtctagtt tagaaagtgg ggtcccatca     240
aggttcagcg gcagtggatc tgggacagaa ttcactctca ccatcagcag cctgcagcct     300
gatgattttg caacttatta ctgccaacag tattatggtt cttctcggac gttcggccaa     360
gggaccaatg tggaaatcaa a                                                381
```

<210> SEQ ID NO 99
<211> LENGTH: 414
<212> TYPE: DNA
<213> ORGANISM: Artificial Sequence
<220> FEATURE:
<223> OTHER INFORMATION: Synthetic: 9H9 VH DNA Sequence with signal
      sequence

<400> SEQUENCE: 99

```
atggaattgg ggctgagctg gttttccctt gttgctattt tagaaggtgt ccagtgtgag      60
gtgcaactgg tggagtctgg gggaggcttg gtccagcctg gggggtccct gagactctcc     120
tgtgcagcct ctggaggcat cattagtacc tattggatga gctgggtccg ccaggctcca     180
gggaaggggc tggaatgggt ggccaacata aagcaagatg gaagtgagaa atattatgtg     240
gactctgtga agggccgatt caccatctcc agagacaacg ccaagaactc actgtatttg     300
caaatgaaca gcctgagagt cgaggacacg gctatgtatt actgtgcgag agatcgtcca     360
gtggctggtg cgtcggccct ctggggccag ggaaccctgg tcaccgtctc ctca           414
```

<210> SEQ ID NO 100
<211> LENGTH: 381
<212> TYPE: DNA
<213> ORGANISM: Artificial Sequence
<220> FEATURE:
<223> OTHER INFORMATION: Synthetic: 9H9 VL DNA Sequence with signal
      sequence

<400> SEQUENCE: 100

```
atgagggtcc ccgctcagct cctggggctc ctgctgctct ggctcccagg tgccaaatgt      60
gacatccaga tgacccagtc tccttccacc ctgtctgcat ctgtaggaga cagagtcacc     120
atcacttgcc gggccagtca gagtattagt ggctggttgg cctggtatca gcagaaacca     180
gggaaagccc ctaagctcct gatctataag gcgtctagtt tagaaagtgg ggtcccatca     240
aggttcagcg gcagtggatc tgggacagaa ttcactctca ccatcagcag cctgcagcct     300
gatgattttg caacttatta ctgccaacag tattatggtt cttctcggac gttcggccaa     360
gggaccaatg tggaaatcaa a                                                381
```

<210> SEQ ID NO 101
<211> LENGTH: 357
<212> TYPE: DNA
<213> ORGANISM: Artificial Sequence
<220> FEATURE:
<223> OTHER INFORMATION: Synthetic: 7H7 VH DNA Sequence without signal
      sequence

<400> SEQUENCE: 101

```
gaggtgcaac tggtggagtc tggggggaggc ttggtccagc ctggggggtc cctgagactc      60
```

```
tcctgtgcag cctctggagg caccattagt acctcttgga tgagctgggt ccgccaggct    120
ccagggaagg ggctggaatg ggtggccaac ataaagcaag atggaagtga gaaatattat    180
gtggactctg tgaagggccg attcaccatc tccagagaca acgccaagaa ctcactgtat    240
ttgcaaatga acagcctgag agtcgaggac acggctatat attactgtgc gagagatcgt    300
ccagtggctg gtgcgtcggc cctctggggc cagggaaccc tggtcaccgt ctcctca      357
```

```
<210> SEQ ID NO 102
<211> LENGTH: 321
<212> TYPE: DNA
<213> ORGANISM: Artificial Sequence
<220> FEATURE:
<223> OTHER INFORMATION: Synthetic: 7H7 VL DNA Sequence  without signal
      sequence

<400> SEQUENCE: 102
```

```
gacatccaga tgacccagtc tccttccacc ctgtctgcat ctgtaggaga cagagtcacc     60
atcacttgcc gggccagtca gagtataagt ggctggttgg cctggtatca gcagaaacaa    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tattatggtt cttctcggac gttcggccaa    300
gggaccaatg tggaaatcaa a                                              321
```

```
<210> SEQ ID NO 103
<211> LENGTH: 357
<212> TYPE: DNA
<213> ORGANISM: Artificial Sequence
<220> FEATURE:
<223> OTHER INFORMATION: Synthetic: 1B3 VH DNA Sequence  without signal
      sequence

<400> SEQUENCE: 103
```

```
gaggtgcaac tggtggagtc tgggggaggc ttggtccagc ctgggggtc cctgagactc       60 tcctgtgcag cctctggagg caccattagt acctcttgga tgagctgggt ccgccaggct    120
ccagggaagg ggctggaatg ggtggccaac ataaagcaag atggaagtga gaaatattat    180
gtggactctg tgaagggccg attcaccatc tccagagaca acgccaagaa ctcactgtat    240
ttgcaaatga acagcctgag agtcgaagac acggctatgt attactgtgc gagagatcgt    300
ccagtggctg gtgcgtcggc cctctggggc cagggaaccc tggtcaccgt ctcctca      357
```

```
<210> SEQ ID NO 104
<211> LENGTH: 321
<212> TYPE: DNA
<213> ORGANISM: Artificial Sequence
<220> FEATURE:
<223> OTHER INFORMATION: Synthetic: 1B3 VL DNA Sequence  without signal
      sequence

<400> SEQUENCE: 104
```

```
gacatccaga tgacccagtc tccttccacc ctgtctgcat ctgtaggaga cagagtcacc     60
atcacttgcc gggccagtca gagtattagt ggctggttgg cctggtatca gcagaaacca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tattatggtt cttctcggac gttcggccaa    300
gggaccaatg tggaaatcaa a                                              321
```

<210> SEQ ID NO 105
<211> LENGTH: 357
<212> TYPE: DNA
<213> ORGANISM: Artificial Sequence
<220> FEATURE:
<223> OTHER INFORMATION: Synthetic: 3B6 VH DNA Sequence without signal
      sequence

<400> SEQUENCE: 105

```
gaggtgcaac tggtggagtc tggggaggc ttggtccagc ctgggggtc cctgagactc       60 tcctgtgcag cctctggagg cacaaccagt acctattgga tgagctgggt ccgccaggct      120
ccagggaagg ggctggaatg ggtggccaac ataaagcaag atggaagtga aaatattat      180 gtggactctg tgaagggccg attcaccatc tccagagaca acgccaagaa ctcactgaat      240
ttgcaaatga acagcctgag agtcgaggac acggctatat attactgtgc gagagatcgt      300
ccagtggctg gtgcgtcggc cctctgggc cagggaaccc tggtcaccgt ctcctca          357
```

<210> SEQ ID NO 106
<211> LENGTH: 321
<212> TYPE: DNA
<213> ORGANISM: Artificial Sequence
<220> FEATURE:
<223> OTHER INFORMATION: Synthetic: 3B6 VL DNA Sequence without signal
      sequence

<400> SEQUENCE: 106

```
gacatccaga tgacccagtc tccttccacc ctgtctgcat ctgtaggaga cagagtcacc       60
atcacttgcc gggccagtca gagtattagt ggctggttgg cctggtatca gcagaaacca      120
gggaaagccc ctaagctcct gatctataag gcgtctagtt tagaaagtgg ggtcccatca      180
aggttcagcg gcagtggatc tgggacagaa ttcactctca ccatcagcag cctgcagcct      240
gatgattttg caacttatta ctgccaacag tattatggtt cttctcggac gttcggccaa      300
gggaccaatg tggaaatcaa a                                                321
```

<210> SEQ ID NO 107
<211> LENGTH: 357
<212> TYPE: DNA
<213> ORGANISM: Artificial Sequence
<220> FEATURE:
<223> OTHER INFORMATION: Synthetic: 8B1 VH DNA Sequence without signal
      sequence

<400> SEQUENCE: 107

```
gaggtgcgac tggtggagtc tggggaggc ttggtccagc ctgggggtc cctgagactc        60 tcctgtgcag cctctggaga cataattagt acccattgga tgagctgggt ccgccaggct      120
ccagggaagg ggctggaatg ggtggccaac ataaaacaag atggaagtga aagtattat      180 gtggactctg tgaagggccg attcaccatc tccagagaca acgccaagaa ctcactgtat      240
ttgcaaatga acaccctgag agtcgaggac acggctatat attactgtac gagagatcgt      300
ccagtggctg gtgcgtcggc cctctgggc cagggaaccc tggtcaccgt ctcctca          357
```

<210> SEQ ID NO 108
<211> LENGTH: 321
<212> TYPE: DNA
<213> ORGANISM: Artificial Sequence
<220> FEATURE:
<223> OTHER INFORMATION: Synthetic: 8B1 VL DNA Sequence without signal
      sequence

<400> SEQUENCE: 108

```
gacatccaga tgacccagtc tccttccacc ctgtctgcat ctgtaggaga cagagtcacc      60
atcacttgcc gggccagtca gagtattagt ggctggttgg cctggtatca gcagaaacca     120
gggaaagccc ctaagctcct gatctataag gcgtctagtt tagaaagtgg ggtcccatta     180
aggttcagcg gcagtggatc tgggacagaa ttcactctca ccatcagcag cctgcagcct     240
gatgattttg caacttatta ctgccaacag tattatggtt cttctcggac gttcggccaa     300
gggaccaatg tggaaatcaa a                                               321
```

<210> SEQ ID NO 109
<211> LENGTH: 357
<212> TYPE: DNA
<213> ORGANISM: Artificial Sequence
<220> FEATURE:
<223> OTHER INFORMATION: Synthetic: 4A3 VH DNA Sequence without signal
      sequence

<400> SEQUENCE: 109

```
gaggtgcaac tggtggagtc tgggggaggc ttggtccagc cggggggggtc cctgagactc     60 tcctgtgcag cctctggagg catcattagt tcctcttgga tgagctgggt ccgccaggct    120
ccagggaagg ggctggaatg ggtggccaac ataaagcaag atggaagtga aaatattat     180 gtggactctg tgaagggccg attcaccatc tccagagaca cgccaaaga cttactgtat     240 ttgcaaatga acagcctgag agtcgaggac acggctttat attactgtgc gagagatcgt    300
ccagtggctg gtgcgtcggc cctctggggc agggaaccc tggtcaccgt ctcctct       357
```

<210> SEQ ID NO 110
<211> LENGTH: 321
<212> TYPE: DNA
<213> ORGANISM: Artificial Sequence
<220> FEATURE:
<223> OTHER INFORMATION: Synthetic: 4A3 VL DNA Sequence without signal
      sequence

<400> SEQUENCE: 110

```
gacatccaga tgacccagtc tccttccacc ctgtctgcat ctgtaggaga cagagtcacc      60
atcacttgcc gggccagtca gagtattagt ggctggttgg cctggtatca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tattatggtt cttctcggac gttcggccaa     300
gggaccaatg tggaaatcaa a                                               321
```

<210> SEQ ID NO 111
<211> LENGTH: 357
<212> TYPE: DNA
<213> ORGANISM: Artificial Sequence
<220> FEATURE:
<223> OTHER INFORMATION: Synthetic: 9H9 VH DNA Sequence without signal
      sequence

<400> SEQUENCE: 111

```
gaggtgcaac tggtggagtc tgggggaggc ttggtccagc ctgggggggtc cctgagactc     60 tcctgtgcag cctctggagg catcattagt acctattgga tgagctgggt ccgccaggct    120
ccagggaagg ggctggaatg ggtggccaac ataaagcaag atggaagtga aaatattat     180 gtggactctg tgaagggccg attcaccatc tccagagaca cgccaagaa ctcactgtat     240 ttgcaaatga acagcctgag agtcgaggac acggctatgt attactgtgc gagagatcgt    300
```

```
ccagtggctg gtgcgtcggc cctctggggc cagggaaccc tggtcaccgt ctcctca         357
```

<210> SEQ ID NO 112
<211> LENGTH: 321
<212> TYPE: DNA
<213> ORGANISM: Artificial Sequence
<220> FEATURE:
<223> OTHER INFORMATION: Synthetic: 9H9 VL DNA Sequence without signal
    sequence

<400> SEQUENCE: 112

```
gacatccaga tgacccagtc tccttccacc ctgtctgcat ctgtaggaga cagagtcacc         60
atcacttgcc gggccagtca gagtattagt ggctggttgg cctggtatca gcagaaacca        120
gggaaagccc ctaagctcct gatctataag gcgtctagtt tagaaagtgg ggtcccatca        180
aggttcagcg gcagtggatc tgggacagaa ttcactctca ccatcagcag cctgcagcct        240
gatgattttg caacttatta ctgccaacag tattatggtt cttctcggac gttcggccaa        300
gggaccaatg tggaaatcaa a                                                  321
```

<210> SEQ ID NO 113
<211> LENGTH: 7
<212> TYPE: PRT
<213> ORGANISM: Artificial Sequence
<220> FEATURE:
<223> OTHER INFORMATION: Synthetic: 3C2 VH CDR1 (Chothia)

<400> SEQUENCE: 113

Thr Gly Ser Ile Ser Gly Tyr
1               5

<210> SEQ ID NO 114
<211> LENGTH: 5
<212> TYPE: PRT
<213> ORGANISM: Artificial Sequence
<220> FEATURE:
<223> OTHER INFORMATION: Synthetic: 3C2 VH CDR2 (Chothia)

<400> SEQUENCE: 114

Tyr Tyr Ser Gly Ser
1               5

<210> SEQ ID NO 115
<211> LENGTH: 10
<212> TYPE: PRT
<213> ORGANISM: Artificial Sequence
<220> FEATURE:
<223> OTHER INFORMATION: Synthetic: 3C2 VH CDR3 (Chothia)

<400> SEQUENCE: 115

Tyr Pro Leu Ile Arg Gly Ala Phe Asp Tyr
1               5                   10

<210> SEQ ID NO 116
<211> LENGTH: 16
<212> TYPE: PRT
<213> ORGANISM: Artificial Sequence
<220> FEATURE:
<223> OTHER INFORMATION: Synthetic: 3C2 VL CDR1 (Chothia)

<400> SEQUENCE: 116

Arg Ser Ser Gln Asn Leu Leu His Thr Asn Gly Tyr Asn Tyr Leu Asp
1               5                   10                  15

-continued

```
<210> SEQ ID NO 117
<211> LENGTH: 7
<212> TYPE: PRT
<213> ORGANISM: Artificial Sequence
<220> FEATURE:
<223> OTHER INFORMATION: Synthetic: 3C2 VL CDR2 (Chothia)

<400> SEQUENCE: 117

Leu Gly Ser Asn Arg Ala Ser
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic: 3C2 VL CDR3 (Chothia)

<400> SEQUENCE: 118

Met Gln Ala Leu Gln Thr Pro Leu Thr
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic: 2B3 VH CDR1 (Chothia)

<400> SEQUENCE: 119

Gly Tyr Thr Phe Thr Gly Tyr
1               5

<210> SEQ ID NO 120
<211> LENGTH: 6
<212> TYPE: PRT
<213> ORGANISM: Artificial Sequence
<220> FEATURE:
<223> OTHER INFORMATION: Synthetic: 2B3 VH CDR2 (Chothia)

<400> SEQUENCE: 120

Asn Pro Asn Ser Gly Gly
1               5

<210> SEQ ID NO 121
<211> LENGTH: 18
<212> TYPE: PRT
<213> ORGANISM: Artificial Sequence
<220> FEATURE:
<223> OTHER INFORMATION: Synthetic: 2B3 VH CDR3 (Chothia)

<400> SEQUENCE: 121

Asp Arg Leu Val Leu Pro Trp Phe Gly Glu Ile Phe Pro Asp Ala Phe
1               5                   10                  15

Asp Ile

<210> SEQ ID NO 122
<211> LENGTH: 11
<212> TYPE: PRT
<213> ORGANISM: Artificial Sequence
<220> FEATURE:
<223> OTHER INFORMATION: Synthetic: 2B3 VL CDR1 (Chothia)

<400> SEQUENCE: 122

Arg Ala Ser Gln Ser Ile Arg Ser Asn Leu Ala
1               5                   10
```

<210> SEQ ID NO 123
<211> LENGTH: 7
<212> TYPE: PRT
<213> ORGANISM: Artificial Sequence
<220> FEATURE:
<223> OTHER INFORMATION: Synthetic: 2B3 VL CDR2 (Chothia)

<400> SEQUENCE: 123

Gly Ala Ser Thr Arg Ala Thr
1               5

<210> SEQ ID NO 124
<211> LENGTH: 9
<212> TYPE: PRT
<213> ORGANISM: Artificial Sequence
<220> FEATURE:
<223> OTHER INFORMATION: Synthetic: 2B3 VL CDR3 (Chothia)

<400> SEQUENCE: 124

Gln Gln Tyr Asn Asn Trp Pro Leu Thr
1               5

<210> SEQ ID NO 125
<211> LENGTH: 7
<212> TYPE: PRT
<213> ORGANISM: Artificial Sequence
<220> FEATURE:
<223> OTHER INFORMATION: Synthetic: 7H7 VH CDR1 (Chothia)

<400> SEQUENCE: 125

Gly Gly Thr Ile Ser Thr Ser
1               5

<210> SEQ ID NO 126
<211> LENGTH: 6
<212> TYPE: PRT
<213> ORGANISM: Artificial Sequence
<220> FEATURE:
<223> OTHER INFORMATION: Synthetic: 7H7 VH CDR2 (Chothia)

<400> SEQUENCE: 126

Lys Gln Asp Gly Ser Glu
1               5

<210> SEQ ID NO 127
<211> LENGTH: 10
<212> TYPE: PRT
<213> ORGANISM: Artificial Sequence
<220> FEATURE:
<223> OTHER INFORMATION: Synthetic: 7H7 VH CDR3 (Chothia)

<400> SEQUENCE: 127

Asp Arg Pro Val Ala Gly Ala Ser Ala Leu
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Synthetic: 7H7 VL CDR1 (Chothia)

<400> SEQUENCE: 128

Arg Ala Ser Gln Ser Ile Ser Gly Trp Leu Ala
1               5                   10

-continued

<210> SEQ ID NO 129
<211> LENGTH: 7
<212> TYPE: PRT
<213> ORGANISM: Artificial Sequence
<220> FEATURE:
<223> OTHER INFORMATION: Synthetic: 7H7 VL CDR2 (Chothia)

<400> SEQUENCE: 129

Lys Ala Ser Ser Leu Glu Ser
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic: 7H7 VL CDR3 (Chothia)

<400> SEQUENCE: 130

Gln Gln Tyr Tyr Gly Ser Ser Arg Thr
1               5

<210> SEQ ID NO 131
<211> LENGTH: 7
<212> TYPE: PRT
<213> ORGANISM: Artificial Sequence
<220> FEATURE:
<223> OTHER INFORMATION: Synthetic: 1B3 VH CDR1 (Chothia)

<400> SEQUENCE: 131

Gly Gly Thr Ile Ser Thr Ser
1               5

<210> SEQ ID NO 132
<211> LENGTH: 6
<212> TYPE: PRT
<213> ORGANISM: Artificial Sequence
<220> FEATURE:
<223> OTHER INFORMATION: Synthetic: 1B3 VH CDR2 (Chothia)

<400> SEQUENCE: 132

Lys Gln Asp Gly Ser Glu
1               5

<210> SEQ ID NO 133
<211> LENGTH: 10
<212> TYPE: PRT
<213> ORGANISM: Artificial Sequence
<220> FEATURE:
<223> OTHER INFORMATION: Synthetic: 1B3 VH CDR3 (Chothia)

<400> SEQUENCE: 133

Asp Arg Pro Val Ala Gly Ala Ser Ala Leu
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Synthetic: 1B3 VL CDR1 (Chothia)

<400> SEQUENCE: 134

Arg Ala Ser Gln Ser Ile Ser Gly Trp Leu Ala
1               5                   10

<210> SEQ ID NO 135

```
<211> LENGTH: 7
<212> TYPE: PRT
<213> ORGANISM: Artificial Sequence
<220> FEATURE:
<223> OTHER INFORMATION: Synthetic: 1B3 VL CDR2 (Chothia)

<400> SEQUENCE: 135

Lys Ala Ser Ser Leu Glu Ser
1               5

<210> SEQ ID NO 136
<211> LENGTH: 9
<212> TYPE: PRT
<213> ORGANISM: Artificial Sequence
<220> FEATURE:
<223> OTHER INFORMATION: Synthetic: 1B3 VL CDR3 (Chothia)

<400> SEQUENCE: 136

Gln Gln Tyr Tyr Gly Ser Ser Arg Thr
1               5

<210> SEQ ID NO 137
<211> LENGTH: 7
<212> TYPE: PRT
<213> ORGANISM: Artificial Sequence
<220> FEATURE:
<223> OTHER INFORMATION: Synthetic: 3B6 VH CDR1 (Chothia)

<400> SEQUENCE: 137

Gly Gly Thr Thr Ser Thr Tyr
1               5

<210> SEQ ID NO 138
<211> LENGTH: 6
<212> TYPE: PRT
<213> ORGANISM: Artificial Sequence
<220> FEATURE:
<223> OTHER INFORMATION: Synthetic: 3B6 VH CDR2 (Chothia)

<400> SEQUENCE: 138

Lys Gln Asp Gly Ser Glu
1               5

<210> SEQ ID NO 139
<211> LENGTH: 10
<212> TYPE: PRT
<213> ORGANISM: Artificial Sequence
<220> FEATURE:
<223> OTHER INFORMATION: Synthetic: 3B6 VH CDR3 (Chothia)

<400> SEQUENCE: 139

Asp Arg Pro Val Ala Gly Ala Ser Ala Leu
1               5                   10

<210> SEQ ID NO 140
<211> LENGTH: 11
<212> TYPE: PRT
<213> ORGANISM: Artificial Sequence
<220> FEATURE:
<223> OTHER INFORMATION: Synthetic: 3B6 VL CDR1 (Chothia)

<400> SEQUENCE: 140

Arg Ala Ser Gln Ser Ile Ser Gly Trp Leu Ala
1               5                   10

<210> SEQ ID NO 141
<211> LENGTH: 7
```

```
<212> TYPE: PRT
<213> ORGANISM: Artificial Sequence
<220> FEATURE:
<223> OTHER INFORMATION: Synthetic: 3B6 VL CDR2 (Chothia)

<400> SEQUENCE: 141

Lys Ala Ser Ser Leu Glu Ser
1               5

<210> SEQ ID NO 142
<211> LENGTH: 9
<212> TYPE: PRT
<213> ORGANISM: Artificial Sequence
<220> FEATURE:
<223> OTHER INFORMATION: Synthetic: 3B6 VL CDR3 (Chothia)

<400> SEQUENCE: 142

Gln Gln Tyr Tyr Gly Ser Ser Arg Thr
1               5

<210> SEQ ID NO 143
<211> LENGTH: 7
<212> TYPE: PRT
<213> ORGANISM: Artificial Sequence
<220> FEATURE:
<223> OTHER INFORMATION: Synthetic: 8B1 VH CDR1 (Chothia)

<400> SEQUENCE: 143

Gly Asp Ile Ile Ser Thr His
1               5

<210> SEQ ID NO 144
<211> LENGTH: 6
<212> TYPE: PRT
<213> ORGANISM: Artificial Sequence
<220> FEATURE:
<223> OTHER INFORMATION: Synthetic: 8B1 VH CDR2 (Chothia)

<400> SEQUENCE: 144

Lys Gln Asp Gly Ser Glu
1               5

<210> SEQ ID NO 145
<211> LENGTH: 10
<212> TYPE: PRT
<213> ORGANISM: Artificial Sequence
<220> FEATURE:
<223> OTHER INFORMATION: Synthetic: 8B1 VH CDR3 (Chothia)

<400> SEQUENCE: 145

Asp Arg Pro Val Ala Gly Ala Ser Ala Leu
1               5                   10

<210> SEQ ID NO 146
<211> LENGTH: 11
<212> TYPE: PRT
<213> ORGANISM: Artificial Sequence
<220> FEATURE:
<223> OTHER INFORMATION: Synthetic: 8B1 VL CDR1 (Chothia)

<400> SEQUENCE: 146

Arg Ala Ser Gln Ser Ile Ser Gly Trp Leu Ala
1               5                   10

<210> SEQ ID NO 147
<211> LENGTH: 7
<212> TYPE: PRT
```

```
<213> ORGANISM: Artificial Sequence
<220> FEATURE:
<223> OTHER INFORMATION: Synthetic: 8B1 VL CDR2 (Chothia)

<400> SEQUENCE: 147

Lys Ala Ser Ser Leu Glu Ser
1               5

<210> SEQ ID NO 148
<211> LENGTH: 9
<212> TYPE: PRT
<213> ORGANISM: Artificial Sequence
<220> FEATURE:
<223> OTHER INFORMATION: Synthetic: 8B1 VL CDR3 (Chothia)

<400> SEQUENCE: 148

Gln Gln Tyr Tyr Gly Ser Ser Arg Thr
1               5

<210> SEQ ID NO 149
<211> LENGTH: 7
<212> TYPE: PRT
<213> ORGANISM: Artificial Sequence
<220> FEATURE:
<223> OTHER INFORMATION: Synthetic: 4A3 VH CDR1 (Chothia)

<400> SEQUENCE: 149

Gly Gly Ile Ile Ser Ser Ser
1               5

<210> SEQ ID NO 150
<211> LENGTH: 6
<212> TYPE: PRT
<213> ORGANISM: Artificial Sequence
<220> FEATURE:
<223> OTHER INFORMATION: Synthetic: 4A3 VH CDR2 (Chothia)

<400> SEQUENCE: 150

Lys Gln Asp Gly Ser Glu
1               5

<210> SEQ ID NO 151
<211> LENGTH: 10
<212> TYPE: PRT
<213> ORGANISM: Artificial Sequence
<220> FEATURE:
<223> OTHER INFORMATION: Synthetic: 4A3 VH CDR3 (Chothia)

<400> SEQUENCE: 151

Asp Arg Pro Val Ala Gly Ala Ser Ala Leu
1               5                   10

<210> SEQ ID NO 152
<211> LENGTH: 11
<212> TYPE: PRT
<213> ORGANISM: Artificial Sequence
<220> FEATURE:
<223> OTHER INFORMATION: Synthetic: 4A3 VL CDR1 (Chothia)

<400> SEQUENCE: 152

Arg Ala Ser Gln Ser Ile Ser Gly Trp Leu Ala
1               5                   10

<210> SEQ ID NO 153
<211> LENGTH: 7
<212> TYPE: PRT
<213> ORGANISM: Artificial Sequence
```

```
<220> FEATURE:
<223> OTHER INFORMATION: Synthetic: 4A3 VL CDR2 (Chothia)

<400> SEQUENCE: 153

Lys Ala Ser Ser Leu Glu Ser
1               5

<210> SEQ ID NO 154
<211> LENGTH: 9
<212> TYPE: PRT
<213> ORGANISM: Artificial Sequence
<220> FEATURE:
<223> OTHER INFORMATION: Synthetic: 4A3 VL CDR3 (Chothia)

<400> SEQUENCE: 154

Gln Gln Tyr Tyr Gly Ser Ser Arg Thr
1               5

<210> SEQ ID NO 155
<211> LENGTH: 7
<212> TYPE: PRT
<213> ORGANISM: Artificial Sequence
<220> FEATURE:
<223> OTHER INFORMATION: Synthetic: 9H9 VH CDR1 (Chothia)

<400> SEQUENCE: 155

Gly Gly Ile Ile Ser Thr Tyr
1               5

<210> SEQ ID NO 156
<211> LENGTH: 6
<212> TYPE: PRT
<213> ORGANISM: Artificial Sequence
<220> FEATURE:
<223> OTHER INFORMATION: Synthetic: 9H9 VH CDR2 (Chothia)

<400> SEQUENCE: 156

Lys Gln Asp Gly Ser Glu
1               5

<210> SEQ ID NO 157
<211> LENGTH: 10
<212> TYPE: PRT
<213> ORGANISM: Artificial Sequence
<220> FEATURE:
<223> OTHER INFORMATION: Synthetic: 9H9 VH CDR3 (Chothia)

<400> SEQUENCE: 157

Asp Arg Pro Val Ala Gly Ala Ser Ala Leu
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Synthetic: 9H9 VL CDR1 (Chothia)

<400> SEQUENCE: 158

Arg Ala Ser Gln Ser Ile Ser Gly Trp Leu Ala
1               5                   10

<210> SEQ ID NO 159
<211> LENGTH: 7
<212> TYPE: PRT
<213> ORGANISM: Artificial Sequence
<220> FEATURE:
```

```
<223> OTHER INFORMATION: Synthetic: 9H9 VL CDR2 (Chothia)

<400> SEQUENCE: 159

Lys Ala Ser Ser Leu Glu Ser
1               5

<210> SEQ ID NO 160
<211> LENGTH: 9
<212> TYPE: PRT
<213> ORGANISM: Artificial Sequence
<220> FEATURE:
<223> OTHER INFORMATION: Synthetic: 9H9 VL CDR3 (Chothia)

<400> SEQUENCE: 160

Gln Gln Tyr Tyr Gly Ser Ser Arg Thr
1               5

<210> SEQ ID NO 161
<211> LENGTH: 5
<212> TYPE: PRT
<213> ORGANISM: Artificial Sequence
<220> FEATURE:
<223> OTHER INFORMATION: Synthetic: CD27 antibody  VH CDR1 consensus
      sequence (Kabat)
<220> FEATURE:
<221> NAME/KEY: misc_feature
<222> LOCATION: (4)..(4)
<223> OTHER INFORMATION: X is W or I
<220> FEATURE:
<221> NAME/KEY: misc_feature
<222> LOCATION: (5)..(5)
<223> OTHER INFORMATION: X is S or H

<400> SEQUENCE: 161

Gly Tyr Tyr Xaa Xaa
1               5

<210> SEQ ID NO 162
<211> LENGTH: 17
<212> TYPE: PRT
<213> ORGANISM: Artificial Sequence
<220> FEATURE:
<223> OTHER INFORMATION: Synthetic: CD27 antibody  VH CDR2 consensus
      sequence (Kabat)
<220> FEATURE:
<221> NAME/KEY: misc_feature
<222> LOCATION: (1)..(1)
<223> OTHER INFORMATION: X is Absent or W
<220> FEATURE:
<221> NAME/KEY: misc_feature
<222> LOCATION: (2)..(2)
<223> OTHER INFORMATION: X is Y or I
<220> FEATURE:
<221> NAME/KEY: misc_feature
<222> LOCATION: (4)..(4)
<223> OTHER INFORMATION: X is Y or P
<220> FEATURE:
<221> NAME/KEY: misc_feature
<222> LOCATION: (5)..(5)
<223> OTHER INFORMATION: X is Y or N
<220> FEATURE:
<221> NAME/KEY: misc_feature
<222> LOCATION: (8)..(8)
<223> OTHER INFORMATION: X is S or G
<220> FEATURE:
<221> NAME/KEY: misc_feature
<222> LOCATION: (11)..(11)
<223> OTHER INFORMATION: X is Y or  S
<220> FEATURE:
<221> NAME/KEY: misc_feature
<222> LOCATION: (12)..(12)
<223> OTHER INFORMATION: X is N or A
<220> FEATURE:
```

```
<221> NAME/KEY: misc_feature
<222> LOCATION: (13)..(13)
<223> OTHER INFORMATION: X is P or Q
<220> FEATURE:
<221> NAME/KEY: misc_feature
<222> LOCATION: (14)..(14)
<223> OTHER INFORMATION: X is S or K
<220> FEATURE:
<221> NAME/KEY: misc_feature
<222> LOCATION: (15)..(15)
<223> OTHER INFORMATION: X is L or F
<220> FEATURE:
<221> NAME/KEY: misc_feature
<222> LOCATION: (16)..(16)
<223> OTHER INFORMATION: X is K or Q
<220> FEATURE:
<221> NAME/KEY: misc_feature
<222> LOCATION: (17)..(17)
<223> OTHER INFORMATION: X is S or D

<400> SEQUENCE: 162

Xaa Xaa Asn Xaa Xaa Ser Gly Xaa Thr Asn Xaa Xaa Xaa Xaa Xaa Xaa
1               5                   10                  15

Xaa

<210> SEQ ID NO 163
<211> LENGTH: 21
<212> TYPE: PRT
<213> ORGANISM: Artificial Sequence
<220> FEATURE:
<223> OTHER INFORMATION: Synthetic: CD27 antibody VH CDR3 consensus
      sequence (Kabat)
<220> FEATURE:
<221> NAME/KEY: misc_feature
<222> LOCATION: (1)..(1)
<223> OTHER INFORMATION: X is Absent or D
<220> FEATURE:
<221> NAME/KEY: misc_feature
<222> LOCATION: (2)..(2)
<223> OTHER INFORMATION: X is Absent or R
<220> FEATURE:
<221> NAME/KEY: misc_feature
<222> LOCATION: (3)..(3)
<223> OTHER INFORMATION: X is Absent or L
<220> FEATURE:
<221> NAME/KEY: misc_feature
<222> LOCATION: (4)..(4)
<223> OTHER INFORMATION: X is Absent or V
<220> FEATURE:
<221> NAME/KEY: misc_feature
<222> LOCATION: (5)..(5)
<223> OTHER INFORMATION: X is Absent or L
<220> FEATURE:
<221> NAME/KEY: misc_feature
<222> LOCATION: (6)..(6)
<223> OTHER INFORMATION: X is Absent or P
<220> FEATURE:
<221> NAME/KEY: misc_feature
<222> LOCATION: (7)..(7)
<223> OTHER INFORMATION: X is Absent or W
<220> FEATURE:
<221> NAME/KEY: misc_feature
<222> LOCATION: (8)..(8)
<223> OTHER INFORMATION: X is Absent or F
<220> FEATURE:
<221> NAME/KEY: misc_feature
<222> LOCATION: (9)..(9)
<223> OTHER INFORMATION: X is Absent or G
<220> FEATURE:
<221> NAME/KEY: misc_feature
<222> LOCATION: (10)..(10)
<223> OTHER INFORMATION: X is Absent or E
<220> FEATURE:
<221> NAME/KEY: misc_feature
<222> LOCATION: (11)..(11)
<223> OTHER INFORMATION: X is Absent or I
```

```
<220> FEATURE:
<221> NAME/KEY: misc_feature
<222> LOCATION: (12)..(12)
<223> OTHER INFORMATION: X is Absent, OR Y or F
<220> FEATURE:
<221> NAME/KEY: misc_feature
<222> LOCATION: (14)..(14)
<223> OTHER INFORMATION: X is L or Absent
<220> FEATURE:
<221> NAME/KEY: misc_feature
<222> LOCATION: (15)..(15)
<223> OTHER INFORMATION: X is I or Absent
<220> FEATURE:
<221> NAME/KEY: misc_feature
<222> LOCATION: (16)..(16)
<223> OTHER INFORMATION: X is R or Absent
<220> FEATURE:
<221> NAME/KEY: misc_feature
<222> LOCATION: (17)..(17)
<223> OTHER INFORMATION: X is G or D
<220> FEATURE:
<221> NAME/KEY: misc_feature
<222> LOCATION: (21)..(21)
<223> OTHER INFORMATION: X is Y or I

<400> SEQUENCE: 163

Xaa Xaa Xaa Xaa Xaa Xaa Xaa Xaa Xaa Xaa Xaa Xaa Pro Xaa Xaa Xaa
1               5                   10                  15

Xaa Ala Phe Asp Xaa
            20

<210> SEQ ID NO 164
<211> LENGTH: 20
<212> TYPE: PRT
<213> ORGANISM: Artificial Sequence
<220> FEATURE:
<223> OTHER INFORMATION: Synthetic: CD27 antibody  VL CDR1 consensus
      sequence (Kabat)
<220> FEATURE:
<221> NAME/KEY: misc_feature
<222> LOCATION: (2)..(2)
<223> OTHER INFORMATION: X is S or  A
<220> FEATURE:
<221> NAME/KEY: misc_feature
<222> LOCATION: (5)..(5)
<223> OTHER INFORMATION: X is Absent or S
<220> FEATURE:
<221> NAME/KEY: misc_feature
<222> LOCATION: (6)..(6)
<223> OTHER INFORMATION: X is Absent or I
<220> FEATURE:
<221> NAME/KEY: misc_feature
<222> LOCATION: (7)..(7)
<223> OTHER INFORMATION: X is Absent or R
<220> FEATURE:
<221> NAME/KEY: misc_feature
<222> LOCATION: (8)..(8)
<223> OTHER INFORMATION: X is Absent or S
<220> FEATURE:
<221> NAME/KEY: misc_feature
<222> LOCATION: (11)..(11)
<223> OTHER INFORMATION: X is L or A
<220> FEATURE:
<221> NAME/KEY: misc_feature
<222> LOCATION: (12)..(12)
<223> OTHER INFORMATION: X is H or Absent
<220> FEATURE:
<221> NAME/KEY: misc_feature
<222> LOCATION: (13)..(13)
<223> OTHER INFORMATION: X is T or Absent
<220> FEATURE:
<221> NAME/KEY: misc_feature
<222> LOCATION: (14)..(14)
<223> OTHER INFORMATION: X is N or Absent
<220> FEATURE:
<221> NAME/KEY: misc_feature
```

```
<222> LOCATION: (15)..(15)
<223> OTHER INFORMATION: X is G or Absent
<220> FEATURE:
<221> NAME/KEY: misc_feature
<222> LOCATION: (16)..(16)
<223> OTHER INFORMATION: X is Y or Absent
<220> FEATURE:
<221> NAME/KEY: misc_feature
<222> LOCATION: (17)..(17)
<223> OTHER INFORMATION: X is N or Absent
<220> FEATURE:
<221> NAME/KEY: misc_feature
<222> LOCATION: (18)..(18)
<223> OTHER INFORMATION: X is Y or Absent
<220> FEATURE:
<221> NAME/KEY: misc_feature
<222> LOCATION: (19)..(19)
<223> OTHER INFORMATION: X is L or Absent
<220> FEATURE:
<221> NAME/KEY: misc_feature
<222> LOCATION: (20)..(20)
<223> OTHER INFORMATION: X is D or Absent

<400> SEQUENCE: 164

Arg Xaa Ser Gln Xaa Xaa Xaa Xaa Asn Leu Xaa Xaa Xaa Xaa Xaa
1               5                   10                  15

Xaa Xaa Xaa Xaa
            20

<210> SEQ ID NO 165
<211> LENGTH: 7
<212> TYPE: PRT
<213> ORGANISM: Artificial Sequence
<220> FEATURE:
<223> OTHER INFORMATION: Synthetic: CD27 antibody VL CDR2 consensus
      sequence (Kabat)
<220> FEATURE:
<221> NAME/KEY: misc_feature
<222> LOCATION: (1)..(1)
<223> OTHER INFORMATION: X is L or G
<220> FEATURE:
<221> NAME/KEY: misc_feature
<222> LOCATION: (2)..(2)
<223> OTHER INFORMATION: X is G or A
<220> FEATURE:
<221> NAME/KEY: misc_feature
<222> LOCATION: (4)..(4)
<223> OTHER INFORMATION: X is N or T
<220> FEATURE:
<221> NAME/KEY: misc_feature
<222> LOCATION: (7)..(7)
<223> OTHER INFORMATION: X is S or T

<400> SEQUENCE: 165

Xaa Xaa Ser Xaa Arg Ala Xaa
1               5

<210> SEQ ID NO 166
<211> LENGTH: 9
<212> TYPE: PRT
<213> ORGANISM: Artificial Sequence
<220> FEATURE:
<223> OTHER INFORMATION: Synthetic: CD27 antibody VL CDR3 consensus
      sequence (Kabat)
<220> FEATURE:
<221> NAME/KEY: misc_feature
<222> LOCATION: (1)..(1)
<223> OTHER INFORMATION: X is M or Q
<220> FEATURE:
<221> NAME/KEY: misc_feature
<222> LOCATION: (3)..(3)
<223> OTHER INFORMATION: X is A or Y
<220> FEATURE:
<221> NAME/KEY: misc_feature
```

```
<222> LOCATION: (4)..(4)
<223> OTHER INFORMATION: X is L or N
<220> FEATURE:
<221> NAME/KEY: misc_feature
<222> LOCATION: (5)..(5)
<223> OTHER INFORMATION: X is Q or N
<220> FEATURE:
<221> NAME/KEY: misc_feature
<222> LOCATION: (6)..(6)
<223> OTHER INFORMATION: X is T or W

<400> SEQUENCE: 166

Xaa Gln Xaa Xaa Xaa Xaa Pro Leu Thr
1               5

<210> SEQ ID NO 167
<211> LENGTH: 5
<212> TYPE: PRT
<213> ORGANISM: Artificial Sequence
<220> FEATURE:
<223> OTHER INFORMATION: Synthetic: PD-L1 antibody  VH CDR1 consensus
      sequence (Kabat)
<220> FEATURE:
<221> NAME/KEY: misc_feature
<222> LOCATION: (1)..(1)
<223> OTHER INFORMATION: X is T or S
<220> FEATURE:
<221> NAME/KEY: misc_feature
<222> LOCATION: (2)..(2)
<223> OTHER INFORMATION: X is S or Y or H

<400> SEQUENCE: 167

Xaa Xaa Trp Met Ser
1               5

<210> SEQ ID NO 168
<211> LENGTH: 17
<212> TYPE: PRT
<213> ORGANISM: Artificial Sequence
<220> FEATURE:
<223> OTHER INFORMATION: Synthetic: PD-L1 antibody  VH CDR2 consensus
      sequence (Kabat)

<400> SEQUENCE: 168

Asn Ile Lys Gln Asp Gly Ser Glu Lys Tyr Tyr Val Asp Ser Val Lys
1               5                   10                  15

Gly

<210> SEQ ID NO 169
<211> LENGTH: 10
<212> TYPE: PRT
<213> ORGANISM: Artificial Sequence
<220> FEATURE:
<223> OTHER INFORMATION: Synthetic: PD-L1 antibody  VH CDR3 consensus
      sequence (Kabat)

<400> SEQUENCE: 169

Asp Arg Pro Val Ala Gly Ala Ser Ala Leu
1               5                   10

<210> SEQ ID NO 170
<211> LENGTH: 11
<212> TYPE: PRT
<213> ORGANISM: Artificial Sequence
<220> FEATURE:
<223> OTHER INFORMATION: Synthetic: PD-L1 antibody  VL CDR1 consensus
      sequence (Kabat)

<400> SEQUENCE: 170
```

```
Arg Ala Ser Gln Ser Ile Ser Gly Trp Leu Ala
1               5                   10
```

```
<210> SEQ ID NO 171
<211> LENGTH: 7
<212> TYPE: PRT
<213> ORGANISM: Artificial Sequence
<220> FEATURE:
<223> OTHER INFORMATION: Synthetic: PD-L1 antibody  VL CDR2 consensus
      sequence (Kabat)

<400> SEQUENCE: 171

Lys Ala Ser Ser Leu Glu Ser
1               5
```

```
<210> SEQ ID NO 172
<211> LENGTH: 9
<212> TYPE: PRT
<213> ORGANISM: Artificial Sequence
<220> FEATURE:
<223> OTHER INFORMATION: Synthetic: PD-L1 antibody  VL CDR3 consensus
      sequence (Kabat)

<400> SEQUENCE: 172

Gln Gln Tyr Tyr Gly Ser Ser Arg Thr
1               5
```

```
<210> SEQ ID NO 173
<211> LENGTH: 260
<212> TYPE: PRT
<213> ORGANISM: Homo sapiens
<220> FEATURE:
<221> NAME/KEY: misc_feature
<222> LOCATION: (1)..(260)
<223> OTHER INFORMATION: CD27 amino acid sequence

<400> SEQUENCE: 173

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
                20                  25                  30

Trp Ala Gln Gly Lys Leu Cys Cys Gln Met Cys Glu Pro Gly Thr Phe
            35                  40                  45

Leu Val Lys Asp Cys Asp Gln His Arg Lys Ala Ala Gln Cys Asp Pro
        50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
                100                 105                 110

Arg Asp Lys Glu Cys Thr Glu Cys Asp Pro Leu Pro Asn Pro Ser Leu
            115                 120                 125

Thr Ala Arg Ser Ser Gln Ala Leu Ser Pro His Pro Gln Pro Thr His
        130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190
```

```
Leu Val Ile Phe Ser Gly Met Phe Leu Val Phe Thr Leu Ala Gly Ala
            195                 200                 205

Leu Phe Leu His Gln Arg Arg Lys Tyr Arg Ser Asn Lys Gly Glu Ser
        210                 215                 220

Pro Val Glu Pro Ala Glu Pro Cys Arg Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
            260

<210> SEQ ID NO 174
<211> LENGTH: 193
<212> TYPE: PRT
<213> ORGANISM: Homo sapiens
<220> FEATURE:
<221> NAME/KEY: misc_feature
<222> LOCATION: (1)..(193)
<223> OTHER INFORMATION: CD70 amino acid sequence

<400> SEQUENCE: 174

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro

<210> SEQ ID NO 175
<211> LENGTH: 288
<212> TYPE: PRT
<213> ORGANISM: Homo sapiens
<220> FEATURE:
<221> NAME/KEY: misc_feature
<222> LOCATION: (1)..(288)
<223> OTHER INFORMATION: PD1 amino acid sequence

<400> SEQUENCE: 175

Met Gln Ile Pro Gln Ala Pro Trp Pro Val Val Trp Ala Val Leu Gln
1               5                   10                  15
```

-continued

```
Leu Gly Trp Arg Pro Gly Trp Phe Leu Asp Ser Pro Asp Arg Pro Trp
             20                  25                  30

Asn Pro Pro Thr Phe Ser Pro Ala Leu Leu Val Val Thr Glu Gly Asp
         35                  40                  45

Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 176
<211> LENGTH: 176
<212> TYPE: PRT
<213> ORGANISM: Homo sapiens
<220> FEATURE:
<221> NAME/KEY: misc_feature
<222> LOCATION: (1)..(176)
<223> OTHER INFORMATION: PD-L1 amino acid sequence (isoform b precursor)

<400> SEQUENCE: 176

Met Arg Ile Phe Ala Val Phe Ile Phe Met Thr Tyr Trp His Leu Leu
1               5                  10                  15

Asn Ala Pro Tyr Asn Lys Ile Asn Gln Arg Ile Leu Val Val Asp Pro
            20                  25                  30

Val Thr Ser Glu His Glu Leu Thr Cys Gln Ala Glu Gly Tyr Pro Lys
        35                  40                  45

Ala Glu Val Ile Trp Thr Ser Ser Asp His Gln Val Leu Ser Gly Lys
    50                  55                  60

Thr Thr Thr Thr Asn Ser Lys Arg Glu Glu Lys Leu Phe Asn Val Thr
65                  70                  75                  80
```

```
Ser Thr Leu Arg Ile Asn Thr Thr Asn Glu Ile Phe Tyr Cys Thr
                85                  90                  95

Phe Arg Arg Leu Asp Pro Glu Glu Asn His Thr Ala Glu Leu Val Ile
            100                 105                 110

Pro Glu Leu Pro Leu Ala His Pro Pro Asn Glu Arg Thr His Leu Val
            115                 120                 125

Ile Leu Gly Ala Ile Leu Leu Cys Leu Gly Val Ala Leu Thr Phe Ile
            130                 135                 140

Phe Arg Leu Arg Lys Gly Arg Met Met Asp Val Lys Lys Cys Gly Ile
145                 150                 155                 160

Gln Asp Thr Asn Ser Lys Lys Gln Ser Asp Thr His Leu Glu Glu Thr
                165                 170                 175

<210> SEQ ID NO 177
<211> LENGTH: 127
<212> TYPE: PRT
<213> ORGANISM: Artificial Sequence
<220> FEATURE:
<223> OTHER INFORMATION: Synthetic: 2B3 VH (modified)

<400> SEQUENCE: 177

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Ile His Trp Val Arg Gln Ala Pro Gly Gln Gly Leu Glu Trp Met
            35                  40                  45

Gly Trp Ile Asn Pro Asn Ser Gly Gly Thr Asn Ser Ala Gln Lys Phe
    50                  55                  60

Gln Asp Arg Val Thr Ile Thr Arg Asp Thr Ser Ile Asn Thr Ala Tyr
65                  70                  75                  80

Met Glu Leu Ser Arg Leu Arg Ser Asp Thr Ala Val Tyr Phe Cys
                85                  90                  95

Ala Arg Asp Arg Leu Val Leu Pro Trp Phe Gly Glu Ile Phe Pro Asp
            100                 105                 110

Ala Phe Asp Ile Trp Gly Gln Gly Thr Leu Val Thr Val Ser Ser
            115                 120                 125

<210> SEQ ID NO 178
<211> LENGTH: 107
<212> TYPE: PRT
<213> ORGANISM: Artificial Sequence
<220> FEATURE:
<223> OTHER INFORMATION: Synthetic: 2B3 VL (modified)

<400> SEQUENCE: 178

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Arg Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
            50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95
```

Thr Phe Gly Gly Gly Thr Lys Val Glu Ile Lys
                100                 105

<210> SEQ ID NO 179
<211> LENGTH: 711
<212> TYPE: PRT
<213> ORGANISM: Artificial Sequence
<220> FEATURE:
<223> OTHER INFORMATION: Synthetic: Full 9H9-2B3 (CDX-527) heavy chain
      sequence

<400> SEQUENCE: 179

Glu Val Gln Leu Val Glu Ser Gly Gly Leu Val Gln Pro Gly Gly
1               5                   10                  15

Ser Leu Arg Leu Ser Cys Ala Ala Ser Gly Gly Ile Ile Ser Thr Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Met Tyr Tyr Cys
                85                  90                  95

Ala Arg Asp Arg Pro Val Ala Gly Ala Ser Ala Leu Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr

```
              340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys Gly Ser Ser Gly Gly Gly Ser Glu Ile Val Met Thr Gln Ser
450                 455                 460
Pro Ala Thr Leu Ser Val Ser Pro Gly Glu Arg Ala Thr Leu Ser Cys
465                 470                 475                 480
Arg Ala Ser Gln Ser Ile Arg Ser Asn Leu Ala Trp Tyr Gln Gln Lys
                485                 490                 495
Pro Gly Gln Ala Pro Arg Leu Leu Ile Tyr Gly Ala Ser Thr Arg Ala
            500                 505                 510
Thr Gly Ile Pro Ala Arg Phe Ser Gly Ser Gly Ser Gly Thr Glu Phe
        515                 520                 525
Thr Leu Thr Ile Ser Ser Leu Gln Ser Glu Asn Phe Ala Val Tyr Tyr
        530                 535                 540
Cys Gln Gln Tyr Asn Asn Trp Pro Leu Thr Phe Gly Cys Gly Thr Lys
545                 550                 555                 560
Val Glu Ile Lys Gly Gly Gly Gly Ser Gly Gly Gly Ser Gly Gly
                565                 570                 575
Gly Gly Ser Gly Gly Gly Gly Ser Gln Val Gln Leu Val Gln Ser Gly
            580                 585                 590
Ala Glu Val Lys Lys Pro Gly Ala Ser Val Lys Val Ser Cys Lys Ala
        595                 600                 605
Ser Gly Tyr Thr Phe Thr Gly Tyr Tyr Ile His Trp Val Arg Gln Ala
        610                 615                 620
Pro Gly Gln Cys Leu Glu Trp Met Gly Trp Ile Asn Pro Asn Ser Gly
625                 630                 635                 640
Gly Thr Asn Ser Ala Gln Lys Phe Gln Asp Arg Val Thr Ile Thr Arg
                645                 650                 655
Val Thr Ser Ile Asn Thr Ala Tyr Met Glu Leu Ser Arg Leu Arg Ser
            660                 665                 670
Asp Asp Thr Ala Val Tyr Phe Cys Ala Arg Asp Arg Leu Val Leu Pro
        675                 680                 685
Trp Phe Gly Glu Ile Phe Pro Asp Ala Phe Asp Ile Trp Gly Gln Gly
        690                 695                 700
Thr Leu Val Thr Val Ser Ser
705                 710

<210> SEQ ID NO 180
<211> LENGTH: 214
<212> TYPE: PRT
<213> ORGANISM: Artificial Sequence
<220> FEATURE:
<223> OTHER INFORMATION: Synthetic: 9H9-2B3 (CDX-527) light chain
      sequence
```

<400> SEQUENCE: 180

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Gly Ser Ser Arg
                85                  90                  95

Thr Phe Gly Gln Gly Thr Asn Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 181
<211> LENGTH: 711
<212> TYPE: PRT
<213> ORGANISM: Artificial Sequence
<220> FEATURE:
<223> OTHER INFORMATION: Synthetic: Full 9H9-2B3(DD) heavy chain sequence

<400> SEQUENCE: 181

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ile Ile Ser Thr Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Met Tyr Tyr Cys
                85                  90                  95

Ala Arg Asp Arg Pro Val Ala Gly Ala Ser Ala Leu Trp Gly Gln Gly
            100                 105                 110

Thr Leu Val Thr Val Ser Ser Ala Ser Thr Lys Gly Pro Ser Val Phe
        115                 120                 125
```

-continued

```
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys Gly Ser Ser Gly Gly Gly Ser Glu Ile Val Met Thr Gln Ser
    450                 455                 460
Pro Ala Thr Leu Ser Val Ser Pro Gly Glu Arg Ala Thr Leu Ser Cys
465                 470                 475                 480
Arg Ala Ser Gln Ser Ile Arg Ser Asn Leu Ala Trp Tyr Gln Gln Lys
                485                 490                 495
Pro Gly Gln Ala Pro Arg Leu Leu Ile Tyr Gly Ala Ser Thr Arg Ala
            500                 505                 510
Thr Gly Ile Pro Ala Arg Phe Ser Gly Ser Gly Ser Gly Thr Glu Phe
        515                 520                 525
Thr Leu Thr Ile Ser Ser Leu Gln Ser Glu Asp Phe Ala Val Tyr Tyr
    530                 535                 540
```

```
Cys Gln Gln Tyr Asn Asn Trp Pro Leu Thr Phe Gly Cys Gly Thr Lys
545                 550                 555                 560

Val Glu Ile Lys Gly Gly Gly Ser Gly Gly Gly Ser Gly
                565                 570                 575

Gly Gly Ser Gly Gly Gly Gly Ser Gln Val Gln Leu Val Gln Ser Gly
            580                 585                 590

Ala Glu Val Lys Lys Pro Gly Ala Ser Val Lys Val Ser Cys Lys Ala
            595                 600                 605

Ser Gly Tyr Thr Phe Thr Gly Tyr Tyr Ile His Trp Val Arg Gln Ala
            610                 615                 620

Pro Gly Gln Cys Leu Glu Trp Met Gly Trp Ile Asn Pro Asn Ser Gly
625                 630                 635                 640

Gly Thr Asn Ser Ala Gln Lys Phe Gln Asp Arg Val Thr Ile Thr Arg
            645                 650                 655

Asp Thr Ser Ile Asn Thr Ala Tyr Met Glu Leu Ser Arg Leu Arg Ser
            660                 665                 670

Asp Asp Thr Ala Val Tyr Phe Cys Ala Arg Asp Arg Leu Val Leu Pro
            675                 680                 685

Trp Phe Gly Glu Ile Phe Pro Asp Ala Phe Asp Ile Trp Gly Gln Gly
690                 695                 700

Thr Leu Val Thr Val Ser Ser
705                 710

<210> SEQ ID NO 182
<211> LENGTH: 214
<212> TYPE: PRT
<213> ORGANISM: Artificial Sequence
<220> FEATURE:
<223> OTHER INFORMATION: Synthetic: 9H9-2B3(DD) light chain sequence

<400> SEQUENCE: 182

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Gly Ser Ser Arg
            85                  90                  95

Thr Phe Gly Gln Gly Thr Asn Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
            195                 200                 205

Phe Asn Arg Gly Glu Cys
    210

<210> SEQ ID NO 183
<211> LENGTH: 168
<212> TYPE: PRT
<213> ORGANISM: Artificial Sequence
<220> FEATURE:
<223> OTHER INFORMATION: Synthetic: ECD of huCD27

<400> SEQUENCE: 183

Thr Pro Ala Pro Lys Ser Cys Pro Glu Arg His Tyr Trp Ala Gln Gly
1               5                   10                  15

Lys Leu Cys Cys Gln Met Cys Glu Pro Gly Thr Phe Leu Val Lys Asp
            20                  25                  30

Cys Asp Gln His Arg Lys Ala Ala Gln Cys Asp Pro Cys Ile Pro Gly
        35                  40                  45

Val Ser Phe Ser Pro Asp His His Thr Arg Pro His Cys Glu Ser Cys
    50                  55                  60

Arg His Cys Asn Ser Gly Leu Leu Val Arg Asn Cys Thr Ile Thr Ala
65                  70                  75                  80

Asn Ala Glu Cys Ala Cys Arg Asn Gly Trp Gln Cys Arg Asp Lys Glu
                85                  90                  95

Cys Thr Glu Cys Asp Pro Leu Pro Asn Pro Ser Leu Thr Ala Arg Ser
            100                 105                 110

Ser Gln Ala Leu Ser Pro His Pro Gln Pro Thr His Leu Pro Tyr Val
        115                 120                 125

Ser Glu Met Leu Glu Ala Arg Thr Ala Gly His Met Gln Thr Leu Ala
    130                 135                 140

Asp Phe Arg Gln Leu Pro Ala Arg Thr Leu Ser Thr His Trp Pro Pro
145                 150                 155                 160

Gln Arg Ser Leu Cys Ser Ser Asp
                165

<210> SEQ ID NO 184
<211> LENGTH: 168
<212> TYPE: PRT
<213> ORGANISM: Artificial Sequence
<220> FEATURE:
<223> OTHER INFORMATION: Synthetic: ECD of huCD27 mutated

<400> SEQUENCE: 184

Thr Pro Ala Pro Lys Ser Cys Pro Glu Arg His Tyr Trp Ala Gln Gly
1               5                   10                  15

Lys Leu Cys Cys Gln Met Cys Glu Pro Gly Thr Phe Leu Val Lys Asp
            20                  25                  30

Cys Asp Gln His Arg Lys Ala Ala Gln Cys Asp Pro Cys Ile Pro Gly
        35                  40                  45

Val Ser Phe Ser Pro Asp His His Thr Arg Pro His Cys Glu Ser Cys
    50                  55                  60

Arg His Cys Asn Ser Gly Leu Leu Val Arg Asn Cys Thr Ile Thr Ala
65                  70                  75                  80

Asn Ala Glu Cys Ser Cys Ala Ala Ala Trp Gln Cys Arg Asp Lys Glu
                85                  90                  95

Cys Thr Glu Cys Asp Pro Leu Pro Asn Pro Ser Leu Thr Ala Arg Ser
            100                 105                 110

Ser Gln Ala Leu Ser Pro His Pro Gln Pro Thr His Leu Pro Tyr Val
            115                 120                 125

Ser Glu Met Leu Glu Ala Arg Thr Ala Gly His Met Gln Thr Leu Ala
        130                 135                 140

Asp Phe Arg Gln Leu Pro Ala Arg Thr Leu Ser Thr His Trp Pro Pro
145                 150                 155                 160

Gln Arg Ser Leu Cys Ser Ser Asp
                165

<210> SEQ ID NO 185
<211> LENGTH: 357
<212> TYPE: DNA
<213> ORGANISM: Artificial Sequence
<220> FEATURE:
<223> OTHER INFORMATION: Synthetic: NA sequence of 9H9x2B3(DD) variable
      domain

<400> SEQUENCE: 185

```
gaagtgcaac tggtggagtc gggtggtgga ctcgtgcagc ccggcggatc cctgagactc      60
tcttgtgccg catcgggcgg cattattagc acttactgga tgtcatgggt cagacaggca     120
ccgggaaagg gcttggaatg ggtggcgaat atcaagcagg atggatccga agtactac       180 gtggactccg tgaagggcag attcaccatt tcccgggaca cgccaagaa ctcgctctat     240 ctgcaaatga actcgttgcg ggtggaagat actgccatgt actactgcgc ccgggaccgg     300
cctgtggccg ggcgtcggc cctctggggc agggcactc tggtcaccgt gtcctct         357
```

<210> SEQ ID NO 186
<211> LENGTH: 786
<212> TYPE: DNA
<213> ORGANISM: Artificial Sequence
<220> FEATURE:
<223> OTHER INFORMATION: Synthetic: NA sequence of 9H9x2B3(DD) scFv
      domain

<400> SEQUENCE: 186

```
ggctccagcg ggggtggcgg ttccgagatc gtgatgactc agagcccggc aaccctgtcc      60
gtgtctccgg gggagcgggc tactctttcc tgccgggcat cccagtccat ccggtcgaac     120
cttgcgtggt accaacagaa gcctggacag gcgccccgcc tgctgatcta cggggcgtcg     180
actagggcca ccggcatccc ggcccgcttc tccgggtccg gatccggcac cgaattcacc     240
ctcaccatct cgagcctgca gtccgaaaac ttcgccgtct actactgcca gcagtacaac     300
aactggccgc tgacattcgg atgcggaacc aaagtggaaa tcaagggcgg cggcggatcc     360
ggcggtggcg gcagcggcgg tggaggatcc ggtggcggcg gttcacaagt gcagctggtg     420
cagtcaggcg ccgaagtcaa gaagcccggg gccagcgtga agtcagctg caaggcttcc     480 ggatacacct tcacgggtta ctacattcac tgggttcgcc aagcgcccgg gcagtgtctg     540
gagtggatgg gatggatcaa ccctaactcg ggggaacca actcggccca aaagttccag     600
gaccgggtca ccattacaag agtcacgtcc atcaacactg cctacatgga gttgagccgg     660
ctgcgatcag acgacaccgc cgtgtactc tgcgcgaggg accgcctcgt cctcccgtgg     720 tttgagaga tcttccccgga tgccttcgac atttggggac aggggaccct cgtgactgtg     780
tccagc                                                                 786
```

<210> SEQ ID NO 187
<211> LENGTH: 321
<212> TYPE: DNA

```
<213> ORGANISM: Artificial Sequence
<220> FEATURE:
<223> OTHER INFORMATION: Synthetic: NA sequence of the 9H9x2B3(DD) light
      chain variable domain

<400> SEQUENCE: 187
gatatccaga tgacccagag cccgtccacc ctttccgcga gcgtcggcga cagagtgacc        60
attacttgtc gggcctcgca aagcatctcc ggctggctgg cttggtacca gcaaaagcct       120
ggaaaggccc ctaagctgct gatctacaag gcctcatccc tggagtccgg agtgccttca       180
cgcttttcgg ggagcggatc ggggactgag ttcaccctca ccatttcctc cctgcaaccc       240
gacgatttcg cgacatacta ctgccagcag tactacggtt cctcgcgcac gttcggacag       300
ggcactaacg tcgagatcaa g                                                 321

<210> SEQ ID NO 188
<211> LENGTH: 8
<212> TYPE: PRT
<213> ORGANISM: Artificial Sequence
<220> FEATURE:
<223> OTHER INFORMATION: Synthetic: Ovalbumin peptide

<400> SEQUENCE: 188

Ser Ile Ile Asn Phe Glu Lys Leu
1               5
```